US011639523B2

(12) United States Patent
Zhang et al.

(10) Patent No.: US 11,639,523 B2
(45) Date of Patent: *May 2, 2023

(54) TYPE V CRISPR-CAS SYSTEMS AND USE THEREOF

(71) Applicants: The Broad Institute, Inc., Cambridge, MA (US); MASSACHUSETTS INSTITUTE OF TECHNOLOGY, Cambridge, MA (US)

(72) Inventors: Feng Zhang, Cambridge, MA (US); Jonathan Gootenberg, Cambridge, MA (US); Omar Abudayyeh, Cambridge, MA (US); Julia Joung, Cambridge, MA (US); Alim Ladha, Cambridge, MA (US); Han Altae-Tran, Cambridge, MA (US); Guilhem Faure, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/894,678

(22) Filed: Jun. 5, 2020

(65) Prior Publication Data
US 2021/0292721 A1    Sep. 23, 2021

Related U.S. Application Data

(60) Provisional application No. 62/993,494, filed on Mar. 23, 2020, provisional application No. 63/018,487, filed on Apr. 30, 2020, provisional application No. 63/019,406, filed on May 3, 2020, provisional application No. 63/032,470, filed on May 29, 2020.

(51) Int. Cl.
*C12Q 1/6844* (2018.01)
*C12N 9/22* (2006.01)
*C12Q 1/6806* (2018.01)
*C12N 9/12* (2006.01)
*C12N 9/78* (2006.01)
*B01L 3/00* (2006.01)
*B01L 7/00* (2006.01)

(52) U.S. Cl.
CPC ...... *C12Q 1/6844* (2013.01); *B01L 3/502715* (2013.01); *B01L 7/52* (2013.01); *C12N 9/1276* (2013.01); *C12N 9/22* (2013.01); *C12N 9/78* (2013.01); *C12Q 1/6806* (2013.01); *B01L 2300/0816* (2013.01); *C12N 2310/20* (2017.05); *C12Q 2600/156* (2013.01); *C12Q 2600/16* (2013.01); *C12Y 207/07049* (2013.01); *G01N 2333/165* (2013.01)

(58) Field of Classification Search
CPC .... C12N 9/22; C12N 2310/20; C12N 9/1276; C12N 9/78; C12Y 207/07049
See application file for complete search history.

(56) References Cited

U.S. PATENT DOCUMENTS

| | | |
|---|---|---|
| 7,312,053 B2 | 12/2007 | Tada et al. |
| 9,470,699 B2 | 10/2016 | Peeters |
| 9,556,466 B2 | 1/2017 | Lee et al. |
| 10,253,365 B1 | 4/2019 | Doudna et al. |
| 2004/0197797 A1 | 10/2004 | Inoko et al. |
| 2005/0100885 A1 | 5/2005 | Crooke et al. |
| 2009/0104218 A1 | 4/2009 | Tettelin et al. |
| 2012/0053329 A1 | 3/2012 | Yamamoto |
| 2014/0142160 A1 | 5/2014 | Lee et al. |
| 2015/0011430 A1 | 1/2015 | Saxonov |
| 2015/0211058 A1 | 7/2015 | Carstens |
| 2017/0081659 A1 | 3/2017 | Felgner et al. |
| 2017/0312751 A1 | 11/2017 | Glezer et al. |
| 2018/0274017 A1 | 9/2018 | Abudayyeh et al. |
| 2018/0298445 A1 | 10/2018 | Abudayyeh et al. |
| 2018/0305773 A1 | 10/2018 | Abudayyeh et al. |
| 2018/0363026 A1 | 12/2018 | Desharnais et al. |
| 2019/0218604 A1 | 7/2019 | Liang et al. |
| 2021/0095271 A1 | 4/2021 | Li et al. |
| 2021/0108267 A1* | 4/2021 | Zhang .................. C12Q 1/6876 |
| 2021/0292824 A1* | 9/2021 | Zhang ...................... C12N 9/22 |
| 2022/0049242 A1 | 2/2022 | Ismagilov et al. |

FOREIGN PATENT DOCUMENTS

| | | |
|---|---|---|
| CN | 101864483 A | 10/2010 |
| CN | 102747148 A | 10/2012 |
| CN | 106544444 A | 3/2017 |
| CN | 111187856 A | 5/2020 |
| EP | 3237637 | 11/2017 |
| WO | 2011010740 A1 | 1/2011 |

(Continued)

OTHER PUBLICATIONS

L .Li et al. "CRISPR-Cas12b-assisted nucleic acid detection platform", bioRxiv preprint doi: https://doi.org/10.1101/362889, pp. 1-12 (Year: 2018).*
Supporting Covid-19 Research, https://www.neb.com/covid-19/solutions-available-from-new-england-biolabs-supporting-covid-19-research, May 21, 2020, 4 pages.
Abudayyeh et al., "A Cytosine Deaminase for Programmable Single-base RNA Editing", Science, vol. 365, Issue 6451, Jul. 26, 2019, 8 pages.
Abudayyeh et al., "C2C2 is a Single-Component Programmable RNA-Guided RNA-Targeting CRISPR Effector", Science, vol. 353, No. 6299, Aug. 5, 2016, 23 pages.

(Continued)

*Primary Examiner* — Ganapathirama Raghu
(74) *Attorney, Agent, or Firm* — F. Brent Nix, Esq.; Johnson, Marcou, Isaacs & Nix, LLC

(57) ABSTRACT

Engineered or non-naturally occurring systems and compositions comprising a novel Cas12b and a guide molecule. Also provided include methods of use the systems and compositions, including in treating and diagnosing diseases.

14 Claims, 46 Drawing Sheets

Specification includes a Sequence Listing.

(56) References Cited

FOREIGN PATENT DOCUMENTS

| WO | 2011/133952 A2 | 10/2011 | | |
|---|---|---|---|---|
| WO | 2013080154 A1 | 6/2013 | | |
| WO | 2014/093622 A2 | 6/2014 | | |
| WO | 2017/219027 A1 | 12/2017 | | |
| WO | 2018/107129 A1 | 6/2018 | | |
| WO | 2018/204764 A1 | 8/2018 | | |
| WO | 2018/170340 A1 | 9/2018 | | |
| WO | 2019/071048 A1 | 4/2019 | | |
| WO | 2019/071051 A1 | 4/2019 | | |
| WO | 2019/126716 A1 | 6/2019 | | |
| WO | 2020/087631 | * | 5/2020 | |
| WO | 2020118444 A1 | 6/2020 | | |
| WO | WO 2021/087203 A1 | * | 5/2021 | ............... C12N 9/22 |

OTHER PUBLICATIONS

Abudayyeh et al., "RNA Targeting with CRISPR-Cas13a", Nature, vol. 550, No. 7675, Oct. 4, 2017, 30 pages.

Anzalone et al., "Search-and-replace Genome Editing Without Double-Strand Breaks or Donor DNA", Nature, vol. 576, No. 7785, Dec. 5, 2019, 30 pages.

Ben-Assa et al., "SARS-CoV-2 On-the-spot Virus Detection Directly from Patients", Department of Cell Biology and Cancer Science, Rappaport Faculty of Medicine, Technion, May 7, 2020, 13 pages.

Bhadra et al., "High-surety Isothermal Amplification and Detection of SARS-COV-2, including with Crude Enzymes", Department of Molecular Biosciences, College of Natural Sciences, The University of Texas at Austin, Austin, TX 78712, USA, May 7, 2020, 15 pages.

Broughton et al., "CRISPR-Cas12-Based Detection of SARS-CoV-2", Nature Biotechnology, Apr. 16, 2020, 8 pages.

Carr et al., "Genome Engineering", Nature Biotechnology, vol. 27, No. 12, Dec. 9, 2009, 1151-1162.

Chen et al., "CRISPR-Cas12 a Target Binding Unleashes Indiscriminate Single-Stranded DNase Activity", Science, vol. 360, Issue 6387, Apr. 27, 2018, 5 pages.

Cox et al., "RNA Editing with CRISPR-Cas13", Science, vol. 358, No. 6366, Nov. 24, 2017, 23 pages.

Ding et al., "All-in-One Dual CRISPR-Cas12a (AIOD-CRISPR) Assay: A Case for Rapid, Ultrasensitive and Visual Detection of Novel Coronavirus SARS-CoV-2 and HIV", Department of Biomedical Engineering, University of Connecticut Health Center, 263, Farmington Ave., Farmington, CT, 06030, United States, Mar. 21, 2020, 19 pages.

Doman et al., "Evaluation and Minimization of Cas9-Independent Off-arget DNA Editing by Cytosine Base Editors", Nature Biotechnology, vol. 38, No. 5, May 2020, 620-628.

East-Seletsky et al., "Two Distinct RNase Activities of CRISPR-C2c2 Enable Guide-RNA Processing and RNA Detection", Nature, vol. 538, No. 7624, Oct. 13, 2016, 17 pages.

Gaudelli et al., "Programmable Base Editing of A•T to G•C in Genomic DNA without DNA Cleavage", Nature, vol. 551, No. 7681, Nov. 23, 2017, 37 pages.

Gootenberg et al., "Multiplexed and Portable Nucleic Acid Detection Platform with Cas13, Cas12a, and Csm6", Science, vol. 360, No. 6387, Feb. 15, 2018, 14 pages.

Gootenberg et al., "Nucleic Acid Detection with CRISPR-Cas13a/C2c2", Science, vol. 356, No. 6336, Apr. 28, 2017, 6 pages.

Guo et al., "SARS-CoV-2 Detection with CRISPR Diagnostics", Cell Discovery, vol. 6, No. 34, May 19, 2020, 4 pages.

Kashir et al., "Loop Mediated Isothermal Amplification (lamp) Assays as a Rapid Diagnostic for Covid-19", Medical Hypotheses, vol. 141, Apr. 23, 2020, 22 pages.

Komor et al., "Programmable Editing of a Target Base in Genomic DNA without Double-Stranded DNA Cleavage", Nature, vol. 533, No. 7603, May 19, 2016, 25 pages.

Lalli et al., "Rapid and Extraction-free Detection of SARS-CoV-2 from Saliva with Colorimetric LAMP", Department of Genetics, May 11, 2020, 25 pages.

Li et al., "Design and Assessment of Engineered CRISPR-Cpf1 and Its Use for Genome Editing", Nature Protocols, vol. 13, No. 5, May 2018, 48 pages.

Li et al., "Synthetic Oligonucleotides Inhibit CRISPR-Cpf1-Mediated Genome Editing", Cell Reports, vol. 25, No. 12, Dec. 18, 2018, 26 pages.

Liang et al., "Development and Characterization of Stable Anaerobic Thermophilic Methanogenic Microbiomes Fermenting Switchgrass at Decreasing Residence Times", Biotechnology for Biofuels, vol. 11, No. 243, 2018, 18 pages.

Lucia et al., "An Ultrasensitive, Rapid, and Portable Coronavirus SARS-CoV-2 Sequence Detection Method Based on CRISPR-Cas12", INPA-National Scientific and Technical Research Council (Conicet)—Argentina, Mar. 2, 2020, 10 pages.

Makarova et al., "Evolutionary Classification of CRISPR-Cas Systems: A Burst of Class 2 and Derived Variants", Nature Reviews Microbiology, vol. 18, No. 2, Dec. 19, 2019, 67-83.

Myhrvold et al., "Field-deployable Viral Diagnostics using CRISPR-Cas13", Science, vol. 360, Issue 6387, Apr. 27, 2018, 11 pages.

Yu et al., "Rapid Colorimetric Detection of COVID-19 Coronavirus using A Reverse Transcriptional Loop-mediated Isothermal Amplification (RT-LAMP) Diagnostic Platform: iLACO", Applied Biology Laboratory, Shenyang University of Chemical Technology, 110142, Shenyang, China, Feb. 24, 2020, 19 pages.

Osterdahl et al., "Detecting SARS-CoV-2 at Point of Care: Preliminary Data Comparing Loop-mediated Isothermal Amplification (LAMP) to PCR", Department of Ageing & Health, Guy's and St Thomas' NHS Foundation Trust, London, UK, Apr. 4, 2020, 9 pages.

Park et al., "Development of Reverse Transcription Loop-mediated Isothermal Amplification (RT-LAMP) Assays Targeting SARS-CoV-2", Center for Convergent Research of Emerging Virus Infection, Korea Research Institute of Chemical Technology, Daejeon 34114, Republic of Korea, Mar. 24, 2020, 20 pages.

Richter et al., "Phage-assisted Evolution of an Adenine Base Editor with Improved Cas Domain Compatibility and Activity", Nature Biotechnology, 2020, 18 pages.

Zhang et al., "Rapid Molecular Detection of SARS-CoV-2 (COVID-19) Virus RNA Using Colorimetric LAMP", New England Biolabs, 240 County Road, Ipswich MA USA 01938, Feb. 29, 2020, 14 pages.

Shmakov et al., "Diversity and Evolution of Class 2 CRISPR-Cas Systems", Nature Reviews Microbiology, vol. 15, No. 3, Mar. 2017, 30 pages.

Smargon et al., "Cas13b Is a Type VI-B CRISPR-Associated RNA-Guided RNase Differentially Regulated by Accessory Proteins Csx27 and Csx28", Molecular Cell, vol. 65, Issue 4, Feb. 16, 2017, 21 pages.

Teng et al., "Repurposing CRISPR-Cas12b for Mammalian Genome Engineering", Cell Discovery, vol. 4, No. 63, Nov. 27, 2018, 15 pages.

Thi et al., "Screening for SARS-CoV-2 Infections with Colorimetric RT-Lamp and Lamp Sequencing", Schaller Research Groups, Center of Infectious Diseases, Department of Virology, Heidelberg University Hospital, Heidelberg, Germany, May 9, 2020, 28 pages.

Wang et al., "One-pot Detection of COVID-19 with Real-time Reverse-transcription Loop-mediated Isothermal Amplification (RT-Lamp) Assay and Visual RT-Lamp Assay", Key Laboratory of Biomarker Based Rapid-detection Technology for Food Safety of Henan Province, Xuchang University, Xuchang 461000, China, Apr. 22, 2020, 7 pages.

Yu et al., "Rapid Detection of COVID-19 Coronavirus Using a Reverse Transcriptional Loop-Mediated Isothermal Amplification (RT-LAMP) Diagnostic Platform", Clinical Chemistry, May 21, 2020, 3 pages.

Yang et al., "Engineering and Optimizing Deaminase Fusions for Genome Editing", Nature Communication, vol. 7, Issue 13330,, Nov. 2, 2016, 11 pages.

Gruber, et al., "The Vienna RNA Websuite", Nucleic Acids Research, vol. 36, 2008, W70-W74.

Invitation to Pay Additional Fees for corresponding International Application No. PCT/US2021/017985 dated May 3, 2021, all enclosed pages cited.

(56) References Cited

OTHER PUBLICATIONS

Broughton James P., A protocol for rapid detection of the 2019 novel coronavirus SARS-CoV-2 using CRISPR diagnostics: SARS-CoV-2 Detectr; Mammoth Biosciences Feb. 2020; all enclosed pages cited.
Giuffrida, et al., "Integration of Isothermal Amplification Methods in Microfluidic Devices: Recent Advances," Biosensors and Bioelectronics, 90 (2017), all enclosed pages cited.
Gorgannezhad, et al., Microfluidic-Based Acid Amplification Systems in Microbiology, Micromachines (Basel). Jun. 2019; 10(6): 408, all enclosed pages cited.
Li, et al., HOLMESv2: A CRISPR-Cas12b-Assisted Platform for Nucleic Acid Detection and DNA Methylation Quantitation, ACS Synth Biol. Oct. 18, 2019; 8 (10): 2228-2237. doi: 10.1021/accsynbio.9b00209.
NCBI accession No. MW308137.1, Nov. 30, 2020.
Non-Final Office action of co-pending U.S. Appl. No. 16/894,664 dated Dec. 11, 2020; all enclosed pages cited.
Spiess, et al. "Trehalose is a Potent PCR Enhancer: Lowering of DNA Melting Temperature and Thermal Stabilization of Taq Polymerase by the Disaccharide Trehalose," 50(7) Clinical Chemistry (2004), pp. 1256-1259.
Wang, et al., "Rapid and Sensitive Detection of Severe Acute Respiratory Syndrome Coronavirus by Rolling Circle Amplification," Journal of Clinical Microbiology, May 2005, all enclosed pages cited.
Non-Final Office Action of corresponding U.S. Appl. No. 116/894,670 dated Dec. 31, 2020, all enclosed pages cited.
Final Office Action of corresponding U.S. Appl. No. 16/894,670 dated Apr. 15, 2021, all enclosed pages cited.
Final Office Action of corresponding U.S. Appl. No. 16/894,664 dated Apr. 28, 2021, all enclosed pages cited.
Sentamat, et al., "One-step RNA extraction for RT-qPCR detection of 2019-nCoV," bioRxiv preprint https://doi.org.10.1101/2020.04.02.023384, Oct. 21, 2020, all enclosed pages cited.
Schermer, et al., "Rapid SARS-CoV-2 testing in primary material based on a novel multiplex RT-Lamp assay," PLoS One, vol. 15, No. 11: e0238612, Nov. 2, 2020, all enclosed pages cited.
Schellenberg, et al. "Extraction-free RT-Lamp to detect SARS-CoV-2 is less sensitive but highly specific compared to standard RT-PCT in 101 samples," Journal of Clinical Virology, vol. 136: 104764, Feb. 16, 2021, all enclosed pages cited.
International Search Report and Written Opinion of corresponding International Application No. PCT/US2021/017985 dated Jul. 20, 2021, all enclosed pages cited.
Final Office Action of corresponding U.S. Appl. No. 16/894,664 dated Aug. 6, 2021, all enclosed pages cited.
Non-Final Office Action of related U.S. Appl. No. 16/894,664 dated Feb. 17, 2022, all enclosed pages cited.
Final Office Action of related U.S. Appl. No. 16/894,670 dated Mar. 10, 2022, all enclosed pages cited.
Non-Final Office Action for U.S. Appl. No. 16/894,670 dated Dec. 3, 2021, all enclosed pages cited.
Notice of Allowance from corresponding U.S. Appl. No. 16/894,670 dated May 13, 2022, all enclosed pages cited.
Restriction Requirement from corresponding U.S. Appl. No. 17/731,019 dated Sep. 14, 2022, all enclosed pages cited.
Final Office Action from corresponding U.S. Appl. No. 16/894,664 dated Aug. 9, 2022, all enclosed pages cited.
Restriction Requirement from corresponding U.S. Appl. No. 17/731,019 dated Jan. 19, 2023.
Final Office Action from corresponding U.S. Appl. No. 16/894,664 dated Jan. 23, 2023.

\* cited by examiner

| SHERLOCK Lateral flow | SAR-CoV-2 infection status | | | Predictive value |
|---|---|---|---|---|
| | Pos. | Neg | Total | |
| Pos. | 35 (True pos.) | 0 (False pos.) | 35 | PPV = 100% |
| Neg. | 1 (False neg.) | 15 (True neg.) | 16 | NPV = 94% |
| Total | 36 | 15 | | |
| | Sensitivity 97% | Specificity 100% | | |

FIG. 27

| Patient | P1 | P2 | P3 | P4 | P5 | P6 | P7 | P8 | P9 | P10 | P11 | P12 | P13 | P14 | P15 | P16 | P17 | P18 | P19 | P20 | P21 | P22 |
|---|---|---|---|---|---|---|---|---|---|---|---|---|---|---|---|---|---|---|---|---|---|---|
| Positive NP swabs | | | | | | | | | | | | | | | | | | | | | | |
| Ct (CDC N1) | 32.7 | 23.4 | 20.2 | 23.6 | 24.2 | 23.1 | 20.2 | 19.6 | 24.3 | 16.4 | 24.6 | 17.2 | 32.7 | 27.3 | 22.0 | 20.2 | 35.6 | 27.7 | 19.4 | 18.6 | 29.1 | 20.0 |
| Ct (CDC N2) | 34.3 | 24.7 | 21.7 | 24.9 | 25.3 | 24.3 | 21.2 | 20.2 | 25.3 | 19.4 | 25.8 | 18.4 | 33.7 | 28.7 | 22.6 | 21.7 | 36.2 | 28.8 | 20.3 | 19.5 | 30.1 | 20.7 |

| Patient | P23 | P24 | P25 | P26 | P27 | P28 | P29 | P30 | P31 | P32 | P33 | P34 | P35 | P36 | P37 | P38 | P39 | P40 | P41 | P42 | P43 |
|---|---|---|---|---|---|---|---|---|---|---|---|---|---|---|---|---|---|---|---|---|---|
| Positive NP swabs | | | | | | | | | | | | | | | | | | | | | |
| Ct (CDC N1) | 32.1 | 32.2 | 30.3 | 28.5 | 24.6 | 35.8 | 37.3 | 35.2 | 28.3 | 26.0 | 28.7 | 36.2 | 27.1 | 18.6 | 32.7 | 34.6 | 27.6 | 27.4 | 28.5 | 28.6 | 30.7 |
| Ct (CDC N2) | 33.4 | 32.7 | 31.1 | 29.4 | 25.6 | 38.0 | 38.4 | 36.4 | 29.2 | 27.3 | 30.3 | 39.0 | 28.0 | 19.2 | 33.9 | 35.8 | 29.0 | 28.5 | 29.3 | 29.6 | 31.7 |

| Patient | N1 | N2 | N3 | N4 | N5 | N6 | N7 | N8 | N9 | N10 | N11 | N12 | N13 | N14 | N15 |
|---|---|---|---|---|---|---|---|---|---|---|---|---|---|---|---|
| Negative NP swabs | | | | | | | | | | | | | | | |

FIG. 35A

**SAR-CoV-2 infection status
(3/3 replicates)**

|  |  | Pos. | Neg. | Total | Predictive value |
|---|---|---|---|---|---|
| SHERLOCK Lateral flow | Pos. | 34 (True pos.) | 0 (False pos.) | 34 | PPV=100% |
| | Neg. | 9 (False neg.) | 15 (True neg.) | 24 | NPV=62.5% |
| | Total | 43 | 15 | | |

Sensitivity 79%   Specificity 100%

**SAR-CoV-2 infection status
(1/3 replicates)**

|  |  | Pos. | Neg. | Total | Predictive value |
|---|---|---|---|---|---|
| SHERLOCK Lateral flow | Pos. | 39 (True pos.) | 0 (False pos.) | 39 | PPV=100% |
| | Neg. | 4 (False neg.) | 15 (True neg.) | 19 | NPV=79% |
| | Total | 43 | 15 | | |

Sensitivity 91%   Specificity 100%

**SAR-CoV-2 infection status
(filtered for CDC N1 Ct < 32)**

|  |  | Pos. | Neg. | Total | Predictive value |
|---|---|---|---|---|---|
| SHERLOCK Lateral flow | Pos. | 34 (True pos.) | 0 (False pos.) | 34 | PPV=100% |
| | Neg. | 0 (False neg.) | 15 (True neg.) | 15 | NPV=100% |
| | Total | 34 | 15 | | |

Sensitivity 100%   Specificity 100%

FIG. 35B

| Patient | 1 | 2 | 3 | 4 | 5 | 6 | 7 | 8 | 9 | 10 | 11 | 12 |
|---|---|---|---|---|---|---|---|---|---|---|---|---|
| Positive NP swabs | | | | | | | | | | | | |
| Ct (CDC N1) | 32.7 | 23.4 | 20.2 | 23.6 | 24.2 | 23.1 | 20.2 | 19.6 | 24.3 | 18.4 | 24.6 | 17.2 |
| Ct (CDC N2) | 34.3 | 24.7 | 21.7 | 24.9 | 25.3 | 24.3 | 21.2 | 20.2 | 25.3 | 19.4 | 25.8 | 18.4 |

| Patient | 13 | 14 | 15 | 16 | 17 | 18 | 19 | 20 | 21 | 22 |
|---|---|---|---|---|---|---|---|---|---|---|
| Positive NP swabs | | | | | | | | | | |
| Ct (CDC N1) | 32.7 | 27.3 | 22.0 | 20.2 | 35.8 | n.d. | 27.7 | 19.4 | 18.6 | 29.1 |
| Ct (CDC N2) | 33.7 | 28.6 | 22.8 | 21.7 | 36.2 | n.d. | 28.8 | 20.3 | 19.5 | 30.0 |

Lysis: 5 min at 95 °C

| Patient | 13 | 14 | 15 |
|---|---|---|---|
| Negative NP swabs | | | |

| Patient | 16 | 17 |
|---|---|---|
| Negative NP swabs | | |

| | | SAR-CoV-2 infection status | | | |
|---|---|---|---|---|---|
| | | Positive | Negative | Total | Predictive value |
| Lateral Flow Readout | Positive | 61 (True positive) | 0 (False positive) | 61 | PPV = 100% |
| | Negative | 2 (False negative) | 15 (True negative) | 17 | NPV = 88% |
| | Total | 63 | 16 | | |
| | | Sensitivity 97% | Specificity 100% | | |

FIG. 42B

TYPE V CRISPR-CAS SYSTEMS AND USE THEREOF

CROSS REFERENCE TO RELATED APPLICATIONS

This application claims the benefit of U.S. Provisional Application Nos. 62/993,494 filed Mar. 23, 2020, 63/018,487 filed Apr. 30, 2020, 63/019,406 filed May 3, 2020 and 63/032,470 filed May 29, 2020. The entire contents of the above-identified applications are hereby fully incorporated herein by reference.

STATEMENT REGARDING FEDERALLY SPONSORED RESEARCH

This invention was made with government support under grant nos. HL141201 and MH110049 awarded by National Institutes of Health. The government has certain rights in the invention.

REFERENCE TO AN ELECTRONIC SEQUENCE LISTING

The contents of the electronic sequence listing ("BROD-5150US_ST25.txt"; Size is 13,432,782 bytes and it was created on Jun. 5, 2020) is herein incorporated by reference in its entirety.

TECHNICAL FIELD

The subject matter disclosed herein is generally directed to systems, methods and compositions related to CRISPR-Cas systems and components thereof.

BACKGROUND

Nucleic acids are a universal signature of biological information. The ability to rapidly detect nucleic acids with high sensitivity and single-base specificity on a portable platform has the potential to revolutionize diagnosis and monitoring for many diseases, provide valuable epidemiological information, and serve as a generalizable scientific tool. Although many methods have been developed for detecting nucleic acids (Du et al., 2017; Green et al., 2014; Kumar et al., 2014; Pardee et al., 2014; Pardee et al., 2016; Urdea et al., 2006), they inevitably suffer from trade-offs among sensitivity, specificity, simplicity, and speed.

Sensitive and rapid detection of nucleic acids is important for clinical diagnostics and biotechnological applications. Particularly when responding to outbreaks, such as the novel coronavirus, which has been referred to as 2019-nCoV and SARS-CoV-2, which causes COVID 2019, time is of the essence. Sabeti, Early Detection Is Key to Combating the Spread of Coronavirus, Time (Feb. 6, 2020). The 2019-nCoV has killed hundreds in a 2-month time span, and response to the escalating outbreak, particularly where there are indications that both symptomatic and asymptomatic patients with 2019-nCov may transmit the disease. Wang, et al., A precision medicine approach to managing Wuhan Coronavirus pneumonia, Prec. Clin. Med, doi:10.1093/pcmedi/pbaa002. Current coronavirus testing kits sent to states and other countries do not work properly, according to the U.S. Centers for Disease Control and Prevention. Grady, "Coronavirus Test Kits Sent to States, 30 Countries Are Flawed, C.D.C. Says," New York Times, Feb. 12, 2020. Moreover the test being used provides results in four hours from initial sample processing to results. cdc.gov/media/releases/2020/p0206-coronavirus-diagnostic-test-kits.

Highly accurate test results at better processing speeds, particularly that are field-deployable would aid in addressing the outbreak. Currently, the novel coronavirus SARS-CoV-2 has resulted in an international public health emergency, spreading to over 180 countries and infecting more than 300,000 individuals. Testing for the presence of the virus is of utmost importance to both reduce the basic reproductive rate of the virus (R0) and inform best clinical practices for affected patients. However, understanding the full extent of the virus outbreak has remained challenging due to bottlenecks in the diagnosis of infection.

Previously, Applicants developed a platform for nucleic acid detection using CRISPR enzymes called SHERLOCK (Specific High Sensitivity Enzymatic Reporter unLOCKing) (Gootenberg, 2018; Gootenberg, 2017), which combines pre-amplification with the RNA-guided RNase CRISPR-Cas13(Abudayyeh, 2016; East-Seletsky, 2016; Shmakov, 2015; Smargon, 201; Shmakov, 2017) and DNase CRISPR-Cas12(Zetsche, 2015 599; Chen, 2018) for sensing of nucleic acids via fluorescence or portable lateral flow.

SUMMARY

In one aspect, the present disclosure provides a non-naturally occurring or engineered composition comprising: a Cas12b protein from *Alicyclobacillus acidiphilis*; and a guide molecule derived from another CRISPR-Cas system and capable of forming a complex with the Cas12b protein and directing the complex to bind to a target polynucleotide.

In some embodiments, the guide molecule is derived from *Alicyclobacillus acidoterrestris*. In some embodiments, the guide sequence comprises one of SEQ ID NOs: 61957-61961. In some embodiments, the Cas12b protein is fused to one or more localization signals. In some embodiments, the Cas12b protein is catalytically inactive. In some embodiments, the functional domain is a nickase, a nucleotide deaminase or a reverse transcriptase. In some embodiments, the functional domain is a reverse transcriptase and the guide molecule is a prime editor guide molecule. In some embodiments, the composition further comprises a detection construct comprising a non-target polynucleotide, wherein the Cas protein exhibits collateral activity and cleaves the non-target polynucleotide component once activated by the target polynucleotide. In some embodiments, the composition further comprises one or more isothermal amplification reagents. In some embodiments, the isothermal amplification reagents are LAMP reagents. In some embodiments, the guide molecule is designed to bind to a polynucleotide sequence of SARS-CoV-2. In some embodiments, the LAMP reagents comprise primers selected from SEQ ID NOs: 61983-61988 and guide molecules is SEQ ID NO: 61989.

In another aspect, the present disclosure provides a vector system comprising one or more polynucleotide sequences encoding the Cas12b protein and the guide molecule in the composition herein, optionally wherein the polynucleotide sequences are codon optimized for expression in a eukaryotic cell.

In another aspect, the present disclosure provides a cell comprising the composition or the vector herein, or progeny thereof. In another aspect, the present disclosure provides a method of targeting one or more target polynucleotides, the method comprising contacting the one or more target polynucleotides with a non-naturally occurring or engineered composition herein, wherein targeting comprises modifying the one or more target polynucleotides comprises increasing or decreasing expression of the one or more genes in the one or more target polynucleotides, insertion of a recombination template or a portion thereof to the tar one or more target polynucleotides. In some embodiments, the Cas12b is a catalytically inactive Cas12b fused to a functional domain. In some embodiments, the functional domain is a nickase, a reverse transcriptase, or a nucleotide deaminase. In some embodiments, the functional domain is a reverse transcriptase and the guide molecule is a primer editor guide molecule.

In another aspect, the present disclosure provides a method for detecting a target polynucleotide in a sample, comprising contacting the sample with the composition herein, wherein the Cas protein exhibits collateral activity and cleaves the detection construct once activated by the target polynucleotide, and the cleaved detection construct generate a signal; and detecting the signal thereby determining presence of the target polynucleotide in the sample.

In another aspect, the present disclosure provides a kit for modifying or detecting a target polynucleotide in a sample, comprising the composition or the vector system herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 2B Detection of synthetic COVID-19 sequence using a two-step SHERLOCK reaction (25 min RPA followed by 30 min Cas13 reaction). Readout using lateral flow strip.

FIG. 3A—Quick Extract at a final concentration of 5% did not negatively affect the RT-qPCR reaction FIG. 3B RNA samples prepared using Quick Extract supported similarly sensitive detection of coronavirus as QIAmp Viral RNA Miniprep.

POC-SHERLOCK lateral flow test for SARS and MERS N genes compared to NTC. All inputs were at 1,000 copies per reaction.

Figure 19:
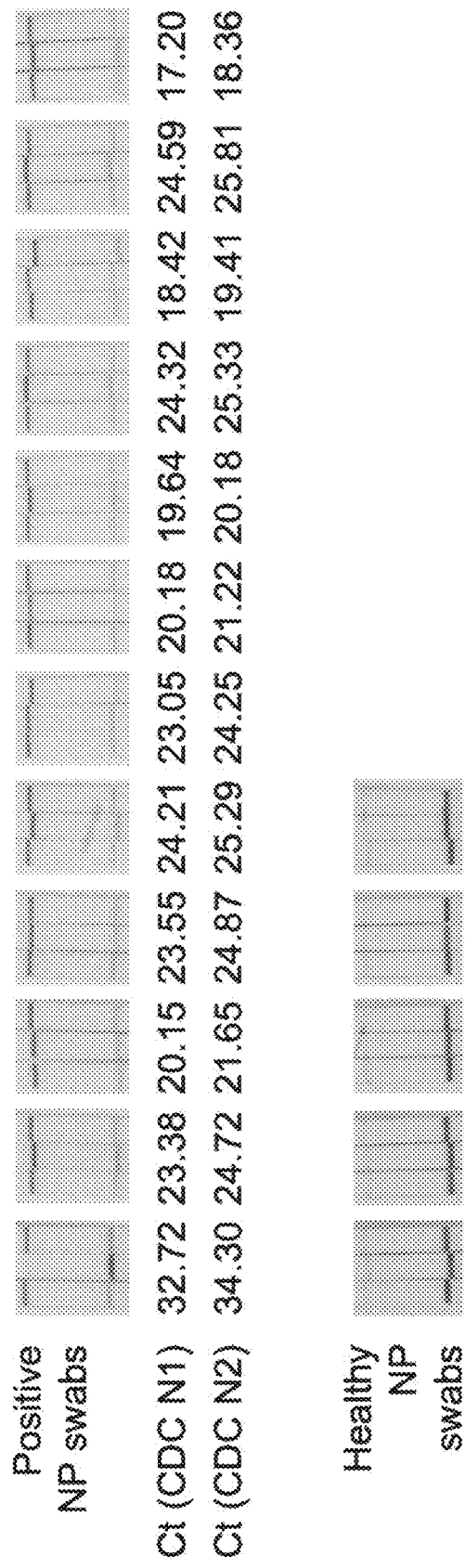
FIG. 19—Shows a comparison of positive SHERLOCK tests to results obtained from qRT-PCR assays.

FIG. 27—POC-SHERLOCK COVID-19 detection results for patient samples tested in FIG. 19. The results yield a sensitivity of 97% and specificity of 100%.

Figure 28:
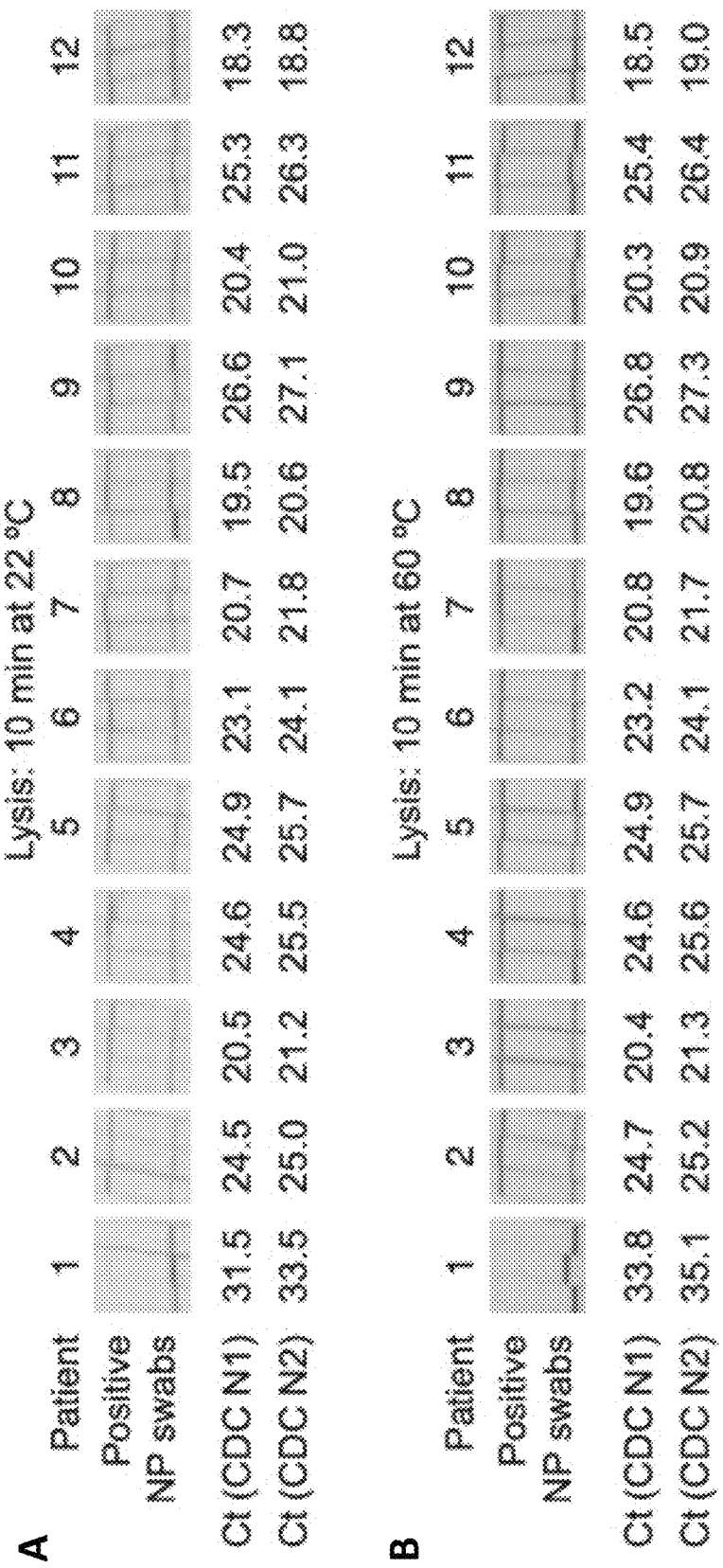

FIG. 28—COVID-19 POC-SHERLOCK detection with SARS-CoV-2 positive patient nasopharyngeal swabs. (A) POC-SHERLOCK COVID-19 detection of 12 different SARS-CoV-2 positive patient nasopharyngeal swabs with three replicates for each sample. Prior to POC-SHERLOCK, nasopharyngeal swabs were lysed using QE for 5 minutes at 22° C. Listed below are Ct values determined by RT-PCR using the CDC N1 and N2 assays. (B) POC-SHERLOCK COVID-19 detection of 12 different SARS-CoV-2 positive patient nasopharyngeal swabs with three replicates for each sample. Prior to POC-SHERLOCK, nasopharyngeal swabs were lysed using QE for 5 minutes at 60° C. Listed below are Ct values determined by RT-PCR using the CDC N1 and N2 assays.

Figure 29:
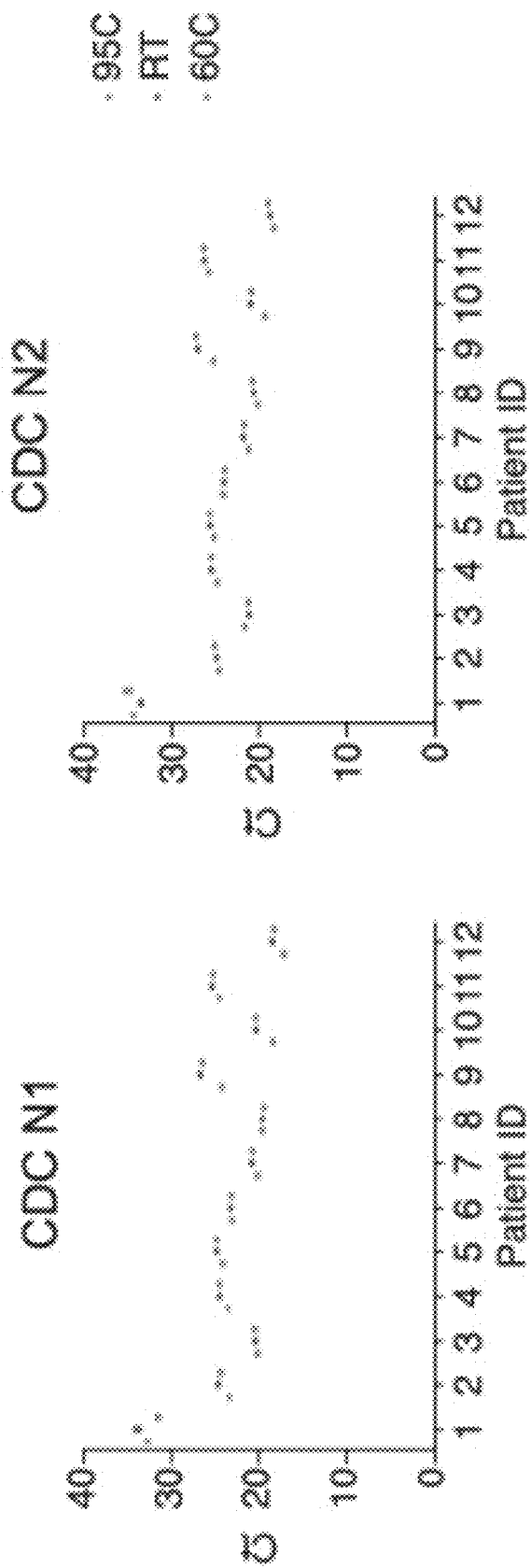

FIG. 29—Comparison of different lysis temperatures for SARS-CoV-2 positive patient nasopharyngeal swab extraction as measured by Ct values from RT-PCR using the CDC N1 and N2 assays. For patients 9 and 10, due to the low volume of samples provided, samples tested with 22° C. and 60° C. lysis conditions were diluted 1:2 prior to POC-SHERLOCK and RT-qPCR.

Figure 30A:
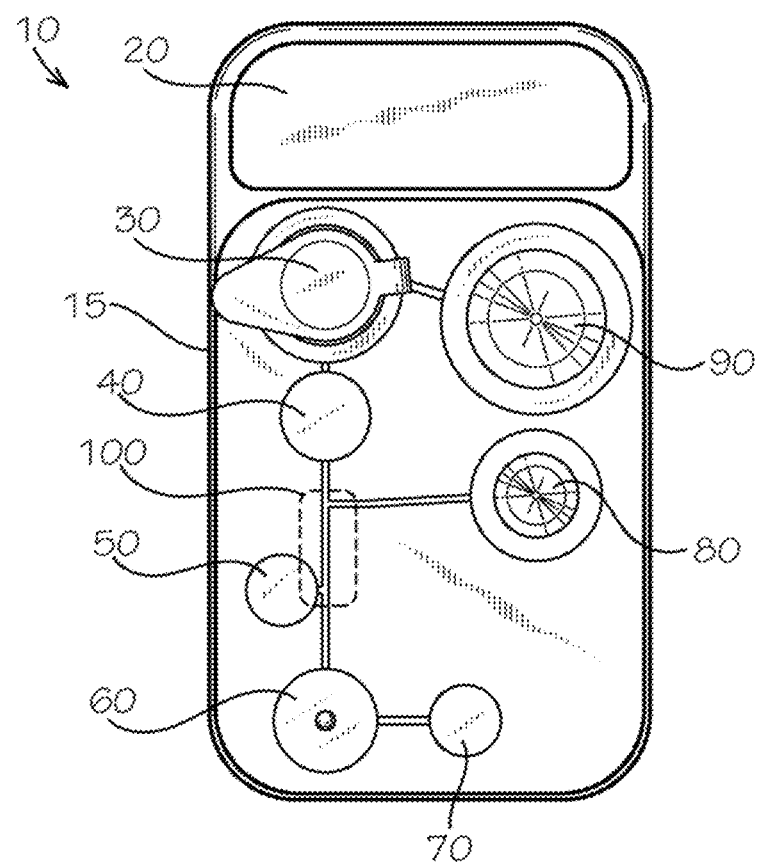
Figure 30B:
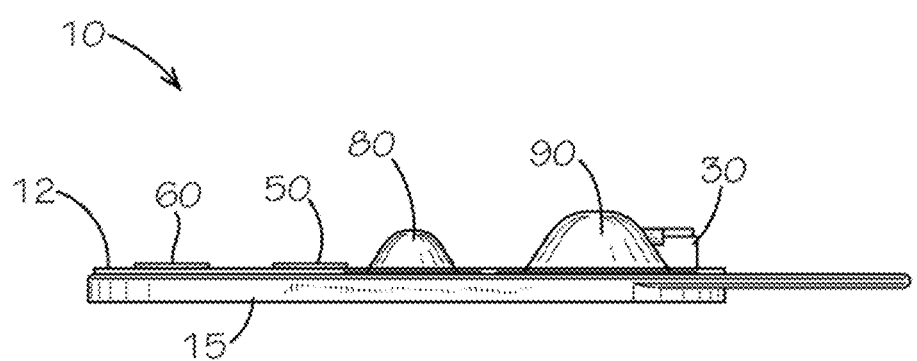

FIGS. 30A-30B—shows the top view (FIG. 30A) and side view (FIG. 30B) of an exemplary cartridge (10) according to the invention.

Figure 31A:
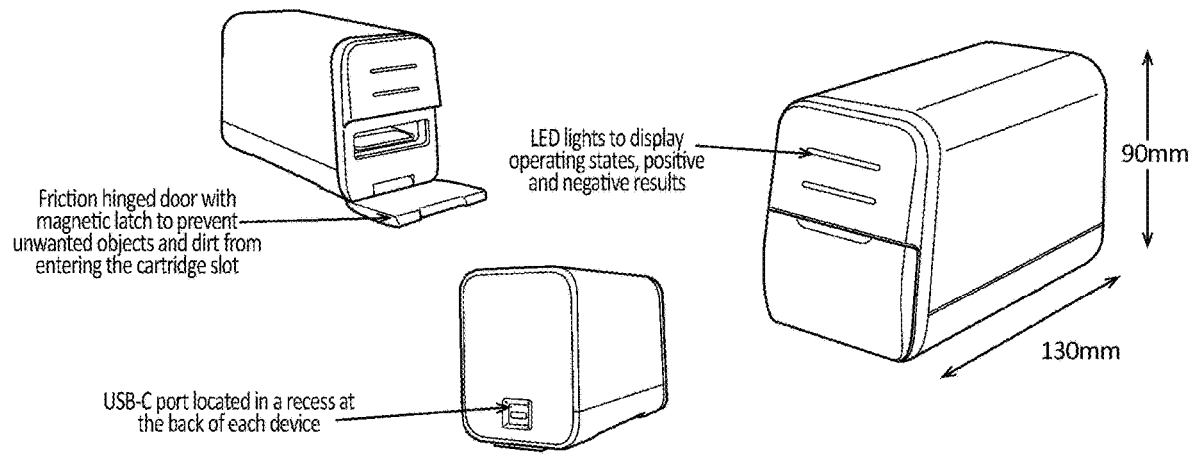
Figure 31B:
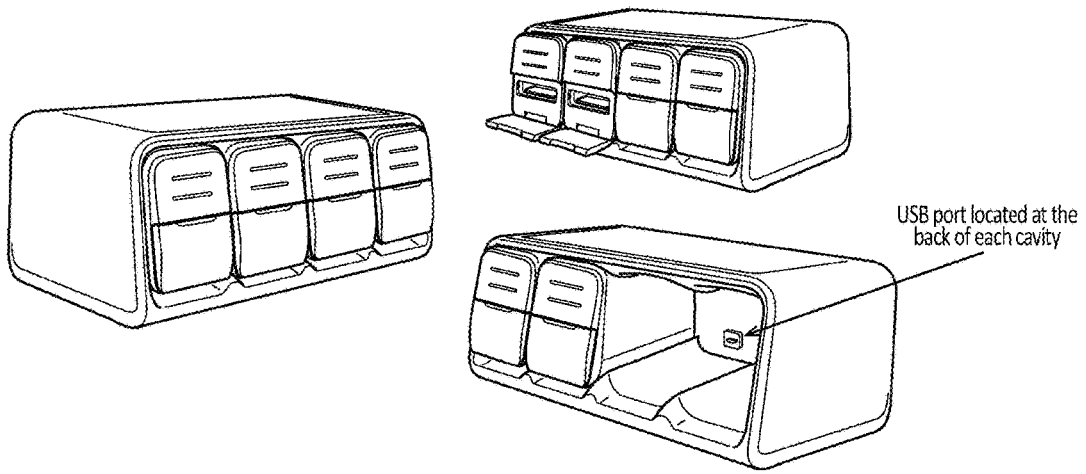
Figure 31C:
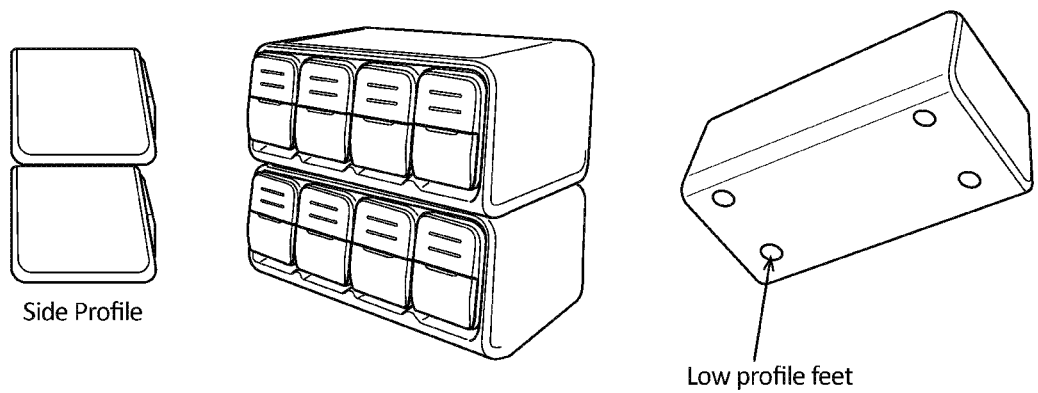

FIGS. 31A-31C—FIG. 31A provides an exemplary front loading device, upper left shows a friction hinged door with magnetic latch to prevent unwanted objects and dirt from entering the cartridge slot, upper right, device showing use of LED lights to display operating states, positive and negative results; lower image depicts rear of device with USB-C port located in a recess; FIG. 31B shows three views of a quad-dock for a front loading device, showing USB port located at the back of each cavity; FIG. 31C shows stacking docs for 8 devices, on the left, a side profile, center front view, and rights, low profile feet on the bottom of the dock.

Figure 32:
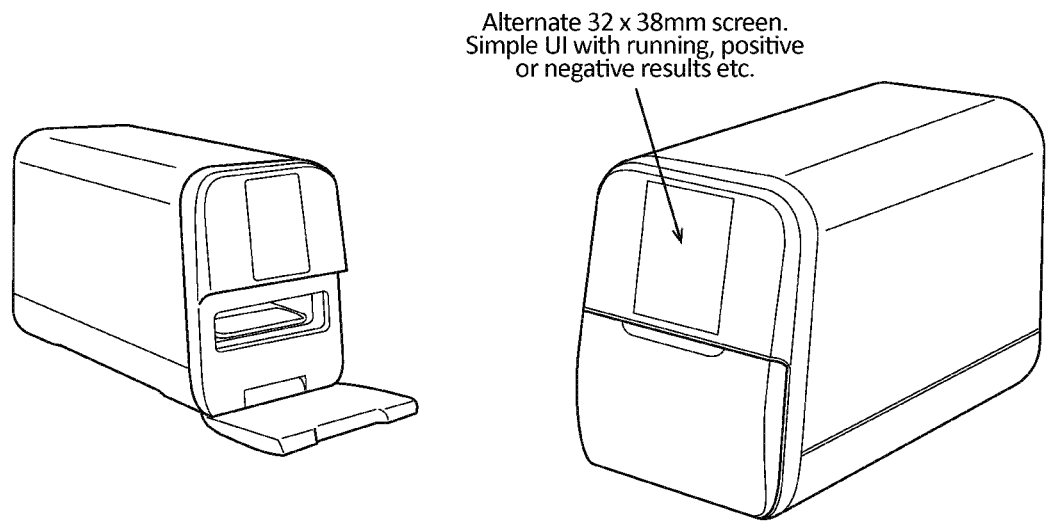
Figure 33:
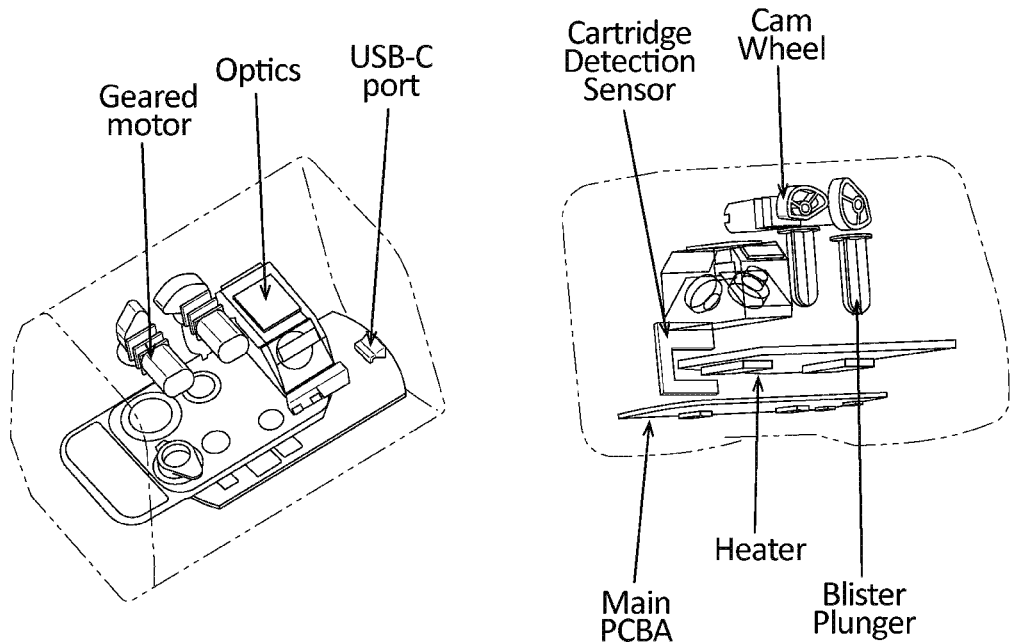

FIG. 32—shows alternate front-loading device with screen, left with front hinge open; right, with front hinge closed with alternate screen and simple user interface with running, positive, negative results or other display information FIG. 33—depicts front loading internal details, tope view (left) shows geared otor, optics and USB-C port; profile view (right) shows cartridge detection sensor, cam wheel, main PCBA, heater and plunger.

Figure 34A:
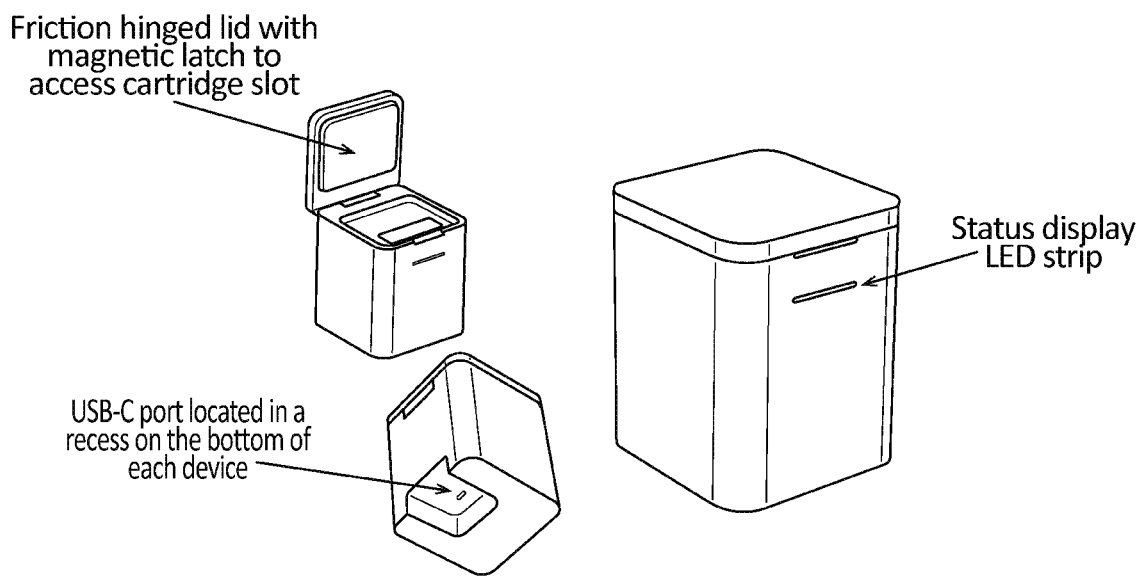
Figure 34B:
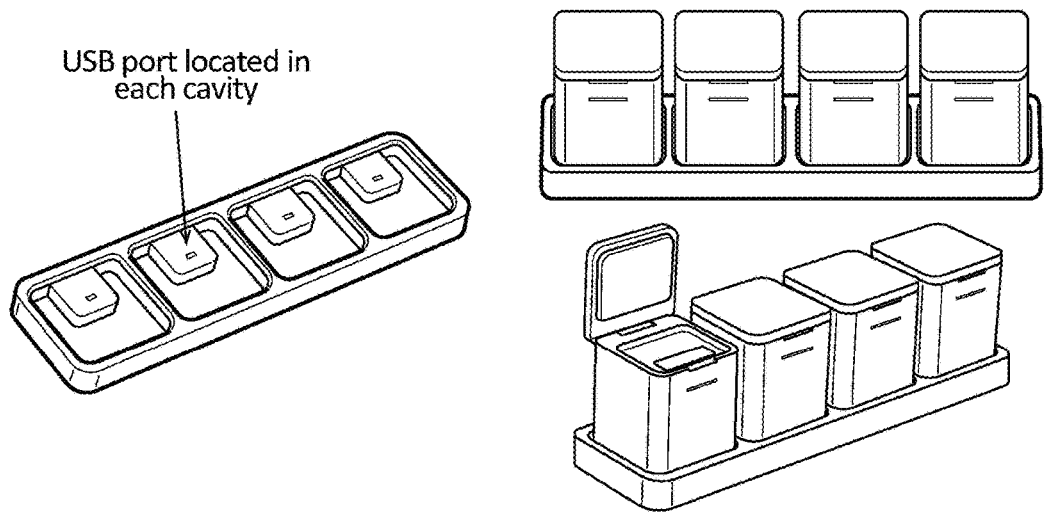
Figure 34C:
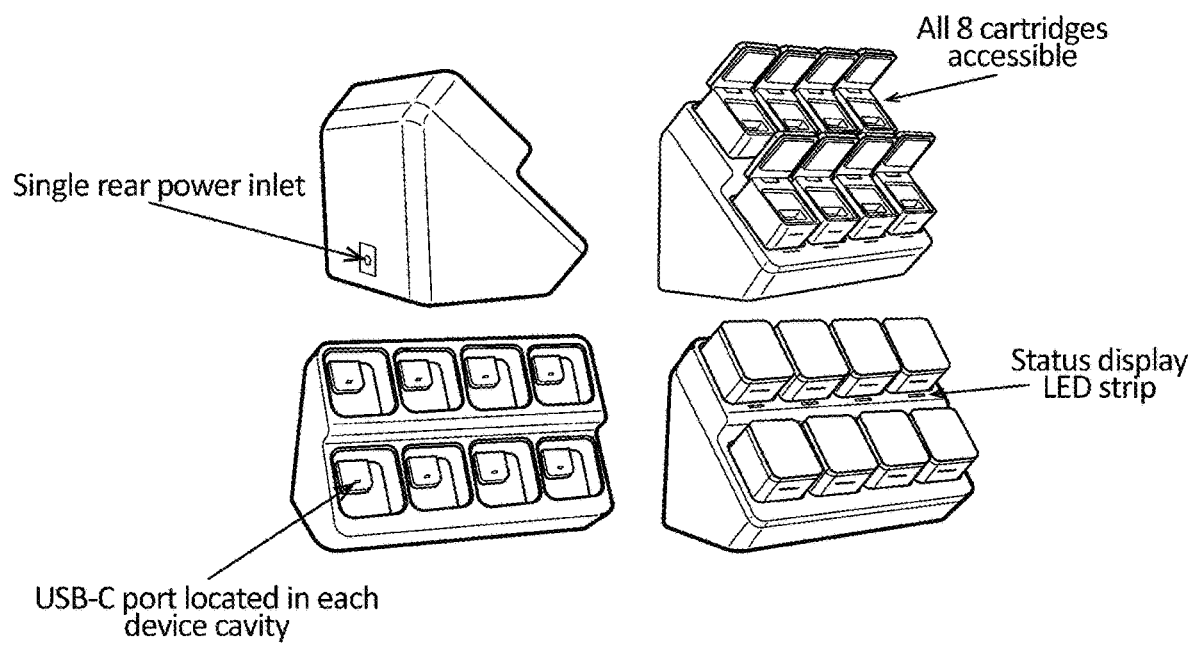

FIGS. 34A-34C—FIG. 34A shows top loading device detains, friction hinged lid with magnetic latch to access cartridge slot (upper left), USB-C port in recess on the bottom of each device (lower left), front view of a top loading details (right) shows status display LED strip; FIG. 34B top loading device quad-dock, USB port located in each cavity (left), quad dock with four top loading devices in closed lid orientation (upper right), quad dock with four top loading devices with one device in open lid orientation (lower right); FIG. 34C top loading device octo-dock, rear view showing single rear power inlet (upper left), All 8 devices in octo-dock in open orientation (upper right), USB-C port located in each device cavity (lower left), and status display LED strip on octo dock with 8 devices in closed orientation (lower right).

FIG. 35A-35B—Expanded patient cohort testing from an example embodiment showing results of patient nasopharyngeal swab samples (FIG. 35A) with calculated predictive values, sensitivity and specificity (FIG. 35B)

Figure 36:
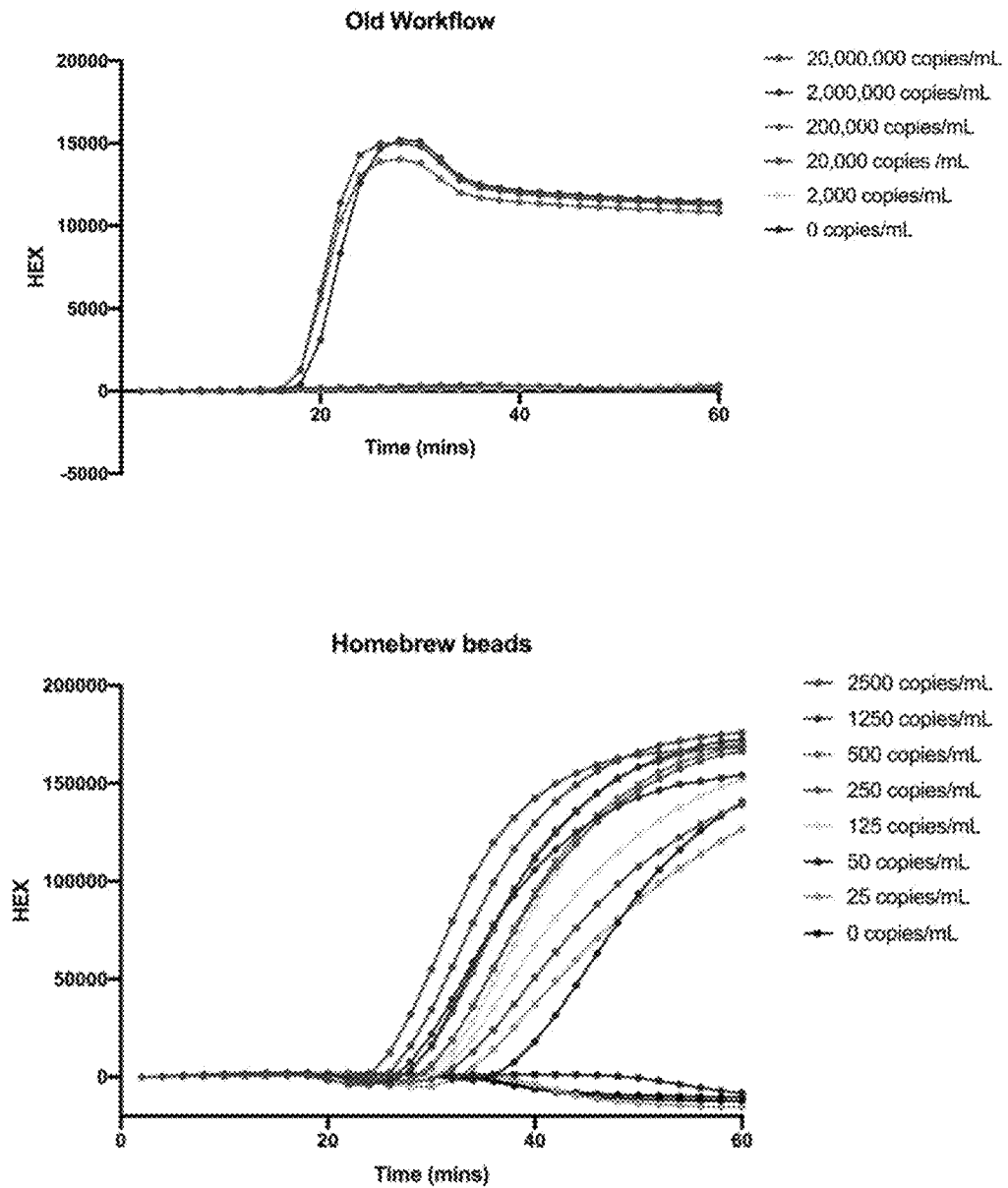
Figure 37A:
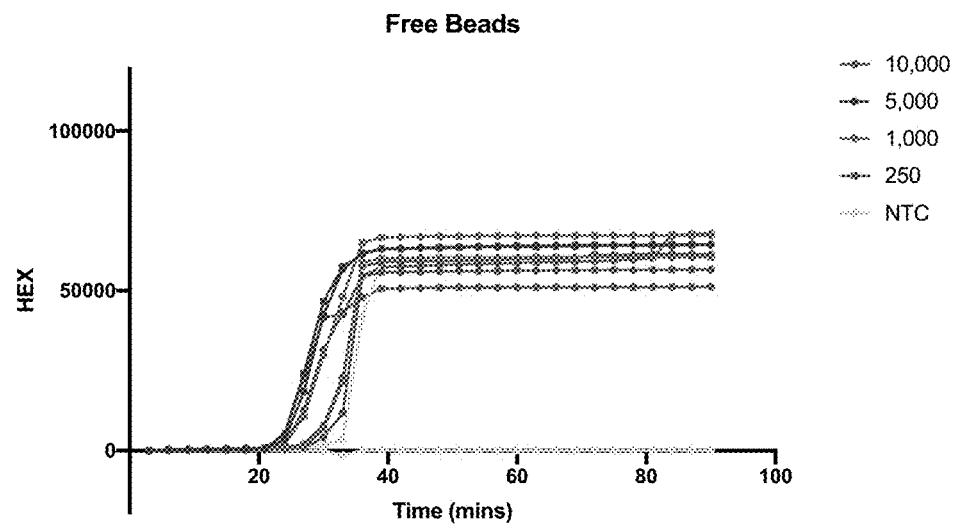
Figure 37B:
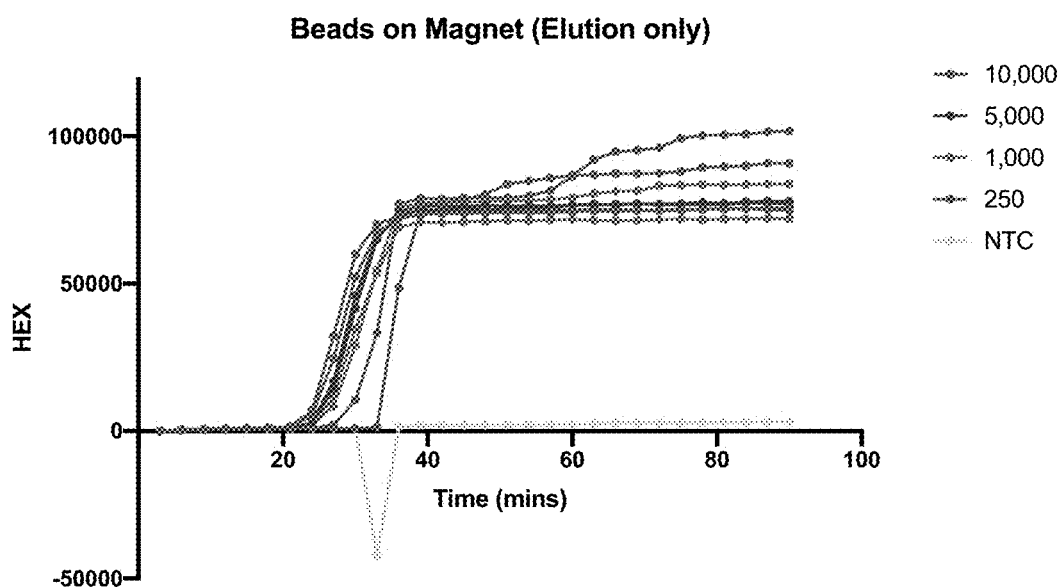
Figure 37C:
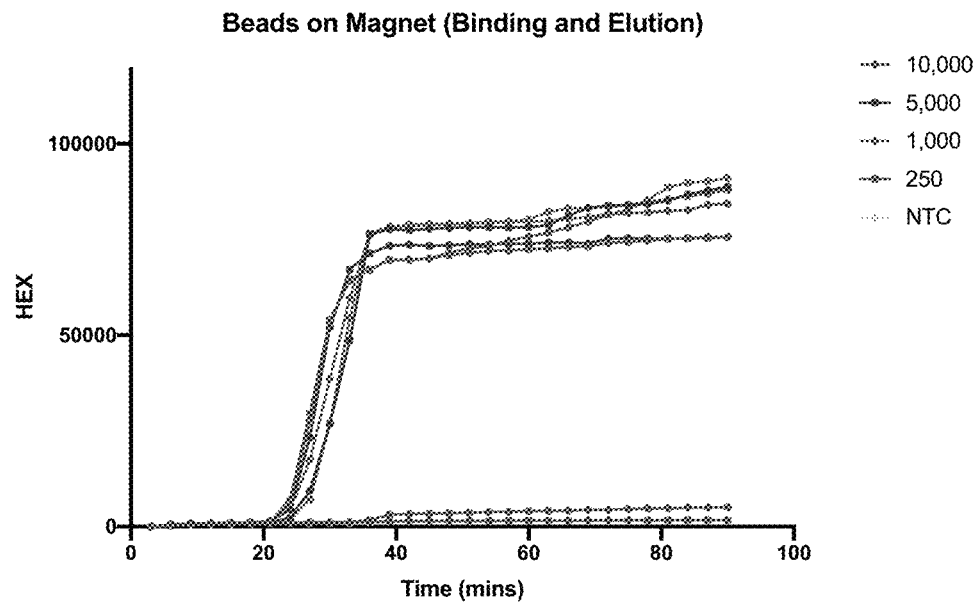

FIG. 36—Concentration with magnetic beads. Upper panel shows old workflow, lower panel with homebrew beads FIGS. 37A-37C—Simplifying bead purification for POC application shows no mixing is required after addition of STOPCovid Master Mix FIG. 37A Free Beads, FIG. 37B beads on magnet (Elution only), FIG. 37C beads on magnet (binding and elution)

Figure 38A:
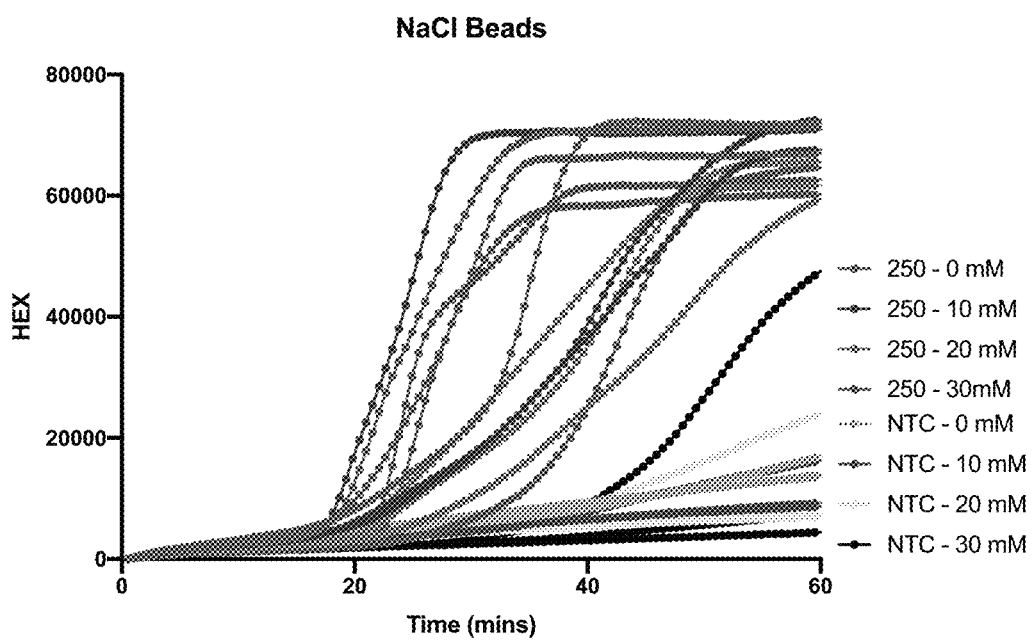
Figure 38B:
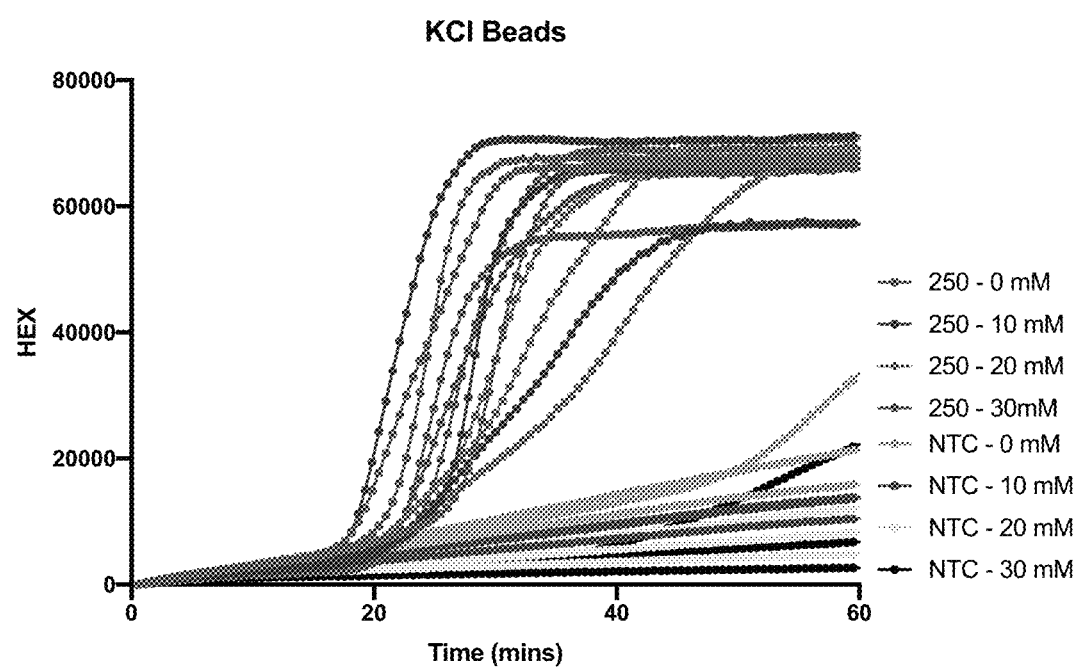

FIGS. 38A-38B—Simplifying Bead purification for POC application shows removing the wash step requires significant reduction in salt concentration in the reaction buffer. FIG. 38A NaCl beads; FIG. 38B KCl beads.

Figure 39:
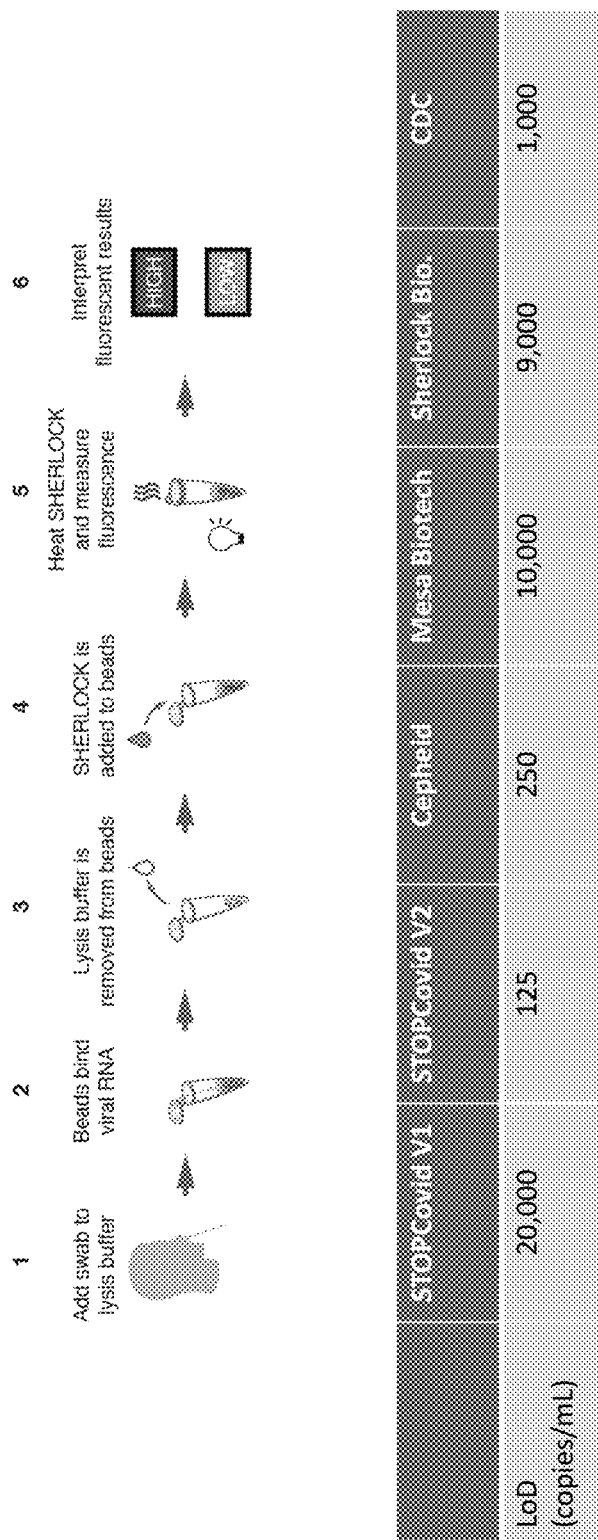

FIG. 39—An example workflow demonstrating increased sensitivity while minimizing complexity.

Figure 40:
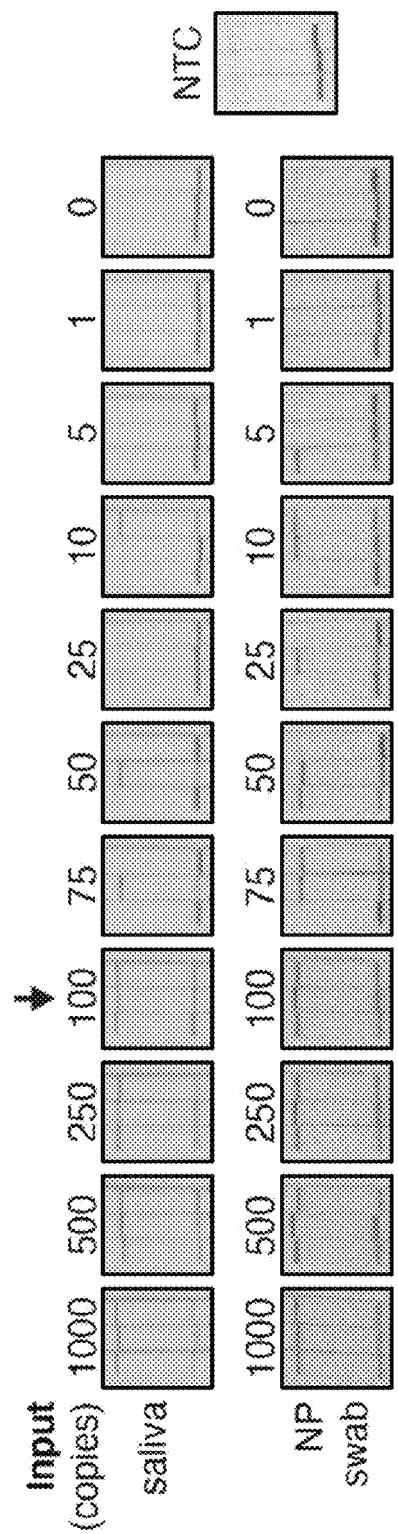
Figure 41:
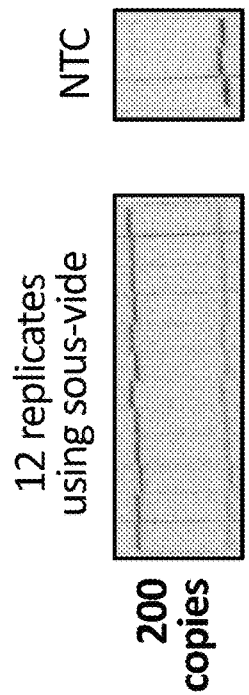
Figure 41:
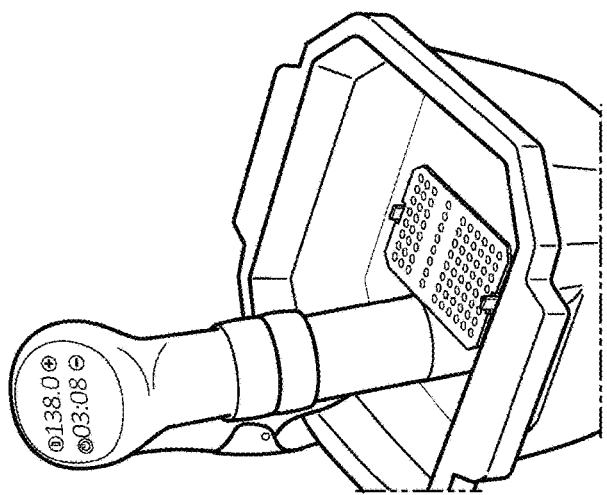
Figure 42A:
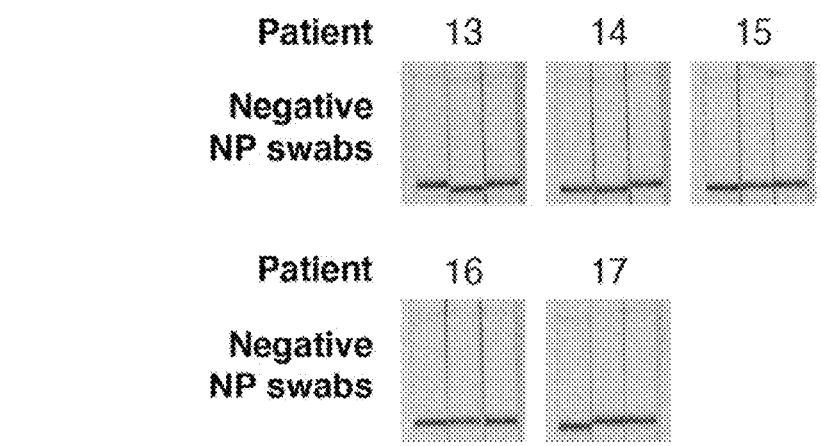
Figure 43:
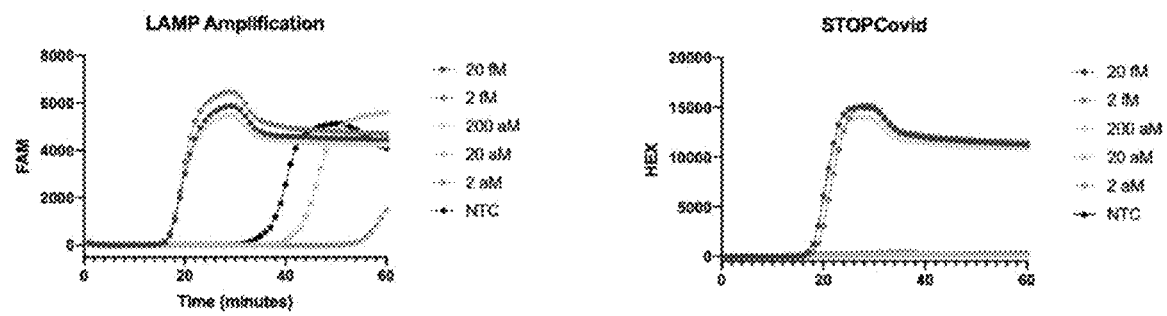

FIG. 40—Shows data from an example embodiment demonstrating limit of detection (LOD) of 100 genomes per reaction from saliva or nasopharyngeal swabs FIG. 41—Shows results of 12 replicates (right) using sous-vide waterbath (left) for STOPCOvid reaction FIGS. 42A-42B—Shows data from an example embodiment demonstrating an ability to achieve 97% sensitivity and 100% specificity on patient nasopharyngeal swab samples FIG. 43—Shows CRISPR detection may improve upon LAMP by increased specificity.

Figure 44:
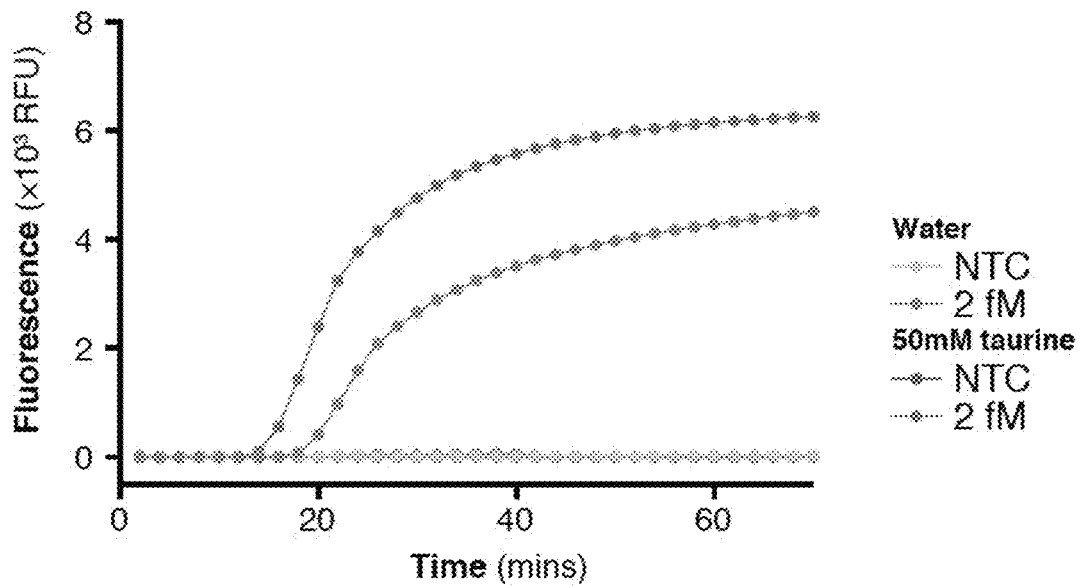

FIG. 44—Provides data showing an ability to detect target in 20 to 30 minutes

Figure 45:
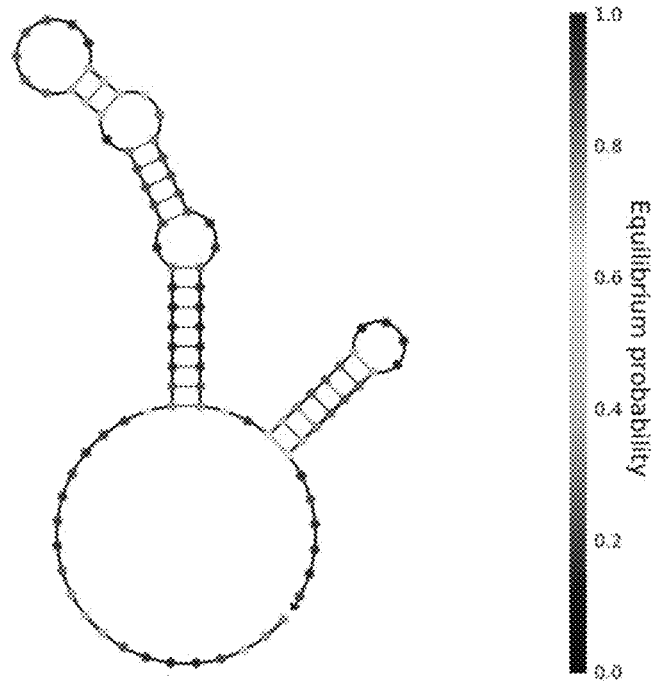
Figure 45:
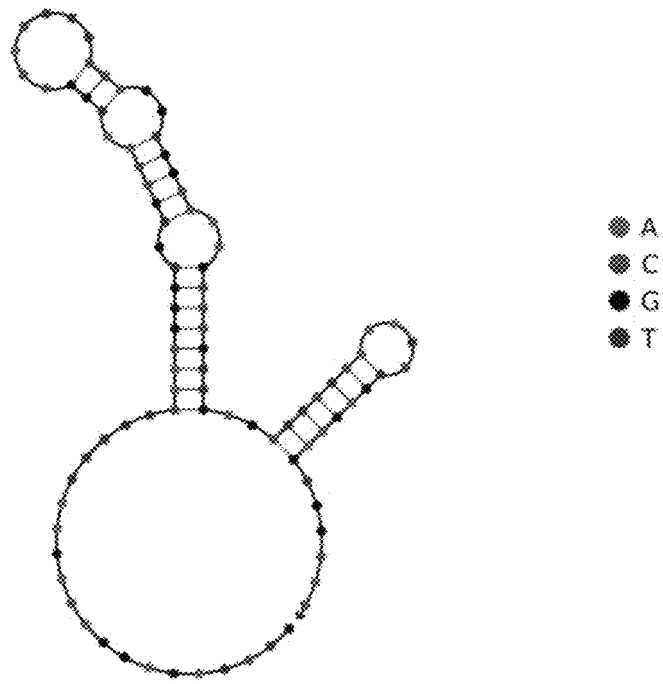

FIG. 45—Shows secondary structure of guide of *Alicyclobacillus acidoterrestris* (Aac) that is used with *Alicyclobacillus acidiphilus* (Aap) Cas12b in exemplary CRISPR Systems.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboraotry Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

In an aspect, the present disclosure provides novel DNA-targeting CRISPR-Cas systems and components thereof. In some embodiments, provided herein are compositions and systems comprising class 2 Type V Cas proteins, such as Cas12b and orthologs thereof. In some cases, the Cas proteins may exhibit target-specific nuclease activity and/or collateral activity at a temperature of at least 50° C. In some embodiments, the compositions and systems further comprise one or more guide molecules. The guide molecules may comprise a guide sequence capable of forming a complex with the Cas protein and directing the complex to bind to a target polynucleotide.

In some embodiments, the compositions comprise (a) a Cas12b protein and (b) a guide molecule comprising a guide sequence derived from another CRISPR-Cas system and capable of forming a complex with the Cas12b protein and directing the complex to bind to a target polynucleotide. In some cases, the guide sequence in (b) is derived from an organism comprising an ortholog protein sharing at least 90% homology (e.g., identity) with the Cas12b protein. In some examples, the present disclosure provides a non-naturally occurring engineered composition comprising a Cas12b protein from *Alicyclobacillus acidiphilis* and a guide molecule comprising a guide sequence derived from another CRISPR-Cas system and capable of forming a complex with the Cas12b protein and directing the complex to bind to a target polynucleotide. In some examples, the guide sequence is derived from *Alicyclobacillus acidoterrestris*.

In some aspects, the present disclosure provides polynucleotide sequences encoding the Cas proteins and the guide molecules, vector or vector systems comprising and delivery systems comprising such. Also provided herein are cells, cell lines, tissues, organs, or organisms comprising the compositions and systems.

In another aspect, the present disclosure provides applications of the compositions and systems. In some embodiments, the applications include methods of modifying one or more polynucleotides, e.g., for treating a disease. For example, such methods may comprise administering an effective amount of the compositions or systems to a subject in need thereof. In certain embodiments, the applications include methods of detecting one or more target polynucleotides in a sample from a subject. For example, such methods may comprise contacting the sample with the compositions or systems, which can then generate a detectable signal indicating the presence or absence of the target polynucleotide(s). The presence or absence of the target polynucleotide(s) may be used to diagnose a disease.

Compositions

In certain aspects, embodiments disclosed herein are directed to compositions and kits that consolidate extraction-free lysis and amplification of target nucleic acids into a single reaction volume. In certain example embodiments, the extraction-free lysis reagents can be used to extract nucleic acids from cells and/or viral particles. In contrast to existing protocols, the extraction-free lysis solution does not require isolation of the nucleic acid prior to further amplification. The extractaction-free lysis reagents may be mixed with amplification reagents such as standard RT-PCR amplification reactions. An example extraction-free lysis solution is described in Example 3.

In certain example embodiments, the extraction-free lysis solution is combined with amplification reagents into a single volume. In certain example embodiments, the amplification reagents are isothermal amplification reagents. In certain other example embodiments, the isothermal amplification reagents are LAMP isothermal amplification reagents. In certain example embodiments, the LAMP isothermal amplification reagents may include primers for the target nucleic acids discussed in further detail below. In certain example embodiments, the LAMP amplification reagents include primer sets selected from SEQ ID NOs: 1-40499. In certain example embodiments, the LAMP amplification reagents may include primers to SARS-COV2. In certain example embodiments, the primers are SEQ ID NOs: 61983-61988. LAMP reagents may further comprise colorimetric and/or fluorescent detection reagents, such as hydroxy napthol blue (see, e.g. Goto, M., et al., Colorimetric detection of loop-mediated isothermal amplification reaction by using hydroxy naphthol blue. Biotechniques, 2009. 46(3): p. 167-72.) leuco triphenylmethane dyes (see, e.g. Miyamoto, S., et al., Method for colorimetric detection of double-stranded nucleic acid using leuco triphenylmethane dyes. Anal Biochem, 2015. 473: p. 28-33) and pH-sensitive dyes (see, e.g. Tanner, N. A., Y. Zhang, and T. C. Evans, Jr., Visual detection of isothermal nucleic acid amplification using pH-sensitive dyes. Biotechniques, 2015. 58(2): p. 59-68); as well as fluorescent detection (see, e.g. Yu et al., *Clinical Chemistry*, hvaa102, doi:10.1093/clinchem/hvaa102 12 May 2020), including use of quenching probes (see, e.g. Shirato et al., *J Virol Methods*. 2018 August; 258:41-48. doi: 10.1016/j.jviromet.2018.05.006).

In certain embodiments, extraction-free lysis solution and isothermal amplification reagents may be lyophilized in a single reaction volume, to be reconstituted by addition of a sample to be assayed. In certain other embodiments, the extraction-free lysis solution and isothermal amplification reagents may be lyophilized and stored on a cartridge or lateral flow strip, as discussed in further detail below.

In certain example embodiments, the single lysis reaction compositions and kits may further comprise one or more Cas proteins possessing collateral activity and a detection construct. Pairing with one or more Cas proteins may increase sensitivity or specificity of the assay. In certain example embodiments, the one or more Cas proteins may be thermostable Cas proteins. Example Cas proteins are disclosed in further detail below. In some examples, the construct comprises a non-target polynucleotide, and the Cas protein exhibits collateral activity and cleaves the non-target polynucleotide component once activated by a target polynucleotide.

In certain example embodiments, the single lysis amplification reaction compositions and kits may comprise optimized primers and/or one or more additives. In an aspect, the design optimizes the primers used in the amplification, In particular aspects, the isothermal amplification is used alone. In another aspect, the isothermal amplification is used with CRISPR-Cas systems. In either approach, design considerations can follow a rational design for optimization of the reactions. Optimization of the methods as disclosed herein can include first screening primers to identify one or more sets of primers that work well for a particular target, Cas protein and/or reaction. Once the primers have been screened, titration of magnesium concentration can be performed to identify an optimal magnesium concentration for higher signal to noise readout. Once an optimum magnesium concentration is identified, additional additives are screened at around 20-25% of the reaction, and once additives are identified, these additives, such as those additives identified in FIG. 17, can be evaluated and varied in concentration to identify optimal reaction kinetics for specific reaction parameters. In an example, varying additives with specific primers, target, Cas protein (when CRISPR system is used), temperature, and other additive concentrations within the reaction can be identified. Optimization can be made with the goal of reducing the number of steps and buffer exchanges that have to occur in the reaction, simplifying the reaction and reducing the risks of contamination at transfer steps. In an aspect, addition of inhibitors, such as proteinase K can be considered so that buffer exchanges can be reduced. Similarly, optimizing the salt levels as well as the type of salt utilized can further facilitate and optimize the one-pot detections disclosed herein. In an aspect, potassium chloride can be utilized rather than sodium chloride when such amplification approaches are used with bead concentration in a lysis step.

In certain embodiments, the compositions and kits may further comprise nucleic acid binding bead. The bead may be used to capture, concentrate or otherwise enrich for particular material. The bead may be magnetic, and may be provided to capture nucleic acid material. In another aspect, the bead is a silica bead. Beads may be utilized in an extraction step of the methods disclosed herein. Beads can be optionally used with the methods described herein, including with the one-pot methods that allow for concentration of viral nucleic acids from large volume samples, such as saliva or swab samples to allow for a single one-pot reaction method. Concentration of desired target molecules can be increased by about 10-fold, 50-fold, 100-fold, 200-fold, 500-fold, 800-fold, 1000-fold, 1500-fold, 2000-fold, 2500-fold, 3000-fold, or more.

Magnetic beads in a PEG and salt solution are preferred in an aspect, and in embodiments bind to viral RNA and/or DNA which allows for concentration and lysis concurrently. Silica beads can be used in another aspect. Capture moieties such as oligonucleotide functionalized beads are envisioned for use. The beads may be using with the extraction reagents, allowed to incubate with a sample and the lysis/extraction buffer, thereby concentrating target molecules on the beads. When used with a cartridge device detailed elsewhere herein, a magnet can be activated and the beads collected, with optional flushing of the extraction buffer and one or more washes performed. Advantageously, the beads can be used in the one-pot methods and systems without additional washings of the beads, allowing for a more efficient process without increased risks of contamination in multi-step processes. Beads can be utilized with the isothermal amplifications detailed herein, and the beads can flow into an amplification chamber of the cartridge or be maintained in the pot for the amplification step. Upon heating, nucleic acid can be released off the beads.

In some embodiments, the compositions and systems further comprise one or more isothermal amplification reagents. In one example, the isothermal amplification reagents are LAMP reagents. In certain examples, the compositions and systems comprise LAMP reagents comprising one or more primers selected from SEQ ID NOs: 61983-61988 and guide molecules is SEQ ID NO: 61989.

Example CRISPR-Cas Systems

The compositions and systems herein may comprise one or more Cas proteins. A Cas protein may be a component of a CRISPR-Cas system and encoded by a CRISPR-associated ("Cas") gene.

In some embodiments, the Cas protein is a class 2 Type V Cas protein, e.g., a Type V-B Cas protein. Examples of the Type V-B protein include those described in Makarova et al. "Evolutionary classification of CRISPR-Cas systems: a burst of class 2 and derived variants" Nature Reviews Microbiology, 18:67-81 (February 2020), incorporated in its entirety herein by reference, and particularly as described in FIG. 2, p. 75.

In some embodiments, the Cas protein is Cas12b (also known as C2c1). The Cas12b gene can be found in several diverse bacterial genomes, typically in the same locus with cas1, cas2, and cas4 genes and a CRISPR cassette. Thus, the layout of this putative novel CRISPR-Cas system appears to be similar to that of type II-B. Furthermore, similar to Cas9, the Cas12b protein contains an active RuvC-like nuclease, an arginine-rich region, and a Zn finger (absent in Cas9).

Thermostable Proteins

In certain example embodiments, the protein selected may be more thermostable at higher temperatures. Exemplary proteins may comprise any Cas protein with collateral effect when used with particular methodologies disclosed herein. In an aspect, the Cas protein is a thermostable protein. The thermostable Cas protein may be a Type V, for example, a Cas12 protein. In embodiments, the thermostable protein, upon activation, comprises collateral cleavage. A thermostable protein as used herein comprises a protein that retains catalytic activity at a temperature at or above 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C. In certain example embodiments, the protein is thermostable at or above 55° C.

Methods for identification of thermostable proteins are detailed herein, and may comprise identifying Cas proteins from thermophilic bacterial species. Upon identification of a particular Cas protein from a species, Cas proteins form similar species may be identified.

In certain embodiments, the thermostable CRISPR-Cas protein is a Cas 12 protein from Table 1:BROD_5090P4_Cas12b_sequences.txt, or at least 80% identity to a polypeptide from Table 1: (BROD_5090P4_Cas12b_sequences.txt.

In an embodiment, the thermostable Cas protein is a Cas12 protein selected from a protein in Table 1.

TABLE 1

Cas 12 proteins (65C) Ga0209381_1004188 | GENOME_ACCESSION
(66C)_a0212093_1 | Ga0212093_1006934 | GENOME_ACCESSION
3300022548 | Ga0212092_1000015 | GENOME_ACCESSION
a0117933_1071983 | Ga0117933_1071983 | GENOME_ACCESSION
a0212092_1024084 | Ga0212092_1024084 | GENOME_ACCESSION
a0212093_1001507 | Ga0212093_1001507 | GENOME_ACCESSION
a0212120_1000874 | Ga0212120_1000874 | GENOME_ACCESSION
a0212125_1004414 | Ga0212125_1004414 | GENOME_ACCESSION
a0212125_1006348 | Ga0212125_1006348 | GENOME_ACCESSION
ABHJ01000011.1_o | *Hydrogenivirga* sp. 128-5-R1-1 1102927038514
AGIV01000002.1_o | *Rhodothermus marinus* SG0.5JP17-171 Rhoma_Contig848_C
BDSM01000053.1_o | *Microcystis* sp. 0824 DNA
BFBB01000008.1_o | *Leptospira* sp. YH101 DNA
BHZK01000001.1_o | *Parageobacillus thermoglucosidasius* TG4 DNA
CP000240.1_organ | *Synechococcus* sp. JA-2-3B'a(2-13)
CP001229.1_organ | *Sulfurihydrogenibium azorense* Az-Ful
CP011339.1_organ | *Microcystis panniformis* FACHB-1757
CP020382.1_organ | *Rhodothermaceae bacterium* RA chromosome
CP040694.1_organ | *Elizabethkingia* sp. JS20170427COW chromosome
DCUT01000059.1_o | TPA_asm
DHGN01000237.1_o | TPA_asm
FQUK01000003.1_o *Thermomonas hydrothermalis* strain DSM 14834 genome assembly
Ga0063162_1014580 | GENOME_ACCESSION
Ga0065719_107896 | GENOME_ACCESSION
Ga0065719_116807 | GENOME_ACCESSION
Ga0067045_1002454 | GENOME_ACCESSION
Ga0067045_1004962 | GENOME_ACCESSION]
Ga0068669_1023596 | GENOME_ACCESSION
Ga0068707_1002163 | GENOME_ACCESSION
Ga0068707_1009867 | GENOME_ACCESSION
Ga0068707_1024093 | GENOME_ACCESSION
Ga0071330_1110381 | GENOME_ACCESSION
Ga0072682_101461 | GENOME_ACCESSION
Ga0073928_10004924 | GENOME_ACCESSION
Ga0073932_1022770 | GENOME_ACCESSION
Ga0079044_1002244 | GENOME_ACCESSION
Ga0079639_1009487 | GENOME_ACCESSION
Ga0099914_10727 | GENOME_ACCESSION
Ga0101790_149349 | GENOME_ACCESSION
Ga0102924_1013089 | GENOME_ACCESSION
Ga0103818_10095 | GENOME_ACCESSION
Ga0105154_1006902 | GENOME_ACCESSION
Ga0105158_1004615 | GENOME_ACCESSION
Ga0114945_10008792 | GENOME_ACCESSION
Ga0116141_10037070 | GENOME_ACCESSION TABLE 1-continued

| Cas 12 proteins |
|---|
| Ga0116143_10029534 | GENOME_ACCESSION |
| Ga0116146_1004071 | GENOME_ACCESSION |
| Ga0116159_1001590 | GENOME_ACCESSION |
| Ga0116160_1008286 | GENOME_ACCESSION |
| Ga0116161_1004008 | GENOME_ACCESSION |
| Ga0116167_1006930 | GENOME_ACCESSION |
| Ga0116184_10002336 | GENOME_ACCESSION |
| Ga0116185_1015740 | GENOME_ACCESSION |
| Ga0116188_1022712 | GENOME_ACCESSION |
| Ga0116210_1003377 | GENOME_ACCESSION |
| Ga0123519_10000481 | GENOME_ACCESSION |
| Ga0123519_10002165 | GENOME_ACCESSION |
| Ga0123519_10002912 | GENOME_ACCESSION |
| Ga0123519_10003344 | GENOME_ACCESSION |
| Ga0123519_10003852 | GENOME_ACCESSION |
| Ga0123519_10021143 | GENOME_ACCESSION |
| Ga0123519_10027137 | GENOME_ACCESSION |
| Ga0123519_10057643 | GENOME_ACCESSION |
| Ga0123519_10064432 | GENOME_ACCESSION |
| Ga0124943_1106748 | GENOME_ACCESSION |
| Ga0124945_1030784 | GENOME_ACCESSION |
| Ga0133944_1001807 | GENOME_ACCESSION |
| Ga0134095_1000962 | GENOME_ACCESSION |
| Ga0137716_10003017 | GENOME_ACCESSION |
| Ga0137716_10003038 | GENOME_ACCESSION |
| Ga0137716_10003531 | GENOME_ACCESSION |
| Ga0137716_10006890 | GENOME_ACCESSION |
| Ga0137716_10009026 | GENOME_ACCESSION |
| Ga0137716_10009341 | GENOME_ACCESSION |
| Ga0137716_10027208 | GENOME_ACCESSION |
| Ga0137716_10032400 | GENOME_ACCESSION |
| Ga0137716_10033855 | GENOME_ACCESSION |
| Ga0137716_10038387 | GENOME_ACCESSION |
| Ga0137716_10042212 | GENOME_ACCESSION |
| Ga0137716_10061480 | GENOME_ACCESSION |
| Ga0172363_10016551 | GENOME_ACCESSION |
| Ga0172365_10006450 | GENOME_ACCESSION |
| Ga0172382_10012866 | GENOME_ACCESSION |
| Ga0180300_10000403 | GENOME_ACCESSION |
| Ga0180301_10011215 | GENOME_ACCESSION |
| Ga0180435_10008691 | GENOME_ACCESSION |
| Ga0180446_1198 | GENOME_ACCESSION |
| Ga0181613_1004254 | GENOME_ACCESSION |
| Ga0181613_1005053 | GENOME_ACCESSION |
| Ga0181858_1004277 | GENOME_ACCESSION |
| Ga0182014_10001887 | GENOME_ACCESSION |
| Ga0186994_110 | GENOME_ACCESSION |
| Ga0187028_105 | GENOME_ACCESSION |
| Ga0187073_104 | GENOME_ACCESSION |
| Ga0187107_1033 | GENOME_ACCESSION |
| Ga0187121_108 | GENOME_ACCESSION |
| Ga0187143_105 | GENOME_ACCESSION |
| Ga0187864_10009485 | GENOME_ACCESSION |
| Ga0190309_1003062 | GENOME_ACCESSION |
| Ga0190334_1000016 | GENOME_ACCESSION |
| Ga0190361_1000443 | GENOME_ACCESSION |
| Ga0190361_1001609 | GENOME_ACCESSION |
| Ga0190361_1003780 | GENOME_ACCESSION 27 |
| Ga0190361_1003780 | GENOME_ACCESSION 31 |
| Ga0190363_1000125 | GENOME_ACCESSION |
| Ga0194111_10067953 | GENOME_ACCESSION |
| Ga0207429_10023 | GENOME_ACCESSION |
| Ga0207433_10006213 | GENOME_ACCESSION |
| Ga0207433_10011113 | GENOME_ACCESSION |
| Ga0207433_10012523 | GENOME_ACCESSION |
| Ga0207433_10020534 | GENOME_ACCESSION |
| Ga0207433_10021674 | GENOME_ACCESSION |
| Ga0207433_10022806 | GENOME_ACCESSION |
| Ga0207433_10030792 | GENOME_ACCESSION |
| Ga0207433_10045901 | GENOME_ACCESSION |
| Ga0207433_10075234 | GENOME_ACCESSION |
| Ga0207433_10075916 | GENOME_ACCESSION |
| Ga0207433_10082276 | GENOME_ACCESSION |
| Ga0207747_1007959 | GENOME_ACCESSION |
| Ga0207868_1000002 | GENOME_ACCESSION |
| Ga0208151_102415 | GENOME_ACCESSION |
| Ga0208195_1004385 | GENOME_ACCESSION |
| Ga0208357_1002034 | GENOME_ACCESSION |

TABLE 1-continued

| Cas 12 proteins |
|---|
| Ga0208429_100128 | GENOME_ACCESSION |
| Ga0208429_100584 | GENOME_ACCESSION |
| Ga0208429_100770 | GENOME_ACCESSION |
| Ga0208461_1008711 | GENOME_ACCESSION |
| Ga0208609_100002 | GENOME_ACCESSION |
| Ga0208683_103187 | GENOME_ACCESSION |
| Ga0208683_103849 | GENOME_ACCESSION |
| Ga0208683_104403 | GENOME_ACCESSION |
| Ga0208940_1001448 | GENOME_ACCESSION |
| Ga0209012_1000842 | GENOME_ACCESSION |
| Ga0209012_1001252 | GENOME_ACCESSION |
| Ga0209012_1015334 | GENOME_ACCESSION |
| Ga0209018_1000172 | GENOME_ACCESSION |
| Ga0209101_1000507 | GENOME_ACCESSION |
| Ga0209101_1006392 | GENOME_ACCESSION |
| Ga0209102_1000334 | GENOME_ACCESSION |
| Ga0209102_1003688 | GENOME_ACCESSION |
| Ga0209143_1000788 | GENOME_ACCESSION |
| Ga0209143_1002248 | GENOME_ACCESSION |
| Ga0209143_1006289 | GENOME_ACCESSION |
| Ga0209162_1014546 | GENOME_ACCESSION |
| Ga0209171_10000726 | GENOME_ACCESSION |
| Ga0209172_10015399 | GENOME_ACCESSION |
| Ga0209201_1007464 | GENOME_ACCESSION |
| Ga0209207_1001084 | GENOME_ACCESSION |
| Ga0209207_1006579 | GENOME_ACCESSION |
| Ga0209224_1000001 | GENOME_ACCESSION |
| Ga0209225_1002268 | GENOME_ACCESSION |
| Ga0209399_10016114 | GENOME_ACCESSION |
| Ga0209410_1010848 | GENOME_ACCESSION |
| Ga0209467_1000554 | GENOME_ACCESSION |
| Ga0209507_1000982 | GENOME_ACCESSION |
| Ga0209513_1002134 | GENOME_ACCESSION |
| Ga0209542_10001012 | GENOME_ACCESSION |
| Ga0209542_10007289 | GENOME_ACCESSION |
| Ga0209669_100016| GENOME_ACCESSION |
| Ga0209669_101200 | GENOME_ACCESSION |
| Ga0209750_1000252 | GENOME_ACCESSION |
| Ga0209827_10659006 | GENOME_ACCESSION |
| Ga0209980_10011112 | GENOME_ACCESSION |
| Ga0210049_1040060 | GENOME_ACCESSION |
| Ga0210051_1028938 | GENOME_ACCESSION |
| Ga0210057_1032582 | GENOME_ACCESSION |
| Ga0214474_1011027| GENOME_ACCESSION |
| Ga0255343_1026926 | GENOME_ACCESSION |
| Ga0255346_1002844 | GENOME_ACCESSION |
| Ga0255355_1000451 | GENOME_ACCESSION |
| Ga0255811_11272827 | GENOME_ACCESSION |
| Ga0255812_10127107 | GENOME_ACCESSION |
| Ga0272445_1000517 | GENOME_ACCESSION |
| Ga0272446_1000057 | GENOME_ACCESSION |
| Ga0272446_1000164 | GENOME_ACCESSION |
| Ga0272446_1001728 | GENOME_ACCESSION 137 |
| Ga0272446_1001728 | GENOME_ACCESSION 249 |
| Ga0272446_1001929 | GENOME_ACCESSION |
| Ga0272446_1017314 | GENOME_ACCESSION |
| Ga0272447_1003507 | GENOME_ACCESSION |
| Ga0272448_1000001 | GENOME_ACCESSION |
| Ga0272448_1000002 | GENOME_ACCESSION |
| Ga0272448_1000009 | GENOME_ACCESSION |
| Ga0272448_1000011 | GENOME_ACCESSION |
| Ga0272448_1000062 | GENOME_ACCESSION |
| Ga0272448_1000167 | GENOME_ACCESSION |
| Ga0272448_1002516 | GENOME_ACCESSION |
| Ga0272448_1011735 | GENOME_ACCESSION |
| Ga0272448_1059621 | GENOME_ACCESSION |
| Ga0272448_1067731 | GENOME_ACCESSION |
| Ga0272449_1002236 | GENOME_ACCESSION |
| Ga0272449_1004365 | GENOME_ACCESSION |
| Ga0272449_1006528 | GENOME_ACCESSION |
| Ga0272449_1019852 | GENOME_ACCESSION |
| Ga0302046_10000852 | GENOME_ACCESSION |
| Ga0302192_10026063 | GENOME_ACCESSION |
| Ga0302246_1000265 | GENOME_ACCESSION |
| Ga0302251_1001844 | GENOME_ACCESSION |
| Ga0302253_1002416 | GENOME_ACCESSION |
| Ga0307340_100872 | GENOME_ACCESSION |
| Ga0308310_1004946 | GENOME_ACCESSION |

TABLE 1-continued

| Cas 12 proteins |
|---|
| Ga0308310_1013800 | GENOME_ACCESSION |
| Ga0308411_10001123 | GENOME_ACCESSION |
| Ga0308411_10021369 | GENOME_ACCESSION |
| Ga0308414_1002480 | GENOME_ACCESSION |
| Ga0308414_1007395 | GENOME_ACCESSION |
| Ga0308414_1018540 | GENOME_ACCESSION |
| Ga0308415_1006042 | GENOME_ACCESSION |
| Ga0308419_1006240 | GENOME_ACCESSION |
| Ga0308419_1011938 | GENOME_ACCESSION |
| Ga0310136_000087 | GENOME_ACCESSION |
| Ga0310138_009337 | GENOME_ACCESSION |
| Ga0310146_00181 | GENOME_ACCESSION |
| Ga0310828_1006812 | GENOME_ACCESSION |
| Ga0311022_13670299 | GENOME_ACCESSION |
| Ga0315269_0011078 | GENOME_ACCESSION |
| Ga0315269_0014929 | GENOME_ACCESSION |
| Ga0315269_0030078 | GENOME_ACCESSION |
| Ga0315277_10001015 | GENOME_ACCESSION |
| Ga0315280_10009663 | GENOME_ACCESSION |
| Ga0315280_10032046 | GENOME_ACCESSION |
| Ga0315282_10006339 | GENOME_ACCESSION |
| Ga0315282_10053614 | GENOME_ACCESSION |
| Ga0315285_10079970 | GENOME_ACCESSION |
| Ga0315288_10142264 | GENOME_ACCESSION |
| Ga0315298_1000517 | GENOME_ACCESSION |
| Ga0315298_1001941 | GENOME_ACCESSION |
| Ga0315298_1005332 | GENOME_ACCESSION |
| Ga0315298_1007399 | GENOME_ACCESSION |
| Ga0315298_1007594 | GENOME_ACCESSION |
| Ga0315298_1015991 | GENOME_ACCESSION |
| Ga0315903_10087816 | GENOME_ACCESSION |
| Ga0334883_1024988 | GENOME_ACCESSION |
| Ga0334884_1015165 | GENOME_ACCESSION |
| Ga0370516_000963 | GENOME_ACCESSION |
| Ga0370516_004838 | GENOME_ACCESSION |
| Ga0370516_008232 | GENOME_ACCESSION |
| Ga0370516_009639 | GENOME_ACCESSION |
| Ga0370516_018229 | GENOME_ACCESSION |
| Ga0370516_020865 | GENOME_ACCESSION |
| Ga0373397_000168 | GENOME_ACCESSION |
| Ga0373621_000479 | GENOME_ACCESSION |
| Ga0373621_007959 | GENOME_ACCESSION |
| Ga0373621_010685 | GENOME_ACCESSION |
| Ga0373621_017562 | GENOME_ACCESSION |
| Ga0373621_020135 | GENOME_ACCESSION |
| Ga0373621_023545 | GENOME_ACCESSION |
| Ga0373621_050562 | GENOME_ACCESSION |
| Ga0373637_0010996 | GENOME_ACCESSION |
| Ga0373637_0021496 | GENOME_ACCESSION |
| Ga0373637_0024972 | GENOME_ACCESSION |
| Ga0373637_0031827 | GENOME_ACCESSION |
| Ga0373637_0034837 | GENOME_ACCESSION |
| Ga0373637_0065620 | GENOME_ACCESSION |
| Ga0374803_055 | GENOME_ACCESSION |
| GCA_000092125.1 | *Meiothermus silvanus* DSM 9946 plasmid pMESIL02 |
| GCA_000444055.1 | *Alicyclobacillus acidoterrestris* ATCC 49025 contig_23 |
| GCA_000444055.1 | *Alicyclobacillus acidoterrestris* ATCC 49025 contig_26 |
| GCA_000832185.1_ASM83218v1 | *Bacillus thermoamylovorans* strain B4167 NODE_88 |
| GCA_002951815.1_ASM295181v1 | *Sulfobacillus thermotolerans* strain Kr chromosome |
| GCA_004343255.1_ASM434325v1 | *Laceyella sacchari* strain DSM 43356 Ga0244645_102 |
| GCA_006503695.1 | *Tepidiphilus succinatimandens* strain DSM 15512 Scaffold2 |
| GCA_006503695.1_ASM650369v1 | *Tepidiphilus succinatimandens* strain DSM 15512 Scaffold2 |
| GCA_900116805.1 | *Alicyclobacillus macrosporangiidus* strain DSM 17980 genome assembly |
| GCA_900129915.1 | *Tepidibacter thalassicus* DSM 15285 genome assembly |
| JGI12383J13903_1002647 | GENOME_ACCESSION |
| JGI24108J20142_1001595 | GENOME_ACCESSION |
| JGI24721J44947_10029740 | GENOME_ACCESSION |
| JGI24721J44947_10039167 | GENOME_ACCESSION |
| JGI26463J51803_1000081 | GENOME_ACCESSION |
| KE386988.1_organ | *Desulfatirhabdium butyrativorans* DSM 18734 genomic scaffold G492DRAFT_scaffold00017.17 |
| KE387196.1_organ | *Tuberibacillus calidus* DSM 17572 genomic scaffold H532DRAFT_scaffold00017.11 |
| LGRA01000008.1_o | *Azospirillum* sp. TSO35-2 Contig02 |
| LNAA02000020.1_o | *Oscillatoriales cyanobacterium* MTP1 Contig_26 |
| mgm4742482.3 | NODE_1674_length_13888_cov_4.96582_ID_49155357 | GENOME_ACCESSION |

TABLE 1-continued

Cas 12 proteins

MHOL01000010.1_o | *Candidatus Staskawiczbacteria* bacterium
RIFCSPHIGHO2A_01_FULL_34_27 rifcsphigho2_01_scaffold_2126
MHPA01000001.1_o | *Candidatus Staskawiczb* acted a bacterium
RIFCSPLOWO2_01_FULL_38_12b rifcsplowo2_01_scaffold_12327
MTKY01071110.1_o | Anaerobic digester metagenome soeholt_digester_71110
MVGR01000004.1_o | *Microcystis aeruginosa* KW Contig4
NICF_comb_assmDRAFT_10010420 | GENOME_ACCESSION
NJDI01000010.1_o | *Archaeoglobales archaeon* ex4484_92
ex4484_82_scaffold_1630_length_14867_count_1478
OGCG01005283.1_o | hot springs metagenome genome assembly
OGCG01007631.1_o | hot springs metagenome genome assembly
OKRQ01000045.1_o | freshwater metagenome genome assembly
OQOO01000421.1_o | human oral metagenome genome assembly
OQUW01.1 | hot springs metagenome genome assembly
OQUW01000094.1_o | hot springs metagenome genome assembly
OQUW01000235.1_o | hot springs metagenome genome assembly
OQUW01001775.1_o | hot springs metagenome genome assembly
ORXB01007227.1_o | sediment metagenome genome assembly
OVXJ01001238.1_o | sediment metagenome genome assembly
QNAW01000106.1_o | *Thermodesulfobacteria* bacterium isolate B8_G2
B8_Guay2_scaffold_12966
UOVV01006324.1_o | compost metagenome genome assembly
UPSJ01002360.1_o | activated sludge metagenome genome assembly
YNPsite07_CeleraDRAF_scfl119010704098 | GENOME_ACCESSION In certain embodiments, the Cas protein is a Cas12b from a thermostable species, for example *Alicyclobacillus acidiphilus* (Aap). Cas 12a proteins can be identified from similar organisms as identified in any of BROD_5090P4_Cas12b_sequences.txt. In certain embodiments, the thermostable CRISPR-Cas protein is a Cas13a. In an aspect, the Cas12b thermostable protein is from FIG. 1A of U.S. Provisional Application 62/967,408, filed Jan. 29, 2020, entitled "Novel CRISPR Enzymes and Systems" which were identified from stable anaerobic thermophilic methanogenic microbiomes fermenting switchgrass, supporting their thermostability. See, Liang et al., Biotechnol Biofuels 2018; 11: 243 doi: 10.1186/s13068-018-1238-1. Similarly, the 0J26742 10014101 clusters with the verified thermophilic sourced Cas13a sequences detailed in FIG. 1A of U.S. Provisional Application 62/967,408, filed Jan. 29, 2020, entitled "Novel CRISPR Enzymes and Systems". The nucleic acid identified at loci 123519_10037894 was identified from a study focusing on 70° C. organism. In certain example embodiments, the Cas13 ortholog has at least two HEPN domains and at least 80% identity to a polypeptide encoded by the nucleic acid sequence 0123519_10037894 or 0J26742_10014101.

Certain example embodiments disclosed herein provide are based on low-cost CRISPR-based diagnostic that enables single-molecule detection of DNA or RNA with single-nucleotide specificity (Gootenberg, 2018; Gootenberg, et al, Science. 2017 Apr. 28; 356(6336):438-442 (2017); Myhrvold, et al., Science 360, 444-448 (2018)). Nucleic acid detection with SHERLOCK relies on the collateral activity of Type VI and Type V Cas proteins, such as Cas13 and Cas12, which unleashes promiscuous cleavage of reporters upon target detection (Gootenberg et al., 2018)(Abudayyeh, et al., Science. 353(6299)(2016); East-Seletsky et al. *Nature* 538:270-273 (2016); Smargon et al. Mol Cell 65(4):618-630 (2017)). Certain embodiments disclosed herein, are capable of single-molecule detection in less than an hour and can be used for multiplexed target detection when using CRISPR enzymes with orthogonal cleavage preference, such as *Alicyclobacillus acidiphilus* (Aap) Cas 12b and *Brevibacillus* sp. SYSU G02855 (BrCas12b); (Gootenberg, 2018; Myhrvold et al. Science 360(6387):444-448 (2018); Gootenberg, 2017; Chen et al. *Science* 360(6387):436-439 (2018); Li et al. *Cell Rep* 25(12):3262-3272 (2018); Li et al. *Nat Protoc* 13(5):899-914 (2018)). Guide molecules used herein are designed using a model for high activity-based Cas guide selection for coronavirus would facilitate design of optimal diagnostic assays, especially in applications requiring high-activity guides like lateral flow detection, and enable guide RNA design for in vivo polynucleotides targeting applications.

Embodiments disclosed herein utilize Cas proteins possessing non-specific nuclease collateral activity to cleave detectable reporters upon target recognition, providing sensitive and specific diagnostics, including single nucleotide variants, detection based on rRNA sequences, screening for drug resistance, monitoring microbe outbreaks, genetic perturbations, and screening of environmental samples, as described, for example, in PCT/US18/054472 filed Oct. 22, 2018 at [0183]-[0327], incorporated herein by reference. Reference is made to WO 2017/219027, WO2018/107129, US20180298445, US 2018-0274017, US 2018-0305773, WO 2018/170340, U.S. application Ser. No. 15/922,837, filed Mar. 15, 2018 entitled "Devices for CRISPR Effector System Based Diagnostics", PCT/US18/50091, filed Sep. 7, 2018 "Multi-Effector CRISPR Based Diagnostic Systems", PCT/US18/66940 filed Dec. 20, 2018 entitled "CRISPR Effector System Based Multiplex Diagnostics", PCT/US18/054472 filed Oct. 4, 2018 entitled "CRISPR Effector System Based Diagnostic", U.S. Provisional 62/740,728 filed Oct. 3, 2018 entitled "CRISPR Effector System Based Diagnostics for Hemorrhagic Fever Detection", U.S. Provisional 62/690,278 filed Jun. 26, 2018 and U.S. Provisional 62/767,059 filed Nov. 14, 2018 both entitled "CRISPR Double Nickase Based Amplification, Compositions, Systems and Methods", U.S. Provisional 62/690,160 filed Jun. 26, 2018 and 62/767,077 filed Nov. 14, 2018, both entitled "CRISPR/CAS and Transposase Based Amplification Compositions, Systems, And Methods", U.S. Provisional 62/690,257 filed Jun. 26, 2018 and 62/767,052 filed Nov. 14, 2018 both entitled "CRISPR Effector System Based Amplification Methods, Systems, And Diagnostics", U.S. Provisional 62/767,076 filed Nov. 14, 2018 entitled "Multiplexing Highly Evolving Viral Variants With SHERLOCK" and 62/767,070 filed Nov.

14, 2018 entitled "Droplet SHERLOCK." Reference is further made to WO2017/127807, WO2017/184786, WO 2017/184768, WO 2017/189308, WO 2018/035388, WO 2018/170333, WO 2018/191388, WO 2018/213708, WO 2019/005866, PCT/US18/67328 filed Dec. 21, 2018 entitled "Novel CRISPR Enzymes and Systems", PCT/US18/67225 filed Dec. 21, 2018 entitled "Novel CRISPR Enzymes and Systems" and PCT/US18/67307 filed Dec. 21, 2018 entitled "Novel CRISPR Enzymes and Systems", U.S. 62/712,809 filed Jul. 31, 2018 entitled "Novel CRISPR Enzymes and Systems", U.S. 62/744,080 filed Oct. 10, 2018 entitled "Novel Cas12b Enzymes and Systems" and U.S. 62/751,196 filed Oct. 26, 2018 entitled "Novel Cas12b Enzymes and Systems", U.S. Pat. No. 715,640 filed August 7, 2-18 entitled "Novel CRISPR Enzymes and Systems", WO 2016/205711, U.S. Pat. No. 9,790,490, WO 2016/205749, WO 2016/205764, WO 2017/070605, WO 2017/106657, and WO 2016/149661, WO2018/035387, WO2018/194963, Cox DBT, et al., RNA editing with CRISPR-Cas13, Science. 2017 Nov. 24; 358(6366):1019-1027; Gootenberg J S, et al., Multiplexed and portable nucleic acid detection platform with Cas13, Cas12a, and Csm6., Science. 2018 Apr. 27; 360(6387):439-444; Gootenberg J S, et al., Nucleic acid detection with CRISPR-Cas13a/C2c2., Science. 2017 Apr. 28; 356(6336):438-442; Abudayyeh O O, et al., RNA targeting with CRISPR-Cas13, Nature. 2017 Oct. 12; 550 (7675):280-284; Smargon A A, et al., Cas13b Is a Type VI-B CRISPR-Associated RNA-Guided RNase Differentially Regulated by Accessory Proteins Csx27 and Csx28. Mol Cell. 2017 Feb. 16; 65(4):618-630.e7; Abudayyeh O O, et al., C2c2 is a single-component programmable RNA-guided RNA-targeting CRISPR effector, Science. 2016 Aug. 5; 353(6299):aaf5573; Yang L, et al., Engineering and optimizing deaminase fusions for genome editing. Nat Commun. 2016 Nov. 2; 7:13330, Myhrvold et al., Field deployable viral diagnostics using CRISPR-Cas13, Science 2018 360, 444-448, Shmakov et al. "Diversity and evolution of class 2 CRISPR-Cas systems," Nat Rev Microbiol. 2017 15(3):169-182, each of which is incorporated herein by reference in its entirety.

In general, a CRISPR-Cas or CRISPR system as used herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system).

In certain embodiments, protospacer flanking site, or protospacer flanking sequence (PFS) directs binding of the effector proteins (e.g. Cas12b) as disclosed herein to the target locus of interest. A PFS is a region that can affect the efficacy of Cas mediated targeting, and may be adjacent to the protospacer target in certain Cas proteins, while other orthologs do not require a specific PFS. In a preferred embodiment, the CRISPR effector protein may recognize a 3' PFS. In certain embodiments, the CRISPR effector protein may recognize a 3' PFS which is 5'H, wherein H is A, C or U. See, e.g. Abudayyeh, 2016. In certain embodiments, the effector protein may be *Leptotrichia shahii* Cas12b, more preferably *Alicyclobacillus acidiphilis* Cas12b.

In the context of formation of a CRISPR complex, "target molecule" or "target sequence" or "target nucleic acid" refers to a molecule harboring a sequence, or a sequence to which a guide sequence is designed to have complementarity, where hybridization between a target sequence and a guide sequence promotes the formation of a CRISPR complex. A target sequence may comprise DNA polynucleotides. The term "target DNA" refers to a DNA polynucleotide being or comprising the target sequence. In other words, the target DNA may be a DNA polynucleotide or a part of a DNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell. A target sequence may comprise DNA polynucleotides.

As such, a CRISPR system may comprise polynucleotide-targeting effector proteins. A CRISPR system may comprise DNA-targeting effector proteins. In some embodiments, a CRISPR system may comprise a combination of RNA- and DNA-targeting effector proteins, or effector proteins that target both RNA and DNA.

Cas12b Orthologs

The present invention encompasses the use of a Cas12b effector proteins, derived from a Cas12b locus denoted as subtype V-B. Presently, the subtype V-B loci encompasses cas1-Cas4 fusion, cas2, a distinct gene denoted Cas12b and a CRISPR array. Cas12b (CRISPR-associated protein Cas12b) is a large protein (about 1100-1300 amino acids) that contains a RuvC-like nuclease domain homologous to the corresponding domain of Cas9 along with a counterpart to the characteristic arginine-rich cluster of Cas9. However, Cas12b lacks the HNH nuclease domain that is present in all Cas9 proteins, and the RuvC-like domain is contiguous in the Cas12b sequence, in contrast to Cas9 where it contains long inserts including the HNH domain. Accordingly, in particular embodiments, the CRISPR-Cas enzyme comprises only a RuvC-like nuclease domain.

The programmability, specificity, and collateral activity of the RNA-guided Cas12b also make it an ideal switchable nuclease for non-specific cleavage of nucleic acids. In one embodiment, a Cas12b system is engineered to provide and take advantage of collateral non-specific cleavage of DNA. In another embodiment, a Cas12b system is engineered to provide and take advantage of collateral non-specific cleavage of ssDNA. Accordingly, engineered Cas12b systems provide platforms for nucleic acid detection and transcriptome manipulation, and inducing cell death. Cas12b is developed for use as a mammalian transcript knockdown and binding tool. Cas12b is capable of robust collateral cleavage of DNA when activated by sequence-specific targeted DNA binding.

In certain embodiments, Cas12b is provided or expressed in an in vitro system or in a cell, transiently or stably, and targeted or triggered to non-specifically cleave cellular nucleic acids. In one embodiment, Cas12b is engineered to knock down ssDNA, for example viral ssDNA. In another embodiment, Cas12b is engineered to knock down RNA. The system can be devised such that the knockdown is dependent on a target DNA present in the cell or in vitro system, or triggered by the addition of a target nucleic acid to the system or cell.

In embodiments, the Cas12b protein also encompasses a homologs or an orthologs of Cas12b proteins described herein. The terms "ortholog" and "homolog" are well known in the art. By means of further guidance, a "homolog" of a protein as used herein is a protein of the same species which performs the same or a similar function as the protein it is a homologue of. Homologous proteins may but need not be structurally related, or are only partially structurally related. An "ortholog" of a protein as used herein is a protein of a different species which performs the same or a similar function as the protein it is an orthologue of. Orthologous proteins may but need not be structurally related, or are only partially structurally related. In particular embodiments, the homologue or orthologue of a Cas protein such as referred to herein has a sequence homology or identity of at least 80%, more preferably at least 85%, even more preferably at least 90%, such as for instance at least 95% with a Cas protein. In further embodiments, the homologue or orthologue of a Cas protein such as referred to herein has a sequence identity of at least 80%, more preferably at least 85%, even more preferably at least 90%, such as for instance at least 95% with the wild type Cas protein. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225.). See also Shmakov et al. (2015) for application in the field of CRISPR-Cas loci. Homologous proteins may but need not be structurally related, or are only partially structurally related.

In certain embodiments, the Cas protein may comprise at least 80% sequence identity to a polypeptide as described in International Patent Publication WO 2016/205749 at FIG. 17-21, FIG. 41A-41M, 44A-44E, incorporated herein by reference. Its cleavage relies on a tracr RNA to recruit a guide RNA comprising a guide sequence and a direct repeat, where the guide sequence hybridizes with the target nucleotide sequence to form a DNA/RNA heteroduplex. Based on current studies, Cas12b nuclease activity also requires relies on recognition of PAM sequence. Cas12b PAM sequences are T-rich sequences. In some embodiments, the PAM sequence is 5' TTN 3' or 5' ATTN 3', wherein N is any nucleotide. In a particular embodiment, the PAM sequence is 5' TTC 3'. In a particular embodiment, the PAM is in the sequence of *Plasmodium falciparum*.

In particular embodiments, the effector protein is a Cas12b effector protein from an organism from a genus comprising *Alicyclobacillus, Desulfovibrio, Desulfonatronum, Opitutaceae, Tuberibacillus, Bacillus, Brevibacillus, Candidatus, Desulfatirhabdium, Citrobacter, Elusimicrobia, Methylobacterium, Omnitrophica, Phycisphaerae, Planctomycetes, Spirochaetes,* and *Verrucomicrobiaceae*. A protein or nucleic acid "from" or "derived from" a species means that the protein or nucleic acid has a sequence identical to an endogenous protein or nucleic acid or a portion thereof in the species. The protein or nucleic acid from the species may be directly obtained from an organism of the species (e.g., by isolation), or may be produced, e.g., by recombination production or chemical synthesis.

In further particular embodiments, the Cas12b effector protein is from a species selected from *Alicyclobacillus acidoterrestris* (e.g., ATCC 49025), *Alicyclobacillus con-taminans* (e.g., DSM 17975), *Alicyclobacillus macrosporangiidus* (e.g. DSM 17980), *Bacillus hisashii* strain C4, *Candidatus Lindowbacteria* bacterium RIFCSPLOWO2, *Desulfovibrio inopinatus* (e.g., DSM 10711), *Desulfonatronum thiodismutans* (e.g., strain MLF-1), *Elusimicrobia* bacterium RIFOXYA12, *Omnitrophica* WOR_2 bacterium RIFCSPHIGHO2, *Opitutaceae* bacterium TAV5, *Phycisphaerae* bacterium ST-NAGAB-D1, *Planctomycetes* bacterium RBG_13_46_10, *Spirochaetes* bacterium GWB1_27_13, *Verrucomicrobiaceae* bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060).

In one aspect, the CRISPR-Cas protein is a Cas12b from BROD_5090P4_Cas12b_sequences.txt. In certain embodiments, the CRISPR-Cas protein is a Cas12b from a thermostable species, for example *Alicyclobacillus acidiphilus* (AapCas12b). When the Aap protein is utilized, a related guide can be used, for example from the same or another *Alicyclobacillus* species, e.g. *Alicyclobacillus acidoterrestrus* (AacCas12b). In an aspect, the guide comprises at least 95%, 96%, 97% or more sequence identity to the DR and/or the tracr sequence from Aac. In certain embodiments, the AapCas12b protein comprises a sequence with at least 80%, at least 85%, at least 90%, or at least 95% identity to, or comprising the sequence:

(SEQ ID NO: 61990)
MAVKSMKVKLRLDNMPEIRAGLWKLHTEVNAGVRYYTEWLSLLRQENLYR

RSPNGDGEQECYKTAEECKAELLERLRARQVENGHCGPAGSDDELLQLAR

QLYELLVPQAIGAKGDAQQIARKFLSPLADKDAVGGLGIAKAGNKPRWVR

MREAGEPGWEEEKAKAEARKSTDRTADVLRALADFGLKPLMRVYTDSDMS

SVQWKPLRKGQAVRTWDRDMFQQAIERMMSWESWNQRVGEAYAKLVEQKS

RFEQKNFVGQEHLVQLVNQLQQDMKEASHGLESKEQTAHYLTGRALRGSD

KVFEKWEKLDPDAPFDLYDTEIKNVQRRNTRRFGSHDLFAKLAEPKYQAL

WREDASFLTRYAVYNSIVRKLNHAKMFATFTLPDATAHPIWTRFDKLGGN

LHQYTFLFNEFGEGRHAIRFQKLLTVEDGVAKEVDDVTVPISMSAQLDDL

LPRDPHELVALYFQDYGAEQHLAGEFGGAKIQYRRDQLNHLHARRGARDV

YLNLSVRVQSQSEARGERRPPYAAVFRLVGDNHRAFVHFDKLSDYLAEHP

DDGKLGSEGLLSGLRVMSVDLGLRTSASISVFRVARKDELKPNSEGRVPF

CFPIEGNENLVAVHERSQLLKLPGETESKDLRAIREERQRTLRQLRTQLA

YLRLLVRCGSEDVGRRERSWAKLIEQPMDANQMTPDWREAFEDELQKLKS

LYGICGDREWTEAVYESVRRVWRHMGKQVRDWRKDVRSGERPKIRGYQKD

VVGGNSIEQIEYLERQYKFLKSWSFFGKVSGQVIRAEKGSRFAITLREHI

DHAKEDRLKKLADRIIMEALGYVYALDDERGKGKWVAKYPPCQLILLEEL

SEYQFNNDRPPSENNQLMQWSHRGVFQELLNQAQVHDLLVGTMYAAFSSR

FDARTGAPGIRCRRVPARCAREQNPEPFPWWLNKFVAEHKLDGCPLRADD

LIPTGEGEFFVSPFSAEEGDFHQIHADLNAAQNLQRRLWSDFDISQIRLR

CDWGEVDGEPVLIPRTTGKRTADSYGNKVFYTKTGVTYYERERGKKRRKV

```
FAQEELSEEEAELLVEADEAREKSVVLMRDPSGIINRGDWTRQKEFWSMV

NQRIEGYLVKQIRSRVRLQESACENTGDI.
```

In an aspect, the Cas protein is a Cas12b from Aap, and the guide molecule is derived from Aac, or an *Alicyclobacillus* CRISPR-Cas system direct repeat and tracrRNA. In certain embodiments, the guide is designed with a spacer sequence to target SARS-CoV-2. While any portion of the SARS-CoV-2 can be targeted, as described elsewhere herein, in an aspect, the spacer is designed to target the Nucleocapsid protein of the SARS-CoV-2.

In some examples, the compositions and system herein may comprise a Cas protein derived from a first species and a guide molecule comprising a guide sequence derived from a second species. In some cases, the Cas protein derived from the first species shares at least 60%, at least 70%, at least 80%, at least 90%, at least 95%, or at least 99% homology (e.g., identity) with a Cas protein derived from the second species. In some cases, the guide molecule comprises a tracrRNA derived from the first species and a crRNA derived from the second species.

In some examples, the compositions and system herein may comprise a Cas protein and a guide molecule comprising a guide sequence derived from another CRISPR-Cas system different from the CRISPR-Cas system of the Cas protein.

A spacer sequence may be attached to the 3' end to target a desired target polynucleotide sequence. In a particular example, the Cas protein is a Cas12b from Aap, and the guide molecule is derived from Aac.

In an aspect, the CRISPR-Cas protein is a BrCas12b. In certain embodiments, the BrCas12b protein comprises a sequence with at least 80%, at least 85%, at least 90%, at least 95% identity to, or comprising the sequence:

```
                                   (SEQ ID NO: 61963)
MPVRSFKVKLVTRSGDAEHMLQLRRGLWKTHEIVNQGIAYYMNKLALMRQ

EPYAGKSREVVRLELLHSLRAQQKRNNWTGDAGTDDEILNLSRRLYELLV

PSAIGEKGDAQMLSRKFLSPLVDPNSEGGKGTAKSGRKPRWMKMREEGHP

DWEAEREKDRAKKAADPTASILNDLEAFGLRPLFPLFTDEQKGIQWLPKQ

KRQFVRTFDRDMFQQALERMLSWESWNRRVAEEYQKLQAQRDELYAKYLA

DGGAWLEALQSFEKQREVELAEESFAAKSEYLITRRQIRGWKQVYEKWSQ

LPEHAAQEQFWQVVADVQTSLPGAFGDPKVYQFLSQPEHHHIWRGYPNRL

FHYSDYNGVRKKLQRARHDATFTLPDPVEHPLWIRFDARGGNIHDYEISQ

NGKQYQVTFSRLLWPENETWVERENVTVAIGASQQLKRQIRLDGYADKKQ

KVRYRDYSSGIELTGVLGGAKIQFDRRHLRKASNRLADGETGPVYLNVVV

DIEPFLAMRNGRLQTPIGQVLQVNTKDWPKVTGYKPAELISWIQNSPLAV

GTGVNTIEAGMRVMSVDLGQRSAAAVSIFEVMRQKPAEQETKLFYPIAVT

GLYAVHRRSLLLRLPGEKISDEIEQQRKIRAHARSLVRYQIRLLADVLRL

HTRGTAEQRRAKLDELLATLQTKQELDQKLWQTELEKLFDYIHEPAERWQ

QALVAAHRTLEPVIGQAVRHWRKSLRIDRKGLAGMSMWNIEELEETRKLL

IAWSKHSRVPGEPNRLDKEETFAPQQLQHIQNVKDDRLKQMANLLVMTAL

GYKYDEAEKQWKEAYPACQMILFEDLSRYRFALDRPRRENNRLMKWAHRS

IPRLVYLQGELFGIQVGDVYSAYTSRFHAKTGAPGIRCHALKEEDLQPNS

YVVKQLIKDGFIREDQTGSLKPGQIVPWSGGELFVTLADRSGSRLAVIHA

DINAAQNLQKRFWQQNTEIFRVPCKVTTSGLIPAYDKMKKLFGKGYFAKI

NQTDTSEVYVWEHSAKMKGKTTPADPAEEGVFDESLTDEMEELEDSQEGY

KTLFRDPSGFFWSSDRWLPQKEFWFWVKRRIEKKLREQLQ.
```

In an aspect, when the CRISPR-Cas protein is a BrCas12b, the tracrRNA can be selected from one of tracrRNA design 1-tracrRNA design 6 as detailed below:

```
tracrRdesign 1:
                                   (SEQ ID NO: 61964)
TGCAGGTTAGTGGAAATATAGATAGCCGTTGTGACTGAGTGACGTGTTAG

GTCACCGTAGCACATGACACAACTGCACTGGTCAGCCTGTAGCTAACCAC

CTTCATTATATCTAGTTTTTCCAAC tracrRNA design 2:
                                   (SEQ ID NO: 61965)
GTTGTGACTGAGTGACGTGTTAGGTCACCGTAGCACATGACACAACTGCA

CTGGTCAGCCTGTAGCTAACCACCTTCATTATATCTAGTTTTTCCAAC tracrRNA design 3:
                                   (SEQ ID NO: 61966)
TGACACAACTGCACTGGTCAGCCTGTAGCTAACCACCTTCATTATATCTA

GTTTTTCCAAC tracrRNA design 4:
                                   (SEQ ID NO: 61967)
GAAGGTGGTTAGCTACAGGCTGACCAGTGCAGTTGTGTCATGTGCTACGG

TGACCTAACACGTCACTCAGTCACAACGGCTATCTATATTTCCACTAAC tracrRNA design 5:
                                   (SEQ ID NO: 61968)
GTTGGAAAAACTAGATATAATGAAGGTGGTTAGCTACAGGCTGACCAGTG

CAGTTGTGTCATGTGCTACGGTGACCTAACACGTCACTCAGTCACAACGG

CTATCTATATTTCCACTAAC tracrRNA design 6:
                                   (SEQ ID NO: 61969)
GTGCAGTTGTGTCATGTGCTACGGTGACCTAACACGTCACTCAGTCACAA

CGGCTATCTATATTTCCACTAAC
```

In an aspect, when BrCas12b is utilized, the crRNA design can be selected from one of crRNAdesign 1 to crRNA design 3, wherein N represents the spacer design:

```
crRNA design 1:
                                   (SEQ ID NO: 61970)
GTCCGTTTCGTTAGTGGAAATGTAGATGGTTAGCACNNNNNNNNNNNNNN

NNNNNNNNNNNNNN crRNA design 2:
                                   (SEQ ID NO: 61971)
TAGTGGAAATGTAGATGGTTAGCACNNNNNNNNNNNNNNNNNNNNNNNNN

NN crRNA design 3
                                   (SEQ ID NO: 61972)
GTTAGTGGAAATCTAGATGGTTAGCACNNNNNNNNNNNNNNNNNNNNNNN

NNNN
```

In certain example embodiments, the guide sequence comprises or is one of SEQ ID NOs:40500-61643.

The effector protein may comprise a chimeric effector protein comprising a first fragment from a first effector protein (e.g., a Cas12b) ortholog and a second fragment from a second effector (e.g., a Cas12b) protein ortholog, and wherein the first and second effector protein orthologs are different. At least one of the first and second effector protein (e.g., a Cas12b) orthologs may comprise an effector protein (e.g., a Cas12b) from an organism comprising *Alicyclobacillus, Desulfovibrio, Desulfonatronum, Opitutaceae, Tuberibacillus, Bacillus, Brevibacillus, Candidatus, Desulfatirhabdium, Elusimicrobia, Citrobacter, Methylobacterium, Omnitrophicai, Phycisphaerae, Planctomycetes, Spirochaetes,* and *Verrucomicrobiaceae*; e.g., a chimeric effector protein comprising a first fragment and a second fragment wherein each of the first and second fragments is selected from a Cas12b of an organism comprising *Alicyclobacillus, Desulfovibrio, Desulfonatronum, Opitutaceae, Tuberibacillus, Bacillus, Brevibacillus, Candidatus, Desulfatirhabdium, Elusimicrobia, Citrobacter, Methylobacterium, Omnitrophicai, Phycisphaerae, Planctomycetes, Spirochaetes,* and *Verrucomicrobiaceae* wherein the first and second fragments are not from the same bacteria; for instance a chimeric effector protein comprising a first fragment and a second fragment wherein each of the first and second fragments is selected from a Cas12b of *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus lindowbacteria bacterium* RIFCSPLOWO2, *Desulfovibrio inopinatus* (e.g., DSM 10711), *Desulfonatronum thiodismutans* (e.g., strain MLF-1), *Elusimicrobia bacterium* RIFOXYA12, *Omnitrophica WOR_2 bacterium* RIFCSPHIGHO2, *Opitutaceae bacterium* TAV5, *Phycisphaerae bacterium* ST-NAGAB-D1, *Planctomycetes bacterium* RBG_13_46_10, *Spirochaetes bacterium* GWB1_27_13, *Verrucomicrobiaceae bacterium* UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060), wherein the first and second fragments are not from the same bacteria.

In a more preferred embodiment, the Cas12b is derived from a bacterial species selected from *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus lindowbacteria bacterium* RIFCSPLOWO2, *Desulfovibrio inopinatus* (e.g., DSM 10711), *Desulfonatronum thiodismutans* (e.g., strain MLF-1), *Elusimicrobia bacterium* RIFOXYA12, *Omnitrophica WOR_2 bacterium* RIFCSPHIGHO2, *Opitutaceae bacterium* TAV5, *Phycisphaerae bacterium* ST-NAGAB-D1, *Planctomycetes bacterium* RBG_13_46_10, *Spirochaetes bacterium* GWB1_27_13, *Verrucomicrobiaceae bacterium* UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060). In certain embodiments, the Cas12b is derived from a bacterial species selected from *Alicyclobacillus acidoterrestris* (e.g., ATCC 49025), or *Alicyclobacillus contaminans* (e.g., DSM 17975).

In particular embodiments, the homolog or ortholog of Cas12b as referred to herein has a sequence homology or identity of at least 80%, more preferably at least 85%, even more preferably at least 90%, such as for instance at least 95% with Cas12b. In further embodiments, the homologue or orthologue of Cas12b as referred to herein has a sequence identity of at least 80%, more preferably at least 85%, even more preferably at least 90%, such as for instance at least 95% with the wild type Cas12b. Where the Cas12b has one or more mutations (mutated), the homologue or orthologue of said Cas12b as referred to herein has a sequence identity of at least 80%, more preferably at least 85%, even more preferably at least 90%, such as for instance at least 95% with the mutated Cas12b.

In an embodiment, the Cas12b protein may be an ortholog of an organism of a genus which includes, but is not limited to *Alicyclobacillus, Desulfovibrio, Desulfonatronum, Opitutaceae, Tuberibacillus, Bacillus, Brevibacillus, Candidatus, Desulfatirhabdium, Elusimicrobia, Citrobacter, Methylobacterium, Omnitrophicai, Phycisphaerae, Planctomycetes, Spirochaetes,* and *Verrucomicrobiaceae*; in particular embodiments, the type V Cas protein may be an ortholog of an organism of a species which includes, but is not limited to *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus Lindowbacteria bacterium* RIFCSPLOWO2, *Desulfovibrio inopinatus* (e.g., DSM 10711), *Desulfonatronum thiodismutans* (e.g., strain MLF-1), *Elusimicrobia bacterium* RIFOXYA12, *Omnitrophica WOR_2 bacterium* RIFCSPHIGHO2, *Opitutaceae bacterium* TAV5, *Phycisphaerae bacterium* ST-NAGAB-D1, *Planctomycetes bacterium* RBG_13_46_10, *Spirochaetes bacterium* GWB1_27_13, *Verrucomicrobiaceae bacterium* UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060). In particular embodiments, the homolog or ortholog of Cas12b as referred to herein has a sequence homology or identity of at least 80%, more preferably at least 85%, even more preferably at least 90%, such as for instance at least 95% with one or more of the Cas12b sequences disclosed herein. In further embodiments, the homologue or orthologue of Cas12b as referred to herein has a sequence identity of at least 80%, more preferably at least 85%, even more preferably at least 90%, such as for instance at least 95% with the wild type AacCas12b or BthCas12b.

In particular embodiments, the Cas12b protein of the invention has a sequence homology or identity of at least 60%, more particularly at least 70, such as at least 80%, more preferably at least 85%, even more preferably at least 90%, such as for instance at least 95% with AacCas12b or BthCas12b. In further embodiments, the Cas12b protein as referred to herein has a sequence identity of at least 60%, such as at least 70%, more particularly at least 80%, more preferably at least 85%, even more preferably at least 90%, such as for instance at least 95% with the wild type AacCas12b. In particular embodiments, the Cas12b protein of the present invention has less than 60% sequence identity with AacCas12b. The skilled person will understand that this includes truncated forms of the Cas12b protein whereby the sequence identity is determined over the length of the truncated form.

In certain methods according to the present invention, the Cas protein is preferably mutated with respect to a corresponding wild-type enzyme such that the mutated Cas protein lacks the ability to cleave one or both DNA strands of a target locus containing a target sequence. In particular embodiments, one or more catalytic domains of the Cas12b protein are mutated to produce a mutated Cas protein which cleaves only one DNA strand of a target sequence.

In particular embodiments, the Cas protein may be mutated with respect to a corresponding wild-type enzyme such that the mutated Cas protein lacks substantially all DNA cleavage activity. In some embodiments, a Cas protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

In certain embodiments of the methods provided herein the Cas protein is a mutated Cas protein which cleaves only one DNA strand, i.e. a nickase. More particularly, in the context of the present invention, the nickase ensures cleavage within the non-target sequence, i.e. the sequence which is on the opposite DNA strand of the target sequence and which is 3' of the PAM sequence. By means of further guidance, and without limitation, an arginine-to-alanine substitution (R911A) in the Nuc domain of Cas12b from *Alicyclobacillus acidoterrestris* converts Cas12b from a nuclease that cleaves both strands to a nickase (cleaves a single strand). It will be understood by the skilled person that where the enzyme is not AacCas12b, a mutation may be made at a residue in a corresponding position.

Modified Cas Proteins

The Cas proteins may be a modified form compared to a naturally occurring counterpart. The modifications of Cas proteins may or may not cause an altered functionality. By means of example, modifications which do not result in an altered functionality include for instance codon optimization for expression into a particular host (e.g., in a eukaryotic cell), or providing the nuclease with a particular marker (e.g. for visualization). Modifications with may result in altered functionality may also include mutations, including point mutations, insertions, deletions, truncations (including split nucleases), etc. Fusion proteins may without limitation include for instance fusions with heterologous domains or functional domains (e.g. localization signals, catalytic domains, etc.). In certain embodiments, various different modifications may be combined (e.g. a mutated nuclease which is catalytically inactive and which further is fused to a functional domain, such as for instance to induce DNA methylation or another nucleic acid modification, such as including without limitation a break (e.g. by a different nuclease (domain)), a mutation, a deletion, an insertion, a replacement, a ligation, a digestion, a break or a recombination). As used herein, "altered functionality" includes without limitation an altered specificity (e.g. altered target recognition, increased (e.g. "enhanced" Cas proteins) or decreased specificity, or altered PAM recognition), altered activity (e.g. increased or decreased catalytic activity, including catalytically inactive nucleases or nickases), and/or altered stability (e.g. fusions with destabilization domains).

In certain embodiments, the Cas protein may comprise one or more modifications resulting in enhanced activity and/or specificity, such as including mutating residues that stabilize the targeted or non-targeted strand (e.g. eCas9; "Rationally engineered Cas9 nucleases with improved specificity", Slaymaker et al. (2016), Science, 351(6268): 84-88, incorporated herewith in its entirety by reference). In certain embodiments, the altered or modified activity of the engineered CRISPR protein comprises increased targeting efficiency or decreased off-target binding. In certain embodiments, the altered activity of the engineered Cas protein comprises modified cleavage activity. In certain embodiments, the altered activity comprises increased cleavage activity as to the target polynucleotide loci. In certain embodiments, the altered activity comprises decreased cleavage activity as to the target polynucleotide loci. In certain embodiments, the altered activity comprises decreased cleavage activity as to off-target polynucleotide loci. In certain embodiments, the altered or modified activity of the modified nuclease comprises altered helicase kinetics.

In certain embodiments, the modified nuclease comprises a modification that alters association of the protein with the nucleic acid molecule comprising RNA (in the case of a Cas protein), or a strand of the target polynucleotide loci, or a strand of off-target polynucleotide loci. In an aspect of the invention, the engineered Cas protein comprises a modification that alters formation of the CRISPR complex. In certain embodiments, the altered activity comprises increased cleavage activity as to off-target polynucleotide loci. Accordingly, in certain embodiments, there is increased specificity for target polynucleotide loci as compared to off-target polynucleotide loci. In other embodiments, there is reduced specificity for target polynucleotide loci as compared to off-target polynucleotide loci. In certain embodiments, the mutations result in decreased off-target effects (e.g. cleavage or binding properties, activity, or kinetics), such as in case for Cas proteins for instance resulting in a lower tolerance for mismatches between target and guide RNA. Other mutations may lead to increased off-target effects (e.g. cleavage or binding properties, activity, or kinetics). Other mutations may lead to increased or decreased on-target effects (e.g. cleavage or binding properties, activity, or kinetics). In certain embodiments, the mutations result in altered (e.g. increased or decreased) helicase activity, association or formation of the functional nuclease complex (e.g. CRISPR-Cas complex). In certain embodiments, as described above, the mutations result in an altered PAM recognition, e.g., a different PAM may be (in addition or in the alternative) be recognized, compared to the unmodified Cas protein. Particularly preferred mutations include positively charged residues and/or (evolutionary) conserved residues, such as conserved positively charged residues, in order to enhance specificity. In certain embodiments, such residues may be mutated to uncharged residues, such as alanine.

According to the invention, mutants can be generated which lead to inactivation of the enzyme or modify the double strand nuclease to nickase activity, or which alter the PAM recognition specificity of Cas12b. In certain embodiments, this information is used to develop enzymes with reduced off-target effects.

In certain example embodiments, the editing preference is for a specific insert or deletion within the target region. In certain example embodiments, the at least one modification increases formation of one or more specific indels. In certain example embodiments, the at least one modification is in a C-terminal RuvC like domain, the NUC domain, the N-terminal alpha-helical region, the mixed alpha and beta region, or a combination thereof. In certain example embodiments the altered editing preference is indel formation. In certain example embodiments, the at least one modification increases formation of one or more specific insertions.

In certain example embodiments, the at least one modification increases formation of one or more specific insertions. In certain example embodiments, the one or more modifications result in an enzyme which ensures more precise one-base insertions or deletions, such as those described above. More particularly, the one or more modifications may reduce the formations of other types of indels by the enzyme. The ability to generate one-base insertions or deletions can be of interest in a number of applications, such as correction of genetic mutants in diseases caused by small deletions, more particularly where HDR is not possible. For example, correction of the F508del mutation in CFTR via delivery of three sRNA directing insertion of three T's, which is the most common genotype of cystic fibrosis, or correction of Alia Jafar's single nucleotide deletion in CDKL5 in the brain. As the editing method only requires NHEJ, the editing would be possible in post-mitotic cells such as the brain. The ability to generate one base pair insertions/deletions may also be useful in genome-wide CRISPR-Cas negative selection screens. In certain example embodiments, the at least one modification, is a mutation. In certain other example embodiment, the one or more modification may be combined with one or more additional modifications or mutations described below including modifications to increase binding specificity and/or decrease off-target effects.

In certain example embodiments, the engineered Cas protein comprising at least one modification that alters editing preference as compared to wild type may further comprise one or more additional modifications that alters the binding property as to the nucleic acid molecule comprising RNA or the target polypeptide loci, altering binding kinetics as to the nucleic acid molecule or target molecule or target polynucleotide or alters binding specificity as to the nucleic acid molecule. Example of such modifications are summarized in the following paragraph. Based on the above information, mutants can be generated which lead to inactivation of the enzyme or which modify the double strand nuclease to nickase activity. In alternative embodiments, this information is used to develop enzymes with reduced off-target effects.

Positions and types of mutations to be made to the Cas protein may be determined based on information from the crystal structure of the Cas protein, or the structure of the homolog or ortholog of Cas protein. The crystal structure of Cas12b reveals similarity with another Type V Cas protein, Cpf1 (also known as Cas12a). Both Cas12b and Cpf1 has an α-helical recognition lobe (REC) and a nuclease lobe (NUC). The NUC lobe further contains a oligonucleotide-binding (WED/OBD) domain, a RuvC domain, a Nuc domain, and a bridge helix (BH), with structural shuffling and folding to form the intact 3D Cas12b structure (Liu et al. Mol. Cell 65, 310-322). Certain mutations (e.g. R1226A in AsCpf1, R894A in BvCas12b) in the Nuc domain render Cpf1 into a nickase for non-target strand cleavage. Mutations of the catalytic residues (e.g. mutations at D908, E933, D1263 of AsCpf1) in the RuvC domain abolishes catalytic activity of Cpf1 as a nuclease. Further, mutations in the PAM interaction (PI) domain of Cpf1 (e.g. mutations at 5542, K548, N522, and K607 of AsCpf1), have been shown to alter Cpf1 specificities, potentially increasing or reducing off-target cleavage (See Gao et al. Cell Research (2016) 26, 901-913 (2016); Gao et al. Nature Biotechnology 35, 789-792 (2017)). The crystal structure of Cas12b also reveals that Cas12b lacks an identifiable PI domain; rather, it is suggested that Cas12b undergoes conformation adjustment to accommodate the binding of the PAM proximal double stranded DNA for PAM recognition and R-loop formation; Cas12b likely engages the WED/OBD and alpha helix domain to recognize the PAM duplex from both the major and the minor groove sides (Yang et al, Cell 167, 1814-1828 (2016)).

Catalytic Inactive Cas Proteins or Nickases

In some embodiments, the modified Cas protein may have reduced or eliminated nuclease activity compared to a wildtype, non-modified counterpart. In some cases, the Cas protein may be a catalytically inactive (dead) Cas protein. As used herein, a catalytically inactive Cas protein may be a nickase.

The modified Cas have nuclease inactivation of at least 70%, at least 80%, at least 90%, at least 95%, at least 97%, or 100% as compared with the wild type counterpart; or to put in another way, a Cas12b enzyme having advantageously about 0% of the nuclease activity of the non-mutated or wild type Cas12b, or no more than about 3% or about 5% or about 10% of the nuclease activity of the non-mutated or wild type Cas12b enzyme. In some embodiments, a Cas protein is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. In these embodiments, the CRISPR-Cas protein is used as a generic DNA binding protein. This is possible by introducing mutations into the nuclease domains of the Cas12b and orthologs thereof.

Mutations may be made at neighboring residues at amino acids that participate in the nuclease activity. In some embodiments, only the RuvC domain is inactivated, and in other embodiments, another putative nuclease domain is inactivated, wherein the effector protein complex functions as a nickase and cleaves only one DNA strand. In some embodiments, two Cas12b variants (each a different nickase) are used to increase specificity, two nickase variants are used to cleave DNA at a target (where both nickases cleave a DNA strand, while minimizing or eliminating off-target modifications where only one DNA strand is cleaved and subsequently repaired). In preferred embodiments the Cas12b effector protein cleaves sequences associated with or at a target locus of interest as a homodimer comprising two Cas12b effector protein molecules. In a preferred embodiment the homodimer may comprise two Cas12b effector protein molecules comprising a different mutation in their respective RuvC domains.

In certain embodiments, the Cas12b protein is a catalytically inactive Cas12b which comprises a mutation in the RuvC domain. In some embodiments, the catalytically inactive Cas12b protein comprises a mutation corresponding to amino acid positions D570, E848, or D977 in *Alicyclobacillus acidoterrestris* Cas12b. In some embodiments, the catalytically inactive Cas12b protein comprises a mutation corresponding to D570A, E848A, or D977A in *Alicyclobacillus acidoterrestris* Cas12b.

In some embodiments, the catalytically inactive Cas12b protein comprises a mutation corresponding to amino acid positions D574, E828, or D952 in *Bacillus hisashii* Cas12b. In some embodiments, the catalytically inactive Cas12b protein comprises a mutation corresponding to D574A, E828A, or D952A in *Bacillus hisashii* Cas12b.

In some embodiments, the catalytically inactive Cas12b protein comprises a mutation corresponding to amino acid positions D567, E831, or D963 in *Bacillus* sp. V3-13 Cas12b. In some embodiments, the catalytically inactive Cas12b protein comprises a mutation corresponding to D567A, E831A, or D963A in *Bacillus* sp. V3-13 Cas12b.

In certain embodiments, the Cas12b protein is a catalytically inactive Cas12b which comprises a mutation in the RuvC domain. In some embodiments, the catalytically inactive Cas12b protein comprises a mutation corresponding to amino acid positions D570, E848, or D977 in *Alicyclobacillus acidoterrestris* Cas12b. In some embodiments, the catalytically inactive Cas12b protein comprises a mutation corresponding to D570A, E848A, or D977A in *Alicyclobacillus acidoterrestris* Cas12b.

In some embodiments, the catalytically inactive Cas12b protein comprises a mutation corresponding to amino acid positions D574, E828, or D952 in *Bacillus hisashii* Cas12b. In some embodiments, the catalytically inactive Cas12b protein comprises a mutation corresponding to D574A, E828A, or D952A in *Bacillus hisashii* Cas12b.

In some embodiments, the catalytically inactive Cas12b protein comprises a mutation corresponding to amino acid positions D567, E831, or D963 in *Bacillus* sp. V3-13 Cas12b. In some embodiments, the catalytically inactive Cas12b protein comprises a mutation corresponding to D567A, E831A, or D963A in *Bacillus* sp. V3-13 Cas12b.

In certain embodiments, the Cas12b protein is a Cas12b nickase which comprises a mutation in the Nuc domain. In some embodiments, the Cas12b nickase comprises a mutation corresponding to amino acid positions R911, R1000, or R1015 in *Alicyclobacillus acidoterrestris* Cas12b. In some embodiments, the Cas12b nickase comprises a mutation corresponding to R911A, R1000A, or R1015A in *Alicyclobacillus acidoterrestris* Cas12b. In some embodiments, the Cas12b nickase comprises a mutation corresponding to R894A in *Bacillus* sp. V3-13 Cas12b. In certain embodiments, the Cas12b protein recognizes PAMs with increased or decreased specificity as compared with an unmutated or unmodified form of the protein. In some embodiments, the Cas12b protein recognizes altered PAMs as compared with an unmutated or unmodified form of the protein.

In some embodiments, a Cas protein is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. In these embodiments, the CRISPR-Cas protein is used as a generic DNA binding protein. The mutations may be artificially introduced mutations or gain- or loss-of-function mutations.

In addition to the mutations described above, the Cas protein may be additionally modified. As used herein, the term "modified" with regard to a Cas protein generally refers to a CRISPR-Cas protein having one or more modifications or mutations (including point mutations, truncations, insertions, deletions, chimeras, fusion proteins, etc.) compared to the wild type Cas protein from which it is derived. By derived is meant that the derived enzyme is largely based, in the sense of having a high degree of sequence homology with, a wildtype enzyme, but that it has been mutated (modified) in some way as known in the art or as described herein.

The invention contemplates methods of using two or more nickases, in particular a dual or double nickase approach. In some aspects and embodiments, a single type Cas12b nickase may be delivered, for example a modified Cas12b or a modified Cas12b nickase as described herein. This results in the target DNA being bound by two Cas12b nickases. In addition, it is also envisaged that different orthologs may be used, e.g., an Cas12b nickase on one strand (e.g., the coding strand) of the DNA and an ortholog on the non-coding or opposite DNA strand. It may be advantageous to use two different orthologs that require different PAMs and may also have different guide requirements, thus allowing a greater deal of control for the user. In certain embodiments, DNA cleavage will involve at least four types of nickases, wherein each type is guided to a different sequence of target DNA, wherein each pair introduces a first nick into one DNA strand and the second introduces a nick into the second DNA strand. In such methods, at least two pairs of single stranded breaks are introduced into the target DNA wherein upon introduction of first and second pairs of single-strand breaks, target sequences between the first and second pairs of single-strand breaks are excised. In certain embodiments, one or both of the orthologs is controllable, i.e. inducible.

In certain methods according to the present invention, the Cas protein is preferably mutated with respect to a corresponding wild-type enzyme such that the mutated Cas protein lacks the ability to cleave one or both DNA strands of a target locus containing a target sequence. In particular embodiments, one or more catalytic domains of the Cas12b protein are mutated to produce a mutated Cas protein which cleaves only one DNA strand of a target sequence.

In certain embodiments of the methods provided herein the Cas protein is a mutated Cas protein which cleaves only one DNA strand, i.e. a nickase. More particularly, in the context of the present invention, the nickase ensures cleavage within the non-target sequence, i.e. the sequence which is on the opposite DNA strand of the target sequence and which is 3' of the PAM sequence. By means of further guidance, and without limitation, an arginine-to-alanine substitution (R911A) in the Nuc domain of Cas12b from *Alicyclobacillus acidoterrestris* converts Cas12b from a nuclease that cleaves both strands to a nickase (cleaves a single strand). It will be understood by the skilled person that where the enzyme is not AacCas12b, a mutation may be made at a residue in a corresponding position.

Destabilized Cas12b

In certain embodiments, the Cas protein is associated with or fused to a destabilization domain (DD). In some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

Split Designs

In some embodiments, the invention provides split enzymes and reporter molecules, portions of which are provided in hybrid molecules comprising an nucleic acid-binding Cas protein, such as, but not limited to Cas12b. When brought into proximity in the presence of a nucleic acid in a cell, activity of the split reporter or enzyme is reconstituted and the activity can then be measured. A split enzyme reconstituted in such manner can detectably act on a cellular component and/or pathway, including but not limited to an endogenous component or pathway, or exogenous component or pathway. A split reporter reconstituted in such manner can provide a detectable signal, such as but not limited to fluorescent or other detectable moiety. In certain embodiments, a split proteolytic enzyme is provided which when reconstituted acts on one or more components (endogenous or exogenous) in a detectable manner. In one exemplary embodiment, there is provided a method of inducing programmed cell death upon detection of a nucleic acid species in a cell. It will be apparent how such a method could be used to ablate populations of cells, based for example, on the presence of virus in the cells.

In some embodiments, when converted to a nucleic acid binding protein, Cas12b is useful for localizing other functional components to target nucleic acids in a sequence dependent manner. The components can be natural or synthetic. According to the invention dCas12b is used to (i) bring effector modules to specific nucleic acids to modulate the function or transcription, which could be used for large-scale screening, construction of synthetic regulatory circuits and other purposes; (ii) fluorescently tag specific nucleic acids to visualize their trafficking and/or localization; (iii) alter nucleic acid localization through domains with affinity for specific subcellular compartments; and (iv) capture specific nucleic acids (through direct pull down of dCas12b to localize biotin ligase activity) to enrich for proximal molecular partners, including RNAs and proteins. dCas12b can be used to i) organize components of a cell, ii) switch components or activities of a cell on or off, and iii) control cellular states based on the presence or amount of a specific transcript present in a cell.

According to the invention, there is provided a method of inducing cell death in a cell which contains an nucleic acid of interest, which comprises contacting the nucleic acid in the cell with a composition which comprises a first Cas protein linked to an inactive first portion of a proteolytic enzyme capable of inducing cell death, a second Cas protein linked to the complementary portion of the enzyme wherein the enzyme activity of the proteolytic enzyme is reconstituted when the first portion and the complementary portion of the protein are contacted, and a first guide that binds to the first CRISPR protein and hybridizes to a first target sequence of the nucleic acid, and a second guide that binds to the second CRISPR protein and hybridizes to a second target sequence of the nucleic acid. When the target nucleic acid of interest is present, the first and second portions of the proteolytic enzyme are contacted and the proteolytic activity of the enzyme is reconstituted and induces cell death. In one such embodiment of the invention, the proteolytic enzyme is a caspase. In another such embodiment, the proteolytic enzyme is TEV protease, wherein when the proteolytic activity of the TEV protease is reconstituted, a TEV protease substrate is cleaved and/or activated. In an embodiment of the invention, the TEV protease substrate is an engineered procaspase such that when the TEV protease is reconstituted, the procaspase is cleaved and activated, whereby apoptosis occurs. In an embodiment of the invention, a proteolytically cleavable transcription factor can be combined with any downstream reporter gene of choice to yield 'transcription-coupled' reporter systems. In an embodiment, a split protease is used to cleave or expose a degron from a detectable substrate.

According to the invention, there is provided a method of marking or identifying a cell which contains an nucleic acid of interest, which comprises contacting the nucleic acid in the cell with a composition which comprises a first Cas protein linked to an inactive first portion of a proteolytic enzyme, a second CRISPR protein linked to the complementary portion of the enzyme wherein the enzyme activity of the proteolytic enzyme is reconstituted when the first portion and the complementary portion of the protein are contacted, a first guide that binds to the first CRISPR protein and hybridizes to a first target sequence of the nucleic acid, a second guide that binds to the second CRISPR protein and hybridizes to a second target sequence of the nucleic acid, and an indicator which is detectably cleaved by the reconstituted proteolytic enzyme. The first and second portions of the proteolytic enzyme are contacted when the nucleic acid of interest is present in the cell, whereby the activity of the proteolytic enzyme is reconstituted and the indicator is detectably cleaved. In one such embodiment, the detectable indicator is a fluorescent protein, such as, but not limited to green fluorescent protein. In another such embodiment of the invention, the detectable indicator is a luminescent protein, such as, but not limited to luciferase. In an embodiment, the split reporter is based on reconstitution of split fragments of *Renilla reniformis* luciferase (Rluc). In an embodiment of the invention, the split reporter is based on complementation between two nonfluorescent fragments of the yellow fluorescent protein (YFP).

Transcription and Modulation

In one aspect, the present disclosure provides a method of identifying, measuring, and/or modulating the state of a cell or tissue based on the presence or level of a particular nucleic acid in the cell or tissue. In one embodiment, the invention provides a CRISPR-based control system designed to modulate the presence and/or activity of a cellular system or component, which may be a natural or synthetic system or component, based on the presence of a selected nucleic acid species of interest. In general, the control system features an inactivated protein, enzyme or activity that is reconstituted when a selected nucleic acid species of interest is present. In an embodiment of the invention, reconstituting an inactivated protein, enzyme or activity involves bringing together inactive components to assemble an active complex.

Split Apoptosis Constructs

It is often desirable to deplete or kill cells based on the presence of aberrant endogenous or foreign DNA, either for basic biology applications to study the role of specific cells types or for therapeutic applications such as cancer or infected cell clearance (Baker, D. J., Childs, B. G., Durik, M., Wijers, M. E., Sieben, C. J., Zhong, J., Saltness, R. A., Jeganathan, K. B., Verzosa, G. C., Pezeshki, A., et al. (2016). Naturally occurring p16(Ink4a)-positive cells shorten healthy lifespan. Nature 530, 184-189.). This targeted cell killing can be achieved by fusing split apoptotic domains to Cas12b proteins, which upon binding to the DNA are reconstituted, leading to death of cells specifically expressing targeted genes or sets of genes. In certain embodiments, the apoptotic domains may be split Caspase 3 (Chelur, D. S., and Chalfie, M. (2007). Targeted cell killing by reconstituted caspases. Proc. Natl. Acad. Sci. U.S.A 104, 2283-2288.). Other possibilities are the assembly of Caspases, such as bringing two Caspase 8 (Pajvani, U. B., Trujillo, M. E., Combs, T. P., Iyengar, P., Jelicks, L., Roth, K. A., Kitsis, R. N., and Scherer, P. E. (2005). Fat apoptosis through targeted activation of caspase 8: a new mouse model of inducible and reversible lipoatrophy. Nat. Med. 11, 797-803.) or Caspase 9 (Straathof, K. C., Pulè, M. A., Yotnda, P., Dotti, G., Vanin, E. F., Brenner, M. K., Heslop, H. E., Spencer, D. M., and Rooney, C. M. (2005). An inducible caspase 9 safety switch for T-cell therapy. Blood 105, 4247-4254.) effectors in proximity via Cas12b binding. It is also possible to reconstitute a split TEV (Gray, D. C., Mahrus, S., and Wells, J. A. (2010). Activation of specific apoptotic caspases with an engineered small-molecule-activated protease. Cell 142, 637-646.) via Cas12b binding on a transcript. This split TEV can be used in a variety of readouts, including luminescent and fluorescent readouts (Wehr, M. C., Laage, R., Bolz, U., Fischer, T. M., Grunewald, S., Scheek, S., Bach, A., Nave, K.-A., and Rossner, M. J. (2006). Monitoring regulated protein-protein interactions using split TEV. Nat. Methods 3, 985-993.). One embodiment involves the reconstitution of this split TEV to cleave modified pro-caspase 3 or pro-caspase 7 (Gray, D. C., Mahrus, S., and Wells, J. A. (2010). Activation of specific apoptotic caspases with an engineered small-molecule-activated protease. Cell 142, 637-646), resulting in cell death.

Inducible apoptosis. According to the invention, guides can be used to locate Cas12b complexes bearing functional domains to induce apoptosis. The Cas12b can be any ortholog. In one embodiment, functional domains are fused at the C-terminus of the protein. The Cas12b is catalytically inactive for example via mutations that knock out nuclease activity. The adaptability of system can be demonstrated by employing various methods of caspase activation, and optimization of guide spacing along a target nucleic acid. Caspase 8 and caspase 9 (aka "initiator" caspases) activity can be induced using Cas12b complex formation to bring together caspase 8 or caspase 9 enzymes associated with Cas12b. Alternatively, caspase 3 and caspase 7 (aka "effector" caspases) activity can be induced when Cas12b complexes bearing tobacco etch virus (TEV) N-terminal and C-terminal portions ("snipper") are maintained in proximity, activating the TEV protease activity and leading to cleavage and activation of caspase 3 or caspase 7 pro-proteins. The system can employ split caspase 3, with heterodimerization of the caspase 3 portions by attachment to Cas12b complexes bound to a target nucleic acid.

Split-Detection Constructs

A system of the invention further includes guides for localizing the Cas protein with linked enzyme portions on a transcript of interest that may be present in a cell or tissue. According, the system includes a first guide that binds to the first Cas protein and hybridizes to the transcript of interest and a second guide that binds to the second Cas protein and hybridizes to the nucleic acid of interest. In most embodiments, it is preferred that the first and second guide hybridize to the nucleic acid of interest at adjacent locations. The locations can be directly adjacent or separated by a few nucleotides, such as separated by 1 nt, 2 nts, 3 nts, 4 nts, 5 nts, 6 nts, 7 nts, 8 nts, 9 nts, 10 nts, 11 nts, 12 nts, or more. In certain embodiments, the first and second guides can bind to locations separated on a nucleic acid by an expected stem loop. Though separated along the linear nucleic acid, the nucleic acid may take on a secondary structure that brings the guide target sequences into close proximity.

In an embodiment of the invention, the proteolytic enzyme comprises a caspase. In an embodiment of the invention, the proteolytic enzyme comprises an initiator caspase, such as but not limited caspase 8 or caspase 9. Initiator caspases are generally inactive as a monomer and gain activity upon homodimerization. In an embodiment of the invention, the proteolytic enzyme comprises an effector caspase, such as but not limited to caspase 3 or caspase 7. Such initiator caspases are normally inactive until cleaved into fragments. Once cleaved the fragments associate to form an active enzyme. In one exemplary embodiment, the first portion of the proteolytic enzyme comprises caspase 3 p12 and the complementary portion of the proteolytic enzyme comprises caspase 3 p17.

In an embodiment of the invention, the proteolytic enzyme is chosen to target a particular amino acid sequence and a substrate is chosen or engineered accordingly. A non-limiting example of such a protease is tobacco etch virus (TEV) protease. Accordingly, a substrate cleavable by TEV protease, which in some embodiments is engineered to be cleavable, serves as the system component acted upon by the protease. In one embodiment, the NEV protease substrate comprises a procaspase and one or more TEV cleavage sites. The procaspase can be, for example, caspase 3 or caspase 7 engineered to be cleavable by the reconstituted TEV protease. Once cleaved, the procaspase fragments are free to take on an active confirmation.

In an embodiment of the invention, the TEV substrate comprises a fluorescent protein and a TEV cleavage site. In another embodiment, the TEV substrate comprises a luminescent protein and a TEV cleavage site. In certain embodiments, the TEV cleavage site provides for cleavage of the substrate such that the fluorescent or luminescent property of the substrate protein is lost upon cleavage. In certain embodiments, the fluorescent or luminescent protein can be modified, for example by appending a moiety which interferes with fluorescence or luminescence which is then cleaved when the TEV protease is reconstituted.

According to the invention, there is provided a method of providing a proteolytic activity in a cell which contains a nucleic acid of interest, which comprises contacting the nucleic acid in the cell with a composition which comprises a first Cas protein linked to an inactive first portion of a proteolytic enzyme, and a second Cas protein linked to the complementary portion of the proteolytic enzyme wherein the activity of the proteolytic enzyme is reconstituted when the first portion and the complementary portion of the protein are contacted, and a first guide that binds to the first CRISPR protein and hybridizes to a first target sequence of the nucleic acid, and a second guide that binds to the second Cas protein and hybridizes to a second target sequence of the nucleic acid. When the target nucleic acid of interest is present, the first and second portions of the proteolytic enzyme are contacted, the proteolytic activity of the enzyme is reconstituted, and a substrate of the enzyme is cleaved.

Split-fluorophore constructs are useful for imaging with reduced background via reconstitution of a split fluorophore upon binding of two Cas12b proteins to a transcript. These split proteins include iSplit (Filonov, G. S., and Verkhusha, V. V. (2013). A near-infrared BiFC reporter for in vivo imaging of protein-protein interactions. Chem. Biol. 20, 1078-1086.), Split Venus (Wu, B., Chen, J., and Singer, R. H. (2014). Background free imaging of single mRNAs in live cells using split fluorescent proteins. Sci. Rep. 4, 3615.), and Split superpositive GFP (Blakeley, B. D., Chapman, A. M., and McNaughton, B. R. (2012). Split-superpositive GFP reassembly is a fast, efficient, and robust method for detecting protein-protein interactions in vivo. Mol. Biosyst. 8, 2036-2040.).

Truncations

In certain example embodiments, the Cas12 protein may be truncated. In certain example embodiments, the truncated version may be a deactivated or dead Cas12 protein. The Cas12 protein may be modified on the N-terminus, C-terminus, or both. In one example embodiment, at least 1, at least 10, at least 20, at least 30, at least 40, at least 50, at least 60, at least 70, at least 80, at least 90, at least 100, at least 150, or at least 200 amino acids are removed from the N-terminus, C-terminus, or combination thereof. In certain example embodiments, 1-10, 1-20, 1-30, 1-40, 1-50, 1-60, 1-70, 1-80, 1-90, 1-100, 1-110, 1-120, 1-130, 1-140, 1-150, 1-160, 1-170, 1-180, 1-190, 1-200, 1-220, 1-230, 1-240, 1-250, 200-250, 100-200, 110-200, 120-200, 130-200, 140-200, 150-200, 160-200, 170-200, 180-200, 190-200, 10-100, 20-100, 30-100, 40-100, 50-100, 60-100, 70-100, 80-100, 90-100, or 150-250 amino acids are removed the N-terminus, C-terminus or a combination thereof. In certain example embodiments, the amino acid positions are those of AapCas12b or amino acids of orthologs corresponding thereto. In certain example embodiments, the truncations may be fused or otherwise attached to nucleotide deaminase and used in the base editing embodiments disclosed in further detail below.

Functional Domains

The Cas protein or variants thereof (e.g., a catalytically inactive form) may be associated with one or more functional domains (e.g., via fusion protein or suitable linkers). In an embodiment, the Cas protein, or an ortholog or homolog thereof, may be used as a generic nucleic acid binding protein with fusion to or being operably linked to one or more functional domains. In one example, the functional domain is a deaminase. In another example, the functional domain is a transposase. In another example, the functional domain is a reverse transcriptase.

In some embodiments, one or more functional domains are associated with a Cas protein via an adaptor protein, for example as used with the modified guides of Konnerman et al. (Nature 517, 583-588, 29 Jan. 2015). In some embodiments, the one or more functional domains is attached to the adaptor protein so that upon binding of the Cas effector protein to the gRNA and target, the functional domain is in a spatial orientation allowing for the functional domain to function in its attributed function.

Examples of functional domains include deaminase domain, transposase domain, reverse transcriptase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease. In some preferred embodiments, the functional domain is a transcriptional activation domain, such as, without limitation, VP64, p65, MyoD1, HSF1, RTA, SETT/9 or a histone acetyltransferase. In some embodiments, the functional domain is a transcription repression domain, preferably KRAB. In some embodiments, the transcription repression domain is SID, or concatemers of SID (e.g. SID4X). In some embodiments, the functional domain is an epigenetic modifying domain, such that an epigenetic modifying enzyme is provided. In some embodiments, the functional domain is an activation domain, which may be the P65 activation domain.

Nuclear Localization Sequences

In some embodiments, the Cas protein is fused to one or more nuclear localization sequences (NLSs), such as about or more than 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas protein comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 61,991); the NLS from nucleoplasmin (e.g. the nucleoplasmin bipartite NLS with the sequence KRPAATKKAGQAKKKK (SEQ ID NO: 61,992); the c-myc NLS having the amino acid sequence PAAKRVKLD (SEQ ID NO: 61,993) or RQRRNELKRSP (SEQ ID NO: 61,994); the hRNPA1 M9 NLS having the sequence NQSSNFGPMKGGNFGGRSSGPYGGGGQYFAKPRNQGGY (SEQ ID NO: 61,995); the sequence RMRIZFKNKGKDTAELRRRRVEVSVELRKAKKDEQILKRRNV (SEQ ID NO: 61,996) of the IBB domain from importin-alpha; the sequences VSRKRPRP (SEQ ID NO: 61,997) and PPKKARED (SEQ ID NO: 61,998) of the myoma T protein; the sequence PQPKKKPL (SEQ ID NO: 61,999) of human p53; the sequence SALIKKKKKMAP (SEQ ID NO: 62,000) of mouse c-abl IV; the sequences DRLRR (SEQ ID NO: 62,001) and PKQKKRK (SEQ ID NO: 62,002) of the influenza virus NS1; the sequence RKLKKKIKKL (SEQ ID NO: 62,003) of the Hepatitis virus delta antigen; the sequence REKKKFLKRR (SEQ ID NO: 62,004) of the mouse Mx1 protein; the sequence KRKGDEVDGVDEVAKKKSKK (SEQ ID NO: 62,005) of the human poly (ADP-ribose) polymerase; and the sequence RKCLQAGMNLEARKTKK (SEQ ID NO: 62,006) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs. In certain embodiments of the herein described Cas effector protein complexes and systems the codon optimized Cas effector proteins comprise an NLS attached to the C-terminal of the protein. In certain embodiments, other localization tags may be fused to the Cas protein, such as without limitation for localizing the Cas to particular sites in a cell, such as organelles, such mitochondria, plastids, chloroplast, vesicles, Golgi, (nuclear or cellular) membranes, ribosomes, nucleolus, ER, cytoskeleton, vacuoles, centrosome, nucleosome, granules, centrioles, etc.

In certain embodiments of the invention, at least one nuclear localization signal (NLS) is attached to the nucleic acid sequences encoding the Cas proteins. In preferred embodiments at least one or more C-terminal or N-terminal NLSs are attached (and hence nucleic acid molecule(s) coding for the Cas protein can include coding for NLS(s) so that the expressed product has the NLS(s) attached or connected). In a preferred embodiment a C-terminal NLS is attached for optimal expression and nuclear targeting in eukaryotic cells, preferably human cells. The invention also encompasses methods for delivering multiple nucleic acid components, wherein each nucleic acid component is specific for a different target locus of interest thereby modifying multiple target loci of interest. The nucleic acid component of the complex may comprise one or more protein-binding RNA aptamers. The one or more aptamers may be capable of binding a bacteriophage coat protein.

Linkers

In some preferred embodiments, the functional domain is linked to a dead-Cas to target and activate epigenomic sequences such as promoters or enhancers. One or more guides directed to such promoters or enhancers may also be provided to direct the binding of the CRISPR enzyme to such promoters or enhancers.

The term "associated with" is used here in relation to the association of the functional domain to the Cas effector protein or the adaptor protein. It is used in respect of how one molecule 'associates' with respect to another, for example between an adaptor protein and a functional domain, or between the Cas effector protein and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the Cas effector protein or adaptor protein is associated with a functional domain by binding thereto. In other embodiments, the Cas effector protein or adaptor protein is associated with a functional domain because the two are fused together, optionally via an intermediate linker.

The term "linker" as used in reference to a fusion protein refers to a molecule which joins the proteins to form a fusion protein. Generally, such molecules have no specific biological activity other than to join or to preserve some minimum distance or other spatial relationship between the proteins. However, in certain embodiments, the linker may be selected to influence some property of the linker and/or the fusion protein such as the folding, net charge, or hydrophobicity of the linker.

Suitable linkers for use in the methods of the present invention are well known to those of skill in the art and include, but are not limited to, straight or branched-chain carbon linkers, heterocyclic carbon linkers, or peptide linkers. However, as used herein the linker may also be a covalent bond (carbon-carbon bond or carbon-heteroatom bond). In particular embodiments, the linker is used to separate the Cas protein and the nucleotide deaminase by a distance sufficient to ensure that each protein retains its required functional property. Preferred peptide linker sequences adopt a flexible extended conformation and do not exhibit a propensity for developing an ordered secondary structure. In certain embodiments, the linker can be a chemical moiety which can be monomeric, dimeric, multimeric or polymeric. Preferably, the linker comprises amino acids. Typical amino acids in flexible linkers include Gly, Asn and Ser. Accordingly, in particular embodiments, the linker comprises a combination of one or more of Gly, Asn and Ser amino acids. Other near neutral amino acids, such as Thr and Ala, also may be used in the linker sequence. Exemplary linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180. For example, GlySer linkers GGS, GGGS or GSG can be used. GGS, GSG, GGGS (SEQ ID NO: 62,007) or GGGGS (SEQ ID (SEQ ID NO: 62,014) linkers can be used in repeats of 3 (such as (GGS)$_3$ (SEQ ID NO: 62,025), (GGGGS)$_3$) (SEQ ID NO: 62,010) or 5 (SEQ ID NO: 62,017), 6 (SEQ ID NO: 62,011), 7 (SEQ ID NO: 62,018), 9 (SEQ ID NO: 62,012) or even 12 (SEQ ID NO: 62,013) or more, to provide suitable lengths. In some cases, the linker may be (GGGGS)$_{3-15}$ (SEQ ID NOs: 62,010-62,013 and 62,015-62,024). For example, in some cases, the linker may be (GGGGS)$_{3-11}$ (SEQ ID NOs: 62010-62012 and 62,014-62,021), e.g., GGGGS (SEQ ID NO: 62,014), (GGGGS)$_2$ (SEQ ID NO: 62,015), (GGGGS)$_3$ (SEQ ID NO: 62,010), (GGGGS)$_4$ (SEQ ID NO: 62,016), (GGGGS)$_5$ (SEQ ID NO: 62,017), (GGGGS)$_6$ (SEQ ID NO: 62,011), (GGGGS)$_7$ (SEQ ID NO: 62,018), (GGGGS)$_8$ (SEQ ID NO: 62,019), (GGGGS)$_9$ (SEQ ID NO: 62,012), (GGGGS)$_{10}$ (SEQ ID NO: 62,020), or (GGGGS)$_{11}$ (SEQ ID NO: 62,021).

In particular embodiments, linkers such as (GGGGS)$_3$ (SEQ ID NO: 62,010) are preferably used herein. (GGGGS)$_6$ (SEQ ID NO: 62,011) (GGGGS)$_9$ (SEQ ID NO: 62,012) or (GGGGS)$_{12}$ (SEQ ID NO: 62,013) may preferably be used as alternatives. Other preferred alternatives are (GGGGS)$_1$ (SEQ ID NO: 62,014), (GGGGS)$_2$ (SEQ ID NO: 62,015), (GGGGS)$_4$ (SEQ ID NO: 62,016), (GGGGS)$_5$ (SEQ ID NO: 62,017), (GGGGS)$_7$ (SEQ ID NO: 62,018), (GGGGS)$_8$ (SEQ ID NO: 62,019), (GGGGS)$_{10}$ (SEQ ID NO: 62,020), or (GGGGS)$_{11}$ (SEQ ID NO: 62,021). In yet a further embodiment, LEPGEKPYKCPECGKSFSQSGALTRHQRTHTR (SEQ ID NO: 62,026) is used as a linker. In yet an additional embodiment, the linker is an XTEN linker. In particular embodiments, the Cas protein is linked to the deaminase protein or its catalytic domain by means of an LEPGEKPYKCPECGKSFSQSGALTRHQRTHTR (SEQ ID NO: 62,026) linker. In further particular embodiments, the Cas protein is linked C-terminally to the N-terminus of a deaminase protein or its catalytic domain by means of an LEPGEKPYKCPECGKSFSQSGALTRHQRTHTR (SEQ ID NO: 62,026) linker. In addition, N- and C-terminal NLSs can also function as linker (e.g., PKKKRKVEAS-SPKKRKVEAS (SEQ ID NO: 62,027).

Examples of linkers are shown below.

| | |
|---|---|
| GGS | GGTGGTAGT |
| GGSx3 (9) | GGTGGTAGTGGAGGGAGCGGCGGTTCA (SEQ ID NO: 62,028) |
| GGSx7 (21) | ggtggaggaggctctggtggaggcggtagcggaggcgga gggtcgGGTGGTAGTGGAGGGAGCGGCGGTTCA (SEQ ID NO: 61,029) |
| XTEN | TCGGGATCTGAGACGCCTGGGACCTCGGAATCGGCTACG CCCGAAAGT (SEQ ID NO: 62,030) |
| Z-EGFR_Short | Gtggataacaaatttaacaaagaaatgtgggcggcgtgg gaagaaattcgtaacctgccgaacctgaacggctggcag atgaccgcgtttattgcgagcctggtggatgatccgagc cagagcgcgaacctgctggcggaagcgaaaaaactgaac gatgcgcaggcgccgaaaaccggcggtggttctggt (SEQ ID NO: 62,031) |
| GSAT | Ggtggttctgccggtggctccggttctggctccagcggt ggcagctctggtgcgtccggcacgggtactgcgggtggc actggcagcggttccggtactggctctggc (SEQ ID NO: 62,032) |

Linkers may be used between the guide RNAs and the functional domain (activator or repressor), or between the Cas protein and the functional domain. The linkers may be used to engineer appropriate amounts of "mechanical flexibility".

In certain embodiments, the one or more functional domains are controllable, e.g., inducible.

Codon Optimization

Aspects of the invention relate to polynucleotide molecules that encode one or more components of one or more CRISPR-Cas systems as described in any of the embodiments herein, wherein at least one or more regions of the polynucleotide molecule may be codon optimized for expression in a eukaryotic cells. In certain embodiments, the polynucleotide molecules that encode one or more components of one or more CRISPR-Cas systems as described in any of the embodiments herein are optimized for expression in a mammalian cell or a plant cell.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in International Patent Publication No. WO 2014/093622 (PCT/US2013/074667) as an example of a codon optimized sequence (from knowledge in the art and this disclosure, codon optimizing coding nucleic acid molecule (s), especially as to effector protein is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA/RNA-targeting Cas protein is codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid.

Guide Sequences

The compositions systems herein may further comprise one or more guide molecules. A guide molecule may comprise a guide sequence capable of forming a complex with the Cas protein and directing the complex to bind to a target polynucleotide.

As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

As used herein, the term "guide sequence," "crRNA," "guide RNA," or "single guide RNA," or "gRNA" refers to a polynucleotide comprising any polynucleotide sequence having sufficient complementarity with a target nucleic acid sequence to hybridize with the target nucleic acid sequence and to direct sequence-specific binding of a polynucleotide-targeting complex comprising the guide sequence and a CRISPR effector protein to the target nucleic acid sequence. In some example embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be DNA encoding any RNA sequence, such as messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmic RNA (scRNA).

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

The guide may be derived from a different species than the Cas protein. In certain embodiments, the Cas protein is a Cas12b from a thermostable species, for example *Alicyclobacillus acidiphilus* (Aap). When the Aap Cas protein is utilized, a related guide can be used, for example from the same or another *Alicyclobacillus* species, e.g. *Alicyclobacillus acidoterrestrus* (Aac). In an aspect, the guide comprises at least 95%, 96%, 97% or more sequence similarity to the DR and/or the tracr sequence from Aac Cas12b. The guide can be designed similarly for other Cas proteins, deriving the guide from a different species than the Cas protein species.

In an aspect, the Cas protein is a Cas12b from Aap, and the guide molecule is derived from Aac, or an *Alicyclobacillus* CRISPR Cas system direct repeat and tracrRNA. In certain embodiments, the guide is designed with a spacer sequence to target a molecule of interest, for example, SARS-CoV-2. While any portion of the SARS-CoV-2 can be targeted, as described elsewhere herein, in an aspect, the spacer is designed to target the Nucleocapsid protein of the SARS-CoV-2. In certain embodiments, the Aac guide has 90%, 91%, 92%, 93%, 94%, 95%, 96%, 97%, 98%, 99% sequence similarity to any one of Type 1 to Type 5 guide sequence below.

In an aspect, the guide comprises:

```
Type 1:
                                       (SEQ ID NO: 61,957)
GTCTAGAGGACAGAATTTTTCAACGGGTGTGCCAATGGCCACTTTCCAGG

TGGCAAAGCCCGTTGAGCTTCTCAAATCTGAGAAGTGGCAC,

Type 2:
                                       (SEQ ID NO: 61,958)
GTCTAAAGGACAGAATTTTTCAACGGGTGTGCCAATGGCCACTTTCCAGG

TGGCAAAGCCCGTTGAACTTCTCAAATCTGAGAAGTGGCAC

Type 3:
                                       (SEQ ID NO: 61,959)
GTCTAGAGGACAGAATTTTTCAACGGGTGTGCCAATGGCCACTTTCCAGG

TGGCAAAGCCCGTTGAACTTCTCAAATCTGAGAAGTGGCAC

Type 4:
                                       (SEQ ID NO: 61,960)
GTCTAAAGGACAGAATTTTTCAACGGGTGTGCCAATGGCCACTTTCCAGG TGGCAAAGCCCGTTGAGCTTCTCAAATCTGAGAAGTGGCAC
or Type 5:
                                       (SEQ ID NO: 61,961)
GTCTAGAGGACAGAATTTTTCAACGGGTGTGCCAATGGCCACTTTCCAGG

TGGCAAAGCCCGTTGAACTTCTCAAATCTGCGAAGTGGCAC.
```

In certain embodiments, preservation of the underlined portions of the following guide sequence are maintained:

```
                                       (SEQ ID NO: 61962)
GTCTAGAGGACAGAATTTTCAACGGGTGTGCCAATGGCCACTTTCCAGG

TGGCAAAGCCCGTTGAGCTTCTCAAATCTGAGAAGTGGCAC.
```

However, importance of particular bases of the guide sequence are not limited to the underlined areas in SEQ ID NO:61962, and mutations of these bases can be performed when structure and activity of the guide sequence can be maintained. Such mutations can be tested and optimized in accordance with the guide optimization methods detailed elsewhere herein. In an aspect, the guide preserves the secondary structure as detailed in FIG. 45. In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62). In a particular example, the guide molecule is designed to bind to a polynucleotide sequence of SARS-CoV-2, e.g., the guide sequence is SEQ ID NO: 61989.

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl(cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target polynucleotide and one or more deoxyribonucleotides and/or nucleotide analogs in a region that binds to Cas12b. In an embodiment of the invention, deoxyribonucleotides and/or nucleotide analogs are incorporated in engineered guide structures, such as, without limitation, stem-loop regions, and the seed region. For Cas guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemicially modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, a nucleic acid-targeting guide is designed or selected to modulate intermolecular interactions among guide molecules, such as among stem-loop regions of different guide molecules. It will be appreciated that nucleotides within a guide that base-pair to form a stem-loop are also capable of base-pairing to form an intermolecular duplex with a second guide and that such an intermolecular duplex would not have a secondary structure compatible with CRISPR complex formation. Accordingly, is useful to select or design DR sequences in order to modulate stem-loop formation and CRISPR complex formation. In some embodiments, about or less than about 75%, 50%, 40%, 30%, 25%, 20%, 15%, 10%, 5%, 1%, or fewer of nucleic acid-targeting guides are in intermolecular duplexes. It will be appreciated that stem-loop variation will often be within limits imposed by DR-CRISPR effector interactions. One way to modulate stem-loop formation or change the equilibrium between stem-loop and intermolecular duplex is to vary nucleotide pairs in the stem of the stem-loop of a DR. For example, in one embodiment, a G-C pair is replaced by an A-U or U-A pair. In another embodiment, an A-U pair is substituted for a G-C or a C-G pair. In another embodiment, a naturally occurring nucleotide is replaced by a nucleotide analog. Another way to modulate stem-loop formation or change the equilibrium between stem-loop and intermolecular duplex is to modify the loop of the stem-loop of a DR. Without be bound by theory, the loop can be viewed as an intervening sequence flanked by two sequences that are complementary to each other. When that intervening sequence is not self-complementary, its effect will be to destabilize intermolecular duplex formation. The same principle applies when guides are multiplexed: while the targeting sequences may differ, it may be advantageous to modify the stem-loop region in the DRs of the different guides. Moreover, when guides are multiplexed, the relative activities of the different guides can be modulated by balancing the activity of each individual guide. In certain embodiments, the equilibrium between intermolecular stem-loops vs. intermolecular duplexes is determined. The determination may be made by physical or biochemical means and can be in the presence or absence of a CRISPR effector.

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

In general, the CRISPR-Cas, or CRISPR system may be as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.source-forge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

Multiplexing Polynucleotides

Provided herein are engineered polynucleotide sequences that can direct the activity of a CRISPR protein to multiple targets using a single crRNA. The engineered polynucleotide sequences, also referred to as a multiplexing polynucleotides, can include two or more direct repeats interspersed with two or more guide sequences. More specifically, the engineered polynucleotide sequences can include a direct repeat sequence having one or more mutations relative to the corresponding wild type direct repeat sequence. The engineered polynucleotide can be configured, for example, as: 5' DR1-G1-DR2-G2 3'. In some embodiments, the engineered polynucleotide can be configured to include three, four, five, or more additional direct repeat and guide sequences, for example: 5' DR1-G1-DR2-G2-DR3-G3 3', 5'' DR1-G1-DR2-G2-DR3-G3-DR4-G4 3', or 5' DR1-G1-DR2-G2-DR3-G3-DR4-G4-DR5-G5 3'.

Regardless of the number of direct repeat sequences, the direct repeat sequences differ from one another. Thus, DR1 can be a wild type sequence and DR2 can include one or more mutations relative to the wild type sequence in accordance with the disclosure provided herein regarding direct repeats for Cas orthologs. The guide sequences can also be the same or different. In some embodiments, the guide sequences can bind to different nucleic acid targets, for example, nucleic acids encoding different polypeptides. The multiplexing polynucleotides can be as described, for example, at [0039]-[0072] in U.S. Application 62/780,748 entitled "CRISPR Cpf1 Direct Repeat Variants" and filed Dec. 17, 2018, incorporated herein in its entirety by reference.

Multiplex design of guide molecules for the detection of coronaviruses and/or other respiratory viruses in a sample to identify the cause of a respiratory infection is envisioned, and design can be according to the methods disclosed herein. Briefly, the design of guide molecules can encompass utilization of training models described herein using a variety of input features, which may include the particular Cas protein used for targeting of the sequences of interest. See U.S. Provisional Application 62/818,702 FIG. 4A, incorporated specifically by reference. Guide molecules can be designed as detailed elsewhere herein. Regarding detection of coronavirus, guide design can be predicated on genome sequences disclosed in Tian et al, "Potent binding of 2019 novel coronavirus spike protein by a SARS coronavirus-specific human monoclonal antibody"; doi: 10.1101/2020.01.28.923011, incorporated by reference, which details human monoclonal antibody, CR3022 binding of the 2019-nCoV RBD (KD of 6.3 nM) or Sequences of the 2019-nCoV are available at GISAID accession no. EPI_ISL_402124 and EPI_ISL_402127-402130, and described in doi:10.1101/2020.01.22.914952, or EP_ISL_402119-402121 and EP_ISL 402123-402124; see also GenBank Accession No. MN908947.3. Guide design can target unique viral genomic regions of SARS-CoV-2 or conserved genomic regions across one or more viruses of the coronavirus family.

Guide Modifications

In certain embodiments, guides of the invention comprise non-naturally occurring nucleic acids and/or non-naturally occurring nucleotides and/or nucleotide analogs, and/or chemical modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified bases include, but are not limited to, 2-aminopurine, 5-bromo-uridine, pseudouridine (Ψ), N1-methylpseudouridine (mePΨ), 5-methoxyuridine(5moU), inosine, 7-methylguanosine. Examples of guide RNA chemical modifications include, without limitation, incorporation of 2'-O-methyl (M), 2'-O-methyl-3'-phosphorothioate (MS), phosphorothioate (PS), S-constrained ethyl(cEt), or 2'-O-methyl-3'-thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015; Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI: 10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target DNA and one or more deoxyribonucleotides and/or nucleotide analogs in a region that binds to Cas12b. In an embodiment of the invention, deoxyribonucleotides and/or nucleotide analogs are incorporated in engineered guide structures, such as, without limitation, 5' and/or 3' end, stem-loop regions, and the seed region. In certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl-3'-phosphorothioate (MS), S-constrained ethyl(cEt), or 2'-O-methyl-3'-thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In certain embodiments, the CRISPR system as provided herein can make use of a crRNA or analogous polynucleotide comprising a guide sequence, wherein the polynucleotide is an RNA, a DNA or a mixture of RNA and DNA, and/or wherein the polynucleotide comprises one or more nucleotide analogs. The sequence can comprise any structure, including but not limited to a structure of a native crRNA, such as a bulge, a hairpin or a stem loop structure. In certain embodiments, the polynucleotide comprising the guide sequence forms a duplex with a second polynucleotide sequence which can be an RNA or a DNA sequence.

In certain embodiments, use is made of chemically modified guide RNAs. Examples of guide RNA chemical modifications include, without limitation, incorporation of 2'-O- methyl (M), 2'-O-methyl 3'phosphorothioate (MS), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33(9):985-9, doi: 10.1038/nbt.3290, published online 29 Jun. 2015). Chemically modified guide RNAs further include, without limitation, RNAs with phosphorothioate linkages and locked nucleic acid (LNA) nucleotides comprising a methylene bridge between the 2' and 4' carbons of the ribose ring.

In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 to 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target RNA may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (T), N1-methylpseudouridine (me1Ψ), 5-methoxyuridine(5moU), inosine, 7-methyl-guanosine, 2'-O-methyl-3'-phosphorothioate (MS), S-constrained ethyl(cEt), phosphorothioate (PS), or 2'-O-methyl-3'-thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 or 10 nucleotides in the 3'-terminus are chemically modified. Such chemical modifications at the 3'-terminus of the Cas12b crRNA improve gene cutting efficiency (see Li, et al., Nature Biomedical Engineering, 2017, 1:0066). In a specific embodiment, 5 nucleotides in the 3'-terminus are replaced with 2'-fluoro analogues. In a specific embodiment, 10 nucleotides in the 3'-terminus are replaced with 2'-fluoro analogues. In a specific embodiment, 5 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU.

A guide sequence, and hence a nucleic acid-targeting guide RNA may be selected to target any target nucleic acid sequence. In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise DNA polynucleotides.

In certain embodiments, the spacer length of the guide RNA is less than 28 nucleotides. In certain embodiments, the spacer length of the guide RNA is at least 18 nucleotides and less than 28 nucleotides. In certain embodiments, the spacer length of the guide RNA is between 19 and 28 nucleotides. In certain embodiments, the spacer length of the guide RNA is between 19 and 25 nucleotides. In certain embodiments, the spacer length of the guide RNA is 20 nucleotides. In certain embodiments, the spacer length of the guide RNA is 23 nucleotides. In certain embodiments, the spacer length of the guide RNA is 25 nucleotides.

In certain embodiments, modulations of cleavage efficiency can be exploited by introduction of mismatches, e.g. 1 or more mismatches, such as 1 or 2 mismatches between spacer sequence and target sequence, including the position of the mismatch along the spacer/target. The more central (i.e. not 3' or 5') for instance a double mismatch is, the more cleavage efficiency is affected. Accordingly, by choosing mismatch position along the spacer, cleavage efficiency can be modulated. By means of example, if less than 100% cleavage of targets is desired (e.g. in a cell population), 1 or more, such as preferably 2 mismatches between spacer and target sequence may be introduced in the spacer sequences. The more central along the spacer of the mismatch position, the lower the cleavage percentage.

In certain example embodiments, the cleavage efficiency may be exploited to design single guides that can distinguish two or more targets that vary by a single nucleotide, such as a single nucleotide polymorphism (SNP), variation, or (point) mutation. The CRISPR effector may have reduced sensitivity to SNPs (or other single nucleotide variations) and continue to cleave SNP targets with a certain level of efficiency. Thus, for two targets, or a set of targets, a guide RNA may be designed with a nucleotide sequence that is complementary to one of the targets i.e. the on-target SNP. The guide RNA is further designed to have a synthetic mismatch. As used herein a "synthetic mismatch" refers to a non-naturally occurring mismatch that is introduced upstream or downstream of the naturally occurring SNP, such as at most 5 nucleotides upstream or downstream, for instance 4, 3, 2, or 1 nucleotide upstream or downstream, preferably at most 3 nucleotides upstream or downstream, more preferably at most 2 nucleotides upstream or downstream, most preferably 1 nucleotide upstream or downstream (i.e. adjacent the SNP). When the CRISPR effector binds to the on-target SNP, only a single mismatch will be formed with the synthetic mismatch and the CRISPR effector will continue to be activated and a detectable signal produced. When the guide RNA hybridizes to an off-target SNP, two mismatches will be formed, the mismatch from the SNP and the synthetic mismatch, and no detectable signal generated. Thus, the systems disclosed herein may be designed to distinguish SNPs within a population. For, example the systems may be used to distinguish pathogenic strains that differ by a single SNP or detect certain disease specific SNPs, such as but not limited to, disease associated SNPs, such as without limitation cancer associated SNPs.

In certain embodiments, the guide RNA is designed such that the SNP is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the SNP is located on position 1, 2, 3, 4, 5, 6, 7, 8, or 9 of the spacer sequence (starting at the 5' end). In certain embodiments, the guide RNA is designed such that the SNP is located on position 2, 3, 4, 5, 6, or 7 of the spacer sequence (starting at the 5' end). In certain embodiments, the guide RNA is designed such that the SNP is located on position 3, 4, 5, or 6 of the spacer sequence (starting at the 5' end). In certain embodiments, the guide RNA is designed such that the SNP is located on position 3 of the spacer sequence (starting at the 5' end).

In certain embodiments, the guide RNA is designed such that the mismatch (e.g. the synthetic mismatch, i.e. an additional mutation besides a SNP) is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the mismatch is located on position 1, 2, 3, 4, 5, 6, 7, 8, or 9 of the spacer sequence (starting at the 5' end). In certain embodiments, the guide RNA is designed such that the mismatch is located on position 4, 5, 6, or 7 of the spacer sequence (starting at the 5' end. In certain embodiments, the guide RNA is designed such that the mismatch is located at position 3, 4, 5, or 6 of the spacer, preferably position 3. In certain embodiments, the guide RNA is designed such that the mismatch is located on position 5 of the spacer sequence (starting at the 5' end).

In certain embodiments, said mismatch is 1, 2, 3, 4, or 5 nucleotides upstream or downstream, preferably 2 nucleotides, preferably downstream of said SNP or other single nucleotide variation in said guide RNA.

In certain embodiments, the guide RNA is designed such that the mismatch is located 2 nucleotides upstream of the SNP (i.e. one intervening nucleotide).

In certain embodiments, the guide RNA is designed such that the mismatch is located 2 nucleotides downstream of the SNP (i.e. one intervening nucleotide).

In certain embodiments, the guide RNA is designed such that the mismatch is located on position 5 of the spacer sequence (starting at the 5' end) and the SNP is located on position 3 of the spacer sequence (starting at the 5' end).

In certain embodiments, the guide RNA comprises a spacer which is truncated relative to a wild type spacer. In certain embodiments, the guide RNA comprises a spacer which comprises less than 28 nucleotides, preferably between and including 20 to 27 nucleotides.

In certain embodiments, the guide RNA comprises a spacer which consists of 20-25 nucleotides or 20-23 nucleotides, such as preferably 20 or 23 nucleotides.

In certain embodiments, the one or more guide RNAs are designed to detect a single nucleotide polymorphism in a target RNA or DNA, or a splice variant of an RNA transcript.

In certain embodiments, the one or more guide RNAs may be designed to bind to one or more target molecules that are diagnostic for a disease state. In some embodiments, the disease may be cancer. In some embodiments, the disease state may be an autoimmune disease. In some embodiments, the disease state may be an infection. In some embodiments, the infection may be caused by a virus, a *bacterium*, a fungus, a protozoa, or a parasite. In specific embodiments, the infection is a viral infection. In specific embodiments, the viral infection is caused by a DNA virus.

The embodiments described herein comprehend inducing one or more nucleotide modifications in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s). The mutations can include the introduction, deletion, or substitution of 1-75 nucleotides at each target sequence of said cell(s) via the guide(s) RNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 40, 45, 50, 75, 100, 200, 300, 400 or 500 nucleotides at each target sequence of said cell(s) via the guide(s) RNA(s).

Typically, in the context of an endogenous CRISPR system, formation of a CRISPR complex (comprising a guide sequence hybridized to a target sequence and complexed with one or more Cas proteins) results in cleavage in or near (e.g. within 1, 2, 3, 4, 5, 6, 7, 8, 9, 10, 20, 50, or more base pairs from) the target sequence, but may depend on for instance secondary structure, in particular in the case of RNA targets.

Methods for Designing Highly Active Guides

A method for designing highly active guide molecules, e.g., guide RNAs, for use in the detection systems may comprise the steps of designing putative guide RNAs tiled across a target molecule of interest; creating a training model based on results of incubating guide RNAs with a Cas12 protein and the target molecule; predicting highly active guide RNAs for the target molecule, wherein the predicting comprises optimizing the nucleotide at each base position in the guide RNA based on the training model; and validating the predicted highly active guide RNAs by incubating the guide RNAs with the Cas12 protein and the target molecule. The method can be as described in U.S. Provisional Application Nos. 62/818,702 and 62/890,555 incorporated by reference in their entirety. Guide RNAs generate by the design methods can be used with the systems for detecting coronavirus as described elsewhere herein.

In some embodiments, the invention provides a method for designing guide RNAs for use in the detection systems described herein. The method may comprise designing putative guide RNAs tiled across a target molecule of interest, such as a coronavirus, viruses that cause respiratory illness, including coronavirus, including 2019-nCov (Covid-19). The method may further comprise creating a training model based on results of incubating guide RNAs with a Cas12 protein and the target molecule. The method may further comprise predicting highly active guide RNAs for the target molecule. Predicting may comprise optimizing the nucleotide at each base position in the guide RNA based on the training model. The method may further comprise validating the predicted highly active guide RNAs by incubating the guide RNAs with the Cas12 protein and the target molecule.

In certain instances, the optimized guide for the target molecule is generated by pooling a set of guides, the guides produced by tiling guides across the target molecule; incubating the set of guides with a Cas polypeptide and the target molecule and measuring cleavage activity of each guide in the set; creating a training model based on the cleavage activity of the set of guides in the incubating step. Steps of predicting highly active guides for the target molecule and identifying the optimized guides by incubating the predicted highly active guides with the Cas polypeptide and the target molecule and selecting optimized guides may also be utilized in generating optimized guides. In embodiments, the training model comprises one or more input features selected from guide sequence, flanking target sequence, normalized positions of the guide in the target and guide GC content. In certain instances, the guide sequence and/or flanking sequence input comprises one hit encoding mono-nucleotide and/or dinucleotide In an embodiments, the training model comprises applying logistic regression model on the activity of the guides across the one or more input features.

In an aspect, the predicting highly active guides for the target molecule comprises selecting guides with an increase in activity of a guide relative to the median activity, or selecting guides with highest guide activity. In certain instances, the increase in activity is measured by an increase in fluorescence. Guides may be selected based on a particular cutoff, in certain instances based on activity relative to a median or above a particular cutoff-, for instance, are selected with a 1.5, 2, 2.5 or 3-fold activity relative to median, or are in the top quartile or quintile for each target tested.

The optimized guides may be generated for a Cas12 ortholog, in some instances, the optimized guide is generated for AapCas12b ortholog.

In some embodiments, the invention provides a method for designing guide RNAs for use in the detection systems described herein. The method may comprise designing putative guide RNAs tiled across a target molecule of interest. The method may further comprise creating a training model based on results of incubating guide RNAs with a Cas12 protein and the target molecule. The method may further comprise predicting highly active guide RNAs for the target molecule. Predicting may comprise optimizing the nucleotide at each base position in the guide RNA based on the training model. The method may further comprise validating the predicted highly active guide RNAs by incubating the guide RNAs with the Cas12 protein and the target molecule.

Guides may be screened for on-target and off-target effects. When using LAMP amplification, the products of LAMP can help identify those guides with more minimal off-target effects relative to on-target products.

The design of putative guide RNAs for target molecules of interest is described elsewhere herein.

The creation of training models is known in the art. Machine learning can be generalized as the ability of a learning machine to perform accurately on new, unseen examples/tasks after having experienced a learning data set. Machine learning may include the following concepts and methods. Supervised learning concepts may include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, Support vector machines; Quadratic classifiers; k-nearest neighbor; Boosting; Decision trees, such as C4.5, Random forests, ID3, CART, SLIQ, SPRINT; Bayesian networks, such as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FP-growth algorithm; Hierarchical clustering, such as Single-linkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training. Reinforcement learning concepts may include; Temporal difference learning; Q-learning; Learning Automata; and SARSA. Deep learning concepts may include; Deep belief networks; Deep Boltzmann machines; Deep Convolutional neural networks; Deep Recurrent neural networks; and Hierarchical temporal memory.

The methods as disclosed herein designing putative guide RNAs may comprise design based on one or more variables, including guide sequence, flanking target sequence, guide position and guide GC content as input features. In certain embodiments, the length of the flanking target region can be considered a freeparameter and can be further selected during cross-validation. Additionally, mono-nucleotide and/or dinucleotide based identities across a guide length and flanking sequence in the target, varying one or more of flanking sequence length, normalized positions of the guide in the target, and GC content of the guide, or a combination thereof.

In embodiments, the training model for the guide design of highly active guides is Cas protein specific. In embodiments, the Cas protein is a Cas13a, Cas13b, a Cas12a and/or a Cas12b protein. In certain embodiments, the protein is LwaCas13a or CcaCas13b. Selection for the best guides can be dependent on each enzyme. In particular embodiments, where majority of guides have activity above background on a per-target basis, selection of guides may be based on 1.5 fold, 2, 2.5, 3 or more fold activity over the median activity. In other instances, the best performing guides may be at or near background fluorescence. In this instance, the guide selection may be based on a top percentile, e.g. quartile or quintile, of performing guides.

Codon optimization is described elsewhere herein. In specific embodiments, the nucleotide at each base position in the guide RNA may be optimized based on the training model, thus allowing for prediction of highly active guide RNAs for the target molecule.

The predicted highly active guide RNAs may then be validated or verified by incubating the guide RNAs with a Cas effector protein, such as Cas12 protein and the target molecule(s) for coronavirus, for example coronavirus sequence that is immunostimulatory to a host immune system, or a target sequence unique to the 2019-nCov, as described elsewhere herein.

In certain embodiments, optimization comprises validation of best performing models for a particular Cas polypeptide across multiple guides may comprise comparing the predicted score of each guide versus actual collateral activity upon target recognition. In embodiments, kinetic data of the best and worst predicted guides are evaluated. In embodiments, lateral flow performance of the predicted guides is evaluated for a target sequence.

Detection Construct

The systems and methods described herein comprise a detection construct. As used herein, a "detection construct" refers to a molecule that can be cleaved or otherwise deactivated by an activated CRISPR system effector protein described herein. The term "detection construct" may also be referred to in the alternative as a "masking construct." Depending on the nuclease activity of the CRISPR effector protein, the masking construct may be a RNA-based masking construct or a DNA-based masking construct. The Nucleic Acid-based masking constructs comprises a nucleic acid element that is cleavable by a CRISPR effector protein. Cleavage of the nucleic acid element releases agents or produces conformational changes that allow a detectable signal to be produced. Example constructs demonstrating how the nucleic acid element may be used to prevent or mask generation of detectable signal are described below and embodiments of the invention comprise variants of the same. Prior to cleavage, or when the masking construct is in an 'active' state, the masking construct blocks the generation or detection of a positive detectable signal. In certain embodiments, detection constructs are designed for cutting motifs of particular Cas proteins. See, International Publication WO 2019/126577, incorporated herein by reference in its entirety, and specifically paragraphs [00314]-[00356], Table 25, and Examples 8-10, for teaching of design of detection constructs for Cas proteins with preferred cutting motifs. For example, when AapCas12b is used, a reporter designed with A and T bases can be utilized because of preferred cleavage specificity. In an aspect, a reporter comprising sequence TTTTTTT is utilized with AapCas12b systems.

It will be understood that in certain example embodiments a minimal background signal may be produced in the presence of an active masking construct. A positive detectable signal may be any signal that can be detected using optical, fluorescent, chemiluminescent, electrochemical or other detection methods known in the art. The term "positive detectable signal" is used to differentiate from other detectable signals that may be detectable in the presence of the masking construct. For example, in certain embodiments a first signal may be detected when the masking agent is present or when a CRISPR system has not been activated (i.e. a negative detectable signal), which then converts to a second signal (e.g. the positive detectable signal) upon detection of the target molecules and cleavage or deactivation of the masking agent, or upon activation of the CRISPR effector protein. The positive detectable signal, then, is a signal detected upon activation of the CRISPR effector protein, and may be, in a colorimetric or fluorescent assay, a decrease in fluorescence or color relative to a control or an increase in fluorescence or color relative to a control, depending on the configuration of the lateral flow substrate, and as described further herein.

In certain example embodiments, the masking construct may comprise a HCR initiator sequence and a cutting motif, or a cleavable structural element, such as a loop or hairpin, that prevents the initiator from initiating the HCR reaction. The cutting motif may be preferentially cut by one of the activated CRISPR effector proteins. Upon cleavage of the cutting motif or structure element by an activated CRISPR effector protein, the initiator is then released to trigger the HCR reaction, detection thereof indicating the presence of one or more targets in the sample. In certain example embodiments, the masking construct comprises a hairpin with a RNA loop. When an activated CRISPR effector protein cuts the RNA loop, the initiator can be released to trigger the HCR reaction.

In certain example embodiments, the masking construct may suppress generation of a gene product. The gene product may be encoded by a reporter construct that is added to the sample. The masking construct may be an interfering RNA involved in a RNA interference pathway, such as a short hairpin RNA (shRNA) or small interfering RNA (siRNA). The masking construct may also comprise microRNA (miRNA). While present, the masking construct suppresses expression of the gene product. The gene product may be a fluorescent protein or other RNA transcript or proteins that would otherwise be detectable by a labeled probe, aptamer, or antibody but for the presence of the masking construct. Upon activation of the effector protein the masking construct is cleaved or otherwise silenced allowing for expression and detection of the gene product as the positive detectable signal. In preferred embodiments, the masking constructs comprise two or more detectable signals, for example, fluorescent signals, that can be read on different channels of a fluorimeter.

In specific embodiments, the masking construct comprises a silencing RNA that suppresses generation of a gene product encoded by a reporting construct, wherein the gene product generates the detectable positive signal when expressed.

In certain example embodiments, the masking construct may sequester one or more reagents needed to generate a detectable positive signal such that release of the one or more reagents from the masking construct results in generation of the detectable positive signal. The one or more reagents may combine to produce a colorimetric signal, a chemiluminescent signal, a fluorescent signal, or any other detectable signal and may comprise any reagents known to be suitable for such purposes. In certain example embodiments, the one or more reagents are sequestered by RNA aptamers that bind the one or more reagents. The one or more reagents are released when the effector protein is activated upon detection of a target molecule and the RNA or DNA aptamers are degraded.

In certain example embodiments, the masking construct may be immobilized on a solid substrate in an individual discrete volume (defined further below) and sequesters a single reagent. For example, the reagent may be a bead comprising a dye. When sequestered by the immobilized reagent, the individual beads are too diffuse to generate a detectable signal, but upon release from the masking construct are able to generate a detectable signal, for example by aggregation or simple increase in solution concentration. In certain example embodiments, the immobilized masking agent is a RNA- or DNA-based aptamer that can be cleaved by the activated effector protein upon detection of a target molecule.

In certain other example embodiments, the masking construct binds to an immobilized reagent in solution thereby blocking the ability of the reagent to bind to a separate labeled binding partner that is free in solution. Thus, upon application of a washing step to a sample, the labeled binding partner can be washed out of the sample in the absence of a target molecule. However, if the effector protein is activated, the masking construct is cleaved to a degree sufficient to interfere with the ability of the masking construct to bind the reagent thereby allowing the labeled binding partner to bind to the immobilized reagent. Thus, the labeled binding partner remains after the wash step indicating the presence of the target molecule in the sample. In certain aspects, the masking construct that binds the immobilized reagent is a DNA or RNA aptamer. The immobilized reagent may be a protein and the labeled binding partner may be a labeled antibody. Alternatively, the immobilized reagent may be streptavidin and the labeled binding partner may be labeled biotin. The label on the binding partner used in the above embodiments may be any detectable label known in the art. In addition, other known binding partners may be used in accordance with the overall design described herein.

In certain example embodiments, the masking construct may comprise a ribozyme. Ribozymes are RNA molecules having catalytic properties. Ribozymes, both naturally and engineered, comprise or consist of RNA that may be targeted by the effector proteins disclosed herein. The ribozyme may be selected or engineered to catalyze a reaction that either generates a negative detectable signal or prevents generation of a positive control signal. Upon deactivation of the ribozyme by the activated effector protein the reaction generating a negative control signal, or preventing generation of a positive detectable signal, is removed thereby allowing a positive detectable signal to be generated. In one example embodiment, the ribozyme may catalyze a colorimetric reaction causing a solution to appear as a first color. When the ribozyme is deactivated the solution then turns to a second color, the second color being the detectable positive signal. An example of how ribozymes can be used to catalyze a colorimetric reaction are described in Zhao et al. "Signal amplification of glucosamine-6-phosphate based on ribozyme glmS," Biosens Bioelectron. 2014; 16:337-42, and provide an example of how such a system could be modified to work in the context of the embodiments disclosed herein. Alternatively, ribozymes, when present can generate cleavage products of, for example, RNA transcripts. Thus, detection of a positive detectable signal may comprise detection of non-cleaved RNA transcripts that are only generated in the absence of the ribozyme.

In some embodiments, the masking construct may be a ribozyme that generates a negative detectable signal, and wherein a positive detectable signal is generated when the ribozyme is deactivated.

In certain example embodiments, the one or more reagents is a protein, such as an enzyme, capable of facilitating generation of a detectable signal, such as a colorimetric, chemiluminescent, or fluorescent signal, that is inhibited or sequestered such that the protein cannot generate the detectable signal by the binding of one or more DNA or RNA aptamers to the protein. Upon activation of the effector proteins disclosed herein, the DNA or RNA aptamers are cleaved or degraded to an extent that they no longer inhibit the protein's ability to generate the detectable signal. In certain example embodiments, the aptamer is a thrombin inhibitor aptamer. In certain example embodiments the thrombin inhibitor aptamer has a sequence of GGGAACAAAGCUGAAGUACUUACCC (SEQ ID NO:61973). When this aptamer is cleaved, thrombin will become active and will cleave a peptide colorimetric or fluorescent substrate. In certain example embodiments, the colorimetric substrate is para-nitroanilide (pNA) covalently linked to the peptide substrate for thrombin. Upon cleavage by thrombin, pNA is released and becomes yellow in color and easily visible to the eye. In certain example embodiments, the fluorescent substrate is 7-amino-4-methylcoumarin a blue fluorophore that can be detected using a fluorescence detector. Inhibitory aptamers may also be used for horseradish peroxidase (HRP), beta-galactosidase, or calf alkaline phosphatase (CAP) and within the general principals laid out above.

In certain embodiments, RNAse or DNAse activity is detected colorimetrically via cleavage of enzyme-inhibiting aptamers. One potential mode of converting DNAse or RNAse activity into a colorimetric signal is to couple the cleavage of a DNA or RNA aptamer with the reactivation of an enzyme that is capable of producing a colorimetric output. In the absence of RNA or DNA cleavage, the intact aptamer will bind to the enzyme target and inhibit its activity. The advantage of this readout system is that the enzyme provides an additional amplification step: once liberated from an aptamer via collateral activity (e.g. Cas12b collateral activity), the colorimetric enzyme will continue to produce colorimetric product, leading to a multiplication of signal.

In certain embodiments, an existing aptamer that inhibits an enzyme with a colorimetric readout is used. Several aptamer/enzyme pairs with colorimetric readouts exist, such as thrombin, protein C, neutrophil elastase, and subtilisin. These proteases have colorimetric substrates based upon pNA and are commercially available. In certain embodiments, a novel aptamer targeting a common colorimetric enzyme is used. Common and robust enzymes, such as beta-galactosidase, horseradish peroxidase, or calf intestinal alkaline phosphatase, could be targeted by engineered aptamers designed by selection strategies such as SELEX. Such strategies allow for quick selection of aptamers with nanomolar binding efficiencies and could be used for the development of additional enzyme/aptamer pairs for colorimetric readout.

In certain embodiments, the masking construct may be a DNA or RNA aptamer and/or may comprise a DNA or RNA-tethered inhibitor.

In certain embodiments, the masking construct may comprise a DNA or RNA oligonucleotide to which a detectable ligand and a masking component are attached.

In certain embodiments, RNAse or DNase activity is detected colorimetrically via cleavage of RNA-tethered inhibitors. Many common colorimetric enzymes have competitive, reversible inhibitors: for example, beta-galactosidase can be inhibited by galactose. Many of these inhibitors are weak, but their effect can be increased by increases in local concentration. By linking local concentration of inhibitors to DNase RNAse activity, colorimetric enzyme and inhibitor pairs can be engineered into DNase and RNAse sensors. The colorimetric DNase or RNAse sensor based upon small-molecule inhibitors involves three components:

the colorimetric enzyme, the inhibitor, and a bridging RNA or DNA that is covalently linked to both the inhibitor and enzyme, tethering the inhibitor to the enzyme. In the uncleaved configuration, the enzyme is inhibited by the increased local concentration of the small molecule; when the DNA or RNA is cleaved (e.g. by Cas13 or Cas12 collateral cleavage), the inhibitor will be released and the colorimetric enzyme will be activated.

In certain embodiments, the aptamer or DNA- or RNA-tethered inhibitor may sequester an enzyme, wherein the enzyme generates a detectable signal upon release from the aptamer or DNA or RNA tethered inhibitor by acting upon a substrate. In some embodiments, the aptamer may be an inhibitor aptamer that inhibits an enzyme and prevents the enzyme from catalyzing generation of a detectable signal from a substance. In some embodiments, the DNA- or RNA-tethered inhibitor may inhibit an enzyme and may prevent the enzyme from catalyzing generation of a detectable signal from a substrate.

In certain embodiments, RNAse activity is detected colorimetrically via formation and/or activation of G-quadruplexes. G quadruplexes in DNA can complex with heme (iron (III)-protoporphyrin IX) to form a DNAzyme with peroxidase activity. When supplied with a peroxidase substrate (e.g. ABTS: (2,2'-Azinobis [3-ethylbenzothiazoline-6-sulfonic acid]-diammonium salt)), the G-quadruplex-heme complex in the presence of hydrogen peroxide causes oxidation of the substrate, which then forms a green color in solution. An example G-quadruplex forming DNA sequence is: GGGTAGGGCGGGTTGGGA (SEQ ID NO:311). By hybridizing an additional DNA or RNA sequence, referred to herein as a "staple," to this DNA aptamer, formation of the G-quadruplex structure will be limited. Upon collateral activation, the staple will be cleaved allowing the G quadraplex to form and heme to bind. This strategy is particularly appealing because color formation is enzymatic, meaning there is additional amplification beyond collateral activation.

In certain embodiments, the masking construct may comprise an RNA oligonucleotide designed to bind a G-quadruplex forming sequence, wherein a G-quadruplex structure is formed by the G-quadruplex forming sequence upon cleavage of the masking construct, and wherein the G-quadruplex structure generates a detectable positive signal.

In certain example embodiments, the masking construct may be immobilized on a solid substrate in an individual discrete volume (defined further below) and sequesters a single reagent. For example, the reagent may be a bead comprising a dye. When sequestered by the immobilized reagent, the individual beads are too diffuse to generate a detectable signal, but upon release from the masking construct are able to generate a detectable signal, for example by aggregation or simple increase in solution concentration. In certain example embodiments, the immobilized masking agent is a DNA- or RNA-based aptamer that can be cleaved by the activated effector protein upon detection of a target molecule.

In one example embodiment, the masking construct comprises a detection agent that changes color depending on whether the detection agent is aggregated or dispersed in solution. For example, certain nanoparticles, such as colloidal gold, undergo a visible purple to red color shift as they move from aggregates to dispersed particles. Accordingly, in certain example embodiments, such detection agents may be held in aggregate by one or more bridge molecules. At least a portion of the bridge molecule comprises RNA or DNA. Upon activation of the effector proteins disclosed herein, the RNA or DNA portion of the bridge molecule is cleaved allowing the detection agent to disperse and resulting in the corresponding change in color. In certain example embodiments, the detection agent is a colloidal metal. The colloidal metal material may include water-insoluble metal particles or metallic compounds dispersed in a liquid, a hydrosol, or a metal sol. The colloidal metal may be selected from the metals in groups IA, IB, IIB and IIIB of the periodic table, as well as the transition metals, especially those of group VIII. Preferred metals include gold, silver, aluminum, ruthenium, zinc, iron, nickel and calcium. Other suitable metals also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form, derived from an appropriate metal compound, for example the $Al^{3+}$, $Ru^{3+}$, $Zn^{2+}$, $Fe^{3+}$, $Ni^{2+}$ and $Ca^{2+}$ ions.

When the RNA or DNA bridge is cut by the activated CRISPR effector, the aforementioned color shift is observed. In certain example embodiments the particles are colloidal metals. In certain other example embodiments, the colloidal metal is a colloidal gold. In certain example embodiments, the colloidal nanoparticles are 15 nm gold nanoparticles (AuNPs). Due to the unique surface properties of colloidal gold nanoparticles, maximal absorbance is observed at 520 nm when fully dispersed in solution and appear red in color to the naked eye. Upon aggregation of AuNPs, they exhibit a red-shift in maximal absorbance and appear darker in color, eventually precipitating from solution as a dark purple aggregate. In certain example embodiments the nanoparticles are modified to include DNA linkers extending from the surface of the nanoparticle. Individual particles are linked together by single-stranded RNA (ssRNA) or single-stranded DNA bridges that hybridize on each end to at least a portion of the DNA linkers. Thus, the nanoparticles will form a web of linked particles and aggregate, appearing as a dark precipitate. Upon activation of the CRISPR effectors disclosed herein, the ssRNA or ssDNA bridge will be cleaved, releasing the AU NPS from the linked mesh and producing a visible red color. Example DNA linkers and bridge sequences are listed below. Thiol linkers on the end of the DNA linkers may be used for surface conjugation to the AuNPS. Other forms of conjugation may be used. In certain example embodiments, two populations of AuNPs may be generated, one for each DNA linker. This will help facilitate proper binding of the ssRNA bridge with proper orientation. In certain example embodiments, a first DNA linker is conjugated by the 3' end while a second DNA linker is conjugated by the 5' end.

In certain other example embodiments, the masking construct may comprise an RNA or DNA oligonucleotide to which are attached a detectable label and a masking agent of that detectable label. An example of such a detectable label/masking agent pair is a fluorophore and a quencher of the fluorophore. Quenching of the fluorophore can occur as a result of the formation of a non-fluorescent complex between the fluorophore and another fluorophore or non-fluorescent molecule. This mechanism is known as ground-state complex formation, static quenching, or contact quenching. Accordingly, the RNA or DNA oligonucleotide may be designed so that the fluorophore and quencher are in sufficient proximity for contact quenching to occur. Fluorophores and their cognate quenchers are known in the art and can be selected for this purpose by one having ordinary skill in the art. The particular fluorophore/quencher pair is not critical in the context of this invention, only that selection of the fluorophore/quencher pairs ensures masking of the fluorophore. Upon activation of the effector proteins disclosed herein, the RNA or DNA oligonucleotide is cleaved thereby severing the proximity between the fluorophore and quencher needed to maintain the contact quenching effect. Accordingly, detection of the fluorophore may be used to determine the presence of a target molecule in a sample.

In certain other example embodiments, the masking construct may comprise one or more RNA oligonucleotides to which are attached one or more metal nanoparticles, such as gold nanoparticles. In some embodiments, the masking construct comprises a plurality of metal nanoparticles crosslinked by a plurality of RNA or DNA oligonucleotides forming a closed loop. In one embodiment, the masking construct comprises three gold nanoparticles crosslinked by three RNA or DNA oligonucleotides forming a closed loop. In some embodiments, the cleavage of the RNA or DNA oligonucleotides by the CRISPR effector protein leads to a detectable signal produced by the metal nanoparticles.

In certain other example embodiments, the masking construct may comprise one or more RNA or DNA oligonucleotides to which are attached one or more quantum dots. In some embodiments, the cleavage of the RNA or DNA oligonucleotides by the CRISPR effector protein leads to a detectable signal produced by the quantum dots.

In one example embodiment, the masking construct may comprise a quantum dot. The quantum dot may have multiple linker molecules attached to the surface. At least a portion of the linker molecule comprises RNA or DNA. The linker molecule is attached to the quantum dot at one end and to one or more quenchers along the length or at terminal ends of the linker such that the quenchers are maintained in sufficient proximity for quenching of the quantum dot to occur. The linker may be branched. As above, the quantum dot/quencher pair is not critical, only that selection of the quantum dot/quencher pair ensures masking of the fluorophore. Quantum dots and their cognate quenchers are known in the art and can be selected for this purpose by one having ordinary skill in the art. Upon activation of the effector proteins disclosed herein, the RNA or DNA portion of the linker molecule is cleaved thereby eliminating the proximity between the quantum dot and one or more quenchers needed to maintain the quenching effect. In certain example embodiments the quantum dot is streptavidin conjugated. RNA or DNA are attached via biotin linkers and recruit quenching molecules with the sequences/5Biosg/UCUCGUACGUUC/3IAbRQSp/(SEQ ID NO:61975) or /5Biosg/UCUCGUACGUUCUCUCGUACGUUC/3IAbRQSp/ (SEQ ID NO:61976) where /5Biosg/is a biotin tag and/31AbRQSp/is an Iowa black quencher (Iowa Black FQ). Upon cleavage, by the activated effectors disclosed herein the quantum dot will fluoresce visibly.

In specific embodiments, the detectable ligand may be a fluorophore and the masking component may be a quencher molecule.

In a similar fashion, fluorescence energy transfer (FRET) may be used to generate a detectable positive signal. FRET is a non-radiative process by which a photon from an energetically excited fluorophore (i.e. "donor fluorophore") raises the energy state of an electron in another molecule (i.e. "the acceptor") to higher vibrational levels of the excited singlet state. The donor fluorophore returns to the ground state without emitting a fluoresce characteristic of that fluorophore. The acceptor can be another fluorophore or non-fluorescent molecule. If the acceptor is a fluorophore, the transferred energy is emitted as fluorescence characteristic of that fluorophore. If the acceptor is a non-fluorescent molecule the absorbed energy is loss as heat. Thus, in the context of the embodiments disclosed herein, the fluorophore/quencher pair is replaced with a donor fluorophore/acceptor pair attached to the oligonucleotide molecule. When intact, the masking construct generates a first signal (negative detectable signal) as detected by the fluorescence or heat emitted from the acceptor. Upon activation of the effector proteins disclosed herein the RNA oligonucleotide is cleaved and FRET is disrupted such that fluorescence of the donor fluorophore is now detected (positive detectable signal).

In certain example embodiments, the masking construct comprises the use of intercalating dyes which change their absorbance in response to cleavage of long RNAs or DNAs to short nucleotides. Several such dyes exist. For example, pyronine-Y will complex with RNA and form a complex that has an absorbance at 572 nm. Cleavage of the RNA results in loss of absorbance and a color change. Methylene blue may be used in a similar fashion, with changes in absorbance at 688 nm upon RNA cleavage. Accordingly, in certain example embodiments the masking construct comprises a RNA and intercalating dye complex that changes absorbance upon the cleavage of RNA by the effector proteins disclosed herein.

In certain example embodiments, the masking construct may comprise an initiator for an HCR reaction. See e.g. Dirks and Pierce. PNAS 101, 15275-15728 (2004). HCR reactions utilize the potential energy in two hairpin species. When a single-stranded initiator having a portion of complementary to a corresponding region on one of the hairpins is released into the previously stable mixture, it opens a hairpin of one species. This process, in turn, exposes a single-stranded region that opens a hairpin of the other species. This process, in turn, exposes a single stranded region identical to the original initiator. The resulting chain reaction may lead to the formation of a nicked double helix that grows until the hairpin supply is exhausted. Detection of the resulting products may be done on a gel or colorimetrically. Example colorimetric detection methods include, for example, those disclosed in Lu et al. "Ultra-sensitive colorimetric assay system based on the hybridization chain reaction-triggered enzyme cascade amplification ACS Appl Mater Interfaces, 2017, 9(1):167-175, Wang et al. "An enzyme-free colorimetric assay using hybridization chain reaction amplification and split aptamers" Analyst 2015, 150, 7657-7662, and Song et al. "Non-covalent fluorescent labeling of hairpin DNA probe coupled with hybridization chain reaction for sensitive DNA detection." Applied Spectroscopy, 70(4): 686-694 (2016).

In certain example embodiments, the masking construct suppresses generation of a detectable positive signal until cleaved, or modified by an activated CRISPR effector protein. In some embodiments, the masking construct may suppress generation of a detectable positive signal by masking the detectable positive signal, or generating a detectable negative signal instead.

Base Editing

The present disclosure also provides for base editing systems. In general, such a system may comprise a deaminase (e.g., an adenosine deaminase or cytidine deaminase) fused with a nucleic acid-guided nuclease, e.g., Cas protein. The Cas protein may be a dead Cas protein or a Cas nickase protein. In certain examples, the system comprises a mutated form of an adenosine deaminase fused with a dead CRISPR-Cas or CRISPR-Cas nickase. The mutated form of the adenosine deaminase may have both adenosine deaminase and cytidine deaminase activities.

The based editing systems may be capable of modifying a single nucleotide in a target polynucleotide. The modification may repair or correct a G→A or C→T point mutation, a T→C or A→G point mutation, or a pathogenic SNP. Accordingly, the compositions and systems may remedy a disease caused by a G→A or C→T point mutation, a T→C or A→G point mutation, or a pathogenic SNP.

In one aspect, the present disclosure provides an engineered adenosine deaminase. The engineered adenosine deaminase may comprise one or more mutations herein. In some embodiments, the engineered adenosine deaminase has cytidine deaminase activity. In certain examples, the engineered adenosine deaminase has both cytidine deaminase activity and adenosine deaminase. In some cases, the modifications by base editors herein may be used for targeting post-translational signaling or catalysis. In some embodiments, compositions herein comprise nucleotide sequence comprising encoding sequences for one or more components of a base editing system. A base-editing system may comprise a deaminase (e.g., an adenosine deaminase or cytidine deaminase) fused with a Cas protein or a variant thereof.

In some cases, the adenosine deaminase is double-stranded RNA-specific adenosine deaminase (ADAR). Examples of ADARs include those described Yiannis A Savva et al., The ADAR protein family, Genome Biol. 2012; 13(12): 252, which is incorporated by reference in its entirety. In some examples, the ADAR may be hADAR1. In certain examples, the ADAR may be hADAR2. The sequence of hADAR2 may be that described under Accession No. AF525422.1.

In some cases, the deaminase may be a deaminase domain, e.g., a deaminase domain of ADAR ("ADAR-D"). In one example, the deaminase may be the deaminase domain of hADAR2 ("hADAR2-D), e.g., as described in Phelps K J et al., Recognition of duplex RNA by the deaminase domain of the RNA editing enzyme ADAR2. Nucleic Acids Res. 2015 January; 43(2):1123-32, which is incorporated by reference herein in its entirety. In a particular example, the hADAR2-D has a sequence comprising amino acid 299-701 of hADAR2-D, e.g., amino acid 299-701 of the sequence under Accession No. AF525422.1.

In certain examples, the system comprises a mutated form of an adenosine deaminase fused with a dead CRISPR-Cas or CRISPR-Cas nickase. The mutated form of the adenosine deaminase may have both adenosine deaminase and cytidine deaminase activities. In some embodiments, the adenosine deaminase may comprise one or more of the mutations: E488Q based on amino acid sequence positions of hADAR2-D, and mutations in a homologous ADAR protein corresponding to the above. In some embodiments, the adenosine deaminase may comprise one or more of the mutations: E488Q, V351G, based on amino acid sequence positions of hADAR2-D, and mutations in a homologous ADAR protein corresponding to the above. In some embodiments, the adenosine deaminase may comprise one or more of the mutations: E488Q, V351G, S486A, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, K350I, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, K350I, M383L, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, K350I, M383L, D619G, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, K350I, M383L, D619G, S582T, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, K350I, M383L, D619G, S582T, V440I based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, K350I, M383L, D619G, S582T, V440I, S495N based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, K350I, M383L, D619G, S582T, V440I, S495N, K418E based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L332I, I398V, K350I, M383L, D619G, S582T, V440I, S495N, K418E, S661T based on amino acid sequence positions of hADAR2-D, and mutations in a homologous ADAR protein corresponding to the above. In some examples, provided herein includes a mutated adenosine deaminase e.g., an adenosine deaminase comprising one or more mutations of E488Q, V351G, S486A, T375S, S370C, P462A, N597I, L332I, I398V, K350I, M383L, D619G, S582T, V440I, S495N, K418E, S661T, fused with a dead CRISPR-Cas protein or CRISPR-Cas nickase. In some examples, provided herein includes a mutated adenosine deaminase e.g., an adenosine deaminase comprising E488Q, V351G, S486A, T375S, S370C, P462A, N597I, L332I, I398V, K350I, M383L, D619G, S582T, V440I, S495N, K418E, and S661T, fused with a dead CRISPR-Cas protein or a CRISPR-Cas nickase. In some examples, provided herein includes a mutated adenosine deaminase e.g., an adenosine deaminase comprising E488Q, V351G, S486A, T375S, S370C, P462A, N597I, L332I, I398V, K350I, M383L, D619G, S582T, V440I, S495N, K418E, S661T, and S375N fused with a dead CRISPR-Cas protein or a CRISPR-Cas nickase.

In some embodiments, the adenosine deaminase may be a tRNA-specific adenosine deaminase or a variant thereof. In some embodiments, the adenosine deaminase may comprise one or more of the mutations: W23L, W23R, R26G, H36L, N37S, P48S, P48T, P48A, I49V, R51L, N72D, L84F, S97C, A106V, D108N, H123Y, G125A, A142N, S146C, D147Y, R152H, R152P, E155V, I156F, K157N, K161T, based on amino acid sequence positions of *E. coli* TadA, and mutations in a homologous deaminase protein corresponding to the above. In some embodiments, the adenosine deaminase may comprise one or more of the mutations: D108N based on amino acid sequence positions of *E. coli* TadA, and mutations in a homologous deaminase protein corresponding to the above. In some embodiments, the adenosine deaminase may comprise one or more of the mutations: A106V, D108N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, based on amino acid sequence positions of *E. coli* TadA, and mutations in a homologous deaminase protein corresponding to the above. In some embodiments, the adenosine deaminase may comprise one or more of the mutations: A106V, D108N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, A142N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, A142N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, W23R, P48A, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, W23R, P48A, A142N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, W23R, P48A, R152P, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, W23R, P48A, R152P, A142N, based on amino acid sequence positions of *E. coli* TadA, and mutations in a homologous deaminase protein corresponding to the above.

In some examples, the base editing systems may comprise an intein-mediated trans-splicing system that enables in vivo delivery of a base editor, e.g., a split-intein cytidine base editors (CBE) or adenine base editor (ABE) engineered to trans-splice. Examples of the such base editing systems include those described in Colin K. W. Lim et al., Treatment of a Mouse Model of ALS by In Vivo Base Editing, Mol Ther. 2020 Jan. 14. pii: S1525-0016(20)30011-3. doi: 10.1016/j.ymthe.2020.01.005; and Jonathan M. Levy et al., Cytosine and adenine base editing of the brain, liver, retina, heart and skeletal muscle of mice via adeno-associated viruses, Nature Biomedical Engineering volume 4, pages 97-110(2020), which are incorporated by reference herein in their entireties.

Examples of base editing systems include those described in International Patent Publication Nos. WO 2019/071048 (e.g. paragraphs [0933]-[0938]), WO 2019/084063 (e.g., paragraphs [0173]-[0186], [0323]-[0475], [0893]-[1094]), WO 2019/126716 (e.g., paragraphs [0290]-[0425], [1077]-[1084]), WO 2019/126709 (e.g., paragraphs [0294]-[0453]), WO 2019/126762 (e.g., paragraphs [0309]-[0438]), WO 2019/126774 (e.g., paragraphs [0511]-[0670]), Cox DBT, et al., RNA editing with CRISPR-Cas13, Science. 2017 Nov. 24; 358(6366):1019-1027; Abudayyeh 00, et al., A cytosine deaminase for programmable single-base RNA editing, Science 26 Jul. 2019: Vol. 365, Issue 6451, pp. 382-386; Gaudelli N M et al., Programmable base editing of A•T to G•C in genomic DNA without DNA cleavage, Nature volume 551, pages 464-471 (23 Nov. 2017); Komor A C, et al., Programmable editing of a target base in genomic DNA without double-stranded DNA cleavage. Nature. 2016 May 19; 533(7603):420-4; Jordan L. Doman et al., Evaluation and minimization of Cas9-independent off-target DNA editing by cytosine base editors, Nat Biotechnol (2020). doi.org/10.1038/s41587-020-0414-6; and Richter M F et al., Phage-assisted evolution of an adenine base editor with improved Cas domain compatibility and activity, Nat Biotechnol (2020). doi.org/10.1038/s41587-020-0453-z, which are incorporated by reference herein in their entireties.

Prime Editing

The compositions and systems may be used for prime editing. In some embodiments, the compositions and systems may comprise a Cas protein, and reverse transcriptase associated with the Cas, and a guide molecule.

In some embodiments, the Cas proteins herein may be used for prime editing. In some cases, the Cas protein may be a nickase, e.g., a DNA nickase. The Cas protein may be a dCas. In some cases, the Cas has one or more mutations. In some cases, the guide molecule may be a prime editor guide molecule. In some example, the compositions and systems comprise a catalytically inactive Cas12 associated with a reverse transcriptase, and a guide molecule that is a prime editor guide molecule.

The Cas protein may be associated with a reverse transcriptase. The reverse transcriptase may be fused to the C-terminus of a Cas protein. Alternatively or additionally, the reverse transcriptase may be fused to the N-terminus of a Cas protein. The fusion may be via a linker and/or an adaptor protein. In some examples, the reverse transcriptase may be an M-MLV reverse transcriptase or variant thereof. The M-MLV reverse transcriptase variant may comprise one or more mutations. For the examples, the M-MLV reverse transcriptase may comprise D200N, L603W, and T330P. In another example, the M-MLV reverse transcriptase may comprise D200N, L603W, T330P, T306K, and W313F. In a particular example, the fusion of Cas and reverse transcriptase is Cas (with a mutation corresponding to H840A of SpCas9) fused with M-MLV reverse transcriptase (D200N+L603W+T330P+T306K+W313F).

The guide molecule for prime editing may be a prime editor guide molecule (also known as prime editing guide molecule) (pegRNA). In some examples, a pegRNA is a sgRNA comprising a primer binding sequence (PBS) and a template containing a desired RNA sequence (e.g., added at the 3' end).

In some embodiments, the Cas protein herein may target DNA using a guide RNA containing a binding sequence that hybridizes to the target sequence on the DNA. The guide RNA may further comprise an editing sequence that contains new genetic information that replaces target DNA nucleotides. The small sizes of the Cas protein herein may allow easier packaging and delivery of the prime editing system, e.g., with a viral vector, e.g., AAV or lentiviral vector.

A single-strand break (a nick) may be generated on the target DNA by the Cas protein at the target site to expose a 3'-hydroxyl group, thus priming the reverse transcription of an edit-encoding extension on the guide directly into the target site. These steps may result in a branched intermediate with two redundant single-stranded DNA flaps: a 5' flap that contains the unedited DNA sequence, and a 3' flap that contains the edited sequence copied from the guide RNA. The 5' flaps may be removed by a structure-specific endonuclease, e.g., FEN122, which excises 5' flaps generated during lagging-strand DNA synthesis and long-patch base excision repair. The non-edited DNA strand may be nicked to induce bias DNA repair to preferentially replace the non-edited strand. Examples of prime editing systems and methods include those described in Anzalone A V et al., Search-and-replace genome editing without double-strand breaks or donor DNA, Nature. 2019 Oct. 21. doi: 10.1038/s41586-019-1711-4, which is incorporated by reference herein in its entirety.

The Cas protein may be used to prime-edit a single nucleotide on a target DNA. Alternatively or additionally, the Cas protein may be used to prime-edit at least 2, at least 3, at least 4, at least 5, at least 6, at least 7, at least 8, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 200, at least 300, at least 400, at least 500, at least 600, at least 700, at least 800, at least 900, or at least 10000 nucleotides on a target DNA.

Recombination Templates

The compositions and systems herein may further comprise one or more recombination templates. A recombination template, as that term is used herein, refers to a nucleic acid sequence which can be used in conjunction with CRISPR-Cas systems disclosed herein to alter the structure of a target position. In an embodiment, the target nucleic acid is modified to have some or all of the sequence of the recombination template nucleic acid, typically at or near cleavage site(s). In an embodiment, the recombination template nucleic acid is single stranded. In an alternate embodiment, the recombination template nucleic acid is double stranded. In an embodiment, the recombination template nucleic acid is DNA, e.g., double stranded DNA. In an alternate embodiment, the recombination template nucleic acid is single stranded DNA.

In some embodiments, a recombination template is provided to serve as a template in homologous recombination, such as within or near a target sequence nicked or cleaved by a nucleic acid-targeting effector protein as a part of a nucleic acid-targeting complex.

In some embodiments, the recombination template may be used to introduce one or more mutations to the target polynucleotide, correct a premature stop codon in the target polynucleotide, disrupt a splicing site, restore a splicing site, or a combination thereof. The one or more mutations introduced by the donor polynucleotide comprises substitutions, deletions, insertions, or a combination thereof. The one or more mutations causes a shift in an open reading frame on the target polynucleotide.

A recombination template may be a component of another vector as described herein, contained in a separate vector, or provided as a separate polynucleotide. A recombination template polynucleotide may be of any suitable length, such as about or more than about 10, 15, 20, 25, 50, 75, 100, 150, 200, 500, 1000, or more nucleotides in length. In some embodiments, the recombination template polynucleotide is complementary to a portion of a polynucleotide comprising the target sequence. When optimally aligned, a recombination template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a recombination template sequence and a polynucleotide comprising a target sequence are optimally aligned, the nearest nucleotide of the recombination template polynucleotide is within about 1, 5, 10, 15, 20, 25, 50, 75, 100, 200, 300, 400, 500, 1000, 5000, 10000, or more nucleotides from the target sequence.

In an embodiment, the recombination template nucleic acid alters the structure of the target position by participating in homologous recombination. In an embodiment, the recombination template nucleic acid alters the sequence of the target position. In an embodiment, the recombination template nucleic acid results in the incorporation of a modified, or non-naturally occurring base into the target nucleic acid.

The recombination template sequence may undergo a breakage mediated or catalyzed recombination with the target sequence. In an embodiment, the recombination template nucleic acid may include sequence that corresponds to a site on the target sequence that is cleaved by an Cas mediated cleavage event. In an embodiment, the recombination template nucleic acid may include sequence that corresponds to both, a first site on the target sequence that is cleaved in a first Cas mediated event and a second site on the target sequence that is cleaved in a second Cas mediated event.

In certain embodiments, the recombination template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the recombination template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A recombination template nucleic acid having homology with a target position in a target gene may be used to alter the structure of a target sequence. The recombination template sequence may be used to alter an unwanted structure, e.g., an unwanted or mutant nucleotide. The recombination template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The recombination template nucleic acid may include sequence which results in: a change in sequence of 1, 2, 3, 4, 5, 6, 7, 8, 9, 10, 11, 12 or more nucleotides of the target sequence. In an embodiment, the recombination template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the t recombination template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the recombination template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

A recombination template nucleic acid comprises the following components: [5' homology arm]-[replacement sequence]-[3' homology arm]. The homology arms provide for recombination into the chromosome, thus replacing the undesired element, e.g., a mutation or signature, with the replacement sequence. In an embodiment, the homology arms flank the most distal cleavage sites. In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, or 2000 nucleotides 5' from the 5' end of the replacement sequence. In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, or 2000 nucleotides 3' from the 3' end of the replacement sequence.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In certain embodiments, a recombination template nucleic acids for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Devices for Detection Assays

In certain embodiments, the detection assay can be provided on a cartridge or chip. In an aspect, the cartridge can comprise one or more ampoules and one or more wells that are communicatively coupled, allowing for the transfer, exchange or movement of reagents and sample with or without the use of beads through the chambers of the cartridge and facilitating detection assays utilizing systems/devices for facilitating the detection assay on the cartridge.

Cartridge

The cartridge, also referred to herein as a chip, according to the present invention comprises a series of components of ampoules and chambers that are communicatively coupled with one or more other components on the cartridge. The coupling is typically a fluidic communication, for example, via channels. The cartridge may comprise a membrane that seals one or more of the chambers and/or ampoules. In an aspect, the membrane allows for storage of reagents, buffers and other solid or fluid components which cover and seal the cartridge. The membrane can be configured to be punctured, pierced or otherwise released from sealing or covering one or more components of the cartridge by a means for releasing reagents.

As noted above, certain embodiments enable the use of nucleic acid binding beads to concentrate target nucleic acid but that do not require elution of the isolated nucleic acid. Thus, in certain example embodiments, the cartridge may further comprise an activatable magnet, such as an electromagnet. A means for activating the magnet may be located on the device, or the means for supplying the magnet or activating the magnet on the cartridge may be provided by a second device, such as those disclosed in further detail below.

An exemplary cartridge is depicted in FIG. 30A-30B. This embodiment is by way of example only, and it should be understood that other configurations of individual components on the cartridge are also envisioned without departing from the overall scope and function of the invention. The cartridge (10) can comprise two or more ampoules (80,90). A first chamber for receiving a sample (30) is also provided and can be communicatively connected to an ampoule (90)

and a second chamber (40). The second chamber (40) may be a lysis chamber. The lysis chamber can in turn be communicatively connected to a channel (100). The channel (100) may be a metering channel that is communicatively coupled to an ampoule (90) and a third chamber (60). The third chamber (60) may be an amplification chamber. Hydrophobic vents can be disposed on the cartridge (50, 70). FIG. 30B shows the cartridge body (15) with a membrane cover or laminate film (12).

The overall size of the device may be between 10, 15, 20, 25, 30, 35, 40, 45, 55, 60, 65, 70, 75, 80, 85, 90, 95, or 100 mm in width, and 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mm. The sizing of ampoules, chambers, and channels can be selected to be in line with the reaction volumes discussed herein and to fit within the general size parameters of the overall cartridge.

Ampoules

The ampoules, also referred to as blisters, allow for storage and release of reagents throughout the cartridge. Ampoules can include liquid or solid reagents, for example, lysis reagents in one ampoule and reaction reagents in another ampoule. The reagents can be as described elsewhere herein, and can be adapted for the use in the cartridge. The ampoule may be sealed by a film that allows for the bursting, puncture or other release of the contents of the ampoules. See, e.g. Becker, H. & Gartner, C. Microfluidics-enabled diagnostic systems: markets, challenges, and examples. In Microchip Diagnostics: Methods and Protocols (eds Taly, V. et al.) (Springer, New York, 2017); Czurratis et al., doi: 10.1088/0960-1317/25/4/045002. Considerations for ampoules can include as discussed in, for example, Smith, S., et al., Blister pouches for effective reagent storage on microfluidic chips for blood cell counting. Microfluid Nanofluid 20, 163 (2016). DOI:10.1007/s10404-016-1830-2. In an aspect, the seal is a frangible seal formed of a composite-layer film that is assembled to the cartridge main body. While referred to herein as an ampoule, the ampoule may comprise a cavity on a chip which comprises a sealed film that is opened by the release means.

Chambers

The chambers on the chip may located and sized for fluidic communication via channels or other communication means with ampoules and/or other chambers on the chip, see, e.g. FIG. 30A. A chamber for receiving a sample can be provided. The sample can be injected, placed in a receptacle into the chamber for receiving a sample, or otherwise transferred to the chamber. A lysis chamber may comprise, for example, capture beads, that may be used for concentration and/or extraction of the desired target material from the sample. Alternatively, the beads may be comprised in an ampoule comprising lysis reagents that are in fluidic communication with the lysis chamber. An amplification chamber may also be provided with, for example, one or more lyophilized components of the system in the amplification chamber and/or communicatively connected to an ampoule comprising one or more components of the amplification reaction.

When the cartridge comprises a magnet, it may be configured near one or more of the chambers. In an aspect, the magnet is near the lysis well, and may be configured such that the device has a means for activating the magnet. Embodiments comprising a magnet in the cartridge may be utilized with methodologies using magnetic beads for extraction of particular target molecules.

System for Detection Assays

A system configured for use with the cartridge and to perform an assay, also referred to as a sample analysis apparatus, detection system or detection device, is configured system to receive the cartridge and conduct an assay comprising isothermal amplification of nucleic acids and detection of target nucleic acids on the cartridge. The system may comprise: a body; a door housing which may be provided in an opened state or a closed state, and configured to be coupled to the body of the sample analysis apparatus by a hinge or other closure means; a cartridge accommodating unit included in the detection system and configured to accommodate the cartridge. The system may further comprise one or more means for releasing reagents for extractions, amplification and/or detection; one or more heating means for extractions, amplification and/or detection, a means for mixing reagents for extraction, amplification, and/or detections, and/or a means for reading the results of the assay. The device may further comprise a user interface for programming the device and/or readout of the results of the assay.

Means for Release of Reagents

The system may comprise means for releasing reagents for extraction, amplification and/or detection. Release of reagents can be performed by a crushing, puncturing, applying heat or pressure until burst, cutting, or other means for the opening of the ampoule and release of contents. e.g. Becker, H. & Gartner, C. Microfluidics-enabled diagnostic systems: markets, challenges, and examples. In Microchip Diagnostics: Methods and Protocols (eds Taly, V. et al.) (Springer, New York, 2017); Czurratis et al., doi: 10.1088/0960-1317/25/4/045002. Mechanical actuators Heating Means The heating means or heating element can be provided, for example, by electrical or chemical elements. One or more heating means can be utilized, or circuits providing regulation of temperature to one or more locations within the detection device can be utilized. In one preferred embodiment the device is configured to comprise a heating means for heating the lysis (extraction) chamber and at the amplification chamber of the cartridge. In an aspect, the heating element is disposed under the extraction well. The system can be designed with one or more heating means for extraction, amplification and/or detection.

Mixing Means

A means for mixing reagents for extraction, amplification and/or detection can be provided. A means for mixing reagents may comprise a means for mixing one or more fluids, or a fluid with a solid or lyophilized reaction mixture can also be provided. Means for mixing that disturb the laminar flow can be provided. In an aspect, the mixing means is a passive mixer, in another aspect, the mixing means is an active mixer. See, e.g. Nam-Trung Nguyen and Zhigang Wu 2005 J. Micromech. Microeng. 15 R1, doi: 10.1088/0960-1317/15/2/R01 for discussion of mixing approaches. In an aspect, the active mixer can be based on external sources such as pressure, temperature, hydrodynamics (with electrical or magnetic forces), dielectrophoresis, electrokinetics, or acoustics. Examples of passive mixing means can be provided by use of geometric approaches, such as a curved path or channel, see, e.g. U.S. Pat. No. 7,160,025, or an expansion/contraction of a channel cross section or diameter. When the cartridge is utilized with beads, channels and wells are configured and sized for the flow of beads.

Means for Reading the Results of the Assay

A means for reading the results of the assay can be provided in the system. The means for reading the results of the assay will depend in part on the type of detectable signal generated by the assay. In particular embodiments, the assay generates a detectable fluorescent or color readout. In these instances, the means for reading the results of the assay will be an optic means, for example a single channel or multi-channel optical means such as a fluorimeter, colorimeter or other spectroscopic sensor.

A combination of means for reading the results of the assay can be utilized, and may include readings such as turbidity, temperature, magnetic, radio, or electrical properties and or optical properties, including scattering, polarization effects, etc.

The system may further comprise a user interface for programming the device and/or readout of the results of the assay. The user interface may comprise an LED screen. The system can be further configured for a USB port that can allow for docking of four or more devices.

In an aspect, the system comprises a means for activating a magnet that is disposed within or on the cartridge.

Lateral Flow Devices

In certain embodiments, the detection assay can be provided on a lateral flow device, as described in International Publication WO 2019/071051, incorporated herein by reference. The lateral flow device can be adapted to detect one or more coronaviruses and/or other viruses in combination of the coronavirus. The lateral flow device may comprise a flexible substrate, such as a paper substrate or a flexible polymer-based substrate, which can include freeze-dried reagents for detection assays with a visual readout of the assay results. See, WO 2019/071051 at [0145]-[0151] and Example 2, specifically incorporated herein by reference. In an aspect, lyophilized reagents can include preferred excipients that aid in rate of reaction, specificity, or other variables. The excipients may comprise trehalose, histidine, and/or glycine. In certain embodiments, the coronavirus assay can be utilized with isothermal amplification reagents, allowing amplification without complex instrumentation that may be unavailable in the field, as described in WO 2019/071051. Accordingly, the assay can be adapted for field diagnostics, including use of visual readout on a lateral flow device, rapid, sensitive detection and can be deployed for early and direct detection. Colorimetric detection can be utilized and may be particularly suited for field deployable applications, as described in International Application PCT/US2019/015726, published as WO2019/148206. In particular, colorimetric detection can be as described in WO2019/148206 at FIGS. 102, 105, 107-111 and [00306]-[00324], incorporated herein by reference.

In one embodiment, the invention provides a lateral flow device comprising a substrate comprising a first end and a second end. The first end may comprise a sample loading portion, a first region comprising a detectable ligand, two or more CRISPR effector systems, two or more detection constructs, and one or more first capture regions, each comprising a first binding agent. The substrate may also comprise two or more second capture regions between the first region of the first end and the second end, each second capture region comprising a different binding agent. Each of the two or more CRISPR effector systems may comprise a CRISPR effector protein and one or more guide sequences, each guide sequence configured to bind one or more target molecules.

The embodiments disclosed herein are directed to lateral flow detection devices that comprise SHERLOCK systems.

The device may comprise a lateral flow substrate for detecting a SHERLOCK reaction. Substrates suitable for use in lateral flow assays are known in the art. These may include, but are not necessarily limited to membranes or pads made of cellulose and/or glass fiber, polyesters, nitrocellulose, or absorbent pads (J Saudi Chem Soc 19(6):689-705; 2015), and other embodiments further described herein. The SHERLOCK system, i.e. one or more CRISPR systems and corresponding reporter constructs are added to the lateral flow substrate at a defined reagent portion of the lateral flow substrate, typically on one end of the lateral flow substrate. Reporting constructs used within the context of the present invention can comprise a first molecule and a second molecule linked by an RNA or DNA linker. The lateral flow substrate further comprises a sample portion. The sample portion may be equivalent to, continuous with, or adjacent to the reagent portion. In an aspect, the lateral flow substrate can be contained within a further device (see, e.g. FIG. 21). In an aspect, the lateral flow substrate can be utilized for visual readout of a detectable signal in one-pot reactions, e.g. wherein steps of extracting, amplifying and detecting are performed in an individual discrete volume.

Lateral Flow Substrate

In certain example embodiments, a lateral flow device comprises a lateral flow substrate on which detection can be performed. Substrates suitable for use in lateral flow assays are known in the art. These may include, but are not necessarily limited to, membranes or pads made of cellulose and/or glass fiber, polyesters, nitrocellulose, or absorbent pads (*J Saudi Chem Soc* 19(6):689-705; 2015).

Lateral support substrates comprise a first and second end, and one or more capture regions that each comprise binding agents. The first end may comprise a sample loading portion, a first region comprising a detectable ligand, two or more CRISPR effector systems, two or more detection constructs, and one or more first capture regions, each comprising a first binding agent. The substrate may also comprise two or more second capture regions between the first region of the first end and the second end, each second capture region comprising a different binding agent. Each of the two or more CRISPR effector systems may comprise a CRISPR effector protein and one or more guide sequences, each guide sequence configured to bind one or more target molecules. The lateral flow substrates may be configured to detect a SHERLOCK reaction.

Lateral support substrates may be located within a housing (see for example, "Rapid Lateral Flow Test Strips" Merck Millipore 2013). The housing may comprise at least one opening for loading samples and a second single opening or separate openings that allow for reading of detectable signal generated at the first and second capture regions.

The embodiments disclosed herein can be prepared in freeze-dried format for convenient distribution and point-of-care (POC) applications. Such embodiments are useful in multiple scenarios in human health including, for example, viral detection, bacterial strain typing, sensitive genotyping, and detection of disease-associated cell free DNA. Accordingly, the lateral substrate comprising one or more of the elements of the system, including detectable ligands, CRISPR effector systems, detection constructs and binding agents may be freeze-dried to the lateral flow substrate and packaged as a ready to use device. Alternatively, all or a portion of the elements of the system may be added to the reagent portion of the lateral flow substrate at the time of using the device.

First End and Second End of the Substrate

The substrate of the lateral flow device comprises a first and second end. The SHERLOCK system, i.e. one or more CRISPR systems and corresponding reporter constructs are added to the lateral flow substrate at a defined reagent portion of the lateral flow substrate, typically on a first end of the lateral flow substrate. Reporting constructs used within the context of the present invention comprise a first molecule and a second molecule linked by an RNA or DNA linker. The lateral flow substrate further comprises a sample portion. The sample portion may be equivalent to, continuous with, or adjacent to the reagent portion.

In certain example embodiments, the first end comprises a first region. The first region comprises a detectable ligand, two or more CRISPR effector systems, two or more detection constructs, and one or more first capture regions, each comprising a first binding agent.

Capture Regions

The lateral flow substrate can comprise one or more capture regions. In embodiments the first end of the lateral flow substrate comprises one or more first capture regions, with two or more second capture regions between the first region of the first end of the substrate and the second end of the substrate. The capture regions may be provided as a capture line, typically a horizontal line running across the device, but other configurations are possible. The first capture region is proximate to and on the same end of the lateral flow substrate as the sample loading portion.

Binding Agents

Specific binding-integrating molecules comprise any members of binding pairs that can be used in the present invention. Such binding pairs are known to those skilled in the art and include, but are not limited to, antibody-antigen pairs, enzyme-substrate pairs, receptor-ligand pairs, and streptavidin-biotin. In addition to such known binding pairs, novel binding pairs may be specifically designed. A characteristic of binding pairs is the binding between the two members of the binding pair.

A first binding agent that specifically binds the first molecule of the reporter construct is fixed or otherwise immobilized to the first capture region. The second capture region is located towards the opposite end of the lateral flow substrate from the first capture region. A second binding agent is fixed or otherwise immobilized at the second capture region. The second binding agent specifically binds the second molecule of the reporter construct, or the second binding agent may bind a detectable ligand. For example, the detectable ligand may be a particle, such as a colloidal particle, that when it aggregates can be detected visually, and generates a detectable positive signal. The particle may be modified with an antibody that specifically binds the second molecule on the reporter construct. If the reporter construct is not cleaved it will facilitate accumulation of the detectable ligand at the first binding region. If the reporter construct is cleaved the detectable ligand is released to flow to the second binding region. In such an embodiment, the second binding region comprises a second binding agent capable of specifically or non-specifically binding the detectable ligand on the antibody of the detectable ligand. Binding agents can be, for example, antibodies, that recognize a particular affinity tag. Such binding agents can further contain, for example, detectable labels, such as isotope labels and/or nucleic acid barcodes. A barcode is a short sequence of nucleotides (for example, DNA, RNA, or combinations thereof) that is used as an identifier. A nucleic acid barcode may have a length of 4-100 nucleotides and be either single or double-stranded. Methods for identifying cells with barcodes are known in the art. Accordingly, guide RNAs of the CRISPR effector systems described herein may be used to detect the barcode.

Detectable Ligands

The first region is loaded with a detectable ligand, such as those disclosed herein, for example a gold nanoparticle. The detectable ligand may be a particle, such as a colloidal particle, that when it aggregates can be detected visually. The particle may be modified with an antibody that specifically binds the second molecule on the reporter construct. If the reporter construct is not cleaved it will facilitate accumulation of the detectable ligand at the first binding region. If the reporter construct is cleaved the detectable ligand is released to flow to the second binding region. In such an embodiment, the second binding agent is an agent capable of specifically or non-specifically binding the detectable ligand on the antibody on the detectable ligand. Examples of suitable binding agents for such an embodiment include, but are not limited to, protein A and protein G. In some examples, the detectable ligand is a gold nanoparticle, which may be modified with a first antibody, such as an anti-FITC antibody.

Lateral Flow Detection Constructs

The first region also comprises a detection construct. In one example embodiment, a polynucleotide detection construct and a CRISPR effector system (a CRISPR effector protein and one or more guide sequences configured to bind to one or more target sequences) as disclosed herein. In one example embodiment, and for purposes of further illustration, the RNA construct may comprise a FAM molecule on a first end of the detection construction and a biotin on a second end of the detection construct. Upstream of the flow of solution from the first end of the lateral flow substrate is a first test band. The test band may comprise a biotin ligand. Accordingly, when the polynucleotide detection construct is present it its initial state, i.e. in the absence of target, the FAM molecule on the first end will bind the anti-FITC antibody on the gold nanoparticle, and the biotin on the second end of the polynucleotide construct will bind the biotin ligand allowing for the detectable ligand to accumulate at the first test, generating a detectable signal. Generation of a detectable signal at the first band indicates the absence of the target ligand. In the presence of target, the CRISPR effector complex forms and the CRISPR effector protein is activated resulting in cleavage of the RND detection construct. In the absence of intact polynucleotide detection construct the colloidal gold will flow past the second strip. The lateral flow device may comprise a second band, upstream of the first band. The second band may comprise a molecule capable of binding the antibody-labeled colloidal gold molecule, for example an anti-rabbit antibody capable of binding a rabbit anti-FITC antibody on the colloidal gold. Therefore, in the presence of one or more targets, the detectable ligand will accumulate at the second band, indicating the presence of the one or more targets in the sample.

In some embodiments, the first end of the lateral flow device comprises two detection constructs and each of the two detection constructs comprises an RNA or DNA oligonucleotide, comprising a first molecule on a first end and a second molecule on a second end. The first molecule and the second molecule may be linked by an RNA or DNA linker.

In some embodiments, the first molecule on the first end of the first detection construct may be FAM and the second molecule on the second end of the first detection construct may be biotin, or vice versa. In some embodiments, the first molecule on the first end of the second detection construct may be FAM and the second molecule on the second end of the second detection construct may be Digoxigenin (DIG), or vice versa.

In some embodiments, the first end may comprise three detection constructs, wherein each of the three detection constructs comprises an RNA or DNA oligonucleotide, comprising a first molecule on a first end and a second molecule on a second end. In specific embodiments, the first and second molecules on the detection constructs comprise Tye 665 and Alexa 488; Tye 665 and FAM, and Tye 665 and Digoxigenin (DIG), respectively.

In some embodiments, the first end of the lateral flow device comprises two or more CRISPR effector systems, also referred to as a CRISPR-Cas or CRISPR system. In some embodiments, such a CRISPR effector system may include a CRISPR effector protein and one or more guide sequences configured to bind to one or more target sequences.

Samples

When utilizing the detection systems with a lateral flow substrate, samples to be screened are loaded at the sample loading portion of the lateral flow substrate. The samples must be liquid samples or samples dissolved in an appropriate solvent, usually aqueous. The liquid sample reconstitutes the SHERLOCK reagents such that a SHERLOCK reaction can occur. The liquid sample begins to flow from the sample portion of the substrate towards the first and second capture regions.

A sample for use with the invention may be a biological or environmental sample, such as a surface sample, a fluid sample, or a food sample (fresh fruits or vegetables, meats). Food samples may include a beverage sample, a paper surface, a fabric surface, a metal surface, a wood surface, a plastic surface, a soil sample, a freshwater sample, a wastewater sample, a saline water sample, exposure to atmospheric air or other gas sample, or a combination thereof. For example, household/commercial/industrial surfaces made of any materials including, but not limited to, metal, wood, plastic, rubber, or the like, may be swabbed and tested for contaminants. Soil samples may be tested for the presence of pathogenic bacteria or parasites, or other microbes, both for environmental purposes and/or for human, animal, or plant disease testing. Water samples such as freshwater samples, wastewater samples, or saline water samples can be evaluated for cleanliness and safety, and/or potability, to detect the presence of, for example, *Cryptosporidium parvum, Giardia lamblia*, or other microbial contamination. In further embodiments, a biological sample may be obtained from a source including, but not limited to, a tissue sample, saliva, blood, plasma, sera, stool, urine, sputum, mucous, lymph, synovial fluid, spinal fluid, cerebrospinal fluid, ascites, pleural effusion, seroma, pus, bile, aqueous or vitreous humor, transudate, exudate, or swab of skin or a mucosal membrane surface. In some particular embodiments, an environmental sample or biological samples may be crude samples and/or the one or more target molecules may not be purified or amplified from the sample prior to application of the method. Identification of microbes may be useful and/or needed for any number of applications, and thus any type of sample from any source deemed appropriate by one of skill in the art may be used in accordance with the invention.

In particular embodiments, the methods and systems can be utilized for direct detection from patient samples. In an aspect, the methods and systems can further allow for direct detection from patient samples with a visual readout to further facilitate field-deployability. In an aspect, a field deployable version can include, for example the lateral flow devices and systems as described herein, and/or colorimetric detection. The methods and systems can be utilized to distinguish multiple viral species and strains and identify clinically relevant mutations, important with viral outbreaks such as the coronavirus outbreak in Wuhan (2019-nCoV). In an aspect, the sample is from a nasopharyngeal swab or a saliva sample. See., e.g. FIG. 40, see also, Wyllie et al., "Saliva is more sensitive for SARS-CoV-2 detection in COVID-19 patients than nasopharyngeal swabs," DOI: 10.1101/2020.04.16.20067835.

Methods for Detecting and/or Quantifying Target Nucleic Acids

In some embodiments, the invention provides methods for detecting target nucleic acids in a sample. Such methods may comprise contacting a sample with the first end of a lateral flow device as described herein. The first end of the lateral flow device may comprise a sample loading portion, wherein the sample flows from the sample loading portion of the substrate towards the first and second capture regions and generates a detectable signal.

A positive detectable signal may be any signal that can be detected using optical, fluorescent, chemiluminescent, electrochemical or other detection methods known in the art, as described elsewhere herein.

In some embodiments, the lateral flow device may be capable of detecting two different target nucleic acid sequences. In some embodiments, this detection of two different target nucleic acid sequences may occur simultaneously.

In some embodiments, the absence of target nucleic acid sequences in a sample elicits a detectable fluorescent signal at each capture region. In such instances, the absence of any target nucleic acid sequences in a sample may cause a detectable signal to appear at the first and second capture regions.

In some embodiments, the lateral flow device as described herein is capable of detecting three different target nucleic acid sequences. In specific embodiments, when the target nucleic acid sequences are absent from the sample, a fluorescent signal may be generated at each of the three capture regions. In such exemplary embodiments, a fluorescent signal may be absent at the capture region for the corresponding target nucleic acid sequence when the sample contains one or more target nucleic acid sequences.

Samples to be screened are loaded at the sample loading portion of the lateral flow substrate. The samples must be liquid samples or samples dissolved in an appropriate solvent, usually aqueous. The liquid sample reconstitutes the system reagents such that a SHERLOCK reaction can occur. Intact reporter construct is bound at the first capture region by binding between the first binding agent and the first molecule. Likewise, the detection agent will begin to collect at the first binding region by binding to the second molecule on the intact reporter construct. If target molecule(s) are present in the sample, the CRISPR effector protein collateral effect is activated. As activated CRISPR effector protein comes into contact with the bound reporter construct, the reporter constructs are cleaved, releasing the second molecule to flow further down the lateral flow substrate towards the second binding region. The released second molecule is then captured at the second capture region by binding to the second binding agent, where additional detection agent may also accumulate by binding to the second molecule. Accordingly, if the target molecule(s) is not present in the sample, a detectable signal will appear at the first capture region, and if the target molecule(s) is present in the sample, a detectable signal will appear at the location of the second capture region.

In some embodiments, the invention provides a method for quantifying target nucleic acids in samples comprising distributing a sample or set of samples into one or more individual discrete volumes comprising two or more CRISPR systems as described herein. The method may comprise using HDA to amplify one or more target molecules in the sample or set of samples, as described herein. The method may further comprise incubating the sample or set of samples under conditions sufficient to allow binding of the guide RNAs to one or more target molecules. The method may further comprise activating the CRISPR effector protein via binding of the guide RNAs to the one or more target molecules. Activating the CRISPR effector protein may result in modification of the detection construct such that a detectable positive signal is generated. The method may further comprise detecting the one or more detectable positive signals, wherein detection indicates the presence of one or more target molecules in the sample. The method may further comprise comparing the intensity of the one or more signals to a control to quantify the nucleic acid in the sample. The steps of amplifying, incubating, activating, and detecting may all be performed in the same individual discrete volume.

An "individual discrete volume" is a discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents maybe passed in Applicants' through the discrete volume, while other material, such as target molecules, maybe maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate.

Incubating the sample at either the amplification step or the extraction steps as described herein can be performed using heat sources known in the art. Advantageously, the heat source can be readily commercially available heating sources that do not require complicated instrumentation. Exemplary heating systems can include heating blocks, incubators, and/or water baths with temperatures maintained by commercially available sous-vide cookers. In this way, sample diagnostics can be performed without the requirement of expensive and proprietary equipment found primarily in diagnostic laboratory and hospital settings.

In certain example embodiments, paper-based microfluidics may be used for transfer of samples or reagents. For example, paper strips having wax barrier printed at a defined distance from the end of a paper dipstick may be used to define a volume of reagent or sample to be transferred. For example, a wax barrier may be printed across a paper dipstick to define a microliter volume such that when the dipstick is transferred into a volume of a reagent or sample only a microliter of said reagent or sample is absorbed onto the dipstick. The dipstick may be place in a second reagent mix, where the reagent or sample will diffuse into the reaction mixture. Such components allow for preparation and use of the assay without specialized equipment such as pipettors.

Amplifying Target Molecules

The step of amplifying one or more target molecules can comprise amplification systems known in the art. In some embodiments, amplification is isothermal. In certain example embodiments, target RNAs and/or DNAs may be amplified prior to activating the CRISPR effector protein. Any suitable RNA or DNA amplification technique may be used. In certain embodiments, the amplifying step may take less than about 1 hour, 50 minutes, 40 minutes, 30 minutes, 25 minutes, 20 minutes or 15 minutes, which may depend on the sample, starting concentrations and nature of amplification used.

In certain embodiments, the amplifying of the target molecules and the detection of the target molecules can be performed in a single reaction, for example, a 'one-pot' method. Guidance for use of a single-pot approach can be as described in Gootenberg, et al., Science 2018 Apr. 27: 360(6387) 439-444 (using Cas13, Cas12a and Csm6 generally, detecting multiple targets in a single reaction, and specifically performing DNA extraction in a sample and using as input for direct detection at Figure S33); and Ding et al., "All-in-One Dual CRISPR-Cas12a (AIOD-CRISPR) Assay: A Case for Rapid, Ultrasensitive and Visual Detection of Novel Coronavirus SARS-CoV-2 and HIV Virus," doi:10.1101/2020.03.19.998724, biorxiv preprint (utilizing a pair of crRNAs with dual CRISPR-Cas12a detection for a one-pot approach to target-specific nucleic acid detection);

and International Patent Application PCT/US2020/022795, filed Mar. 13, 2020, incorporated herein by reference in its entirety.

In certain example embodiments, the RNA or DNA amplification is an isothermal amplification. In certain example embodiments, the isothermal amplification may be nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM).

The amplifying of target molecules can be optimized by methods as detailed herein. In an aspect, the design optimizes the primers used in the amplification, In particular aspects, the isothermal amplification is used alone. In another aspect, the isothermal amplification is used with CRISPR-Cas systems. In either approach, design considerations can follow a rational design for optimization of the reactions. Optimization of the methods as disclosed herein can include first screening primers to identify one or more sets of primers that work well for a particular target, Cas protein and/or reaction. Once the primers have been screened, titration of magnesium concentration can be performed to identify an optimal magnesium concentration for higher signal to noise readout. Once an optimum magnesium concentration is identified, additional additives are screened at around 20-25% of the reaction, and once additives are identified, these additives, such as those additives identified in FIG. 17, can be evaluated and varied in concentration to identify optimal reaction kinetics for specific reaction parameters. In an example, varying additives with specific primers, target, Cas protein (when CRISPR system is used), temperature, and other additive concentrations within the reaction can be identified. Optimization can be made with the goal of reducing the number of steps and buffer exchanges that have to occur in the reaction, simplifying the reaction and reducing the risks of contamination at transfer steps. In an aspect, addition of inhibitors, such as proteinase K can be considered so that buffer exchanges can be reduced. Similarly, optimizing the salt levels as well as the type of salt utilized can further facilitate and optimize the one-pot detections disclosed herein. In an aspect, potassium chloride can be utilized rather than sodium chloride when such amplification approaches are used with bead concentration in a lysis step.

Loop-Mediated Isothermal Amplification

In certain example embodiments, a loop-mediated isothermal amplification (LAMP) reaction may be used to target nucleic acids, which encompasses both LAMP and RT-LAMP reactions. LAMP can be performed with a four-primer system for isothermal nucleic acid amplification in conjunction with a polymerase. Notomi et al., Nucleic Acids Res. 2000, 28, 12, Nagamine et al., Molecular and Cellular Probes (2002) 16, 223-229, doi: 10.1006/mcpr.2002.0415. When performing LAMP with a 4-primer system, two loop-forming inner primers, denoted as FIP and BIP, are provided with two outer primers, F3 and B3. The inner primers each contain two distinct sequences, one for priming in the first stage of the amplification and the other sequence for self-priming in subsequent amplification states. The two outer primers initiate strand displacement of nucleic acid strands initiated from the FIP and BIP primers, thereby generating formation of loops and strand displacement nucleic acid synthesis utilizing the provided polymerase. LAMP can be conducted with two to six primers, ranging from only the two loop-forming primers, up to at least the addition of 2 additional primers, LF and LB along with the two outer primers and two inner primers. LAMP technologies advantageously have high specificity and can work at a variety of pH and temperature. In a preferred aspect, the LAMP is an isothermal reaction at between about 45° C. to 75° C., 55 to 70° C. or 60° C. to 65° C. Colorimetric LAMP (Y. Zhang et al., doi:10.1101/2020.92.26.20028373), RT-LAMP (Lamb et al., doi: 10.1101/2020.02.19.20025155; and Yang et al., doi:10.1101/2020.03.02.20030130) have been developed for detection of COVID-19, and are incorporated herein by reference in their entirety.

In certain embodiments, the LAMP reagents may include Bst 2.0+RTx or Bst 3.0 from New England Biolabs. In certain embodiments, the LAMP reagents may comprise colorimetric or fluorescent detection. Detection of LAMP products can be accomplished using colorimetric tools, such as hydroxy napthol blue (see, e.g. Goto, M., et al., Colorimetric detection of loop-mediated isothermal amplification reaction by using hydroxy naphthol blue. Biotechniques, 2009. 46(3): p. 167-72.) leuco triphenylmethane dyes (see, e.g. Miyamoto, S., et al., Method for colorimetric detection of double-stranded nucleic acid using leuco triphenylmethane dyes. Anal Biochem, 2015. 473: p. 28-33) and pH-sensitive dyes (see, e.g. Tanner, N. A., Y. Zhang, and T. C. Evans, Jr., Visual detection of isothermal nucleic acid amplification using pH-sensitive dyes. Biotechniques, 2015. 58(2): p. 59-68); as well as fluorescent detection (see, e.g. Yu et al., *Clinical Chemistry*, hvaa102, doi:10.1093/clinchem/hvaa102 12 May 2020), including use of quenching probes (see, e.g. Shirato et al., *J Virol Methods*. 2018 August; 258:41-48. doi: 10.1016/j.jviromet.2018.05.006).

In an aspect, the primer sets for LAMP are designed to amplify one or more target sequences, generating amplicons that comprise the one or more target sequences. Optionally, the primers can comprise barcodes that can be designed as described elsewhere herein. Incubating to a temperature sufficient for LAMP amplification, e.g. 50° C.-72° C., more preferably 55° C. to 65° C., using a polymerase and, optionally a reverse transcriptase (in the event RT-LAMP is utilized). Preferably the enzymes utilized in the LAMP reaction are heat-stabilized. LAMP primer sites have been designed, see, e.g. Park et al., "Development of Reverse Transcription Loop-Mediated Isothermal Amplification Assays Targeting SARS-CoV-2" J. of Mol. Diag. (2020). Optionally, a control template is further provided with the sample, which may differ from the target sequence but share primer binding sites. In an exemplary embodiment, visual read out of the detection results can be accomplished using commercially-available lateral flow substrate, e.g. a commercially available paper substrate.

In a certain embodiments, the LAMP primer can be selected from SEQ ID NOs: 1-40499.

In certain embodiments, the primer deigned to target one or more of *Chlamydia trachomatis* D/UW-3/CX chromosome, complete genome, Hepatitis A virus, complete genome, Hepatitis B virus (strain ayw) genome, Hepatitis C virus (isolate H77) genotype 1, complete cds, Hepatitis C virus genotype 1, complete genome, Hepatitis C virus genotype 2, complete genome, Hepatitis C virus genotype 3, genome, Hepatitis C virus genotype 4, genome, Hepatitis C virus genotype 5, genome, Hepatitis C virus genotype 6, complete genome, Hepatitis C virus genotype 7, complete genome, Hepatitis delta virus, complete genome, Hepatitis E virus, complete genome, Hepatitis E virus rat/R63/DEU/2009, complete genome, Hepatitis GB virus A, complete genome, Hepatitis GB virus B, complete genome, Human adenovirus 54, complete genome, Human adenovirus A, complete genome, Human betaherpesvirus 6A, variant A DNA, complete virion genome, isolate U1102, Human coronavirus 229E, complete genome, Human coronavirus HKU1, complete genome, Human Coronavirus NL63, complete genome, Human coronavirus OC43 strain ATCC VR-759, complete genome, Human gammaherpesvirus 4, complete genome, Human genital-associated circular DNA virus-1 isolate 349, complete genome, Human herpesvirus 1 strain 17, complete genome, Human herpesvirus 2 strain HG52, complete genome, Human herpesvirus 3, complete genome, Human herpesvirus 4, complete genome, Human herpesvirus 5 strain Merlin, complete genome, Human herpesvirus 6B, complete genome, Human herpesvirus 7, complete genome, Human herpesvirus 8 strain GK18, complete genome, Human immunodeficiency virus 1, complete genome, Human immunodeficiency virus 2, complete genome, Human papillomavirus 54, complete genome, Human papillomavirus 116, complete genome, Human papillomavirus-1, complete genome, Human papillomavirus-2, complete genome, Human papillomavirus-18, complete genome, Human papillomavirus-61, complete genome, Human papillomavirus isolate SE379, complete genome, Human papillomavirus KCS, complete genome, Human papillomavirus type 4, complete genome, Human papillomavirus type 6b, complete genome, Human papillomavirus type 7 genomic DNA, Human papillomavirus type 9, complete genome, Human papillomavirus type 10 genomic DNA, Human papillomavirus type 16, complete genome, Human papillomavirus type 26, complete genome, Human papillomavirus type 30 genomic DNA, Human papillomavirus type 32, complete genome, Human papillomavirus type 34, complete genome, Human papillomavirus type 41, complete genome, Human papillomavirus type 48, complete genome, Human papillomavirus type 49, complete genome, Human papillomavirus type 50, complete genome, Human papillomavirus type 53, complete genome, Human papillomavirus type 60, complete genome, Human papillomavirus type 63, complete genome, Human papillomavirus type 71 DNA, complete genome, Human papillomavirus type 85 isolate 114B, complete genome, Human papillomavirus type 88, complete genome, Human papillomavirus type 90, complete genome, Human papillomavirus type 92, complete genome, Human papillomavirus type 96, complete genome, Human papillomavirus type 101, complete genome, Human papillomavirus type 103, complete genome, Human papillomavirus type 108, complete genome, Human papillomavirus type 109, complete genome, Human papillomavirus type 112, complete genome, Human papillomavirus type 121, complete genome, Human papillomavirus type 126, complete genome, Human papillomavirus type 128, complete genome, Human papillomavirus type 129, complete genome, Human papillomavirus type 131, complete genome, Human papillomavirus type 132, complete genome, Human papillomavirus type 134, complete genome, Human papillomavirus type 135, complete genome, Human papillomavirus type 136, complete genome, Human papillomavirus type 137, complete genome, Human papillomavirus type 140, complete genome, Human papillomavirus type 144, complete genome, Human papillomavirus type 154 isolate PV77, complete genome, Human papillomavirus type 156 isolate GC01, complete genome, Human papillomavirus type 161 isolate KC1, complete genome, Human papillomavirus type 163 isolate KC3, complete genome, Human papillomavirus type 166 isolate KC9, complete genome, Human papillomavirus type 167 isolate KC10, complete genome, Human papillomavirus type 172, complete genome, Human papillomavirus type 175 isolate SE87, complete genome, Human, apillomavirus type 178, complete genome, Human papillomavirus type 179 complete genome, isolate SIBX16, Human papillomavirus type 184 complete genome, isolate SIBX17, Human papillomavirus type 187 isolate ACS447, complete genome, Human papillomavirus type 201 isolate HPV201, complete genome, Human papillomavirus type 204 isolate A342, complete genome, Human papillomoavirus type 5, complete genome, Human parainfluenza virus 1, complete genome, Human parainfluenza virus 3, complete genome, Human rhinovirus 1 strain ATCC VR-1559, complete genome, Human rhinovirus 3, complete genome, Human rhinovirus 14, complete genome, Human rhinovirus 89, complete genome, Human rhinovirus C, complete genome, Human rhinovirus NAT001 polyprotein gene, complete cds, Human T-lymphotropic virus 1, complete genome, Influenza A virus (A/California/07/2009(H1N1)) segment 1 polymerase PB2 (PB2) gene, complete cds, Influenza A virus (A/California/07/2009(H1N1)) segment 2 polymerase PB1 (PB1) gene, complete cds; and nonfunctional PB1-F2 protein (PB1-F2) gene, complete sequence, Influenza A virus (A/California/07/2009(H1N1)) segment 3 polymerase PA (PA) gene, complete cds, Influenza A virus (A/California/07/2009(H1N1)) segment 4 hemagglutinin (HA) gene, complete cds, Influenza A virus (A/California/07/2009(H1N1)) segment 5 nucleocapsid protein (NP) gene, complete cds, Influenza A virus (A/California/07/2009(H1N1)) segment 6 neuraminidase (NA) gene, complete cds, Influenza A virus (A/California/07/2009(H1N1)) segment 7 matrix protein 2 (M2) and matrix protein 1 (M1) genes, complete cds, Influenza A virus (A/California/07/2009(H1N1)) segment 8 nuclear export protein (NEP) and nonstructural protein 1 (NS1) genes, complete cds, Influenza A virus (A/Goose/Guangdong/1/96(H5N1)) neuraminidase (NA) gene, complete cds, Influenza A virus (A/Goose/Guangdong/1/96 (H5N1)) nucleocapsid protein (NP) gene, complete cds, Influenza A virus (A/Goose/Guangdong/1/96(H5N1)) polymerase (PB2) gene, complete cds, Influenza A virus (A/goose/Guangdong/1/1996(H5N1)) hemagglutinin (HA) gene, complete cds, Influenza A virus (A/goose/Guangdong/1/1996(H5N1)) polymerase (PA) and PA-X protein (PA-X) genes, complete cds, Influenza A virus (A/goose/Guangdong/1/1996(H5N1)) polymerase (PB1) and PB1-F2 protein (PB1-F2) genes, complete cds, Influenza A virus (A/goose/Guangdong/1/1996(H5N1)) segment 7, complete sequence, Influenza A virus (A/goose/Guangdong/1/1996(H5N1)) segment 8, complete sequence, Influenza A virus (A/Hong Kong/1073/99(H9N2)) segment 5, complete sequence, Influenza A virus (A/Hong Kong/1073/99(H9N2)) segment 7, complete sequence, Influenza A virus (A/Hong Kong/1073/99(H9N2)) segment 8, complete sequence, Influenza A virus (A/Korea/426/1968(H2N2)) segment 1, complete sequence, Influenza A virus (A/Korea/426/1968(H2N2)) segment 2, complete sequence, Influenza A virus (A/Korea/426/1968(H2N2)) segment 3, complete sequence, Influenza A virus (A/Korea/426/1968(H2N2)) segment 4, complete sequence, Influenza A virus (A/Korea/426/1968(H2N2)) segment 5, complete sequence, Influenza A virus (A/Korea/426/1968(H2N2)) segment 6, complete sequence, Influenza A virus (A/Korea/426/1968(H2N2)) segment 7, complete sequence, Influenza A virus (A/Korea/426/1968(H2N2)) segment 8, complete sequence, Influenza A virus (A/New York/392/2004(H3N2)) segment 1, complete sequence, Influenza A virus (A/New York/392/2004(H3N2)) segment 2, complete sequence, Influenza A virus (A/New York/392/2004(H3N2)) segment 3, complete sequence, Influenza A virus (A/New York/392/2004(H3N2)) segment 4, complete sequence, Influenza A virus (A/New York/392/2004(H3N2)) segment 5, complete sequence, Influenza A virus (A/New York/392/2004(H3N2)) segment 6, complete sequence, Influenza A virus (A/New York/392/2004(H3N2)) segment 7, complete sequence, Influenza A virus (A/New York/392/2004(H3N2)) segment 8, complete sequence, Influenza A virus (A/Puerto Rico/8/1934(H1N1)) segment 1, complete sequence, Influenza A virus (A/Puerto Rico/8/1934(H1N1)) segment 2, complete sequence, Influenza A virus (A/Puerto Rico/8/1934(H1N1)) segment 3, complete sequence, Influenza A virus (A/Puerto Rico/8/1934(H1N1)) segment 4, complete sequence, Influenza A virus (A/Puerto Rico/8/1934 (H1N1)) segment 5, complete sequence, Influenza A virus (A/Puerto Rico/8/1934(H1N1)) segment 6, complete sequence, Influenza A virus (A/Puerto Rico/8/1934(H1N1)) segment 7, complete sequence, Influenza A virus (A/Puerto Rico/8/1934(H1N1)) segment 8, complete sequence, Influenza A virus (A/Shanghai/02/2013(H7N9)) segment 1 polymerase PB2 (PB2) gene, complete cds, Influenza A virus (A/Shanghai/02/2013(H7N9)) segment 2 polymerase PB1 (PB1) and PB1-F2 protein (PB1-F2) genes, complete cds, Influenza A virus (A/Shanghai/02/2013(H7N9)) segment 3 polymerase PA (PA) and PA-X protein (PA-X) genes, complete cds, Influenza A virus (A/Shanghai/02/2013(H7N9)) segment 4 hemagglutinin (HA) gene, complete cds, Influenza A virus (A/Shanghai/02/2013(H7N9)) segment 5 nucleocapsid protein (NP) gene, complete cds, Influenza A virus (A/Shanghai/02/2013(H7N9)) segment 6 neuraminidase (NA) gene, complete cds, Influenza A virus (A/Shanghai/02/2013(H7N9)) segment 7 matrix protein 2 (M2) and matrix protein 1 (M1) genes, complete cds, Influenza A virus (A/Shanghai/02/2013(H7N9)) segment 8 nuclear export protein (NEP) and nonstructural protein 1 (NS1) genes, complete cds, Influenza A virus ha gene for Hemagglutinin, genomic RNA, strain A/Hong Kong/1073/99(H9N2), Influenza A virus na gene for neuraminidase, genomic RNA, strain A/Hong Kong/1073/99(H9N2), Influenza A virus pa gene for polymerase PA, genomic RNA, strain A/Hong Kong/1073/99(H9N2), Influenza A virus 01 gene for polymerase Pb1, genomic RNA, strain A/Hong Kong/1073/99 (H9N2), Influenza A virus pb2 gene for polymerase Pb2, genomic RNA, strain A/Hong Kong/1073/99(H9N2), Influenza B virus (B/Lee/1940) segment 2, complete sequence, Influenza B virus (B/Lee/1940) segment 3, complete sequence, Influenza B virus (B/Lee/1940) segment 4, complete sequence, Influenza B virus (B/Lee/1940) segment 5, complete sequence, Influenza B virus (B/Lee/1940) segment 6, complete sequence, Influenza B virus (B/Lee/1940) segment 7, complete sequence, Influenza B virus (B/Lee/1940) segment 8, complete sequence, Influenza B virus RNA 1, complete sequence, Influenza C virus (C/Ann Arbor/1/50) HEF gene for hemagglutinin-esterase-fusion, complete cds, Influenza C virus (C/Ann Arbor/1/50) M1, CM2 genes for matrix protein, CM2 protein, complete cds, Influenza C virus (C/Ann Arbor/1/50) P3 gene for polymerase 3, complete cds, Influenza C virus (C/Ann Arbor/1/50) PB1 gene for polymerase 1, complete cds, Influenza C virus (C/Ann Arbor/1/50) PB2 gene for polymerase 2, complete cds, Influenza C virus (C/Ann Arbor/1/50) segment 5, complete sequence, Influenza C virus (C/Ann Arbor/1/50) segment 7, complete sequence, *Neisseria gonorrhoeae* strain WHO F chromosome 1, Respiratory syncytial virus, complete genome, SARS coronavirus, complete genome, or *Streptococcus pyogenes* strain NCTC8198 chromosome 1.

NASBA

In certain example embodiments, the RNA or DNA amplification is NASBA, which is initiated with reverse transcription of target RNA by a sequence-specific reverse primer to create a RNA/DNA duplex. RNase H is then used to degrade the RNA template, allowing a forward primer containing a promoter, such as the T7 promoter, to bind and initiate elongation of the complementary strand, generating a double-stranded DNA product. The RNA polymerase promoter-mediated transcription of the DNA template then creates copies of the target RNA sequence. Importantly, each of the new target RNAs can be detected by the guide RNAs thus further enhancing the sensitivity of the assay. Binding of the target RNAs by the guide RNAs then leads to activation of the CRISPR effector protein and the methods proceed as outlined above. The NASBA reaction has the additional advantage of being able to proceed under moderate isothermal conditions, for example at approximately 41° C., making it suitable for systems and devices deployed for early and direct detection in the field and far from clinical laboratories.

RPA

In certain other example embodiments, a recombinase polymerase amplification (RPA) reaction may be used to amplify the target nucleic acids. RPA reactions employ recombinases which are capable of pairing sequence-specific primers with homologous sequence in duplex DNA. If target DNA is present, DNA amplification is initiated and no other sample manipulation such as thermal cycling or chemical melting is required. The entire RPA amplification system is stable as a dried formulation and can be transported safely without refrigeration. RPA reactions may also be carried out at isothermal temperatures with an optimum reaction temperature of 37-42° C. The sequence specific primers are designed to amplify a sequence comprising the target nucleic acid sequence to be detected. In certain example embodiments, a RNA polymerase promoter, such as a T7 promoter, is added to one of the primers. This results in an amplified double-stranded DNA product comprising the target sequence and a RNA polymerase promoter. After, or during, the RPA reaction, a RNA polymerase is added that will produce RNA from the double-stranded DNA templates. The amplified target RNA can then in turn be detected by the CRISPR effector system. In this way target DNA can be detected using the embodiments disclosed herein. RPA reactions can also be used to amplify target RNA. The target RNA is first converted to cDNA using a reverse transcriptase, followed by second strand DNA synthesis, at which point the RPA reaction proceeds as outlined above.

Transposase Based Amplification

Embodiments disclosed herein provide systems and methods for isothermal amplification of target nucleic acid sequences by contacting oligonucleotides containing the target nucleic acid sequence with a transposon complex. The oligonucleotides may be single stranded or double stranded RNA, DNA, or RNA/DNA hybrid oligonucleotides. The transposon complex comprises a transposase and a transposon sequence comprising one or more RNA polymerase promoters. The transposase facilitates insertion of the one or more RNA polymerase promoters into the oligonucleotide. A RNA polymerase promoter can then transcribe the target nucleic acid sequence from the inserted one or more RNA polymerase promoters. One advantage of this system is that there is no need to heat or melt double-stranded DNA templates, since RNA polymerase polymerases require a double-stranded template. Such isothermal amplification is fast and simple, obviating the need for complicated and expensive instrumentation for denaturation and cooling. In certain example embodiment the RNA polymerase promoter is a native of modified T7 RNA promoter.

The term "transposon", as used herein, refers to a nucleic acid segment, which is recognized by a transposase or an integrase enzyme and which is an essential component of a functional nucleic acid-protein complex (e.g. a transposome) capable of transposition. The term "transposase" as used herein refers to an enzyme, which is a component of a functional nucleic acid-protein complex capable of transposition and which is mediating transposition. The term "transposase" also refers to integrases from retrotransposons or of retroviral origin. Transposon complexes form between a transposase enzyme and a fragment of double stranded DNA that contains a specific binding sequence for the enzyme, termed "transposon end". The sequence of the transposon binding site can be modified with other bases, at certain positions, without affecting the ability for transposon complex to form a stable structure that can efficiently transpose into target DNA.

In embodiments provided herein, the transposon complex may comprise a transposase and a transposon sequence comprising one or more RNA polymerase promoters. The term "promoter" refers to a region of DNA involved in binding the RNA polymerase to initiate transcription. In specific embodiments, the RNA polymerase promoter may be a T7 RNA polymerase promoter. The T7 RNA promoter may be inserted into the double-stranded polynucleotide using the transposase. In some embodiments, insertion of the T7 RNA polymerase promoter into the oligonucleotide may be random.

The frequency of transposition is very low for most transposons, which use complex mechanisms to limit activity. Tn5 transposase, for example, utilizes a DNA binding sequence that is suboptimal and the C-terminus of the transposase interferes with DNA binding. Mechanisms involved in Tn5 transposition have been carefully characterized by Reznikoff and colleagues. Tn5 transposes by a cut-and-paste mechanism. The transposon has two pairs of 19 bp elements that are utilized by the transposase: outside elements (OE) and inside elements (IE). One transposase monomer binds to each of the two elements that are utilized. After a monomer is bound to each end of the transposon, the two monomers dimerize, forming a synapse. Vectors with donor backbones of at least 200 bp, but less than 1000 bp, are most functional for transposition in bacteria. Transposon cleavage occurs by trans catalysis and only when monomers bound to each DNA end are in a synaptic complex. Tn5 transposes with a relaxed target site selection and can therefore insert into target DNA with little to no target sequence specificity.

The natural downregulation of Tn5 transposition can be overcome by selection of a hyperactive transposase and by optimizing the transposase-binding elements [York et al. 1998]. A mosaic element (ME), made by modification of three bases of the wild type OE, led to a 50-fold increase in transposition events in bacteria as well as cell-free systems. The combined effect of the optimized ME and hyperactive mutant transposase is estimated to result in a 100-fold increase in transposition activity. Goryshin et al showed that preformed Tn5 transposition complexes could be functionally introduced into bacterial or yeast by electroporation [Goryshin et al. 2000]. Linearization of the DNA, to have inverted repeats precisely positioned at both ends of the transposon, allowed Goryshin and coworkers to bypass the cutting step of transposition thus enhancing transposition efficiency.

In some embodiments, the transposase may be used to tagment the oligonucleotide sequence comprising the target sequence. The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

In some embodiments, the transposase may be a Tn5 transposase. In some embodiments, the transposase may be a variant of a Tn5 transposase, or an engineered transposase. Transposases may be engineered using any method known in the art. The engineered transposase may be optimized to function at a temperature ranging from 30° C. to 45° C., 35° C. to 40° C. or any temperature in between. The engineered transposase may be optimized to release from the oligonucleotide at a faster rate compared to a wild type transposase.

In some embodiments, the transposase may be a Tn5 transposase, a Mu transposase, or a Tn7 transposase. Transposition efficiency in vitro may vary depending on the transposon system used. Generally, Tn5 and Mu transposases effect higher levels of transposition efficiency. In some embodiments, insertion may be random. In some embodiments, insertion may occur in GC rich regions of the target sequence.

In some embodiments, the transposon sequence may comprise two 19 base pair Mosaic End (ME) Tn5 transposase recognition sequences. Tn5 transposases will generally transpose any DNA sequence contained between such short 19 base pair ME Tn5 transposase recognition sequences.

In some embodiments, use of a transposase allows for separation of a double-stranded polynucleotide in the absence of heat or melting. Embodiments can be as described in PCT/US2019/039195, entitled CRISPR/Cas and Transposase Based Amplification Compositions, Systems and Methods, incorporated herein by reference.

Nickase Dependent Amplification

In an embodiment of the invention may comprise nickase-based amplification. The nicking enzyme may be a CRISPR protein. Accordingly, the introduction of nicks into dsDNA can be programmable and sequence-specific. In an embodiment of the invention, two guides can be designed to target opposite strands of a dsDNA target. According to the invention, the nickase can be Cpf1, Cas12b, Cas9 or any ortholog or CRISPR protein that cleaves or is engineered to cleave a single strand of a DNA duplex. The nicked strands may then be extended by a polymerase. In an embodiment, the locations of the nicks are selected such that extension of the strands by a polymerase is towards the central portion of the target duplex DNA between the nick sites. In certain embodiments, primers are included in the reaction capable of hybridizing to the extended strands followed by further polymerase extension of the primers to regenerate two dsDNA pieces: a first dsDNA that includes the first strand Cas12b guide site or both the first and second strand Cas12b guide sites, and a second dsDNA that includes the second strand Cas12b guide site or both the first and second strand Cas12b guide sites. These pieces continue to be nicked and extended in a cyclic reaction that exponentially amplifies the region of the target between nicking sites.

The amplification can be isothermal and selected for temperature. In one embodiment, the amplification proceeds rapidly at 37 degrees. In other embodiments, the temperature of the isothermal amplification may be chosen by selecting a polymerase (e.g. Bsu, Bst, Phi29, klenow fragment etc.). operable at a different temperature.

Thus, whereas nicking isothermal amplification techniques use nicking enzymes with fixed sequence preference (e.g. in nicking enzyme amplification reaction or NEAR), which requires denaturing of the original dsDNA target to allow annealing and extension of primers that add the nicking substrate to the ends of the target, use of a CRISPR nickase wherein the nicking sites can be programed via guide RNAs means that no denaturing step is necessary, enabling the entire reaction to be truly isothermal. This also simplifies the reaction because these primers that add the nicking substrate are different than the primers that are used later in the reaction, meaning that NEAR requires two primer sets (i.e. 4 primers) while Cas12b nicking amplification only requires one primer set (i.e. two primers). This makes nicking Cas12b amplification much simpler and easier to operate without complicated instrumentation to perform the denaturation and then cooling to the isothermal temperature.

In an aspect, the isothermal amplification reagents may be utilized with a thermostable CRISPR-Cas protein. The combination of thermostable protein and isothermal amplification reagents may be utilized to further improve reaction times for detection and diagnostics.

Accordingly, in certain example embodiments the systems disclosed herein may include amplification reagents. Different components or reagents useful for amplification of nucleic acids are described herein. For example, an amplification reagent as described herein may include a buffer, such as a Tris buffer. A Tris buffer may be used at any concentration appropriate for the desired application or use, for example including, but not limited to, a concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art will be able to determine an appropriate concentration of a buffer such as Tris for use with the present invention.

A salt, such as magnesium chloride ($MgCl_2$), potassium chloride (KCl), or sodium chloride (NaCl), may be included in an amplification reaction, such as PCR, in order to improve the amplification of nucleic acid fragments. Although the salt concentration will depend on the particular reaction and application, in some embodiments, nucleic acid fragments of a particular size may produce optimum results at particular salt concentrations. Larger products may require altered salt concentrations, typically lower salt, in order to produce desired results, while amplification of smaller products may produce better results at higher salt concentrations. One of skill in the art will understand that the presence and/or concentration of a salt, along with alteration of salt concentrations, may alter the stringency of a biological or chemical reaction, and therefore any salt may be used that provides the appropriate conditions for a reaction of the present invention and as described herein.

Other components of a biological or chemical reaction may include a cell lysis component in order to break open or lyse a cell for analysis of the materials therein. A cell lysis component may include, but is not limited to, a detergent, a salt as described above, such as NaCl, KCl, ammonium sulfate [$(NH_4)_2SO_4$], or others. Detergents that may be appropriate for the invention may include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40). Concentrations of detergents may depend on the particular application, and may be specific to the reaction in some cases. Amplification reactions may include dNTPs and nucleic acid primers used at any concentration appropriate for the invention, such as including, but not limited to, a concentration of 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, or the like. Likewise, a polymerase useful in accordance with the invention may be any specific or general polymerase known in the art and useful or the invention, including Taq polymerase, Q5 polymerase, or the like.

In some embodiments, amplification reagents as described herein may be appropriate for use in hot-start amplification. Hot start amplification may be beneficial in some embodiments to reduce or eliminate dimerization of adaptor molecules or oligos, or to otherwise prevent unwanted amplification products or artifacts and obtain optimum amplification of the desired product. Many components described herein for use in amplification may also be used in hot-start amplification. In some embodiments, reagents or components appropriate for use with hot-start amplification may be used in place of one or more of the composition components as appropriate. For example, a polymerase or other reagent may be used that exhibits a desired activity at a particular temperature or other reaction condition. In some embodiments, reagents may be used that are designed or optimized for use in hot-start amplification, for example, a polymerase may be activated after transposition or after reaching a particular temperature. Such polymerases may be antibody-based or aptamer-based. Polymerases as described herein are known in the art. Examples of such reagents may include, but are not limited to, hot-start polymerases, hot-start dNTPs, and photo-caged dNTPs. Such reagents are known and available in the art. One of skill in the art will be able to determine the optimum temperatures as appropriate for individual reagents.

Amplification of nucleic acids may be performed using specific thermal cycle machinery or equipment, and may be performed in single reactions or in bulk, such that any desired number of reactions may be performed simultaneously. In some embodiments, amplification may be performed using microfluidic or robotic devices, or may be performed using manual alteration in temperatures to achieve the desired amplification. In some embodiments, optimization may be performed to obtain the optimum reactions conditions for the particular application or materials. One of skill in the art will understand and be able to optimize reaction conditions to obtain sufficient amplification.

In certain embodiments, detection of DNA with the methods or systems of the invention requires transcription of the (amplified) DNA into RNA prior to detection.

It will be evident that detection methods of the invention can involve nucleic acid amplification and detection procedures in various combinations. The nucleic acid to be detected can be any naturally occurring or synthetic nucleic acid, including but not limited to DNA and RNA, which may be amplified by any suitable method to provide an intermediate product that can be detected. Detection of the intermediate product can be by any suitable method including but not limited to binding and activation of a CRISPR protein which produces a detectable signal moiety by direct or collateral activity.

Helicase-Dependent Amplification

In helicase-dependent amplification, a helicase enzyme is used to unwind a double stranded nucleic acid to generate templates for primer hybridization and subsequent primer-extension. This process utilizes two oligonucleotide primers, each hybridizing to the 3'-end of either the sense strand containing the target sequence or the anti-sense strand containing the reverse-complementary target sequence. The HDA reaction is a general method for helicase-dependent nucleic acid amplification.

In combining this method with a CRISPR-SHERLOCK system, the target nucleic acid may be amplified by opening R-loops of the target nucleic acid using first and second CRISPR/Cas complexes. The first and second strand of the target nucleic acid may thus be unwound using a helicase, allowing primers and polymerase to bind and extend the DNA under isothermal conditions.

The term "helicase" refers here to any enzyme capable of unwinding a double stranded nucleic acid enzymatically. For example, helicases are enzymes that are found in all organisms and in all processes that involve nucleic acid such as replication, recombination, repair, transcription, translation and RNA splicing. (Kornberg and Baker, DNA Replication, W. H. Freeman and Company ($2^{nd}$ ed. (1992)), especially chapter 11). Any helicase that translocates along DNA or RNA in a 5' to 3' direction or in the opposite 3' to 5' direction may be used in present embodiments of the invention. This includes helicases obtained from prokaryotes, viruses, archaea, and eukaryotes or recombinant forms of naturally occurring enzymes as well as analogues or derivatives having the specified activity. Examples of naturally occurring DNA helicases, described by Kornberg and Baker in chapter 11 of their book, DNA Replication, W. H. Freeman and Company ($2^{nd}$ ed. (1992)), include *E. coli* helicase I, II, III, & IV, Rep, DnaB, PriA, PcrA, T4 Gp41helicase, T4 Dda helicase, T7 Gp4 helicases, SV40 Large T antigen, yeast RAD. Additional helicases that may be useful in HDA include RecQ helicase (Harmon and Kowalczykowski, *J. Biol. Chem.* 276:232-243 (2001)), thermostable UvrD helicases from *T. tengcongensis* (disclosed in this invention, Example XII) and *T. thermophilus* (Collins and McCarthy, *Extremophiles.* 7:35-41. (2003)), thermostable DnaB helicase from *T. aquaticus* (Kaplan and Steitz, *J. Biol. Chem.* 274:6889-6897 (1999)), and MCM helicase from archaeal and eukaryotic organisms ((Grainge et al., *Nucleic Acids Res.* 31:4888-4898 (2003)).

A traditional definition of a helicase is an enzyme that catalyzes the reaction of separating/unzipping/unwinding the helical structure of nucleic acid duplexes (DNA, RNA or hybrids) into single-stranded components, using nucleoside triphosphate (NTP) hydrolysis as the energy source (such as ATP). However, it should be noted that not all helicases fit this definition anymore. A more general definition is that they are motor proteins that move along the single-stranded or double stranded nucleic acids (usually in a certain direction, 3' to 5' or 5 to 3, or both), i.e. translocases, that can or cannot unwind the duplexed nucleic acid encountered. In addition, some helicases simply bind and "melt" the duplexed nucleic acid structure without an apparent translocase activity.

Helicases exist in all living organisms and function in all aspects of nucleic acid metabolism. Helicases are classified based on the amino acid sequences, directionality, oligomerization state and nucleic-acid type and structure preferences. The most common classification method was developed based on the presence of certain amino acid sequences, called motifs. According to this classification helicases are divided into 6 super families: SF1, SF2, SF3, SF4, SF5 and SF6. SF1 and SF2 helicases do not form a ring structure around the nucleic acid, whereas SF3 to SF6 do. Superfamily classification is not dependent on the classical taxonomy.

DNA helicases are responsible for catalyzing the unwinding of double-stranded DNA (dsDNA) molecules to their respective single-stranded nucleic acid (ssDNA) forms. Although structural and biochemical studies have shown how various helicases can translocate on ssDNA directionally, consuming one ATP per nucleotide, the mechanism of nucleic acid unwinding and how the unwinding activity is regulated remains unclear and controversial (T. M. Lohman, E. J. Tomko, C. G. Wu, "Non-hexameric DNA helicases and translocases: mechanisms and regulation," Nat Rev Mol Cell Biol 9:391-401 (2008)). Since helicases can potentially unwind all nucleic acids encountered, understanding how their unwinding activities are regulated can lead to harnessing helicase functions for biotechnology applications.

The term "HDA" refers to Helicase Dependent Amplification, which is an in vitro method for amplifying nucleic acids by using a helicase preparation for unwinding a double stranded nucleic acid to generate templates for primer hybridization and subsequent primer-extension. This process utilizes two oligonucleotide primers, each hybridizing to the 3'-end of either the sense strand containing the target sequence or the anti-sense strand containing the reverse-complementary target sequence. The HDA reaction is a general method for helicase-dependent nucleic acid amplification.

The invention comprises use of any suitable helicase known in the art. These include, but are not necessarily limited to, UvrD helicase, CRISPR-Cas3 helicase, *E. coli* helicase I, *E. coli* helicase II, *E. coli* helicase III, *E. coli* helicase IV, Rep helicase, DnaB helicase, PriA helicase, PcrA helicase, T4 Gp41 helicase, T4 Dda helicase, SV40 Large T antigen, yeast RAD helicase, RecD helicase, RecQ helicase, thermostable *T. tengcongensis* UvrD helicase, thermostable *T. thermophilus* UvrD helicase, thermostable *T. aquaticus* DnaB helicase, Dda helicase, papilloma virus E1 helicase, archaeal MCM helicase, eukaryotic MCM helicase, and T7 Gp4 helicase.

In particularly preferred embodiments, the helicase comprises a super mutation. In particular embodiments, Although the *E coli* mutation has been described, the mutations were generated by sequence alignment (e.g. D409A/D410A for TteUvrd) and result in thermophilic enzymes working at lower temperatures like 37° C., which is advantageous for amplification methods and systems described herein. In some embodiments, the super mutations is an aspartate to alanine mutation, with position based on sequence alignment. In some embodiments, the super mutant helicase is selected from WP 003870487.1 *Thermoanaerobacter* ethanolicus 403/404, WP_049660019.1 *Bacillus* sp. FJAT-27231 407/408, WP_034654680.1 *Bacillus megaterium* 415/416, WP_095390358.1 *Bacillus simplex* 407/408, and WP_055343022.1 *Paeniclostridium sordellii* 402/403.

Incubating

Methods of detection and/or extraction using the systems disclosed herein can comprise incubating the sample or set of samples under conditions sufficient to allow binding of the guide RNAs to one or more target molecules. Extraction can comprise incubating the sample under conditions sufficient to allow release of viral RNA or DNA molecules amplified from the viral RNA present in the sample, which may comprise incubating at 22° C. to 60° C. for 30 to 70 minutes or at 90° C.-100° C. for about 10 minutes.

In certain example embodiments, the incubation time of the amplifying and detecting in the present invention may be shortened. The assay may be performed in a period of time required for an enzymatic reaction to occur. One skilled in the art can perform biochemical reactions in 5 minutes (e.g., 5 minute ligation). Incubating may occur at one or more temperatures over timeframes between about 10 minutes and 90 minutes, preferably less than 90 minutes, 75 minutes, 60 minutes, 45 minutes, 30 minutes, 25 minutes, 20 minutes, 15 minutes, or 10 minutes depending on sample, reagents and components of the system. In some embodiments, incubating for the amplification is performed at one or more temperatures between about 20° C. and 80° C., in some embodiments, about 37° C. In some embodiments, incubating for the amplification is performed at one or more temperatures between about 55° C. and 65° C., between about 59° C. and 61° C., in some embodiments, about 60° C.

Activating

In certain example embodiment, activating of the Cas protein occurs via binding of the CRISPR-Cas complex via the guide molecule to the one or more target molecules, wherein activating the CRISPR effector protein results in modification of the detection construct such that a detectable positive signal is generated.

Detecting a Signal

Detecting may comprise visual observance of a positive signal relative to a control. Detecting may comprise a loss of signal or presence of signal at one or more capture regions, for example colorimetric detection, or fluorescent detection. In certain example embodiments, further modifications may be introduced that further amplify the detectable positive signal. For example, activated CRISPR effector protein collateral activation may be used to generate a secondary target or additional guide sequence, or both. In one example embodiment, the reaction solution would contain a secondary target that is spiked in at high concentration. The secondary target may be distinct from the primary target (i.e. the target for which the assay is designed to detect) and in certain instances may be common across all reaction volumes. A secondary guide sequence for the secondary target may be protected, e.g. by a secondary structural feature such as a hairpin with an RNA loop, and unable to bind the second target or the CRISPR effector protein. Cleavage of the protecting group by an activated CRISPR effector protein (i.e. after activation by formation of complex with the primary target(s) in solution) and formation of a complex with free CRISPR effector protein in solution and activation from the spiked in secondary target. In certain other example embodiments, a similar concept is used with free guide sequence to a secondary target and protected secondary target. Cleavage of a protecting group off the secondary target would allow additional CRISPR effector protein, guide sequence, secondary target sequence to form. In yet another example embodiment, activation of CRISPR effector protein by the primary target(s) may be used to cleave a protected or circularized primer, which would then be released to perform an isothermal amplification reaction, such as those disclosed herein, on a template for either secondary guide sequence, secondary target, or both. Subsequent transcription of this amplified template would produce more secondary guide sequence and/or secondary target sequence, followed by additional CRISPR effector protein collateral activation.

Quantifying

In particular methods, comparing the intensity of the one or more signals to a control is performed to quantify the nucleic acid in the sample. The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue, fluid, or cells isolated from a subject, such as a normal patient or the patient having a condition of interest.

The intensity of a signal is "significantly" higher or lower than the normal intensity if the signal is greater or less, respectively, than the normal or control level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the signal can be considered "significantly" higher or lower than the normal and/or control signal if the amount is at least about two, and preferably at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, two times, three times, four times, five times, or more, or any range in between, such as 5%-100%, higher or lower, respectively, than the normal and/or control signal. Such significant modulation values can be applied to any metric described herein, such as altered level of expression, altered activity, changes in biomarker inhibition, changes in test agent binding, and the like.

In some embodiments, the detectable positive signal may be a loss of fluorescent signal or colorimetric relative to a control, as described herein. In some embodiments, the detectable positive signal may be detected on a lateral flow device, as described herein.

Applications of Detection Methods

Systems and methods can be designed for the detection and diagnosis of microbes, including bacterial, fungi and viral microbes. In an aspect, the systems may comprise multiplex detection of multiple variants of viral infections, including coronavirus, different viruses which may be related coronaviruses or respiratory viruses, or a combination thereof. In embodiments, assays can be performed for a variety of viruses and viral infections, including acute respiratory infections using the disclosure detailed herein. The systems can comprise two or more CRISPR Cas systems to multiplex, as described elsewhere herein, to detect a plurality of respiratory infections or viral infections, including coronavirus. The coronavirus is a positive-sense single stranded RNA family of viruses, infecting a variety of animals and humans. SARS-CoV is one type of coronavirus infection, as well as MERS-CoV Detection of one or more coronaviruses are envisioned, including the 2019-nCoV detected in Wuhan City. Sequences of the 2019-nCoV are available at GISAID accession no. EPI_ISL_402124 and EPI_ISL_402127-402130, and described in DOI: 10.1101/

2020.01.22.914952. Further deposits of the SARS-CoV-2 deposited in the GISAID platform include EP_ISL_402119-402121 and EP_ISL_402123-402124; see also GenBank Accession No. MN908947.3.

Target molecule detection can comprise two or more detection systems utilizing RNA targeting Cas effector proteins; DNA targeting Cas effector proteins, or a combination thereof. The RNA-targeting effector proteins may be a Cas13 protein, such as Cas13a, Cas13b, or Cas13c, including one of the thermostable Cas13a proteins described herein. The DNA-targeting effector protein may be a Type V protein, e.g. Cas12 protein such as Cpf1 and Cas12b. The Cas protein may preferably be thermostable, such as BrCas12b or Aap Cas12b. Multiplexing systems can be designed such that different Cas proteins with different sequence specificities or other motif cutting preferences can be used, including, in certain embodiments, at least one Cas. thermostable protein described herein. See International Publication WO 2019/126577. Type VI and Type V Cas proteins are known to possess different cutting motif preferences. See Gootenberg et al. "Multiplexed and portable nucleic acid detection platform with Cas13b, Cas12a, and Csm6." Science. Apr. 27, 2018, 360:439-444; International Publication WO 2019/051318. Thus, embodiments disclosed herein may further comprise multiplex embodiments comprising two or more Type VI Cas proteins with different cutting preferences, or one or more Type VI Cas proteins and one or more Type V Cas proteins.

Multiplex approaches and selection of Cas effector proteins can be as described in International Publication WO 2019/126577 at [0415]-[0416] and Examples 1-10, incorporated herein by reference. In certain example embodiments, the coronavirus assay comprises a Type VI Cas protein disclosed herein and guide molecule comprising a guide sequence configured to directed binding of the CRISPR-Cas complex to a target molecule and a labeled detection molecule ("RNA-based masking construct"). A multiplex embodiment can be designed to track one or more variants of coronavirus or one or more variants of coronavirus, including SARS-CoV-2, in combination with other viruses, for example, Human respiratory syncytial virus, Middle East respiratory syndrome (MERS) coronavirus, Severe acute respiratory syndrome-related (SARS) coronavirus, and influenza. In embodiments, assays can be done in multiplex to detect multiple variants of coronavirus, different viruses which may be related coronaviruses or respiratory viruses, or a combination thereof. In an aspect, each assay can take place in an individual discrete volume. An "individual discrete volume" is a discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electromagnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents maybe passed in Applicants' through the discrete volume, while other material, such as target molecules, maybe maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate.

In certain example embodiments, the systems, devices, and methods, disclosed herein are directed to detecting the presence of one or more microbial agents in a sample, such as a biological sample obtained from a subject. In certain example embodiments, the microbe may be a *bacterium*, a fungus, a yeast, a protozoan, a parasite, or a virus. Accordingly, the methods disclosed herein can be adapted for use in other methods (or in combination) with other methods that require quick identification of microbe species, monitoring the presence of microbial proteins (antigens), antibodies, antibody genes, detection of certain phenotypes (e.g. bacterial resistance), monitoring of disease progression and/or outbreak, and antibiotic screening. Because of the rapid and sensitive diagnostic capabilities of the embodiments disclosed here, detection of microbe species type, down to a single nucleotide difference, and the ability to be deployed as a POC device, the embodiments disclosed herein may be used as guide therapeutic regimens, such as a selection of the appropriate antibiotic or antiviral. The embodiments disclosed herein may also be used to screen environmental samples (air, water, surfaces, food etc.) for the presence of microbial contamination.

Disclosed is a method to identify microbial species, such as bacterial, viral, fungal, yeast, or parasitic species, or the like. Particular embodiments disclosed herein describe methods and systems that will identify and distinguish microbial species within a single sample, or across multiple samples, allowing for recognition of many different microbes. The present methods allow the detection of pathogens and distinguishing between two or more species of one or more organisms, e.g., bacteria, viruses, yeast, protozoa, and fungi or a combination thereof, in a biological or environmental sample, by detecting the presence of a target nucleic acid sequence in the sample. A positive signal obtained from the sample indicates the presence of the microbe. Multiple microbes can be identified simultaneously using the methods and systems of the invention, by employing the use of more than one effector protein, wherein each effector protein targets a specific microbial target sequence. In this way, a multi-level analysis can be performed for a particular subject in which any number of microbes can be detected at once, for example, a subject with unknown respiratory infection, having symptoms of coronavirus, or an individual at risk or having been exposed to coronavirus. In some embodiments, simultaneous detection of multiple microbes may be performed using a set of probes that can identify one or more microbial species.

Microbe Detection

In some embodiments, a method for detecting microbes in samples is provided comprising distributing a sample or set of samples into one or more individual discrete volumes, the individual discrete volumes comprising a CRISPR system as described herein; incubating the sample or set of samples under conditions sufficient to allow binding of the one or more guide RNAs to one or more microbe-specific targets; activating the CRISPR effector protein via binding of the one or more guide RNAs to the one or more target molecules, wherein activating the CRISPR effector protein results in modification of the RNA-based masking construct such that a detectable positive signal is generated; and detecting the detectable positive signal, wherein detection of the detectable positive signal indicates a presence of one or more target molecules in the sample. The one or more target molecules may be mRNA, gDNA (coding or non-coding), trRNA, or rRNA comprising a target nucleotide sequence that may be used to distinguish two or more microbial species/strains from one another. The one or more target molecules also include DNA molecules derived from the RNA molecules, e.g., by reverse transcription and amplification. The guide RNAs may be designed to detect target sequences. The embodiments disclosed herein may also utilize certain steps to improve hybridization between guide RNA and target RNA sequences. Methods for enhancing ribonucleic acid hybridization are disclosed in WO 2015/085194, entitled "Enhanced Methods of Ribonucleic Acid Hybridization" which is incorporated herein by reference. The microbe-specific target may be RNA or DNA or a protein. If DNA method may further comprise the use of DNA primers that introduce a RNA polymerase promoter as described herein. If the target is a protein than the method will utilized aptamers and steps specific to protein detection described herein.

Detection of Single Nucleotide Variants

In some embodiments, one or more identified target sequences may be detected using guide RNAs that are specific for and bind to the target sequence as described herein. The systems and methods of the present invention can distinguish even between single nucleotide polymorphisms present among different microbial species and therefore, use of multiple guide RNAs in accordance with the invention may further expand on or improve the number of target sequences that may be used to distinguish between species. For example, in some embodiments, the one or more guide RNAs may distinguish between microbes at the species, genus, family, order, class, phylum, kingdom, or phenotype, or a combination thereof.

Detection Based on rRNA Sequences

In certain example embodiments, the devices, systems, and methods disclosed herein may be used to distinguish multiple microbial species in a sample. In certain example embodiments, identification may be based on ribosomal RNA sequences, including the 16S, 23S, and 5S subunits. Methods for identifying relevant rRNA sequences are disclosed in U.S. Patent Application Publication No. 2017/0029872. In certain example embodiments, a set of guide RNA may designed to distinguish each species by a variable region that is unique to each species or strain. Guide RNAs may also be designed to target RNA genes that distinguish microbes at the genus, family, order, class, phylum, kingdom levels, or a combination thereof. In certain example embodiments where amplification is used, a set of amplification primers may be designed to flanking constant regions of the ribosomal RNA sequence and a guide RNA designed to distinguish each species by a variable internal region. In certain example embodiments, the primers and guide RNAs may be designed to conserved and variable regions in the 16S subunit respectfully. Other genes or genomic regions that uniquely variable across species or a subset of species such as the RecA gene family, RNA polymerase β subunit, may be used as well. Other suitable phylogenetic markers, and methods for identifying the same, are discussed for example in Wu et al. arXiv:1307.8690 [q-bio.GN].

In certain example embodiments, a method or diagnostic is designed to screen microbes across multiple phylogenetic and/or phenotypic levels at the same time. For example, the method or diagnostic may comprise the use of multiple CRISPR systems with different guide RNAs. A first set of guide RNAs may distinguish, for example, between mycobacteria, gram positive, and gram negative bacteria. These general classes can be even further subdivided. For example, guide RNAs could be designed and used in the method or diagnostic that distinguish enteric and non-enteric within gram negative bacteria. A second set of guide RNA can be designed to distinguish microbes at the genus or species level. Thus a matrix may be produced identifying all mycobacteria, gram positive, gram negative (further divided into enteric and non-enteric) with each genus of species of bacteria identified in a given sample that fall within one of those classes. The foregoing is for example purposes only. Other means for classifying other microbe types are also contemplated and would follow the general structure described above.

Screening for Drug Resistance

In certain example embodiments, the devices, systems and methods disclosed herein may be used to screen for microbial genes of interest, for example antibiotic and/or antiviral resistance genes. Guide RNAs may be designed to distinguish between known genes of interest. Samples, including clinical samples, may then be screened using the embodiments disclosed herein for detection of such genes. The ability to screen for drug resistance at POC would have tremendous benefit in selecting an appropriate treatment regime. In certain example embodiments, the antibiotic resistance genes are carbapenemases including KPC, NDM1, CTX-M15, OXA-48. Other antibiotic resistance genes are known and may be found for example in the Comprehensive Antibiotic Resistance Database (Jia et al. "CARD 2017: expansion and model-centric curation of the Comprehensive Antibiotic Resistance Database." Nucleic Acids Research, 45, D566-573).

Ribavirin is an effective antiviral that hits a number of RNA viruses. Several clinically important viruses have evolved ribavirin resistance including Foot and Mouth Disease Virus doi:10.1128/JVI.03594-13; polio virus (Pfeifer and Kirkegaard. PNAS, 100(12):7289-7294, 2003); and hepatitis C virus (Pfeiffer and Kirkegaard, J. Virol. 79(4): 2346-2355, 2005). A number of other persistent RNA viruses, such as hepatitis and HIV, have evolved resistance to existing antiviral drugs: hepatitis B virus (lamivudine, tenofovir, entecavir) doi:10/1002/hep22900; hepatitis C virus (telaprevir, BILN2061, ITMN-191, SCh6, boceprevir, AG-021541, ACH-806) doi:10.1002/hep.22549; and HIV (many drug resistance mutations) hivb.standford.edu. The embodiments disclosed herein may be used to detect such variants among others.

Aside from drug resistance, there are a number of clinically relevant mutations that could be detected with the embodiments disclosed herein, such as persistent versus acute infection in LCMV (doi:10.1073/pnas.1019304108), and increased infectivity of Ebola (Diehl et al. Cell. 2016, 167(4):1088-1098.

As described herein elsewhere, closely related microbial species (e.g. having only a single nucleotide difference in a given target sequence) may be distinguished by introduction of a synthetic mismatch in the gRNA.

Monitoring Microbe Outbreaks

In some embodiments, a CRISPR system or methods of use thereof as described herein may be used to determine the evolution of a pathogen outbreak. The method may comprise detecting one or more target sequences from a plurality of samples from one or more subjects, wherein the target sequence is a sequence from a microbe causing the outbreaks. Such a method may further comprise determining a pattern of pathogen transmission, or a mechanism involved in a disease outbreak caused by a pathogen.

The pattern of pathogen transmission may comprise continued new transmissions from the natural reservoir of the pathogen or subject-to-subject transmissions (e.g. human-to-human transmission) following a single transmission from the natural reservoir or a mixture of both. In one embodiment, the pathogen transmission may be bacterial or viral transmission, in such case, the target sequence is preferably a microbial genome or fragments thereof. In one embodiment, the pattern of the pathogen transmission is the early pattern of the pathogen transmission, i.e. at the beginning of the pathogen outbreak. Determining the pattern of the pathogen transmission at the beginning of the outbreak increases likelihood of stopping the outbreak at the earliest possible time thereby reducing the possibility of local and international dissemination.

Determining the pattern of the pathogen transmission may comprise detecting a pathogen sequence according to the methods described herein. Determining the pattern of the pathogen transmission may further comprise detecting shared intra-host variations of the pathogen sequence between the subjects and determining whether the shared intra-host variations show temporal patterns. Patterns in observed intrahost and interhost variation provide important insight about transmission and epidemiology (Gire, et al., 2014).

Detection of shared intra-host variations between the subjects that show temporal patterns is an indication of transmission links between subject (in particular between humans) because it can be explained by subject infection from multiple sources (superinfection), sample contamination recurring mutations (with or without balancing selection to reinforce mutations), or co-transmission of slightly divergent viruses that arose by mutation earlier in the transmission chain (Park, et al., Cell 161(7):1516-1526, 2015). Detection of shared intra-host variations between subjects may comprise detection of intra-host variants located at common single nucleotide polymorphism (SNP) positions. Positive detection of intra-host variants located at common (SNP) positions is indicative of superinfection and contamination as primary explanations for the intra-host variants. Superinfection and contamination can be parted on the basis of SNP frequency appearing as inter-host variants (Park, et al., 2015). Otherwise superinfection and contamination can be ruled out. In this latter case, detection of shared intra-host variations between subjects may further comprise assessing the frequencies of synonymous and nonsynonymous variants and comparing the frequency of synonymous and nonsynonymous variants to one another. A nonsynonymous mutation is a mutation that alters the amino acid of the protein, likely resulting in a biological change in the microbe that is subject to natural selection. Synonymous substitution does not alter an amino acid sequence. Equal frequency of synonymous and nonsynonymous variants is indicative of the intra-host variants evolving neutrally. If frequencies of synonymous and nonsynonymous variants are divergent, the intra-host variants are likely to be maintained by balancing selection. If frequencies of synonymous and nonsynonymous variants are low, this is indicative of recurrent mutation. If frequencies of synonymous and nonsynonymous variants are high, this is indicative of co-transmission (Park, et al., 2015).

Like Ebola virus, Lassa virus (LASV) can cause hemorrhagic fever with high case fatality rates. Andersen et al. generated a genomic catalog of almost 200 LASV sequences from clinical and rodent reservoir samples (Andersen, et al., Cell Volume 162, Issue 4, p 738-750, 13 Aug. 2015). Andersen et al. show that whereas the 2013-2015 EVD epidemic is fueled by human-to-human transmissions, LASV infections mainly result from reservoir-to-human infections. Andersen et al. elucidated the spread of LASV across West Africa and show that this migration was accompanied by changes in LASV genome abundance, fatality rates, codon adaptation, and translational efficiency. The method may further comprise phylogenetically comparing a first pathogen sequence to a second pathogen sequence, and determining whether there is a phylogenetic link between the first and second pathogen sequences. The second pathogen sequence may be an earlier reference sequence. If there is a phylogenetic link, the method may further comprise rooting the phylogeny of the first pathogen sequence to the second pathogen sequence. Thus, it is possible to construct the lineage of the first pathogen sequence. (Park, et al., 2015).

The method may further comprise determining whether the mutations are deleterious or adaptive. Deleterious mutations are indicative of transmission-impaired viruses and dead-end infections, thus normally only present in an individual subject. Mutations unique to one individual subject are those that occur on the external branches of the phylogenetic tree, whereas internal branch mutations are those present in multiple samples (i.e. in multiple subjects). Higher rate of nonsynonymous substitution is a characteristic of external branches of the phylogenetic tree (Park, et al., 2015).

In internal branches of the phylogenetic tree, selection has had more opportunity to filter out deleterious mutants. Internal branches, by definition, have produced multiple descendent lineages and are thus less likely to include mutations with fitness costs. Thus, lower rate of nonsynonymous substitution is indicative of internal branches (Park, et al., 2015).

Synonymous mutations, which likely have less impact on fitness, occurred at more comparable frequencies on internal and external branches (Park, et al., 2015).

By analyzing the sequenced target sequence, such as viral genomes, it is possible to discover the mechanisms responsible for the severity of the epidemic episode such as during the 2014 Ebola outbreak. For example, Gire et al. made a phylogenetic comparison of the genomes of the 2014 outbreak to all 20 genomes from earlier outbreaks suggests that the 2014 West African virus likely spread from central Africa within the past decade. Rooting the phylogeny using divergence from other ebolavirus genomes was problematic (6, 13). However, rooting the tree on the oldest outbreak revealed a strong correlation between sample date and root-to-tip distance, with a substitution rate of $8 \times 10-4$ per site per year (13). This suggests that the lineages of the three most recent outbreaks all diverged from a common ancestor at roughly the same time, around 2004, which supports the hypothesis that each outbreak represents an independent zoonotic event from the same genetically diverse viral population in its natural reservoir. They also found out that the 2014 EBOV outbreak might be caused by a single transmission from the natural reservoir, followed by human-to-human transmission during the outbreak. Their results also suggested that the epidemic episode in Sierra Leon might stem from the introduction of two genetically distinct viruses from Guinea around the same time (Gire, et al., 2014).

It has been also possible to determine how the Lassa virus spread out from its origin point, in particular thanks to human-to-human transmission and even retrace the history of this spread 400 years back (Andersen, et al., *Cell* 162(4): 738-50, 2015).

In relation to the work needed during the 2013-2015 EBOV outbreak and the difficulties encountered by the medical staff at the site of the outbreak, and more generally, the method of the invention makes it possible to carry out sequencing using fewer selected probes such that sequencing can be accelerated, thus shortening the time needed from sample taking to results procurement. Further, kits and systems can be designed to be usable on the field so that diagnostics of a patient can be readily performed without need to send or ship samples to another part of the country or the world.

In any method described above, sequencing the target sequence or fragment thereof may be used any of the sequencing processes described above. Further, sequencing the target sequence or fragment thereof may be a near-real-time sequencing. Sequencing the target sequence or fragment thereof may be carried out according to previously described methods (Experimental Procedures: Matranga et al., 2014; and Gire, et al., 2014). Sequencing the target sequence or fragment thereof may comprise parallel sequencing of a plurality of target sequences. Sequencing the target sequence or fragment thereof may comprise Illumina sequencing.

Analyzing the target sequence or fragment thereof that hybridizes to one or more of the selected probes may be an identifying analysis, wherein hybridization of a selected probe to the target sequence or a fragment thereof indicates the presence of the target sequence within the sample.

Currently, primary diagnostics are based on the symptoms a patient has. However, various diseases may share identical symptoms so that diagnostics rely much on statistics. For example, malaria triggers flu-like symptoms: headache, fever, shivering, joint pain, vomiting, hemolytic anemia, jaundice, hemoglobin in the urine, retinal damage, and convulsions. These symptoms are also common for septicemia, gastroenteritis, and viral diseases. Amongst the latter, Ebola hemorrhagic fever has the following symptoms fever, sore throat, muscular pain, headaches, vomiting, diarrhea, rash, decreased function of the liver and kidneys, internal and external hemorrhage.

When a patient is presented to a medical unit, for example in tropical Africa, basic diagnostics will conclude to malaria because statistically, malaria is the most probable disease within that region of Africa. The patient is consequently treated for malaria although the patient might not actually have contracted the disease and the patient ends up not being correctly treated. This lack of correct treatment can be life-threatening especially when the disease the patient contracted presents a rapid evolution. It might be too late before the medical staff realizes that the treatment given to the patient is ineffective and comes to the correct diagnostics and administers the adequate treatment to the patient.

The method of the invention provides a solution to this situation. Indeed, because the number of guide RNAs can be dramatically reduced, this makes it possible to provide on a single chip selected probes divided into groups, each group being specific to one disease, such that a plurality of diseases, e.g. viral infection, can be diagnosed at the same time. Thanks to the invention, more than 3 diseases can be diagnosed on a single chip, preferably more than 4, 5, 6, 7, 8, 9, 10, 11, 12, 13, 14, 15, 16, 17, 18, 19, 20 diseases at the same time, preferably the diseases that most commonly occur within the population of a given geographical area. Since each group of selected probes is specific to one of the diagnosed diseases, a more accurate diagnosis can be performed, thus diminishing the risk of administering the wrong treatment to the patient.

In other cases, a disease such as a viral infection may occur without any symptoms, or had caused symptoms but they faded out before the patient is presented to the medical staff. In such cases, either the patient does not seek any medical assistance or the diagnostics is complicated due to the absence of symptoms on the day of the presentation.

The present invention may also be used in concert with other methods of diagnosing disease, identifying pathogens and optimizing treatment based upon detection of nucleic acids, such as mRNA in crude, non-purified samples.

The method of the invention also provides a powerful tool to address this situation. Indeed, since a plurality of groups of selected guide RNAs, each group being specific to one of the most common diseases that occur within the population of the given area, are comprised within a single diagnostic, the medical staff only need to contact a biological sample taken from the patient with the chip. Reading the chip reveals the diseases the patient has contracted.

In some cases, the patient is presented to the medical staff for diagnostics of particular symptoms. The method of the invention makes it possible not only to identify which disease causes these symptoms but at the same time determine whether the patient suffers from another disease he was not aware of.

This information might be of utmost importance when searching for the mechanisms of an outbreak. Indeed, groups of patients with identical viruses also show temporal patterns suggesting a subject-to-subject transmission links.

Example Microbes

The embodiment disclosed herein may be used to detect a number of different microbes. The term microbe as used herein includes bacteria, fungus, protozoa, parasites and viruses.

Bacteria

The following provides an example list of the types of microbes that might be detected using the embodiments disclosed herein. In certain example embodiments, the microbe is a *bacterium*. Examples of bacteria that can be detected in accordance with the disclosed methods include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii* biovar *sobria (Aeromonas sobria)*, and *Aeromonas caviae*), *Anaplasma phagocytophilum, Anaplasma marginate Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtherias, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli) Enterococcus* sp. (such as *Enterococcus faecalis* and *Enterococcus faecium*) *Ehrlichia* sp. (such as *Ehrlichia chafeensia* and *Ehrlichia canis*), *Epidermophyton floccosum, Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus), Helicobacter* sp. (such as *Helicobacter pylori, Helicobacter cinaedi* and *Helicobacter fennelliae), Kingella kingii, Klebsiella* sp. (such as *Klebsiella pneumoniae, Klebsiella granulomatis* and *Klebsiella oxytoca), Lactobacillus* sp., *Listeria monocytogenes, Leptospira interrogans, Legionella pneumophila, Leptospira interrogans, Peptostreptococcus* sp., *Mannheimia hemolytica, Microsporum canis, Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis, Mycobacterium intracellulare, Mycobacterium avium, Mycobacterium bovis*, and *Mycobacterium marinum*), *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Pityrosporum orbiculare (Malassezia furfur), Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi), Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes,* Group A streptococci, *Streptococcus pyogenes,* Group B streptococci, *Streptococcus agalactiae,* Group C streptococci, *Streptococcus anginosus, Streptococcus equismilis,* Group D streptococci, *Streptococcus bovis,* Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Trichophyton rubrum, T mentagrophytes, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii), Yersinia* sp. (such as *Yersinia enterocolitica, Yersinia pestis*, and *Yersinia pseudotuberculosis*) and *Xanthomonas maltophilia* among others.

Fungi

In certain example embodiments, the microbe is a fungus or a fungal species. Examples of fungi that can be detected in accordance with the disclosed methods include without limitation any one or more of (or any combination of), *Aspergillus, Blastomyces, Candidiasis, Coccidiodomycosis, Cryptococcus neoformans, Cryptococcus gatti,* sp. *Histoplasma* sp. (such as *Histoplasma capsulatum), Pneumocystis* sp. (such as *Pneumocystis jirovecii*), *Stachybotrys* (such as *Stachybotrys chartarum*), *Mucroymcosis, Sporothrix*, fungal eye infections ringworm, *Exserohilum, Cladosporium*.

In certain example embodiments, the fungus is a yeast. Examples of yeast that can be detected in accordance with disclosed methods include without limitation one or more of (or any combination of), *Aspergillus* species (such as *Aspergillus fumigatus, Aspergillus flavus* and *Aspergillus clavatus*), *Cryptococcus* sp. (such as *Cryptococcus neoformans, Cryptococcus gattii, Cryptococcus laurentii* and *Cryptococcus albidus*), a *Geotrichum* species, a *Saccharomyces* species, a *Hansenula* species, a *Candida* species (such as *Candida albicans*), a *Kluyveromyces* species, a *Debaryomyces* species, a *Pichia* species, or combination thereof. In certain example embodiments, the fungi is a mold. Example molds include, but are not limited to, a *Penicillium* species, a *Cladosporium* species, a *Byssochlamys* species, or a combination thereof.

Protozoa

In certain example embodiments, the microbe is a protozoa. Examples of protozoa that can be detected in accordance with the disclosed methods and devices include without limitation any one or more of (or any combination of), *Euglenozoa, Heterolobosea, Diplomonadida, Amoebozoa, Blastocystic*, and *Apicomplexa*. Example *Euglenoza* include, but are not limited to, *Trypanosoma cruzi* (Chagas disease), *T. brucei gambiense, T. brucei rhodesiense, Leishmania braziliensis, L. infantum, L. mexicana, L. major, L. tropica*, and *L. donovani*. Example Heterolobosea include, but are not limited to, *Naegleria fowleri*. Example Diplomonadids include, but are not limited to, Giardia intestinalis (*G. lamblia, G. duodenalis*). Example Amoebozoa include, but are not limited to, *Acanthamoeba castellanii, Balamuthia madrillaris, Entamoeba histolytica*. Example Blastocysts include, but are not limited to, *Blastocystic hominis*. Example *Apicomplexa* include, but are not limited to, *Babesia microti, Cryptosporidium parvum, Cyclospora cayetanensis, Plasmodium falciparum, P. vivax, P. ovale, P. malariae*, and *Toxoplasma gondii*.

Parasites

In certain example embodiments, the microbe is a parasite. Examples of parasites that can be detected in accordance with disclosed methods include without limitation one or more of (or any combination of), an *Onchocerca* species and a *Plasmodium* species.

Viruses

In certain example embodiments, the systems, devices, and methods, disclosed herein are directed to detecting viruses in a sample. The embodiments disclosed herein may be used to detect viral infection (e.g. of a subject or plant), or determination of a viral strain, including viral strains that differ by a single nucleotide polymorphism. The virus may be a DNA virus, a RNA virus, or a retrovirus. Non-limiting example of viruses useful with the present invention include, but are not limited to Ebola, measles, SARS, Chikungunya, hepatitis, Marburg, yellow fever, MERS, Dengue, Lassa, influenza, rhabdovirus or HIV. A hepatitis virus may include hepatitis A, hepatitis B, or hepatitis C. An influenza virus may include, for example, influenza A or influenza B. An HIV may include HIV 1 or HIV 2. In certain example embodiments, the viral sequence may be a human respiratory syncytial virus, Sudan ebola virus, Bundibugyo virus, Tai Forest ebola virus, Reston ebola virus, Achimota, *Aedes* flavivirus, Aguacate virus, Akabane virus, Alethinophid reptarenavirus, Allpahuayo mammarenavirus, Amapari mmarenavirus, Andes virus, Apoi virus, Aravan virus, Aroa virus, Arumwot virus, Atlantic salmon paramyxovirus, Australian bat lyssavirus, Avian bornavirus, Avian metapneumovirus, Avian paramyxoviruses, penguin or Falkland Islandsvirus, BK polyomavirus, Bagaza virus, Banna virus, Bat herpesvirus, Bat sapovirus, Bear Canon mammarenavirus, Beilong virus, Betacoronavirus, Betapapillomavirus 1-6, Bhanja virus, Bokeloh bat lyssavirus, Borna disease virus, Bourbon virus, Bovine hepacivirus, Bovine parainfluenza virus 3, Bovine respiratory syncytial virus, Brazoran virus, Bunyamwera virus, Caliciviridae virus. California encephalitis virus, Candiru virus, Canine distemper virus, Canine pneumovirus, Cedar virus, Cell fusing agent virus, Cetacean morbillivirus, Chandipura virus, Chaoyang virus, Chapare mammarenavirus, Chikungunya virus, Colobus monkey papillomavirus, Colorado tick fever virus, Cowpox virus, Crimean-Congo hemorrhagic fever virus, *Culex* flavivirus, Cupixi mammarenavirus, Dengue virus, Dobrava-Belgrade virus, Donggang virus, Dugbe virus, Duvenhage virus, Eastern equine encephalitis virus, Entebbe bat virus, Enterovirus A-D, European bat lyssavirus 1-2, Eyach virus, Feline morbillivirus, Fer-de-Lance paramyxovirus, Fitzroy River virus, Flaviviridae virus, Flexal mammarenavirus, GB virus C, Gairo virus, Gemycircularvirus, Goose paramyxovirus SF02, Great Island virus, Guanarito mammarenavirus, Hantaan virus, Hantavirus Z10, Heartland virus, Hendra virus, Hepatitis A/B/C/E, Hepatitis delta virus, Human bocavirus, Human coronavirus, Human endogenous retrovirus K, Human enteric coronavirus, Human genital-associated circular DNA virus-1, Human herpesvirus 1-8, Human immunodeficiency virus 1/2, Human mastadenovirus A-G, Human papillomavirus, Human parainfluenza virus 1-4, Human paraechovirus, Human picornavirus, Human smacovirus, Ikoma lyssavirus, Ilheus virus, Influenza A-C, Ippy mammarenavirus, Irkut virus, J-virus, JC polyomavirus, Japanese encephalitis virus, Junin mammarenavirus, KI polyomavirus, Kadipiro virus, Kamiti River virus, Kedougou virus, Khuj and virus, Kokobera virus, Kyasanur forest disease virus, Lagos bat virus, Langat virus, Lassa mammarenavirus, Latino mammarenavirus, Leopards Hill virus, Liao ning virus, Ljungan virus, Lloviu virus, Louping ill virus, Lujo mammarenavirus, Luna mammarenavirus, Lunk virus, Lymphocytic choriomeningitis mammarenavirus, Lyssavirus Ozernoe, MSSI2\0.225 virus, Machupo mammarenavirus, Mamastrovirus 1, Manzanilla virus, Mapuera virus, Marburg virus, Mayaro virus, Measles virus, Menangle virus, Mercadeo virus, Merkel cell polyomavirus, Middle East respiratory syndrome coronavirus, Mobala mammarenavirus, Modoc virus, Moijang virus, Mokolo virus, Monkeypox virus, Montana *myotis* leukoenchalitis virus, Mopeia lassa virus reassortant 29, Mopeia mammarenavirus, Morogoro virus, Mossman virus, Mumps virus, Murine pneumonia virus, Murray Valley encephalitis virus, Nariva virus, Newcastle disease virus, Nipah virus, Norwalk virus, Norway rat hepacivirus, Ntaya virus, O'nyong-nyong virus, Oliveros mammarenavirus, Omsk hemorrhagic fever virus, Oropouche virus, Parainfluenza virus 5, Parana mammarenavirus, Parramatta River virus, Peste-des-petits-ruminants virus, Pichande mammarenavirus, Picornaviridae virus, Pirital mammarenavirus, Piscihepevirus A, Porcine parainfluenza virus 1, porcine rubulavirus, Powassan virus, Primate T-lymphotropic virus 1-2, Primate erythroparvovirus 1, Punta Toro virus, Puumala virus, Quang Binh virus, Rabies virus, Razdan virus, Reptile bornavirus 1, Rhinovirus A-B, Rift Valley fever virus, Rinderpest virus, Rio Bravo virus, Rodent Torque Teno virus, Rodent hepacivirus, Ross River virus, Rotavirus A-I, Royal Farm virus, Rubella virus, Sabia mammarenavirus, Salem virus, Sandfly fever Naples virus, Sandfly fever Sicilian virus, Sapporo virus, Sathuperi virus, Seal anellovirus, Semliki Forest virus, Sendai virus, Seoul virus, Sepik virus, Severe acute respiratory syndrome-related coronavirus, Severe fever with thrombocytopenia syndrome virus, Shamonda virus, Shimoni bat virus, Shuni virus, Simbu virus, Simian torque teno virus, Simian virus 40-41, Sin Nombre virus, Sindbis virus, Small anellovirus, Sosuga virus, Spanish goat encephalitis virus, Spondweni virus, St. Louis encephalitis virus, Sunshine virus, TTV-like mini virus, Tacaribe mammarenavirus, Taila virus, Tamana bat virus, Tamiami mammarenavirus, Tembusu virus, Thogoto virus, Thottapalayam virus, Tick-borne encephalitis virus, Tioman virus, Togaviridae virus, Torque teno *canis* virus, Torque teno douroucouli virus, Torque teno *felis* virus, Torque teno midi virus, Torque teno sus virus, Torque teno tamarin virus, Torque teno virus, Torque teno *zalophus* virus, Tuhoko virus, Tula virus, Tupaia paramyxovirus, Usutu virus, Uukuniemi virus, Vaccinia virus, Variola virus, Venezuelan equine encephalitis virus, Vesicular stomatitis Indiana virus, WU Polyomavirus, Wesselsbron virus, West Caucasian bat virus, West Nile virus, Western equine encephalitis virus, Whitewater Arroyo mammarenavirus, Yellow fever virus, Yokose virus, Yug Bogdanovac virus, Zaire ebolavirus, Zika virus, or *Zygosaccharomyces bailii* virus Z viral sequence. Examples of RNA viruses that may be detected include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is Coronavirus, SARS, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

In certain example embodiments, the virus may be a plant virus selected from the group comprising Tobacco mosaic virus (TMV), Tomato spotted wilt virus (TSWV), Cucumber mosaic virus (CMV), Potato virus Y (PVY), the RT virus Cauliflower mosaic virus (CaMV), Plum pox virus (PPV), Brome mosaic virus (BMV), Potato virus X (PVX), Citrus tristeza virus (CTV), Barley yellow dwarf virus (BYDV), Potato leafroll virus (PLRV), Tomato bushy stunt virus (TBSV), rice tungro spherical virus (RTSV), rice yellow mottle virus (RYMV), rice hoja blanca virus (RHBV), maize rayado fino virus (MRFV), maize dwarf mosaic virus (MDMV), sugarcane mosaic virus (SCMV), Sweet potato feathery mottle virus (SPFMV), sweet potato sunken vein closterovirus (SPSVV), Grapevine fanleaf virus (GFLV), Grapevine virus A (GVA), Grapevine virus B (GVB), Grapevine fleck virus (GFkV), Grapevine leafroll-associated virus-1, -2, and -3, (GLRaV-1, -2, and -3), *Arabis* mosaic virus (ArMV), or *Rupestris* stem pitting-associated virus (RSPaV). In a preferred embodiment, the target RNA molecule is part of said pathogen or transcribed from a DNA molecule of said pathogen. For example, the target sequence may be comprised in the genome of an RNA virus. It is further preferred that CRISPR effector protein hydrolyzes said target RNA molecule of said pathogen in said plant if said pathogen infects or has infected said plant. It is thus preferred that the CRISPR system is capable of cleaving the target RNA molecule from the plant pathogen both when the CRISPR system (or parts needed for its completion) is applied therapeutically, i.e. after infection has occurred or prophylactically, i.e. before infection has occurred.

In certain example embodiments, the virus may be a retrovirus. Example retroviruses that may be detected using the embodiments disclosed herein include one or more of or any combination of viruses of the Genus Alpharetrovirus, Betaretrovirus, Gammaretrovirus, Deltaretrovirus, Epsilonretrovirus, Lentivirus, Spumavirus, or the Family Metaviridae, Pseudoviridae, and Retroviridae (including HIV), Hepadnaviridae (including Hepatitis B virus), and Caulimoviridae (including Cauliflower mosaic virus).

In certain example embodiments, the virus is a DNA virus. Example DNA viruses that may be detected using the embodiments disclosed herein include one or more of (or any combination of) viruses from the Family Myoviridae, Podoviridae, Siphoviridae, Alloherpesviridae, Herpesviridae (including human herpes virus, and Varicella Zorter virus), Malocoherpesviridae, Lipothrixviridae, Rudiviridae, Adenoviridae, Ampullaviridae, Ascoviridae, Asfarviridae (including African swine fever virus), Baculoviridae, Cicaudaviridae, Clavaviridae, Corticoviridae, Fuselloviridae, Globuloviridae, Guttaviridae, Hytrosaviridae, Iridoviridae, Maseilleviridae, Mimiviridae, Nudiviridae, Nimaviridae, Pandoraviridae, Papillomaviridae, Phycodnaviridae, Plasmaviridae, Polydnaviruses, Polyomaviridae (including Simian virus 40, JC virus, BK virus), Poxviridae (including Cowpox and smallpox), Sphaerolipoviridae, Tectiviridae, Turriviridae, Dinodnavirus, Salterprovirus, Rhizidovirus, among others. In some embodiments, a method of diagnosing a species-specific bacterial infection in a subject suspected of having a bacterial infection is described as obtaining a sample comprising bacterial ribosomal ribonucleic acid from the subject; contacting the sample with one or more of the probes described, and detecting hybridization between the bacterial ribosomal ribonucleic acid sequence present in the sample and the probe, wherein the detection of hybridization indicates that the subject is infected with *Escherichia coli, Klebsiella pneumoniae, Pseudomonas aeruginosa, Staphylococcus aureus, Acinetobacter baumannii, Candida albicans, Enterobacter cloacae, Enterococcus faecalis, Enterococcus faecium, Proteus mirabilis, Staphylococcus agalactiae,* or *Staphylococcus maltophilia* or a combination thereof.

Coronavirus

Systems and methods of the presently disclosed invention are designed to detect coronavirus, in an aspect, the target sequence is the 2019-nCoV, also referred to herein as SARS-CoV-2, which causes COVID-19. The coronavirus is a positive-sense single stranded RNA family of viruses, infecting a variety of animals and humans. SARS-CoV is one type of coronavirus infection, as well as MERS-CoV. Detection of one or more coronaviruses are envisioned, including the SARS-CoV-2 detected in Wuhan City. Sequences of the sARS-CoV-2 are available at GISAID accession no. EPI_ISL_402124 and EPI_ISL_402127-402130, and described in DOI: 10.1101/2020.01.22.914952. Further deposits of the SARS-CoV2 are deposited in the GISAID platform include EP_ISL_402119-402121 and EP_ISL 402123-402124; see also GenBank Accession No. MN908947.3. In an aspect, one may use known SARS and SARS-related coronaviruses or other viruses from one or more hosts to generate a non-redundant alignment. Related viruses can be found, for example in bats.

In certain embodiments, the systems are designed to comprise at least one highly active guide polynucleotide which is designed according to the methods disclosed herein. In a preferred embodiment, the guide polynucleotide binds to at least one target sequence that is a unique coronavirus genomic sequence, thereby identifying the presence of coronavirus to the exclusion of other viruses. The systems and methods can be designed to detect a plurality of respiratory infections or viral infections, including coronavirus.

In an aspect the at least one guide polynucleotide binds to a coronavirus sequence encoding a polypeptide that is immunostiumulatory to a host immune system. Immunostiumulatory polypeptides have the ability to enhance, stimulate, or increase response of the immune system, typically by inducing the activation or activity of a components of the immune system (e.g. an immune cell). In embodiments, the immunostimulatory polypeptide contributes to immune-mediated disease in the host. In an aspect, the host is a mammal, for example, a human, a bat, or a pangolin, that may be infected by a coronavirus. Cyranoski, D. Did pangolins spread the China coronavirus to people? Nature, 7 Feb. 2020. In certain embodiments, the guide polynucleotide can be designed to detect SARS-CoV-2 or a variant thereof in meat, live animals and humans so that testing can be performed, for example at markets and other public places where sources of contamination can arise.

Gene targets may comprise ORF1ab, N protein, RNA-dependent RNA polymerase (RdRP), E protein, ORF1b-nsp14, Spike glycoprotein (S), or pancorona targets. Molecular assays have been under development and can be used as a starting point to develop guide molecules for the methods and systems described herein. See, "Diagnostic detection of 2019-nCoV by real-time RT-PCR" Charité, Berlin Germany (17 Jan. 2020)' Detection of 2019 novel coronavirus (2019-nCoV) in suspected human cases by RT-PCR—Hong Kong University (23 Jan. 2020); PCR and sequencing protocol for 2019-nCoV-Department of Medical Sciences, Ministry of Public Health, Thailand (updated 28 Jan. 2020); PCR and sequencing protocols for 2019-nCoV-National Institute of Infectious Diseases Japan (24 Jan. 2020); US CDC panel primer and probes—U.S. CDC, USAV—U.S. CDC, USA (28 Jan. 2020); China CDC Primers and probes for detection 2019-nCoV (24 Jan. 2020), incorporated in their entirety by reference. Further, the guide molecule design may exploit differences or similarities with SARS-CoV. Researchers have recently identified simialrities and fifrferences between 2019-nCoV and SARS-CoV. "Coronavirus Genome Annotation Reveals Amino Acid Differences with Other SARS Viruses," genomeweb, Feb. 10, 2020. For example, guide molecules based on the 8a protein, which was present in SARS-CoV but absent in SARS-CoV-2, can be utilized to differentiate between the viruses. Similarly, the 8b and 3b proteins have different lengths in SARS-CoV and sARS-CoV-2 and can be utilized to design guide molecules to detect non-overlapping proteins of nucleotides encoding in the two viruses. Wu et al., Genome Composition and Divergence of the Novel Coronavirus (2019-nCoV) Originating in China, Cell Host & Microbe (2020), DOI: 10.1016/j.chom.2020.02.001, incorporated herein by reference, including all supplemental information, in particular Table S1.

The systems and methods of detection can be used to identify single nucleotide variants, detection based on rRNA sequences, screening for drug resistance, monitoring microbe outbreaks, genetic perturbations, and screening of environmental samples, as described in PCT/US2018/054472 filed Oct. 22, 2018 at [0183]-[0327], incorporated herein by reference.

In certain example embodiments, the systems, devices, and methods disclosed herein may be used for biomarker detection. For example, the systems, devices and method disclosed herein may be used for SNP detection and/or genotyping. The systems, devices and methods disclosed herein may be also used for the detection of any disease state or disorder characterized by aberrant gene expression. Aberrant gene expression includes aberration in the gene expressed, location of expression and level of expression. Multiple transcripts or protein markers related to cardiovascular, immune disorders, and cancer among other diseases may be detected. In certain example embodiments, the embodiments disclosed herein may be used for cell free DNA detection of diseases that involve lysis. In certain example embodiments, the embodiments could be utilized for faster and more portable detection for pre-natal testing of cell-free DNA. The embodiments disclosed herein may be used for screening panels of different SNPs associated with, among others, different coronaviruses, evolving SARS-CoV2, and other related respiratory viral infections. As described herein elsewhere, closely related genotypes/alleles or biomarkers (e.g. having only a single nucleotide difference in a given target sequence) may be distinguished by introduction of a synthetic mismatch in the gRNA.

In an aspect, the invention relates to a method for detecting target nucleic acids in samples, comprising:

distributing a sample or set of samples into one or more individual discrete volumes, the individual discrete volumes comprising a CRISPR system according to the invention as described herein;

incubating the sample or set of samples under conditions sufficient to allow binding of the one or more guide RNAs to one or more target molecules;

activating the CRISPR effector protein via binding of the one or more guide RNAs to the one or more target molecules, wherein activating the CRISPR effector protein results in modification of the RNA-based masking construct such that a detectable positive signal is generated; and detecting the detectable positive signal, wherein detection of the detectable positive signal indicates a presence of one or more target molecules in the sample.

The sensitivity of the assays described herein are well suited for detection of target nucleic acids in a wide variety of biological sample types, including sample types in which the target nucleic acid is dilute or for which sample material is limited. Methods for field deployable and rapid diagnostic assays can be optimized for the type of sample material utilized. See, e.g. Myhrvold et al., 2018. Biomarker screening may be carried out on a number of sample types including, but not limited to, saliva, urine, blood, feces, sputum, and cerebrospinal fluid. The embodiments disclosed herein may also be used to detect up- and/or down-regulation of genes. For example, a sample may be serially diluted such that only over-expressed genes remain above the detection limit threshold of the assay.

In certain embodiments, the present invention provides steps of obtaining a sample of biological fluid (e.g., urine, blood plasma or serum, sputum, cerebral spinal fluid), and extracting the DNA or RNA. The mutant nucleotide sequence to be detected, may be a fraction of a larger molecule or can be present initially as a discrete molecule.

In certain embodiments, DNA is isolated from plasma/serum of a cancer patient. For comparison, DNA samples isolated from neoplastic tissue and a second sample may be isolated from non-neoplastic tissue from the same patient (control), for example, lymphocytes. The non-neoplastic tissue can be of the same type as the neoplastic tissue or from a different organ source. In certain embodiments, blood samples are collected and plasma immediately separated from the blood cells by centrifugation. Serum may be filtered and stored frozen until DNA/RNA extraction.

In an aspect, sample preparation can comprise methods as disclosed herein to circumvent other RNA extraction methods and can be used with standard amplification techniques such as RT-PCR as well as the CRISPR-Cas detection methods disclosed herein. In an aspect, the method may comprise a one-step extraction-free RNA preparation method that can be used with samples tested for coronavirus, which may be, in an aspect, a RT-qPCR testing method, a lateral flow detection method or other CRISPR-Cas detection method disclosed herein. Advantageously, the RNA extraction method can be utilized directly with other testing protocols. In an aspect, the method comprises use of a nasopharyngeal swab, nasal saline lavage, or other nasal sample with Quick Extract™ DNA Extraction Solution (QE09050), Lucigen. In an aspect, the sample is diluted 2:1, 1:1 or 1:2 sample:DNA extraction solution. The sample: extraction mix is incubated at about 90° C. to about 98° C., preferably about 95° C. The incubation period can be about 2, 3, 4, 5, 6, 7, 8, 9, or 10 minutes, preferably about 4 to 6 minutes, or about 5 minutes. Incubation time and temperature may vary depending on sample size and quality. Current CDC Real-Time RT-PCR Diagnostic Panel are as described at fda.gov/media/134922/download, "CDC 2019-Novel Coronavirus (2019-nCoV) Real-Time RT-PCR Diagnostic Panel." In certain embodiments, the DNA extraction solution can remain with the sample subsequent to incubation and be utilized in the next steps of detection methods. In an aspect, the detection method is an RT-qPCR reaction and the extraction solution is kept at a concentration of less than 10%, 9%, 8%, 7%, 6%, 5%, 4%, 3% of the reaction mixture, where the reaction mixture comprises the detection reaction reagents, sample and extraction solution.

In certain embodiments, a bead is utilized with particular embodiments of the invention and may be included with the extraction solution. The bead may be used to capture, concentrate or otherwise enrich for particular material. The bead may be magnetic, and may be provided to capture nucleic acid material. In another aspect, the bead is a silica bead. Beads may be utilized in an extraction step of the methods disclosed herein. Beads can be optionally used with the methods described herein, including with the one-pot methods that allow for concentration of viral nucleic acids from large volume samples, such as saliva or swab samples to allow for a single one-pot reaction method. Concentration of desired target molecules can be increased by about 10-fold, 50-fold, 100-fold, 200-fold, 500-fold, 800-fold, 1000-fold, 1500-fold, 2000-fold, 2500-fold, 3000-fold, or more.

Magnetic beads in a PEG and salt solution are preferred in an aspect, and in embodiments bind to viral RNA and/or DNA which allows for concentration and lysis concurrently. Silica beads can be used in another aspect. Capture moieties such as oligonucleotide functionalized beads are envisioned for use. The beads may be using with the extraction reagents, allowed to incubate with a sample and the lysis/extraction buffer, thereby concentrating target molecules on the beads. When used with a cartridge device detailed elsewhere herein, a magnet can be activated and the beads collected, with optional flushing of the extraction buffer and one or more washes performed. Advantageously, the beads can be used in the one-pot methods and systems without additional washings of the beads, allowing for a more efficient process without increased risks of contamination in multi-step processes. Beads can be utilized with the isothermal amplifications detailed herein, and the beads can flow into an amplification chamber of the cartridge or be maintained in the pot for the amplification step. Upon heating, nucleic acid can be released off the beads.

In certain example embodiments, target nucleic acids are detected directly from a crude or unprocessed sample, such as blood, serum, saliva, cebrospinal fluid, sputum, or urine. In certain example embodiments, the target nucleic acid is cell free DNA.

Delivery

The present disclosure also provides delivery systems for introducing components of the systems and compositions herein to cells, tissues, organs, or organisms. A delivery system may comprise one or more delivery vehicles and/or cargos. Exemplary delivery systems and methods include those described in paragraphs [00117] to [00278] of Feng Zhang et al., (WO2016106236A1), and pages 1241-1251 and Table 1 of Lino C A et al., Delivering CRISPR: a review of the challenges and approaches, DRUG DELIVERY, 2018, VOL. 25, NO. 1, 1234-1257, which are incorporated by reference herein in their entireties.

In some embodiments, the delivery systems may be used to introduce the components of the systems and compositions to plant cells. For example, the components may be delivered to plant using electroporation, microinjection, aerosol beam injection of plant cell protoplasts, biolistic methods, DNA particle bombardment, and/or *Agrobacterium*-mediated transformation. Examples of methods and delivery systems for plants include those described in Fu et al., Transgenic Res. 2000 February; 9(1):11-9; Klein R M, et al., Biotechnology. 1992; 24:384-6; Casas A M et al., Proc Natl Acad Sci USA. 1993 Dec. 1; 90(23): 11212-11216; and U.S. Pat. No. 5,563,055, Davey M R et al., Plant Mol Biol. 1989 September; 13(3):273-85, which are incorporated by reference herein in their entireties.

Cargos

The delivery systems may comprise one or more cargos. The cargos may comprise one or more components of the systems and compositions herein. A cargo may comprise one or more of the following: i) a plasmid encoding one or more Cas proteins; ii) a plasmid encoding one or more guide RNAs, iii) mRNA of one or more Cas proteins; iv) one or more guide RNAs; v) one or more Cas proteins; vi) any combination thereof. In some examples, a cargo may comprise a plasmid encoding one or more Cas protein and one or more (e.g., a plurality of) guide RNAs. In some cases, the plasmid may also encode a recombination template (e.g., for HDR). In some embodiments, a cargo may comprise mRNA encoding one or more Cas proteins and one or more guide RNAs.

In some examples, a cargo may comprise one or more Cas proteins and one or more guide RNAs, e.g., in the form of ribonucleoprotein complexes (RNP). The ribonucleoprotein complexes may be delivered by methods and systems herein. In some cases, the ribonucleoprotein may be delivered by way of a polypeptide-based shuttle agent. In one example, the ribonucleoprotein may be delivered using synthetic peptides comprising an endosome leakage domain (ELD) operably linked to a cell penetrating domain (CPD), to a histidine-rich domain and a CPD, e.g., as describe in WO2016161516. RNP may also be used for delivering the compositions and systems to plant cells, e.g., as described in Wu J W, et al., Nat Biotechnol. 2015 November; 33(11): 1162-4.

Physical Delivery

In some embodiments, the cargos may be introduced to cells by physical delivery methods. Examples of physical methods include microinjection, electroporation, and hydrodynamic delivery. Both nucleic acid and proteins may be delivered using such methods. For example, Cas protein may be prepared in vitro, isolated, (refolded, purified if needed), and introduced to cells.

Microinjection

Microinjection of the cargo directly to cells can achieve high efficiency, e.g., above 90% or about 100%. In some embodiments, microinjection may be performed using a microscope and a needle (e.g., with 0.5-5.0 µm in diameter) to pierce a cell membrane and deliver the cargo directly to a target site within the cell. Microinjection may be used for in vitro and ex vivo delivery.

Plasmids comprising coding sequences for Cas proteins and/or guide RNAs, mRNAs, and/or guide RNAs, may be microinjected. In some cases, microinjection may be used i) to deliver DNA directly to a cell nucleus, and/or ii) to deliver mRNA (e.g., in vitro transcribed) to a cell nucleus or cytoplasm. In certain examples, microinjection may be used to delivery sgRNA directly to the nucleus and Cas-encoding mRNA to the cytoplasm, e.g., facilitating translation and shuttling of Cas to the nucleus.

Microinjection may be used to generate genetically modified animals. For example, gene editing cargos may be injected into zygotes to allow for efficient germline modification. Such approach can yield normal embryos and full-term mouse pups harboring the desired modification(s). Microinjection can also be used to provide transiently up- or down-regulate a specific gene within the genome of a cell, e.g., using CRISPRa and CRISPRi.

Electroporation

In some embodiments, the cargos and/or delivery vehicles may be delivered by electroporation. Electroporation may use pulsed high-voltage electrical currents to transiently open nanometer-sized pores within the cellular membrane of cells suspended in buffer, allowing for components with hydrodynamic diameters of tens of nanometers to flow into the cell. In some cases, electroporation may be used on various cell types and efficiently transfer cargo into cells. Electroporation may be used for in vitro and ex vivo delivery.

Electroporation may also be used to deliver the cargo to into the nuclei of mammalian cells by applying specific voltage and reagents, e.g., by nucleofection. Such approaches include those described in Wu Y, et al. (2015). Cell Res 25:67-79; Ye L, et al. (2014). Proc Natl Acad Sci USA 111:9591-6; Choi P S, Meyerson M. (2014). Nat Commun 5:3728; Wang J, Quake S R. (2014). Proc Natl Acad Sci 111:13157-62. Electroporation may also be used to deliver the cargo in vivo, e.g., with methods described in Zuckermann M, et al. (2015). Nat Commun 6:7391.

Hydrodynamic Delivery

Hydrodynamic delivery may also be used for delivering the cargos, e.g., for in vivo delivery. In some examples, hydrodynamic delivery may be performed by rapidly pushing a large volume (8-10% body weight) solution containing the gene editing cargo into the bloodstream of a subject (e.g., an animal or human), e.g., for mice, via the tail vein. As blood is incompressible, the large bolus of liquid may result in an increase in hydrodynamic pressure that temporarily enhances permeability into endothelial and parenchymal cells, allowing for cargo not normally capable of crossing a cellular membrane to pass into cells. This approach may be used for delivering naked DNA plasmids and proteins. The delivered cargos may be enriched in liver, kidney, lung, muscle, and/or heart.

Transfection

The cargos, e.g., nucleic acids, may be introduced to cells by transfection methods for introducing nucleic acids into cells. Examples of transfection methods include calcium phosphate-mediated transfection, cationic transfection, liposome transfection, dendrimer transfection, heat shock transfection, magnetofection, lipofection, impalefection, optical transfection, proprietary agent-enhanced uptake of nucleic acid.

Delivery Vehicles

The delivery systems may comprise one or more delivery vehicles. The delivery vehicles may deliver the cargo into cells, tissues, organs, or organisms (e.g., animals or plants). The cargos may be packaged, carried, or otherwise associated with the delivery vehicles. The delivery vehicles may be selected based on the types of cargo to be delivered, and/or the delivery is in vitro and/or in vivo. Examples of delivery vehicles include vectors, viruses, non-viral vehicles, and other delivery reagents described herein.

The delivery vehicles in accordance with the present invention may have a greatest dimension (e.g. diameter) of less than 100 microns (µm). In some embodiments, the delivery vehicles have a greatest dimension of less than 10 µm. In some embodiments, the delivery vehicles may have a greatest dimension of less than 2000 nanometers (nm). In some embodiments, the delivery vehicles may have a greatest dimension of less than 1000 nanometers (nm). In some embodiments, the delivery vehicles may have a greatest dimension (e.g., diameter) of less than 900 nm, less than 800 nm, less than 700 nm, less than 600 nm, less than 500 nm, less than 400 nm, less than 300 nm, less than 200 nm, less than 150 nm, or less than 100 nm, less than 50 nm. In some embodiments, the delivery vehicles may have a greatest dimension ranging between 25 nm and 200 nm.

In some embodiments, the delivery vehicles may be or comprise particles. For example, the delivery vehicle may be or comprise nanoparticles (e.g., particles with a greatest dimension (e.g., diameter) no greater than 1000 nm. The particles may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles). Nanoparticles may also be used to deliver the compositions and systems to plant cells, e.g., as described in International Patent Publication No. WO 2008042156, US Publication Application No. US 20130185823, and International Patent Publication No WO 2015/089419.

Vectors

The systems, compositions, and/or delivery systems may comprise one or more vectors. The present disclosure also include vector systems. A vector system may comprise one or more vectors. A vector or vector system may comprise one or more polynucleotide sequences encoding the components of the compositions herein, e.g., one or more polynucleotide sequences encoding the Cas12b protein and the guide molecule in the compositions herein. The polynucleotide sequences may be codon optimized to express in a eukaryote. In some examples, the polynucleotides may be comprised in a single vector.

In some embodiments, a vector refers to a nucleic acid molecule capable of transporting another nucleic acid to which it has been linked. Vectors include nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. A vector may be a plasmid, e.g., a circular double stranded DNA loop into which additional DNA segments can be inserted, such as by standard molecular cloning techniques. Certain vectors may be capable of autonomous replication in a host cell into which they are introduced (e.g., bacterial vectors having a bacterial origin of replication and episomal mammalian vectors). Some vectors (e.g., non-episomal mammalian vectors) are integrated into the genome of a host cell upon introduction into the host cell, and thereby are replicated along with the host genome. In certain examples, vectors may be expression vectors, e.g., capable of directing the expression of genes to which they are operatively-linked. In some cases, the expression vectors may be for expression in eukaryotic cells. Common expression vectors of utility in recombinant DNA techniques are often in the form of plasmids.

Examples of vectors include pGEX, pMAL, pRIT5, E. coli expression vectors (e.g., pTrc, pET 11d, yeast expression vectors (e.g., pYepSec1, pMFa, NRY88, pYES2, and picZ, Baculovirus vectors (e.g., for expression in insect cells such as SF9 cells) (e.g., pAc series and the pVL series), mammalian expression vectors (e.g., pCDM8 and pMT2PC.

A vector may comprise i) Cas encoding sequence(s), and/or ii) a single, or at least 2, at least 3, at least 4, at least 5, at least 6, at least 7, at least 8, at least 9, at least 10, at least 12, at least 14, at least 16, at least 32, at least 48, at least 50 guide RNA(s) encoding sequences. In a single vector there can be a promoter for each RNA coding sequence. Alternatively or additionally, in a single vector, there may be a promoter controlling (e.g., driving transcription and/or expression) multiple RNA encoding sequences.

Furthermore, that compositions or systems may be delivered via a vector, e.g., a separate vector or the same vector that is encoding the CRISPR complex. When provided by a separate vector, the CRISPR RNA that targets Cas expression can be administered sequentially or simultaneously. When administered sequentially, the CRISPR RNA that targets Cas expression is to be delivered after the CRISPR RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA capable of hybridizing to a first target, such as a genomic locus or loci of interest and undertakes the function(s) desired of the CRISPR-Cas system (e.g., gene engineering); and subsequently the Cas enzyme may then associate with the second gRNA capable of hybridizing to the sequence comprising at least part of the Cas or CRISPR cassette. Where the guide RNA targets the sequences encoding expression of the Cas protein, the enzyme becomes impeded and the system becomes self-inactivating. In the same manner, CRISPR RNA that targets Cas expression applied via, for example liposome, lipofection, particles, microvesicles as explained herein, may be administered sequentially or simultaneously. Similarly, self-inactivation may be used for inactivation of one or more guide RNA used to target one or more targets.

Regulatory Elements

A vector may comprise one or more regulatory elements. The regulatory element(s) may be operably linked to coding sequences of Cas proteins, accessary proteins, guide RNAs (e.g., a single guide RNA, crRNA, and/or tracrRNA), or combination thereof. The term "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). In certain examples, a vector may comprise: a first regulatory element operably linked to a nucleotide sequence encoding a Cas protein, and a second regulatory element operably linked to a nucleotide sequence encoding a guide RNA.

Examples of regulatory elements include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific.

Examples of promoters include one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1a promoter.

Viral Vectors

The cargos may be delivered by viruses. In some embodiments, viral vectors are used. A viral vector may comprise virally-derived DNA or RNA sequences for packaging into a virus (e.g., retroviruses, replication defective retroviruses, adenoviruses, replication defective adenoviruses, and adeno-associated viruses). Viral vectors also include polynucleotides carried by a virus for transfection into a host cell. Viruses and viral vectors may be used for in vitro, ex vivo, and/or in vivo deliveries.

Adeno Associated Virus (AAV)

The systems and compositions herein may be delivered by adeno associated virus (AAV). AAV vectors may be used for such delivery. AAV, of the Dependovirus genus and Parvoviridae family, is a single stranded DNA virus. In some embodiments, AAV may provide a persistent source of the provided DNA, as AAV delivered genomic material can exist indefinitely in cells, e.g., either as exogenous DNA or, with some modification, be directly integrated into the host DNA. In some embodiments, AAV do not cause or relate with any diseases in humans. The virus itself is able to efficiently infect cells while provoking little to no innate or adaptive immune response or associated toxicity.

Examples of AAV that can be used herein include AAV-1, AAV-2, AAV-3, AAV-4, AAV-5, AAV-6, AAV-8, and AAV-9. The type of AAV may be selected with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. AAV-2-based vectors were originally proposed for CFTR delivery to CF airways, other serotypes such as AAV-1, AAV-5, AAV-6, and AAV-9 exhibit improved gene transfer efficiency in a variety of models of the lung epithelium. Examples of cell types targeted by AAV are described in Grimm, D. et al, J. Virol. 82: 5887-5911 (2008)), and shown as follows:

Examples of lentiviruses include human immunodeficiency virus (HIV), which may use its envelope glycoproteins of other viruses to target a broad range of cell types; minimal non-primate lentiviral vectors based on the equine infectious anemia virus (EIAV), which may be used for ocular therapies. In certain embodiments, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the nucleic acid-targeting system herein.

Lentiviruses may be pseudo-typed with other viral proteins, such as the G protein of vesicular stomatitis virus. In doing so, the cellular tropism of the lentiviruses can be altered to be as broad or narrow as desired. In some cases, to improve safety, second- and third-generation lentiviral systems may split essential genes across three plasmids, which may reduce the likelihood of accidental reconstitution of viable viral particles within cells.

In some examples, leveraging the integration ability, lentiviruses may be used to create libraries of cells com-

TABLE 2

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

CRISPR-Cas AAV particles may be created in HEK 293 T cells. Once particles with specific tropism have been created, they are used to infect the target cell line much in the same way that native viral particles do. This may allow for persistent presence of CRISPR-Cas components in the infected cell type, and what makes this version of delivery particularly suited to cases where long-term expression is desirable. Examples of doses and formulations for AAV that can be used include those describe in U.S. Pat. Nos. 8,454,972 and 8,404,658.

Various strategies may be used for delivery the systems and compositions herein with AAVs. In some examples, coding sequences of Cas and gRNA may be packaged directly onto one DNA plasmid vector and delivered via one AAV particle. In some examples, AAVs may be used to deliver gRNAs into cells that have been previously engineered to express Cas. In some examples, coding sequences of Cas and gRNA may be made into two separate AAV particles, which are used for co-transfection of target cells. In some examples, markers, tags, and other sequences may be packaged in the same AAV particles as coding sequences of Cas and/or gRNAs.

Lentiviruses

The systems and compositions herein may be delivered by lentiviruses. Lentiviral vectors may be used for such delivery. Lentiviruses are complex retroviruses that have the ability to infect and express their genes in both mitotic and post-mitotic cells.

prising various genetic modifications, e.g., for screening and/or studying genes and signaling pathways.

Adenoviruses

The systems and compositions herein may be delivered by adenoviruses. Adenoviral vectors may be used for such delivery. Adenoviruses include nonenveloped viruses with an icosahedral nucleocapsid containing a double stranded DNA genome. Adenoviruses may infect dividing and non-dividing cells. In some embodiments, adenoviruses do not integrate into the genome of host cells, which may be used for limiting off-target effects of CRISPR-Cas systems in gene editing applications.

Viral Vehicles for Delivery to Plants

The systems and compositions may be delivered to plant cells using viral vehicles. In particular embodiments, the compositions and systems may be introduced in the plant cells using a plant viral vector (e.g., as described in Scholthof et al. 1996, Annu Rev Phytopathol. 1996; 34:299-323). Such viral vector may be a vector from a DNA virus, e.g., geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). The viral vector may be a vector from an RNA virus, e.g., tobravirus (e.g., tobacco rattle virus, tobacco mosaic virus), potexvirus (e.g., potato virus X), or hordeivirus (e.g., barley stripe mosaic virus). The replicating genomes of plant viruses may be non-integrative vectors.

Non-Viral Vehicles

The delivery vehicles may comprise non-viral vehicles. In general, methods and vehicles capable of delivering nucleic acids and/or proteins may be used for delivering the systems compositions herein. Examples of non-viral vehicles include lipid nanoparticles, cell-penetrating peptides (CPPs), DNA nanoclews, gold nanoparticles, streptolysin O, multifunctional envelope-type nanodevices (MENDs), lipid-coated mesoporous silica particles, and other inorganic nanoparticles.

Lipid Particles

The delivery vehicles may comprise lipid particles, e.g., lipid nanoparticles (LNPs) and liposomes.

Lipid Nanoparticles (LNPs)

LNPs may encapsulate nucleic acids within cationic lipid particles (e.g., liposomes), and may be delivered to cells with relative ease. In some examples, lipid nanoparticles do not contain any viral components, which helps minimize safety and immunogenicity concerns. Lipid particles may be used for in vitro, ex vivo, and in vivo deliveries. Lipid particles may be used for various scales of cell populations.

In some examples. LNPs may be used for delivering DNA molecules (e.g., those comprising coding sequences of Cas and/or gRNA) and/or RNA molecules (e.g., mRNA of Cas, gRNAs). In certain cases, LNPs may be use for delivering RNP complexes of Cas/gRNA.

Components in LNPs may comprise cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), R-3-[(ro-methoxy-poly(ethylene glycol) 2000) carbamoyl]-1,2-dimyristyloxlpropyl-3-amine (PEG-C-DOMG, and any combination thereof. Preparation of LNPs and encapsulation may be adapted from Rosin et al, Molecular Therapy, vol. 19, no. 12, pages 1286-2200, December 2011).

Liposomes

In some embodiments, a lipid particle may be liposome. Liposomes are spherical vesicle structures composed of a uni- or multilamellar lipid bilayer surrounding internal aqueous compartments and a relatively impermeable outer lipophilic phospholipid bilayer. In some embodiments, liposomes are biocompatible, nontoxic, can deliver both hydrophilic and lipophilic drug molecules, protect their cargo from degradation by plasma enzymes, and transport their load across biological membranes and the blood brain barrier (BBB).

Liposomes can be made from several different types of lipids, e.g., phospholipids. A liposome may comprise natural phospholipids and lipids such as 1,2-distearoryl-sn-glycero-3-phosphatidyl choline (DSPC), sphingomyelin, egg phosphatidylcholines, monosialoganglioside, or any combination thereof.

Several other additives may be added to liposomes in order to modify their structure and properties. For instance, liposomes may further comprise cholesterol, sphingomyelin, and/or 1,2-dioleoyl-sn-glycero-3-phosphoethanolamine (DOPE), e.g., to increase stability and/or to prevent the leakage of the liposomal inner cargo.

Stable Nucleic-Acid-Lipid Particles (SNALPs)

In some embodiments, the lipid particles may be stable nucleic acid lipid particles (SNALPs). SNALPs may comprise an ionizable lipid (DLinDMA) (e.g., cationic at low pH), a neutral helper lipid, cholesterol, a diffusible polyethylene glycol (PEG)-lipid, or any combination thereof. In some examples, SNALPs may comprise synthetic cholesterol, dipalmitoylphosphatidylcholine, 3-N-[(w-methoxy polyethylene glycol)2000)carbamoyl]-1,2-dimyrestyloxypropylamine, and cationic 1,2-dilinoleyloxy-3-N,Ndimethylaminopropane. In some examples, SNALPs may comprise synthetic cholesterol, 1,2-distearoyl-sn-glycero-3-phosphocholine, PEG-cDMA, and 1,2-dilinoleyloxy-3-(N;N-dimethyl)aminopropane (DLinDMA)

Other Lipids

The lipid particles may also comprise one or more other types of lipids, e.g., cationic lipids, such as amino lipid 2,2-dilinoleyl-4-dimethylaminoethyl-[1,3]-dioxolane (DLin-KC2-DMA), DLin-KC2-DMA4, C12-200 and colipids disteroylphosphatidyl choline, cholesterol, and PEG-DMG.

Lipoplexes/Polyplexes

In some embodiments, the delivery vehicles comprise lipoplexes and/or polyplexes. Lipoplexes may bind to negatively charged cell membrane and induce endocytosis into the cells. Examples of lipoplexes may be complexes comprising lipid(s) and non-lipid components. Examples of lipoplexes and polyplexes include FuGENE-6 reagent, a non-liposomal solution containing lipids and other components, zwitterionic amino lipids (ZALs), Ca2φ (e.g., forming DNA/$Ca^{2+}$ microcomplexes), polyethenimine (PEI) (e.g., branched PEI), and poly(L-lysine) (PLL).

Cell Penetrating Peptides

In some embodiments, the delivery vehicles comprise cell penetrating peptides (CPPs). CPPs are short peptides that facilitate cellular uptake of various molecular cargo (e.g., from nanosized particles to small chemical molecules and large fragments of DNA).

CPPs may be of different sizes, amino acid sequences, and charges. In some examples, CPPs can translocate the plasma membrane and facilitate the delivery of various molecular cargoes to the cytoplasm or an organelle. CPPs may be introduced into cells via different mechanisms, e.g., direct penetration in the membrane, endocytosis-mediated entry, and translocation through the formation of a transitory structure.

CPPs may have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. Another type of CPPs is the trans-activating transcriptional activator (Tat) from Human Immunodeficiency Virus 1 (HIV-1). Examples of CPPs include to Penetratin, Tat (48-60), Transportan, and (R-AhX-R4) (Ahx refers to aminohexanoyl), Kaposi fibroblast growth factor (FGF) signal peptide sequence, integrin β3 signal peptide sequence, polyarginine peptide Args sequence, Guanine rich-molecular transporters, and sweet arrow peptide. Examples of CPPs and related applications also include those described in U.S. Pat. No. 8,372,951.

CPPs can be used for in vitro and ex vivo work quite readily, and extensive optimization for each cargo and cell type is usually required. In some examples, CPPs may be covalently attached to the Cas protein directly, which is then complexed with the gRNA and delivered to cells. In some examples, separate delivery of CPP-Cas and CPP-gRNA to multiple cells may be performed. CPP may also be used to delivery RNPs.

CPPs may be used to deliver the compositions and systems to plants. In some examples, CPPs may be used to deliver the components to plant protoplasts, which are then regenerated to plant cells and further to plants.

DNA Nanoclews

In some embodiments, the delivery vehicles comprise DNA nanoclews. A DNA nanoclew refers to a sphere-like structure of DNA (e.g., with a shape of a ball of yarn). The nanoclew may be synthesized by rolling circle amplification with palindromic sequences that aide in the self-assembly of the structure. The sphere may then be loaded with a payload. An example of DNA nanoclew is described in Sun W et al, J Am Chem Soc. 2014 Oct. 22; 136(42):14722-5; and Sun W et al, Angew Chem Int Ed Engl. 2015 Oct. 5; 54(41):12029-33. DNA nanoclew may have a palindromic sequences to be partially complementary to the gRNA within the Cas:gRNA ribonucleoprotein complex. A DNA nanoclew may be coated, e.g., coated with PEI to induce endosomal escape.

Gold Nanoparticles

In some embodiments, the delivery vehicles comprise gold nanoparticles (also referred to AuNPs or colloidal gold). Gold nanoparticles may form complex with cargos, e.g., Cas:gRNA RNP. Gold nanoparticles may be coated, e.g., coated in a silicate and an endosomal disruptive polymer, PAsp(DET). Examples of gold nanoparticles include AuraSense Therapeutics' Spherical Nucleic Acid (SNA™) constructs, and those described in Mout R, et al. (2017). ACS Nano 11:2452-8; Lee K, et al. (2017). Nat Biomed Eng 1:889-901.

iTOP

In some embodiments, the delivery vehicles comprise iTOP. iTOP refers to a combination of small molecules drives the highly efficient intracellular delivery of native proteins, independent of any transduction peptide. iTOP may be used for induced transduction by osmocytosis and propanebetaine, using NaCl-mediated hyperosmolality together with a transduction compound (propanebetaine) to trigger macropinocytotic uptake into cells of extracellular macromolecules. Examples of iTOP methods and reagents include those described in D'Astolfo D S, Pagliero R J, Pras A, et al. (2015). Cell 161:674-690.

Polymer-Based Particles

In some embodiments, the delivery vehicles may comprise polymer-based particles (e.g., nanoparticles). In some embodiments, the polymer-based particles may mimic a viral mechanism of membrane fusion. The polymer-based particles may be a synthetic copy of Influenza virus machinery and form transfection complexes with various types of nucleic acids ((siRNA, miRNA, plasmid DNA or shRNA, mRNA) that cells take up via the endocytosis pathway, a process that involves the formation of an acidic compartment. The low pH in late endosomes acts as a chemical switch that renders the particle surface hydrophobic and facilitates membrane crossing. Once in the cytosol, the particle releases its payload for cellular action. This Active Endosome Escape technology is safe and maximizes transfection efficiency as it is using a natural uptake pathway. In some embodiments, the polymer-based particles may comprise alkylated and carboxyalkylated branched polyethylenimine. In some examples, the polymer-based particles are VIROMER, e.g., VIROMER RNAi, VIROMER RED, VIROMER mRNA, VIROMER CRISPR. Example methods of delivering the systems and compositions herein include those described in Bawage S S et al., Synthetic mRNA expressed Cas13a mitigates RNA virus infections, www.biorxiv.org/content/10.1101/370460v1.full doi: doi.org/10.1101/370460, Viromer® RED, a powerful tool for transfection of keratinocytes. doi: 10.13140/RG.2.2.16993.61281, Viromer® Transfection-Factbook 2018: technology, product overview, users' data., doi: 10.13140/RG.2.2.23912.16642.

Streptolysin O (SLO)

The delivery vehicles may be streptolysin O (SLO). SLO is a toxin produced by Group A streptococci that works by creating pores in mammalian cell membranes. SLO may act in a reversible manner, which allows for the delivery of proteins (e.g., up to 100 kDa) to the cytosol of cells without compromising overall viability. Examples of SLO include those described in Sierig G, et al. (2003). Infect Immun 71:446-55; Walev I, et al. (2001). Proc Natl Acad Sci USA 98:3185-90; Teng K W, et al. (2017). Elife 6:e25460.

Multifunctional Envelope-Type Nanodevice (MEND)

The delivery vehicles may comprise multifunctional envelope-type nanodevice (MENDs). MENDs may comprise condensed plasmid DNA, a PLL core, and a lipid film shell. A MEND may further comprise cell-penetrating peptide (e.g., stearyl octaarginine). The cell penetrating peptide may be in the lipid shell. The lipid envelope may be modified with one or more functional components, e.g., one or more of: polyethylene glycol (e.g., to increase vascular circulation time), ligands for targeting of specific tissues/cells, additional cell-penetrating peptides (e.g., for greater cellular delivery), lipids to enhance endosomal escape, and nuclear delivery tags. In some examples, the MEND may be a tetra-lamellar MEND (T-MEND), which may target the cellular nucleus and mitochondria. In certain examples, a MEND may be a PEG-peptide-DOPE-conjugated MEND (PPD-MEND), which may target bladder cancer cells. Examples of MENDs include those described in Kogure K, et al. (2004). J Control Release 98:317-23; Nakamura T, et al. (2012). Acc Chem Res 45:1113-21.

Lipid-Coated Mesoporous Silica Particles

The delivery vehicles may comprise lipid-coated mesoporous silica particles. Lipid-coated mesoporous silica particles may comprise a mesoporous silica nanoparticle core and a lipid membrane shell. The silica core may have a large internal surface area, leading to high cargo loading capacities. In some embodiments, pore sizes, pore chemistry, and overall particle sizes may be modified for loading different types of cargos. The lipid coating of the particle may also be modified to maximize cargo loading, increase circulation times, and provide precise targeting and cargo release. Examples of lipid-coated mesoporous silica particles include those described in Du X, et al. (2014). Biomaterials 35:5580-90; Durfee P N, et al. (2016). ACS Nano 10:8325-45.

Inorganic Nanoparticles

The delivery vehicles may comprise inorganic nanoparticles. Examples of inorganic nanoparticles include carbon nanotubes (CNTs) (e.g., as described in Bates K and Kostarelos K. (2013). Adv Drug Deliv Rev 65:2023-33.), bare mesoporous silica nanoparticles (MSNPs) (e.g., as described in Luo G F, et al. (2014). Sci Rep 4:6064), and dense silica nanoparticles (SiNPs) (as described in Luo D and Saltzman W M. (2000). Nat Biotechnol 18:893-5).

Exosomes

The delivery vehicles may comprise exosomes. Exosomes include membrane bound extracellular vesicles, which can be used to contain and delivery various types of biomolecules, such as proteins, carbohydrates, lipids, and nucleic acids, and complexes thereof (e.g., RNPs). Examples of exosomes include those described in Schroeder A, et al., J Intern Med. 2010 January; 267(1):9-21; El-Andaloussi S, et al., Nat Protoc. 2012 December; 7(12):2112-26; Uno Y, et al., Hum Gene Ther. 2011 June; 22(6):711-9; Zou W, et al., Hum Gene Ther. 2011 April; 22(4):465-75.

In some examples, the exosome may form a complex (e.g., by binding directly or indirectly) to one or more components of the cargo. In certain examples, a molecule of an exosome may be fused with first adapter protein and a component of the cargo may be fused with a second adapter protein. The first and the second adapter protein may specifically bind each other, thus associating the cargo with the exosome. Examples of such exosomes include those described in Ye Y, et al., Biomater Sci. 2020 Apr. 28. doi: 10.1039/d0bm00427h.

Genetically Modified Cells and Organisms

The present disclosure further provides cells comprising one or more components of the systems herein, e.g., the Cas protein and/or guide molecule(s). Also provided include cells modified by the systems and methods herein, and cell cultures, tissues, organs, organism comprising such cells or progeny thereof. The invention in some embodiments comprehends a method of modifying an cell or organism. The cell may be a prokaryotic cell or a eukaryotic cell. The cell may be a mammalian cell. The mammalian cell many be a non-human primate, bovine, porcine, rodent or mouse cell. The cell may be a non-mammalian eukaryotic cell such as poultry, fish or shrimp. The cell may be a therapeutic T cell or antibody-producing B-cell. The cell may also be a plant cell. The plant cell may be of a crop plant such as cassava, corn, sorghum, wheat, or rice. The plant cell may also be of an algae, tree or vegetable. The modification introduced to the cell by the present invention may be such that the cell and progeny of the cell are altered for improved production of biologic products such as an antibody, starch, alcohol or other desired cellular output. The modification introduced to the cell by the present invention may be such that the cell and progeny of the cell include an alteration that changes the biologic product produced.

In some embodiments, one or more polynucleotide molecules, vectors, or vector systems driving expression of one or more elements of a nucleic acid-targeting system or delivery systems comprising one or more elements of the nucleic acid-targeting system are introduced into a host cell such that expression of the elements of the nucleic acid-targeting system direct formation of a nucleic acid-targeting complex at one or more target sites. In certain embodiments of the invention the host cell may be a eukaryotic cell, a prokaryotic cell, or a plant cell.

In particular embodiments, the host cell is a cell of a cell line. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

Further intended are isolated human cells or tissues, plants or non-human animals comprising one or more of the polynucleotide molecules, vectors, vector systems, or cells described in any of the embodiments herein. In an aspect, host cells and cell lines modified by or comprising the compositions, systems or modified enzymes of present invention are provided, including (isolated) stem cells, and progeny thereof.

In certain embodiments, the plants or non-human animals comprise at least one of the CRISPR system components, polynucleotide molecules, vectors, vector systems, or cells described in any of the embodiments herein at least one tissue type of the plant or non-human animal. In certain embodiment, non-human animals comprise at least one of the CRISPR system components, polynucleotide molecules, vectors, vector systems, or cells described in any of the embodiments herein in at least one tissue type. In certain embodiments, the presence of the CRISPR system components is transient, in that they are degraded over time. In certain embodiments, expression of the CRISPR-Cas systems or Cas proteins described in any of the embodiments comprised in polynucleotide molecules, vectors, vector systems, or cells is limited to certain tissue types or regions in the plant or non-human animal. In certain embodiments, the expression of the CRISPR-Cas systems or Cas proteins described in any of the embodiments comprised in polynucleotide molecules, vectors, vector systems, or cells is dependent of a physiological cue. In certain embodiments, expression of the CRISPR-Cas systems or Cas proteins described in any of the embodiments comprised in polynucleotide molecules, vectors, vector systems, or cells may be triggered by an exogenous molecule. In certain embodiments, expression of the CRISPR-Cas systems or Cas proteins described in any of the embodiments comprised in polynucleotide molecules, vectors, vector systems, or cells is dependent on the expression of a non-cas molecule in the plant or non-human animal.

Applications and Uses in General

The systems, the vector systems, the vectors and the compositions described herein may be used in various nucleic acids-targeting applications, altering or modifying synthesis of a gene product, such as a protein, nucleic acids cleavage, nucleic acids editing, nucleic acids splicing; trafficking of target nucleic acids, tracing of target nucleic acids, isolation of target nucleic acids, visualization of target nucleic acids, etc.

In some embodiments, disclosed herein include methods for modifying or targeting one or more target polynucleotides, the method comprising contacting the one or more target polynucleotides with a non-naturally occurring or engineered compositions herein.

The modification or targeting of the one or more target polynucleotides comprises increasing or decreasing expression of the one or more genes in the one or more target polynucleotides. In some embodiments, the modification comprises insertion of a recombination template or a portion thereof to the tar one or more target polynucleotides. The one or more target sequences is in a prokaryotic cell, a eukaryotic cell, or comprised in a nucleic acid molecule in vitro. In some embodiments, the method modifies one or more nucleotides in the one or more target polynucleotides, e.g., with a base editing systems herein. In some embodiments, the modification of the one or more target polynucleotides remedies a disease caused by a G→A or C→T point mutation, a T→C or A→G point mutation, or a pathogenic SNP.

Aspects of the invention thus also encompass methods and uses of the compositions and systems described herein in genome engineering, e.g. for altering or manipulating the expression of one or more genes or the one or more gene products, in prokaryotic or eukaryotic cells, in vitro, in vivo or ex vivo.

Typically, in the context of a nucleic acid-targeting system, formation of a nucleic acid-targeting complex (comprising a guide RNA hybridized to a target sequence and complexed with one or more nucleic acid-targeting effector proteins) results in cleavage of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the Cas protein used, but PAMs are typically 2-5 base pair sequences adjacent the protospacer (that is, the target sequence) Examples of PAM sequences are given in the examples section below, and the skilled person will be able to identify further PAM sequences for use with a given Cas protein. Further, engineering of the PAM Interacting (PI) domain may allow programing of PAM specificity, improve target site recognition fidelity, and increase the versatility of the Cas, genome engineering platform. Cas proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/nature14592.

The target polynucleotide of a CRISPR complex may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Aspects of the invention relate to a method of targeting a polynucleotide, comprising contacting a sample that comprises the polynucleotide with a CRISPR-Cas system or Cas protein as described in any embodiment herein, a delivery system comprising a CRISPR-Cas system or Cas protein as described in any embodiment herein, a polynucleotide comprising a CRISPR-Cas system or Cas protein as described in any embodiment herein, a vector comprising a CRISPR-Cas system or Cas protein as described in any embodiment herein, or a vector system comprising a CRISPR-Cas system or Cas protein as described in any embodiment herein. In certain embodiments, a target polynucleotide is contacted with at least two different CRISPR-Cas systems or Cas proteins. In further embodiments, the two different CRISPR-Cas systems or Cas proteins have different target polynucleotide specificities, or degrees of specificity. In certain embodiments, the two different CRISPR-Cas systems or Cas proteins have a different PAM specificity.

Further intended is the method of targeting a polynucleotide, comprising contacting a sample that comprises the polynucleotide with a CRISPR-Cas system or Cas protein as described in any embodiment herein, a polynucleotide comprising a CRISPR-Cas system or Cas protein as described in any embodiment herein, a delivery system comprising a CRISPR-Cas system or Cas protein as described in any embodiment herein, a vector comprising a CRISPR-Cas system or Cas protein as described in any embodiment herein, or a vector system comprising a CRISPR-Cas system or Cas protein as described in any embodiment herein wherein the method further comprises detection of binding of the CRISPR-Cas system or Cas protein to the polynucleotide.

Also envisaged are methods of targeting a polynucleotide, comprising contacting a sample that comprises the polynucleotide with a CRISPR-Cas system or Cas protein as described in any embodiment herein, a polynucleotide comprising a CRISPR-Cas system or Cas protein as described in any embodiment herein, a vector comprising a CRISPR-Cas system or Cas protein as described in any embodiment herein, or a vector system comprising a CRISPR-Cas system or Cas protein as described in any embodiment herein wherein contacting results in modification of a gene product or modification of the amount or expression of a gene product. In certain embodiments, the expression of the targeted gene product is increased by the method. In certain embodiments, the expression of the targeted gene product is increased by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In certain embodiments, the expression of the targeted gene product is increased at least 1.5-fold, at least 2-fold, at least 3-fold, at least 4-fold, at least 5-fold, at least 10-fold, at least 15-fold, at least 20-fold, at least 25-fold, at least 50-fold, or at least 100-fold. In certain embodiments, the expression of the targeted gene product is reduced by at least 10%, by at least 15%, by at least 20%, by at least 25%, by at least 30%, by at least 35%, by at least 40%, by at least 50%, by at least 60%, by at least 70%, by at least 80%, by at least 90%, or by at least 100%. In certain embodiments, the expression of the targeted gene product is reduced at least 1.5-fold, at least 2-fold, at least 3-fold, y at least 4-fold, at least 5-fold, at least 10-fold, at least 15-fold, at least 20-fold, at least 25-fold, at least 50-fold, or at least 100-fold. In alternative embodiments, the expression of the targeted gene product is reduced by the method. In further embodiments, expression of the targeted gene may be completely eliminated, or may be considered eliminated as remnant expression levels of the targeted gene fall below the detection limit of methods known in the art that are used to quantify, detect, or monitor expression levels of genes.

In one embodiment, this invention provides a method of cleaving a target polynucleotide. The method may comprise modifying a target polynucleotide using a nucleic acid-targeting complex that binds to the target polynucleotide and effect cleavage of said target polynucleotide. In an embodiment, the nucleic acid-targeting complex of the invention, when introduced into a cell, may create a break (e.g., a single or a double strand break) in the polynucleotide sequence. For example, the method can be used to cleave a disease polynucleotide in a cell. For example, an exogenous template comprising a sequence to be integrated flanked by an upstream sequence and a downstream sequence may be introduced into a cell. The upstream and downstream sequences share sequence similarity with either side of the site of integration in the polynucleotide. The exogenous template comprises a sequence to be integrated (e.g., a mutated RNA). The sequence for integration may be a sequence endogenous or exogenous to the cell. Examples of a sequence to be integrated include polynucleotide encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the recombination template are selected to promote recombination between the RNA sequence of interest and the recombination. The upstream sequence is a polynucleotide sequence that shares sequence similarity with the sequence upstream of the targeted site for integration. Similarly, the downstream sequence is a polynucleotide sequence that shares sequence similarity with the polynucleotide sequence downstream of the targeted site of integration. The upstream and downstream sequences in the recombination template can have 75%, 80%, 85%, 90%, 95%, or 100% sequence identity with the targeted sequence. Preferably, the upstream and downstream sequences in the recombination template have about 95%, 96%, 97%, 98%, 99%, or 100% sequence identity with the targeted sequence. In some methods, the upstream and downstream sequences in the recombination template have about 99% or 100% sequence identity with the targeted sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the recombination template may further comprise a marker. Such a marker may make it easy to screen for targeted integrations. Examples of suitable markers include restriction sites, fluorescent proteins, or selectable markers. The recombination template of the invention can be constructed using recombinant techniques (see, for example, Sambrook et al., 2001 and Ausubel et al., 1996). In a method for modifying a target sequence by integrating an recombination template, a break (e.g., double or single stranded break in double or single stranded DNA or RNA) is introduced into the DNA or RNA sequence by the nucleic acid-targeting complex, the break is repaired via homologous recombination with an recombination template such that the template is integrated into the target. The presence of a double-stranded break facilitates integration of the template. In other embodiments, this invention provides a method of modifying expression of a RNA in a eukaryotic cell. The method comprises increasing or decreasing expression of a target polynucleotide by using a nucleic acid-targeting complex that binds to the DNA or RNA (e.g., mRNA or pre-mRNA). In some methods, a target can be inactivated to affect the modification of the expression in a cell. For example, upon the binding of a nucleic acid-targeting complex to a target sequence in a cell, the target is inactivated such that the sequence is not translated, the coded protein is not produced, or the sequence does not function as the wild-type sequence does. For example, a protein or microRNA coding sequence may be inactivated such that the protein or microRNA or pre-microRNA transcript is not produced. The target of a nucleic acid-targeting complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., ncRNA, lncRNA, tRNA, or rRNA). Examples of target RNA include a sequence associated with a signaling biochemical pathway, e.g., a signaling biochemical pathway-associated polynucleotide.

Examples of target polynucleotide include a disease associated polynucleotide. A "disease-associated" polynucleotide refers to any polynucleotide which is yielding translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. disease-associated polynucleotide also refers to a gene possessing mutation(s) or genetic variation that is directly responsible or is in linkage disequilibrium with a gene(s) that is responsible for the etiology of a disease. The translated products may be known or unknown, and may be at a normal or abnormal level. The target RNA of a nucleic acid-targeting complex can be any polynucleotide endogenous or exogenous to the eukaryotic cell. For example, the target RNA can be a RNA residing in the nucleus of the eukaryotic cell. The target polynucleotide can be a sequence coding a gene product (e.g., a protein) or a non-coding sequence (e.g., ncRNA, lncRNA, tRNA, or rRNA).

In some embodiments, the method may comprise allowing the compositions or systems herein to bind to the target DNA or RNA to effect cleavage of said target DNA or RNA thereby modifying the target DNA or RNA, wherein the nucleic acid-targeting complex comprises a nucleic acid-targeting effector protein complexed with a guide RNA hybridized to a target sequence within said target DNA or RNA. In one aspect, the invention provides a method of modifying expression of DNA or RNA in a eukaryotic cell. In some embodiments, the method comprises allowing a nucleic acid-targeting complex to bind to the DNA or RNA such that said binding results in increased or decreased expression of said DNA or RNA; wherein the nucleic acid-targeting complex comprises a nucleic acid-targeting effector protein complexed with a guide RNA. Similar considerations and conditions apply as above for methods of modifying a target DNA or RNA. In fact, these sampling, culturing and re-introduction options apply across the aspects of the present invention. In one aspect, the invention provides for methods of modifying a target DNA or RNA in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells. The Cas proteins as described in any embodiment herein may be used to detect nucleic acid identifiers. Nucleic acid identifiers are non-coding nucleic acids that may be used to identify a particular article. Example nucleic acid identifiers, such as DNA watermarks, are described in Heider and Barnekow. "DNA watermarks: A proof of concept" BMC Molecular Biology 9:40 (2008). The nucleic acid identifiers may also be a nucleic acid barcode. A nucleic-acid based barcode is a short sequence of nucleotides (for example, DNA, RNA, or combinations thereof) that is used as an identifier for an associated molecule, such as a target molecule and/or target nucleic acid. A nucleic acid barcode can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. One or more nucleic acid barcodes can be attached, or "tagged," to a target molecule and/or target nucleic acid. This attachment can be direct (for example, covalent or non-covalent binding of the barcode to the target molecule) or indirect (for example, via an additional molecule, for example, a specific binding agent, such as an antibody (or other protein) or a barcode receiving adaptor (or other nucleic acid molecule). Target molecule and/or target nucleic acids can be labeled with multiple nucleic acid barcodes in combinatorial fashion, such as a nucleic acid barcode concatemer. Typically, a nucleic acid barcode is used to identify target molecules and/or target nucleic acids as being from a particular compartment (for example a discrete volume), having a particular physical property (for example, affinity, length, sequence, etc.), or having been subject to certain treatment conditions. Target molecule and/or target nucleic acid can be associated with multiple nucleic acid barcodes to provide information about all of these features (and more). Methods of generating nucleic acid-barcodes are disclosed, for example, in International Patent Application Publication No. WO/2014/047561.

In an embodiment, a guide RNA and a Cas induce a double strand break for the purpose of inducing HDR-mediated correction. In a further embodiment, two or more guide RNAs complexing with Cas or an ortholog or homolog thereof, may be used to induce multiplexed breaks for purpose of inducing HDR-mediated correction.

Unlike CRISPR-Cas-mediated gene knockout, which permanently eliminates expression by mutating the gene at the DNA level, CRISPR-Cas knockdown allows for temporary reduction of gene expression through the use of artificial transcription factors. Mutating key residues in both DNA cleavage domains of the Cas protein, results in the generation of a catalytically inactive Cas. A catalytically inactive Cas complexes with a guide RNA and localizes to the DNA sequence specified by that guide RNA's targeting domain, however, it does not cleave the target DNA. Fusion of the inactive Cas protein (e.g. the D10A and H840A mutations) to an effector domain, e.g., a transcription repression domain, enables recruitment of the effector to any DNA site specified by the guide RNA. In certain embodiments, Cas may be fused to a transcriptional repression domain and recruited to the promoter region of a gene. Especially for gene repression, it is contemplated herein that blocking the binding site of an endogenous transcription factor would aid in downregulating gene expression. In another embodiment, an inactive Cas can be fused to a chromatin modifying protein. Altering chromatin status can result in decreased expression of the target gene.

In an embodiment, a guide RNA molecule can be targeted to a known transcription response elements (e.g., promoters, enhancers, etc.), a known upstream activating sequences, and/or sequences of unknown or known function that are suspected of being able to control expression of the target DNA.

In some methods, a target polynucleotide can be inactivated to affect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In an aspect, the present disclosure provides methods for detecting a target polynucleotide in a sample, comprising contacting the sample with the compositions or systems (e.g., those comprising one or more detection constructs) herein, wherein the Cas protein exhibits collateral activity and cleaves the detection construct once activated by the target polynucleotide, and the cleaved detection construct generate a signal; and detecting the signal thereby determining presence of the target polynucleotide in the sample.

In an aspect, the present disclosure also provides kits for modifying and/or detecting a target polynucleotide in a sample. The kits may comprise one or more components of the compositions herein.

Non-Homologous End-Joining

In certain embodiments, nuclease-induced non-homologous end-joining (NHEJ) can be used to target gene-specific knockouts. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily be greater than 50 bp, e.g., they can easily reach greater than about 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it may also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving Cas proteins, or an ortholog or homolog thereof, and single strand, or nickase, Cas proteins, or an ortholog or homolog thereof, molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In an embodiment, in which a guide RNA and Cas protein, or an ortholog or homolog thereof, generate a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two guide RNAs complexing with Cas proteins, or an ortholog or homolog thereof, preferably Cas nickases induce two single strand breaks for the purpose of inducing NHEJ-mediated indels, two guide RNAs may be configured to position two single-strand breaks to provide for NHEJ repair a nucleotide of the target position.

In some examples, the systems herein may introduce one or more indels via NHEJ pathway and insert sequence from a combination template via HDR.

Therapeutic Uses and Methods of Treatment

Also provided herein are methods of diagnosing, prognosing, treating, and/or preventing a disease, state, or condition in or of a subject. Generally, the methods of diagnosing, prognosing, treating, and/or preventing a disease, state, or condition in or of a subject can include modifying a polynucleotide in a subject or cell thereof using a composition, system, or component thereof described herein and/or include detecting a diseased or healthy polynucleotide in a subject or cell thereof using a composition, system, or component thereof described herein. In some embodiments, the method of treatment or prevention can include using a composition, system, or component thereof to modify a polynucleotide of an infectious organism (e.g. bacterial or virus) within a subject or cell thereof. In some embodiments, the method of treatment or prevention can include using a composition, system, or component thereof to modify a polynucleotide of an infectious organism or symbiotic organism within a subject. The composition, system, and components thereof can be used to develop models of diseases, states, or conditions. The composition, system, and components thereof can be used to detect a disease state or correction thereof, such as by a method of treatment or prevention described herein. The composition, system, and components thereof can be used to screen and select cells that can be used, for example, as treatments or preventions described herein. The composition, system, and components thereof can be used to develop biologically active agents that can be used to modify one or more biologic functions or activities in a subject or a cell thereof.

In general, the method can include delivering a composition, system, and/or component thereof to a subject or cell thereof, or to an infectious or symbiotic organism by a suitable delivery technique and/or composition. Once administered the components can operate as described elsewhere herein to elicit a nucleic acid modification event. In some aspects, the nucleic acid modification event can occur at the genomic, epigenomic, and/or transcriptomic level. DNA and/or RNA cleavage, gene activation, and/or gene deactivation can occur. Additional features, uses, and advantages are described in greater detail below. On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. In addition to treating and/or preventing a disease in a subject, the compositions may be applied in a wide variety of methods for screening in libraries in cells and functional modeling in vivo (e.g. gene activation of lincRNA and identification of function; gain-of-function modeling; loss-of-function modeling; the use the compositions of the invention to establish cell lines and transgenic animals for optimization and screening purposes).

The composition, system, and components thereof described elsewhere herein can be used to treat and/or prevent a disease, such as a genetic and/or epigenetic disease, in a subject. The composition, system, and components thereof described elsewhere herein can be used to treat and/or prevent genetic infectious diseases in a subject, such as bacterial infections, viral infections, fungal infections, parasite infections, and combinations thereof. The composition, system, and components thereof described elsewhere herein can be used to modify the composition or profile of a microbiome in a subject, which can in turn modify the health status of the subject. The composition, system, described herein can be used to modify cells ex vivo, which can then be administered to the subject whereby the modified cells can treat or prevent a disease or symptom thereof. This is also referred to in some contexts as adoptive therapy.

The composition, system, described herein can be used to treat mitochondrial diseases, where the mitochondrial disease etiology involves a mutation in the mitochondrial DNA.

Also provided is a method of treating a subject, e.g., a subject in need thereof, comprising inducing gene editing by transforming the subject with the polynucleotide encoding one or more components of the composition, system, or complex or any of polynucleotides or vectors described herein and administering them to the subject. A suitable repair template may also be provided, for example delivered by a vector comprising said repair template. The repair template may be a recombination template herein. Also provided is a method of treating a subject, e.g., a subject in need thereof, comprising inducing transcriptional activation or repression of multiple target gene loci by transforming the subject with the polynucleotides or vectors described herein, wherein said polynucleotide or vector encodes or comprises one or more components of composition, system, complex or component thereof comprising multiple Cas effectors. Where any treatment is occurring ex vivo, for example in a cell culture, then it will be appreciated that the term 'subject' may be replaced by the phrase "cell or cell culture."

Also provided is a method of treating a subject, e.g., a subject in need thereof, comprising inducing gene editing by transforming the subject with the Cas effector(s), advantageously encoding and expressing in vivo the remaining portions of the composition, system, (e.g., RNA, guides). A suitable repair template may also be provided, for example delivered by a vector comprising said repair template. Also provided is a method of treating a subject, e.g., a subject in need thereof, comprising inducing transcriptional activation or repression by transforming the subject with the Cas effector(s) advantageously encoding and expressing in vivo the remaining portions of the composition, system, (e.g., RNA, guides); advantageously in some embodiments the CRISPR enzyme is a catalytically inactive Cas effector and includes one or more associated functional domains. Where any treatment is occurring ex vivo, for example in a cell culture, then it will be appreciated that the term 'subject' may be replaced by the phrase "cell or cell culture."

One or more components of the composition and system described herein can be included in a composition, such as a pharmaceutical composition, and administered to a host individually or collectively. Alternatively, these components may be provided in a single composition for administration to a host. Administration to a host may be performed via viral vectors known to the skilled person or described herein for delivery to a host (e.g. lentiviral vector, adenoviral vector, AAV vector). As explained herein, use of different selection markers (e.g. for lentiviral gRNA selection) and concentration of gRNA (e.g. dependent on whether multiple gRNAs are used) may be advantageous for eliciting an improved effect.

Thus, also described herein are methods of inducing one or more polynucleotide modifications in a eukaryotic or prokaryotic cell or component thereof (e.g. a mitochondria) of a subject, infectious organism, and/or organism of the microbiome of the subject. The modification can include the introduction, deletion, or substitution of one or more nucleotides at a target sequence of a polynucleotide of one or more cell(s). The modification can occur in vitro, ex vivo, in situ, or in vivo.

In some embodiments, the method of treating or inhibiting a condition or a disease caused by one or more mutations in a genomic locus in a eukaryotic organism or a non-human organism can include manipulation of a target sequence within a coding, non-coding or regulatory element of said genomic locus in a target sequence in a subject or a non-human subject in need thereof comprising modifying the subject or a non-human subject by manipulation of the target sequence and wherein the condition or disease is susceptible to treatment or inhibition by manipulation of the target sequence including providing treatment comprising delivering a composition comprising the particle delivery system or the delivery system or the virus particle of any one of the above embodiment or the cell of any one of the above embodiment.

Also provided herein is the use of the particle delivery system or the delivery system or the virus particle of any one of the above embodiment or the cell of any one of the above embodiment in ex vivo or in vivo gene or genome editing; or for use in in vitro, ex vivo or in vivo gene therapy. Also provided herein are particle delivery systems, non-viral delivery systems, and/or the virus particle of any one of the above embodiments or the cell of any one of the above embodiments used in the manufacture of a medicament for in vitro, ex vivo or in vivo gene or genome editing or for use in in vitro, ex vivo or in vivo gene therapy or for use in a method of modifying an organism or a non-human organism by manipulation of a target sequence in a genomic locus associated with a disease or in a method of treating or inhibiting a condition or disease caused by one or more mutations in a genomic locus in a eukaryotic organism or a non-human organism.

In some embodiments, polynucleotide modification can include the introduction, deletion, or substitution of 1-75 nucleotides at each target sequence of said polynucleotide of said cell(s). The modification can include the introduction, deletion, or substitution of at least 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence. The modification can include the introduction, deletion, or substitution of at least 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s). The modification can include the introduction, deletion, or substitution of at least 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s). The modification can include the introduction, deletion, or substitution of at least 20, 21, 22, 23, 24, 25, 26, 27, 28, 29, 30, 35, 40, 45, 50, or 75 nucleotides at each target sequence of said cell(s). The modification can include the introduction, deletion, or substitution of at least 40, 45, 50, 75, 100, 200, 300, 400 or 500 nucleotides at each target sequence of said cell(s). The modification can include the introduction, deletion, or substitution of at least 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, or 9900 to 10000 nucleotides at each target sequence of said cell(s).

In some embodiments, the modifications can include the introduction, deletion, or substitution of nucleotides at each target sequence of said cell(s) via nucleic acid components (e.g. guide(s) RNA(s) or sgRNA(s)), such as those mediated by a composition, system, or a component thereof described elsewhere herein. In some embodiments, the modifications can include the introduction, deletion, or substitution of nucleotides at a target or random sequence of said cell(s) via a composition, system, or technique.

In some embodiments, the composition, system, or component thereof can promote Non-Homologous End-Joining (NHEJ). In some embodiments, modification of a polynucleotide by a composition, system, or a component thereof, such as a diseased polynucleotide, can include NHEJ. In some embodiments, promotion of this repair pathway by the composition, system, or a component thereof can be used to target gene or polynucleotide specific knock-outs and/or knock-ins. In some embodiments, promotion of this repair pathway by the composition, system, or a component thereof can be used to generate NHEJ-mediated indels. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. The indel can range in size from 1-50 or more base pairs. In some embodiments the indel can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 base pairs or more. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences.

In some embodiments, composition, system, mediated NHEJ can be used in the method to delete small sequence motifs. In some embodiments, composition, system, mediated NHEJ can be used in the method to generate NHEJ-mediate indels that can be targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp). In an embodiment, in which a guide RNA and Cas effector generate a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position). In an embodiment, in which two guide RNAs complexing with one or more Cas nickases induce two single strand breaks for the purpose of inducing NHEJ-mediated indels, two guide RNAs may be configured to position two single-strand breaks to provide for NHEJ repair a nucleotide of the target position.

For minimization of toxicity and off-target effect, it may be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the D10A mutation) can be delivered with a pair of guide RNAs targeting a site of interest. Guide sequences and strategies to minimize toxicity and off-target effects can be as in International Patent Publication No. WO 2014/093622 (PCT/US2013/074667); or, via mutation. Others are as described elsewhere herein.

Typically, in the context of an endogenous CRISPR or system, formation of a CRISPR or complex (comprising a guide sequence hybridized to a target sequence and complexed with one or more Cas proteins) results in cleavage, nicking, and/or another modification of one or both strands in or near (e.g. within 1, 2, 3, 4, 5, 6, 7, 8, 9, 10, 20, 50, or more base pairs from) the target sequence. In some embodiments, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), can also form part of a CRISPR complex, such as by hybridization along at least a portion of the tracr sequence to all or a portion of a tracr mate sequence that is operably linked to the guide sequence.

In some embodiments, a method of modifying a target polynucleotide in a cell to treat or prevent a disease can include allowing a composition, system, or component thereof to bind to the target polynucleotide, e.g., to effect cleavage, nicking, or other modification as the composition, system, is capable of said target polynucleotide, thereby modifying the target polynucleotide, wherein the composition, system, or component thereof, complex with a guide sequence, and hybridize said guide sequence to a target sequence within the target polynucleotide, wherein said guide sequence is optionally linked to a tracr mate sequence, which in turn can hybridize to a tracr sequence. In some of these embodiments, the composition, system, or component thereof can be or include a CRISPR-Cas effector complexed with a guide sequence. In some embodiments, modification can include cleaving or nicking one or two strands at the location of the target sequence by one or more components of the composition, system, or component thereof.

The cleavage, nicking, or other modification capable of being performed by the composition, system, can modify transcription of a target polynucleotide. In some embodiments, modification of transcription can include decreasing transcription of a target polynucleotide. In some embodiments, modification can include increasing transcription of a target polynucleotide. In some embodiments, the method includes repairing said cleaved target polynucleotide by homologous recombination with an recombination template polynucleotide, wherein said repair results in a modification such as, but not limited to, an insertion, deletion, or substitution of one or more nucleotides of said target polynucleotide. In some embodiments, said modification results in one or more amino acid changes in a protein expressed from a gene comprising the target sequence. In some embodiments, the modification imparted by the composition, system, or component thereof provides a transcript and/or protein that can correct a disease or a symptom thereof, including but not limited to, any of those described in greater detail elsewhere herein.

In some embodiments, the method of treating or preventing a disease can include delivering one or more vectors or vector systems to a cell, such as a eukaryotic or prokaryotic cell, wherein one or more vectors or vector systems include the composition, system, or component thereof. In some embodiments, the vector(s) or vector system(s) can be a viral vector or vector system, such as an AAV or lentiviral vector system, which are described in greater detail elsewhere herein. In some embodiments, the method of treating or preventing a disease can include delivering one or more viral particles, such as an AAV or lentiviral particle, containing the composition, system, or component thereof. In some embodiments, the viral particle has a tissue specific tropism. In some embodiments, the viral particle has a liver, muscle, eye, heart, pancreas, kidney, neuron, epithelial cell, endothelial cell, astrocyte, glial cell, immune cell, or red blood cell specific tropism.

It will be understood that the composition and system, according to the invention as described herein, such as the composition and system, for use in the methods according to the invention as described herein, may be suitably used for any type of application known for composition, system, preferably in eukaryotes. In certain aspects, the application is therapeutic, preferably therapeutic in a eukaryote organism, such as including but not limited to animals (including human), plants, algae, fungi (including yeasts), etc. Alternatively, or in addition, in certain aspects, the application may involve accomplishing or inducing one or more particular traits or characteristics, such as genotypic and/or phenotypic traits or characteristics, as also described elsewhere herein.

Treating Diseases of the Circulatory System

In some embodiments, the composition, system, and/or component thereof described herein can be used to treat and/or prevent a circulatory system disease. Exemplary disease is provided, for example, in Tables 2 and 3. In some embodiments the plasma exosomes of Wahlgren et al. (Nucleic Acids Research, 2012, Vol. 40, No. 17 e130) can be used to deliver the composition, system, and/or component thereof described herein to the blood. In some embodiments, the circulatory system disease can be treated by using a lentivirus to deliver the composition, system, described herein to modify hematopoietic stem cells (HSCs) in vivo or ex vivo (see e.g. Drakopoulou, "Review Article, The Ongoing Challenge of Hematopoietic Stem Cell-Based Gene Therapy for β-Thalassemia," Stem Cells International, Volume 2011, Article ID 987980, 10 pages, doi:10.4061/2011/987980, which can be adapted for use with the composition, system, herein in view of the description herein). In some embodiments, the circulatory system disorder can be treated by correcting HSCs as to the disease using a composition, system, herein or a component thereof, wherein the composition, system, optionally includes a suitable HDR repair template (see e.g. Cavazzana, "Outcomes of Gene Therapy for β-Thalassemia Major via Transplantation of Autologous Hematopoietic Stem Cells Transduced Ex Vivo with a Lentiviral βA-T87Q-Globin Vector."; Cavazzana-Calvo, "Transfusion independence and HMGA2 activation after gene therapy of human β-thalassaemia", Nature 467, 318-322 (16 Sep. 2010) doi:10.1038/nature09328; Nienhuis, "Development of Gene Therapy for Thalassemia, Cold Spring Harbor Perspectives in Medicine, doi: 10.1101/cshperspect.a011833 (2012), LentiGlobin BB305, a lentiviral vector containing an engineered β-globin gene (βA-T87Q); and Xie et al., "Seamless gene correction of β-thalassaemia mutations in patient-specific iPSCs using CRISPR/Cas9 and piggyback" Genome Research gr.173427.114 (2014) www.genome.org/cgi/doi/10.1101/gr.173427.114 (Cold Spring Harbor Laboratory Press; Watts, "Hematopoietic Stem Cell Expansion and Gene Therapy" Cytotherapy 13(10):1164-1171. doi:10.3109/14653249.2011.620748 (2011), which can be adapted for use with the composition, system, herein in view of the description herein). In some embodiments, iPSCs can be modified using a composition, system, described herein to correct a disease polynucleotide associated with a circulatory disease. In this regard, the teachings of Xu et al. (Sci Rep. 2015 Jul. 9; 5:12065. doi: 10.1038/srep12065) and Song et al. (Stem Cells Dev. 2015 May 1; 24(9):1053-65. doi: 10.1089/scd.2014.0347. Epub 2015 Feb. 5) with respect to modifying iPSCs can be adapted for use in view of the description herein with the composition, system, described herein.

The term "Hematopoietic Stem Cell" or "HSC" refers broadly those cells considered to be an HSC, e.g., blood cells that give rise to all the other blood cells and are derived from mesoderm; located in the red bone marrow, which is contained in the core of most bones. HSCs of the invention include cells having a phenotype of hematopoietic stem cells, identified by small size, lack of lineage (lin) markers, and markers that belong to the cluster of differentiation series, like: CD34, CD38, CD90, CD133, CD105, CD45, and also c-kit,—the receptor for stem cell factor. Hematopoietic stem cells are negative for the markers that are used for detection of lineage commitment, and are, thus, called Lin−; and, during their purification by FACS, a number of up to 14 different mature blood-lineage markers, e.g., CD13 & CD33 for myeloid, CD71 for erythroid, CD19 for B cells, CD61 for megakaryocytic, etc. for humans; and, B220 (murine CD45) for B cells, Mac-1 (CD11b/CD18) for monocytes, Gr-1 for Granulocytes, Ter119 for erythroid cells, I17Ra, CD3, CD4, CD5, CD8 for T cells, etc. Mouse HSC markers: CD34lo/−, SCA-1+, Thy1.1+/lo, CD38+, C-kit+, lin−, and Human HSC markers: CD34+, CD59+, Thy1/CD90+, CD38lo/−, C-kit/CD117+, and lin-. HSCs are identified by markers. Hence in embodiments discussed herein, the HSCs can be CD34+ cells. HSCs can also be hematopoietic stem cells that are CD34−/CD38-. Stem cells that may lack c-kit on the cell surface that are considered in the art as HSCs are within the ambit of the invention, as well as CD133+ cells likewise considered HSCs in the art.

In some embodiments, the treatment or prevention for treating a circulatory system or blood disease can include modifying a human cord blood cell with any modification described herein. In some embodiments, the treatment or prevention for treating a circulatory system or blood disease can include modifying a granulocyte colony-stimulating factor-mobilized peripheral blood cell (mPB) with any modification described herein. In some embodiments, the human cord blood cell or mPB can be CD34+. In some embodiments, the cord blood cell(s) or mPB cell(s) modified can be autologous. In some embodiments, the cord blood cell(s) or mPB cell(s) can be allogenic. In addition to the modification of the disease gene(s), allogenic cells can be further modified using the composition, system, described herein to reduce the immunogenicity of the cells when delivered to the recipient. Such techniques are described elsewhere herein and e.g. Cartier, "MINI-SYMPOSIUM: X-Linked Adrenoleukodystrophypa, Hematopoietic Stem Cell Transplantation and Hematopoietic Stem Cell Gene Therapy in X-Linked Adrenoleukodystrophy," Brain Pathology 20 (2010) 857-862, which can be adapted for use with the composition, system, herein. The modified cord blood cell(s) or mPB cell(s) can be optionally expanded in vitro. The modified cord blood cell(s) or mPB cell(s) can be derived to a subject in need thereof using any suitable delivery technique.

The CRISPR-Cas (system may be engineered to target genetic locus or loci in HSCs. In some embodiments, the Cas effector(s) can be codon-optimized for a eukaryotic cell and especially a mammalian cell, e.g., a human cell, for instance, HSC, or iPSC and sgRNA targeting a locus or loci in HSC, such as circulatory disease, can be prepared. These may be delivered via particles. The particles may be formed by the Cas effector protein and the gRNA being admixed. The gRNA and Cas effector protein mixture can be, for example, admixed with a mixture comprising or consisting essentially of or consisting of surfactant, phospholipid, biodegradable polymer, lipoprotein and alcohol, whereby particles containing the gRNA and Cas effector protein may be formed. The invention comprehends so making particles and particles from such a method as well as uses thereof. Particles suitable delivery of the CRISPR-Cas systems in the context of blood or circulatory system or HSC delivery to the blood or circulatory system are described in greater detail elsewhere herein.

In some embodiments, after ex vivo modification the HSCs or iPCS can be expanded prior to administration to the subject. Expansion of HSCs can be via any suitable method such as that described by, Lee, "Improved ex vivo expansion of adult hematopoietic stem cells by overcoming CUL4-mediated degradation of HOXB4." Blood. 2013 May 16; 121(20):4082-9. doi: 10.1182/blood-2012-09-455204. Epub 2013 Mar. 21.

In some embodiments, the HSCs or iPSCs modified can be autologous. In some embodiments, the HSCs or iPSCs can be allogenic. In addition to the modification of the disease gene(s), allogenic cells can be further modified using the composition, system, described herein to reduce the immunogenicity of the cells when delivered to the recipient. Such techniques are described elsewhere herein and e.g. Cartier, "MINI-SYMPOSIUM: X-Linked Adrenoleukodystrophypa, Hematopoietic Stem Cell Transplantation and Hematopoietic Stem Cell Gene Therapy in X-Linked Adrenoleukodystrophy," Brain Pathology 20 (2010) 857-862, which can be adapted for use with the composition, system, herein.

Treating Neurological Diseases

In some embodiments, the compositions, systems, described herein can be used to treat diseases of the brain and CNS. Delivery options for the brain include encapsulation of CRISPR enzyme and guide RNA in the form of either DNA or RNA into liposomes and conjugating to molecular Trojan horses for trans-blood brain barrier (BBB) delivery. Molecular Trojan horses have been shown to be effective for delivery of B-gal expression vectors into the brain of non-human primates. The same approach can be used to delivery vectors containing CRISPR enzyme and guide RNA. For instance, Xia C F and Boado R J, Pardridge W M ("Antibody-mediated targeting of siRNA via the human insulin receptor using avidin-biotin technology." Mol Pharm. 2009 May-June; 6(3):747-51. doi: 10.1021/mp800194) describes how delivery of short interfering RNA (siRNA) to cells in culture, and in vivo, is possible with combined use of a receptor-specific monoclonal antibody (mAb) and avidin-biotin technology. The authors also report that because the bond between the targeting mAb and the siRNA is stable with avidin-biotin technology, and RNAi effects at distant sites such as brain are observed in vivo following an intravenous administration of the targeted siRNA, the teachings of which can be adapted for use with the compositions, systems, herein. In other embodiments, an artificial virus can be generated for CNS and/or brain delivery. See e.g. Zhang et al. (Mol Ther. 2003 January; 7(1):11-8.)), the teachings of which can be adapted for use with the compositions, systems, herein.

Treating Hearing Diseases

In some embodiments the composition and system described herein can be used to treat a hearing disease or hearing loss in one or both ears. Deafness is often caused by lost or damaged hair cells that cannot relay signals to auditory neurons. In such cases, cochlear implants may be used to respond to sound and transmit electrical signals to the nerve cells. But these neurons often degenerate and retract from the cochlea as fewer growth factors are released by impaired hair cells.

In some embodiments, the composition, system, or modified cells can be delivered to one or both ears for treating or preventing hearing disease or loss by any suitable method or technique. Suitable methods and techniques include, but are not limited to those set forth in US Patent Publication No. 20120328580 describes injection of a pharmaceutical composition into the ear (e.g., auricular administration), such as into the luminae of the cochlea (e.g., the Scala media, Sc vestibulae, and Sc tympani), e.g., using a syringe, e.g., a single-dose syringe. For example, one or more of the compounds described herein can be administered by intratympanic injection (e.g., into the middle ear), and/or injections into the outer, middle, and/or inner ear; administration in situ, via a catheter or pump (see e.g. McKenna et al., (U.S. Patent Publication No. 2006/0030837) and Jacobsen et al., (U.S. Pat. No. 7,206,639); administration in combination with a mechanical device such as a cochlear implant or a hearing aid, which is worn in the outer ear (see e.g. U.S. Patent Publication No. 2007/0093878, which provides an exemplary cochlear implant suitable for delivery of the compositions, systems, described herein to the ear). Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, Drug Discovery Today, 10:1299-1306, 2005). In some embodiments, a catheter or pump can be positioned, e.g., in the ear (e.g., the outer, middle, and/or inner ear) of a patient during a surgical procedure. In some embodiments, a catheter or pump can be positioned, e.g., in the ear (e.g., the outer, middle, and/or inner ear) of a patient without the need for a surgical procedure.

In general, the cell therapy methods described in US Patent Publication No. 20120328580 can be used to promote complete or partial differentiation of a cell to or towards a mature cell type of the inner ear (e.g., a hair cell) in vitro. Cells resulting from such methods can then be transplanted or implanted into a patient in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Cells suitable for use in the present invention include, but are not limited to, cells that are capable of differentiating completely or partially into a mature cell of the inner ear, e.g., a hair cell (e.g., an inner and/or outer hair cell), when contacted, e.g., in vitro, with one or more of the compounds described herein. Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, iPS cells, and fat derived stem cells), progenitor cells (e.g., inner ear progenitor cells), support cells (e.g., Deiters' cells, pillar cells, inner phalangeal cells, tectal cells and Hensen's cells), and/or germ cells. The use of stem cells for the replacement of inner ear sensory cells is described in Li et al., (U.S. Patent Publication No. 2005/0287127) and Li et al., (U.S. patent application Ser. No. 11/953,797). The use of bone marrow derived stem cells for the replacement of inner ear sensory cells is described in Edge et al., PCT/US2007/084654. iPS cells are described, e.g., at Takahashi et al., Cell, Volume 131, Issue 5, Pages 861-872 (2007); Takahashi and Yamanaka, Cell 126, 663-76 (2006); Okita et al., Nature 448, 260-262 (2007); Yu, J. et al., Science 318(5858):1917-1920 (2007); Nakagawa et al., Nat. Biotechnol. 26:101-106 (2008); and Zaehres and Scholer, Cell 131(5):834-835 (2007). Such suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

The composition and system may be delivered to the ear by direct application of pharmaceutical composition to the outer ear, with compositions modified from US Patent Publication No. 20110142917. In some embodiments the pharmaceutical composition is applied to the ear canal. Delivery to the ear may also be referred to as aural or otic delivery.

In some embodiments, the compositions, systems, or components thereof and/or vectors or vector systems can be delivered to ear via a transfection to the inner ear through the intact round window by a novel proteidic delivery technology which may be applied to the nucleic acid-targeting system of the present invention (see, e.g., Qi et al., Gene Therapy (2013), 1-9). About 40 µl of 10 mM RNA may be contemplated as the dosage for administration to the ear.

According to Rejali et al. (Hear Res. 2007 June; 228(1-2):180-7), cochlear implant function can be improved by good preservation of the spiral ganglion neurons, which are the target of electrical stimulation by the implant and brain derived neurotrophic factor (BDNF) has previously been shown to enhance spiral ganglion survival in experimentally deafened ears. Rejali et al. tested a modified design of the cochlear implant electrode that includes a coating of fibroblast cells transduced by a viral vector with a BDNF gene insert. To accomplish this type of ex vivo gene transfer, Rejali et al. transduced guinea pig fibroblasts with an adenovirus with a BDNF gene cassette insert, and determined that these cells secreted BDNF and then attached BDNF-secreting cells to the cochlear implant electrode via an agarose gel, and implanted the electrode in the scala tympani. Rejali et al. determined that the BDNF expressing electrodes were able to preserve significantly more spiral ganglion neurons in the basal turns of the cochlea after 48 days of implantation when compared to control electrodes and demonstrated the feasibility of combining cochlear implant therapy with ex vivo gene transfer for enhancing spiral ganglion neuron survival. Such a system may be applied to the nucleic acid-targeting system of the present invention for delivery to the ear.

In some embodiments, the system set forth in Mukherj ea et al. (Antioxidants & Redox Signaling, Volume 13, Number 5, 2010) can be adapted for transtympanic administration of the composition, system, or component thereof to the ear. In some embodiments, a dosage of about 2 mg to about 4 mg of CRISPR Cas for administration to a human.

In some embodiments, the system set forth in [Jung et al. (Molecular Therapy, vol. 21 no. 4, 834-841 April 2013) can be adapted for vestibular epithelial delivery of the composition, system, or component thereof to the ear. In some embodiments, a dosage of about 1 to about 30 mg of CRISPR Cas for administration to a human.

Treating Diseases in Non-Dividing Cells

In some embodiments, the gene or transcript to be corrected is in a non-dividing cell. Exemplary non-dividing cells are muscle cells or neurons. Non-dividing (especially non-dividing, fully differentiated) cell types present issues for gene targeting or genome engineering, for example because homologous recombination (HR) is generally suppressed in the G1 cell-cycle phase. However, while studying the mechanisms by which cells control normal DNA repair systems, Durocher discovered a previously unknown switch that keeps HR "off" in non-dividing cells and devised a strategy to toggle this switch back on. Orthwein et al. (Daniel Durocher's lab at the Mount Sinai Hospital in Ottawa, Canada) recently reported (Nature 16142, published online 9 Dec. 2015) have shown that the suppression of HR can be lifted and gene targeting successfully concluded in both kidney (293T) and osteosarcoma (U2OS) cells. Tumor suppressors, BRCA1, PALB2 and BRAC2 are known to promote DNA DSB repair by HR. They found that formation of a complex of BRCA1 with PALB2-BRAC2 is governed by a ubiquitin site on PALB2, such that action on the site by an E3 ubiquitin ligase. This E3 ubiquitin ligase is composed of KEAP1 (a PALB2-interacting protein) in complex with cullin-3 (CUL3)-RBX1. PALB2 ubiquitylation suppresses its interaction with BRCA1 and is counteracted by the deubiquitylase USP11, which is itself under cell cycle control. Restoration of the BRCA1-PALB2 interaction combined with the activation of DNA-end resection is sufficient to induce homologous recombination in G1, as measured by a number of methods including a CRISPR-Cas-based gene-targeting assay directed at USP11 or KEAP1 (expressed from a pX459 vector). However, when the BRCA1-PALB2 interaction was restored in resection-competent G1 cells using either KEAP1 depletion or expression of the PALB2-KR mutant, a robust increase in gene-targeting events was detected. These teachings can be adapted for and/or applied to the Cas compositions, systems, described herein.

Thus, reactivation of HR in cells, especially non-dividing, fully differentiated cell types is preferred, in some embodiments. In some embodiments, promotion of the BRCA1-PALB2 interaction is preferred in some embodiments. In some embodiments, the target ell is a non-dividing cell. In some embodiments, the target cell is a neuron or muscle cell. In some embodiments, the target cell is targeted in vivo. In some embodiments, the cell is in G1 and HR is suppressed. In some embodiments, use of KEAP1 depletion, for example inhibition of expression of KEAP1 activity, is preferred. KEAP1 depletion may be achieved through siRNA, for example as shown in Orthwein et al. Alternatively, expression of the PALB2-KR mutant (lacking all eight Lys residues in the BRCA1-interaction domain is preferred, either in combination with KEAP1 depletion or alone. PALB2-KR interacts with BRCA1 irrespective of cell cycle position. Thus, promotion or restoration of the BRCA1-PALB2 interaction, especially in G1 cells, is preferred in some embodiments, especially where the target cells are non-dividing, or where removal and return (ex vivo gene targeting) is problematic, for example neuron or muscle cells. KEAP1 siRNA is available from ThermoFischer. In some embodiments, a BRCA1-PALB2 complex may be delivered to the G1 cell. In some embodiments, PALB2 deubiquitylation may be promoted for example by increased expression of the deubiquitylase USP11, so it is envisaged that a construct may be provided to promote or up-regulate expression or activity of the deubiquitylase USP11.

Treating Diseases of the Eye

In some embodiments, the disease to be treated is a disease that affects the eyes. Thus, in some embodiments, the composition, system, or component thereof described herein is delivered to one or both eyes.

The composition, system, can be used to correct ocular defects that arise from several genetic mutations further described in Genetic Diseases of the Eye, Second Edition, edited by Elias I. Traboulsi, Oxford University Press, 2012.

In some embodiments, the condition to be treated or targeted is an eye disorder. In some embodiments, the eye disorder may include glaucoma. In some embodiments, the eye disorder includes a retinal degenerative disease. In some embodiments, the retinal degenerative disease is selected from Stargardt disease, Bardet-Biedl Syndrome, Best disease, Blue Cone Monochromacy, Choroidermia, Cone-rod dystrophy, Congenital Stationary Night Blindness, Enhanced S-Cone Syndrome, Juvenile X-Linked Retinoschisis, Leber Congenital Amaurosis, Malattia Leventinesse, Norrie Disease or X-linked Familial Exudative Vitreoretinopathy, Pattern Dystrophy, Sorsby Dystrophy, Usher Syndrome, Retinitis Pigmentosa, Achromatopsia or Macular dystrophies or degeneration, Retinitis Pigmentosa, Achromatopsia, and age related macular degeneration. In some embodiments, the retinal degenerative disease is Leber Congenital Amaurosis (LCA) or Retinitis Pigmentosa. Other exemplary eye diseases are described in greater detail elsewhere herein.

In some embodiments, the composition, system, is delivered to the eye, optionally via intravitreal injection or subretinal injection. Intraocular injections may be performed with the aid of an operating microscope. For subretinal and intravitreal injections, eyes may be prolapsed by gentle digital pressure and fundi visualized using a contact lens system consisting of a drop of a coupling medium solution on the cornea covered with a glass microscope slide coverslip. For subretinal injections, the tip of a 10-mm 34-gauge needle, mounted on a 5-μl Hamilton syringe may be advanced under direct visualization through the superior equatorial sclera tangentially towards the posterior pole until the aperture of the needle was visible in the subretinal space. Then, 2 μl of vector suspension may be injected to produce a superior bullous retinal detachment, thus confirming subretinal vector administration. This approach creates a self-sealing sclerotomy allowing the vector suspension to be retained in the subretinal space until it is absorbed by the RPE, usually within 48 h of the procedure. This procedure may be repeated in the inferior hemisphere to produce an inferior retinal detachment. This technique results in the exposure of approximately 70% of neurosensory retina and RPE to the vector suspension. For intravitreal injections, the needle tip may be advanced through the sclera 1 mm posterior to the corneoscleral limbus and 2 μl of vector suspension injected into the vitreous cavity. For intracameral injections, the needle tip may be advanced through a corneoscleral limbal paracentesis, directed towards the central cornea, and 2 μl of vector suspension may be injected. For intracameral injections, the needle tip may be advanced through a corneoscleral limbal paracentesis, directed towards the central cornea, and 2 μl of vector suspension may be injected. These vectors may be injected at titers of either $1.0-1.4\times10^{10}$ or $1.0-1.4\times10^{9}$ transducing units (TU)/ml.

In some embodiments, for administration to the eye, lentiviral vectors. In some embodiments, the lentiviral vector is an equine infectious anemia virus (EIAV) vector. Exemplary EIAV vectors for eye delivery are described in Balagaan, J Gene Med 2006; 8: 275-285, Published online 21 Nov. 2005 in Wiley InterScience (www.interscience.wiley.com). DOI: 10.1002/jgm.845; Binley et al., HUMAN GENE THERAPY 23:980-991 (September 2012), which can be adapted for use with the composition, system, described herein. In some embodiments, the dosage can be $1.1\times10^{5}$ transducing units per eye (TU/eye) in a total volume of 100 μl.

Other viral vectors can also be used for delivery to the eye, such as AAV vectors, such as those described in Campochiaro et al., Human Gene Therapy 17:167-176 (February 2006), Millington-Ward et al. (Molecular Therapy, vol.

19 no. 4, 642-649 April 2011; Dalkara et al. (Sci Transl Med 5, 189ra76 (2013)), which can be adapted for use with the composition, system, described herein. In some embodiments, the dose can range from about $10^6$ to $10^{9.5}$ particle units. In the context of the Millington-Ward AAV vectors, a dose of about $2\times10^{11}$ to about $6\times10^{13}$ virus particles can be administered. In the context of Dalkara vectors, a dose of about $1\times10^{15}$ to about $1\times10^{16}$ vg/ml administered to a human.

In some embodiments, the sd-rxRNA® system of RXi Pharmaceuticals may be used/and or adapted for delivering composition, system, to the eye. In this system, a single intravitreal administration of 3 µg of sd-rxRNA results in sequence-specific reduction of PPIB mRNA levels for 14 days. The sd-rxRNA® system may be applied to the nucleic acid-targeting system of the present invention, contemplating a dose of about 3 to 20 mg of CRISPR administered to a human.

In other embodiments, the methods of US Patent Publication No. 20130183282, which is directed to methods of cleaving a target sequence from the human rhodopsin gene, may also be modified to the nucleic acid-targeting system of the present invention.

In other embodiments, the methods of US Patent Publication No. 20130202678 for treating retinopathies and sight-threatening ophthalmologic disorders relating to delivering of the Puf-A gene (which is expressed in retinal ganglion and pigmented cells of eye tissues and displays a unique anti-apoptotic activity) to the sub-retinal or intravitreal space in the eye may be used or adapted. In particular, desirable targets are zgc:193933, prdm1a, spata2, tex10, rbb4, ddx3, zp2.2, Blimp-1 and HtrA2, all of which may be targeted by the composition, system, of the present invention.

Wu (Cell Stem Cell, 13:659-62, 2013) designed a guide RNA that led Cas9 to a single base pair mutation that causes cataracts in mice, where it induced DNA cleavage. Then using either the other wild-type allele or oligos given to the zygotes repair mechanisms corrected the sequence of the broken allele and corrected the cataract-causing genetic defect in mutant mouse. This approach can be adapted to and/or applied to the compositions, systems, described herein.

US Patent Publication No. 20120159653, describes use of zinc finger nucleases to genetically modify cells, animals and proteins associated with macular degeneration (MD), the teachings of which can be applied to and/or adapted for the compositions, systems, described herein.

One aspect of US Patent Publication No. 20120159653 relates to editing of any chromosomal sequences that encode proteins associated with MD which may be applied to the nucleic acid-targeting system of the present invention.

Treating Muscle Diseases and Cardiovascular Diseases

In some embodiments, the composition, system can be used to treat and/or prevent a muscle disease and associated circulatory or cardiovascular disease or disorder. The present invention also contemplates delivering the composition, system, described herein, e.g. Cas effector protein systems, to the heart. For the heart, a myocardium tropic adeno-associated virus (AAVM) is preferred, in particular AAVM41 which showed preferential gene transfer in the heart (see, e.g., Lin-Yanga et al., PNAS, Mar. 10, 2009, vol. 106, no. 10). Administration may be systemic or local. A dosage of about $1\text{-}10\times10^{14}$ vector genomes are contemplated for systemic administration. See also, e.g., Eulalio et al. (2012) Nature 492: 376 and Somasuntharam et al. (2013) Biomaterials 34: 7790, the teachings of which can be adapted for and/or applied to the compositions, systems, described herein.

For example, US Patent Publication No. 20110023139, the teachings of which can be adapted for and/or applied to the compositions, systems, described herein describes use of zinc finger nucleases to genetically modify cells, animals and proteins associated with cardiovascular disease. Cardiovascular diseases generally include high blood pressure, heart attacks, heart failure, and stroke and TIA. Any chromosomal sequence involved in cardiovascular disease or the protein encoded by any chromosomal sequence involved in cardiovascular disease may be utilized in the methods described in this disclosure. The cardiovascular-related proteins are typically selected based on an experimental association of the cardiovascular-related protein to the development of cardiovascular disease. For example, the production rate or circulating concentration of a cardiovascular-related protein may be elevated or depressed in a population having a cardiovascular disorder relative to a population lacking the cardiovascular disorder. Differences in protein levels may be assessed using proteomic techniques including but not limited to Western blot, immunohistochemical staining, enzyme linked immunosorbent assay (ELISA), and mass spectrometry. Alternatively, the cardiovascular-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR). Exemplary chromosomal sequences can be found in Table 2.

The compositions, systems, herein can be used for treating diseases of the muscular system. The present invention also contemplates delivering the composition, system, described herein, effector protein systems, to muscle(s).

In some embodiments, the muscle disease to be treated is a muscle dystrophy such as DMD. In some embodiments, the composition, system, such as a system capable of RNA modification, described herein can be used to achieve exon skipping to achieve correction of the diseased gene. As used herein, the term "exon skipping" refers to the modification of pre-mRNA splicing by the targeting of splice donor and/or acceptor sites within a pre-mRNA with one or more complementary antisense oligonucleotide(s) (AONs). By blocking access of a spliceosome to one or more splice donor or acceptor site, an AON may prevent a splicing reaction thereby causing the deletion of one or more exons from a fully-processed mRNA. Exon skipping may be achieved in the nucleus during the maturation process of pre-mRNAs. In some examples, exon skipping may include the masking of key sequences involved in the splicing of targeted exons by using a composition, system, described herein capable of RNA modification. In some embodiments, exon skipping can be achieved in dystrophin mRNA. In some embodiments, the composition, system, can induce exon skipping at exon 1, 2, 3, 4, 5, 6, 7, 8, 10, 11, 12, 13, 14, 15, 16, 17, 18, 19, 20, 21, 22, 23, 24, 25, 26, 27, 28, 29, 30, 31, 32, 33, 34, 45, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or any combination thereof of the dystrophin mRNA. In some embodiments, the composition, system, can induce exon skipping at exon 43, 44, 50, 51, 52, 55, or any combination thereof of the dystrophin mRNA. Mutations in these exons, can also be corrected using non-exon skipping polynucleotide modification methods.

In some embodiments, for treatment of a muscle disease, the method of Bortolanza et al. Molecular Therapy vol. 19 no. 11, 2055-264 November 2011) may be applied to an AAV expressing CRISPR Cas and injected into humans at a dosage of about $2 \times 10^{15}$ or $2 \times 10^{16}$ vg of vector. The teachings of Bortolanza et al., can be adapted for and/or applied to the compositions, systems, described herein.

In some embodiments, the method of Dumonceaux et al. (Molecular Therapy vol. 18 no. 5, 881-887 May 2010) may be applied to an AAV expressing CRISPR Cas and injected into humans, for example, at a dosage of about $10^{14}$ to about $10^{15}$ vg of vector. The teachings of Dumonceaux described herein can be adapted for and/or applied to the compositions, systems, described herein.

In some embodiments, the method of Kinouchi et al. (Gene Therapy (2008) 15, 1126-1130) may be applied to CRISPR Cas systems described herein and injected into a human, for example, at a dosage of about 500 to 1000 ml of a 40 µM solution into the muscle.

In some embodiments, the method of Hagstrom et al. (Molecular Therapy Vol. 10, No. 2, August 2004) can be adapted for and/or applied to the compositions, systems, herein and injected at a dose of about 15 to about 50 mg into the great saphenous vein of a human.

In some embodiments, the method comprise treating a sickle cell related disease, e.g., sickle cell trait, sickle cell disease such as sickle cell anemia, β-thalassaemia. For example, the method and system may be used to modify the genome of the sickle cell, e.g., by correcting one or more mutations of the β-globin gene. In the case of β-thalassaemia, sickle cell anemia can be corrected by modifying HSCs with the systems. The system allows the specific editing of the cell's genome by cutting its DNA and then letting it repair itself. The Cas protein is inserted and directed by a RNA guide to the mutated point and then it cuts the DNA at that point. Simultaneously, a healthy version of the sequence is inserted. This sequence is used by the cell's own repair system to fix the induced cut. In this way, the CRISPR-Cas allows the correction of the mutation in the previously obtained stem cells. The methods and systems may be used to correct HSCs as to sickle cell anemia using a systems that targets and corrects the mutation (e.g., with a suitable HDR template that delivers a coding sequence for β-globin, advantageously non-sickling β-globin); specifically, the guide RNA can target mutation that give rise to sickle cell anemia, and the HDR can provide coding for proper expression of β-globin. An guide RNA that targets the mutation-and-Cas protein containing particle is contacted with HSCs carrying the mutation. The particle also can contain a suitable HDR template to correct the mutation for proper expression of β-globin; or the HSC can be contacted with a second particle or a vector that contains or delivers the HDR template. The so contacted cells can be administered; and optionally treated/expanded; cf. Cartier. The HDR template can provide for the HSC to express an engineered 3-globin gene (e.g., βA-T87Q), or β-globin.

Treating Diseases of the Liver and Kidney

In some embodiments, the composition, system, or component thereof described herein can be used to treat a disease of the kidney or liver. Thus, in some embodiments, delivery of the CRISPR-Cas system or component thereof described herein is to the liver or kidney.

Delivery strategies to induce cellular uptake of the therapeutic nucleic acid include physical force or vector systems such as viral-, lipid- or complex-based delivery, or nanocarriers. From the initial applications with less possible clinical relevance, when nucleic acids were addressed to renal cells with hydrodynamic high-pressure injection systemically, a wide range of gene therapeutic viral and non-viral carriers have been applied already to target posttranscriptional events in different animal kidney disease models in vivo (Csaba Révész and Péter Hamar (2011). Delivery Methods to Target RNAs in the Kidney, Gene Therapy Applications, Prof. Chunsheng Kang (Ed.), ISBN: 978-953-307-541-9, InTech, Available from: www.intechopen.com/books/gene-therapy-applications/delivery-methods-to-target-rnas-inthe-kidney). Delivery methods to the kidney may include those in Yuan et al. (Am J Physiol Renal Physiol 295: F605-F617, 2008). The method of Yuang et al. may be applied to the CRISPR Cas system of the present invention contemplating a 1-2 g subcutaneous injection of CRISPR Cas conjugated with cholesterol to a human for delivery to the kidneys. In some embodiments, the method of Molitoris et al. (J Am Soc Nephrol 20: 1754-1764, 2009) can be adapted to the CRISRP-Cas system of the present invention and a cumulative dose of 12-20 mg/kg to a human can be used for delivery to the proximal tubule cells of the kidneys. In some embodiments, the methods of Thompson et al. (Nucleic Acid Therapeutics, Volume 22, Number 4, 2012) can be adapted to the CRISPR-Cas system of the present invention and a dose of up to 25 mg/kg can be delivered via i.v. administration. In some embodiments, the method of Shimizu et al. (J Am Soc Nephrol 21: 622-633, 2010) can be adapted to the CRISPR-Cas system of the present invention and a dose of about of 10-20 µmol CRISPR Cas complexed with nanocarriers in about 1-2 liters of a physiologic fluid for i.p. administration can be used.

Other various delivery vehicles can be used to deliver the composition, system to the kidney such as viral, hydrodynamic, lipid, polymer nanoparticles, aptamers and various combinations thereof (see e.g. Larson et al., Surgery, (August 2007), Vol. 142, No. 2, pp. (262-269); Hamar et al., Proc Natl Acad Sci, (October 2004), Vol. 101, No. 41, pp. (14883-14888); Zheng et al., Am J Pathol, (October 2008), Vol. 173, No. 4, pp. (973-980); Feng et al., Transplantation, (May 2009), Vol. 87, No. 9, pp. (1283-1289); Q. Zhang et al., PloS ONE, (July 2010), Vol. 5, No. 7, e11709, pp. (1-13); Kushibikia et al., J Controlled Release, (July 2005), Vol. 105, No. 3, pp. (318-331); Wang et al., Gene Therapy, (July 2006), Vol. 13, No. 14, pp. (1097-1103); Kobayashi et al., Journal of Pharmacology and Experimental Therapeutics, (February 2004), Vol. 308, No. 2, pp. (688-693); Wolfrum et al., Nature Biotechnology, (September 2007), Vol. 25, No. 10, pp. (1149-1157); Molitoris et al., J Am Soc Nephrol, (August 2009), Vol. 20, No. 8 pp. (1754-1764); Mikhaylova et al., Cancer Gene Therapy, (March 2011), Vol. 16, No. 3, pp. (217-226); Y. Zhang et al., J Am Soc Nephrol, (April 2006), Vol. 17, No. 4, pp. (1090-1101); Singhal et al., Cancer Res, (May 2009), Vol. 69, No. 10, pp. (4244-4251); Malek et al., Toxicology and Applied Pharmacology, (April 2009), Vol. 236, No. 1, pp. (97-108); Shimizu et al., J Am Soc Nephrology, (April 2010), Vol. 21, No. 4, pp. (622-633); Jiang et al., Molecular Pharmaceutics, (May-June 2009), Vol. 6, No. 3, pp. (727-737); Cao et al, J Controlled Release, (June 2010), Vol. 144, No. 2, pp. (203-212); Ninichuk et al., Am J Pathol, (March 2008), Vol. 172, No. 3, pp. (628-637); Purschke et al., Proc Natl Acad Sci, (March 2006), Vol. 103, No. 13, pp. (5173-5178).

In some embodiments, delivery is to liver cells. In some embodiments, the liver cell is a hepatocyte. Delivery of the composition and system herein may be via viral vectors, especially AAV (and in particular AAV2/6) vectors. These can be administered by intravenous injection. A preferred target for the liver, whether in vitro or in vivo, is the albumin gene. This is a so-called 'safe harbor" as albumin is expressed at very high levels and so some reduction in the production of albumin following successful gene editing is tolerated. It is also preferred as the high levels of expression seen from the albumin promoter/enhancer allows for useful levels of correct or transgene production (from the inserted recombination template) to be achieved even if only a small fraction of hepatocytes are edited. See sites identified by Wechsler et al. (reported at the 57th Annual Meeting and Exposition of the American Society of Hematology—abstract available online at ash.confex.com/ash/2015/webprogram/Paper86495.html and presented on 6 Dec. 2015) which can be adapted for use with the compositions, systems, herein.

Exemplary liver and kidney diseases that can be treated and/or prevented are described elsewhere herein.

Treating Epithelial and Lung Diseases

In some embodiments, the disease treated or prevented by the composition and system described herein can be a lung or epithelial disease. The compositions and systems described herein can be used for treating epithelial and/or lung diseases. The present invention also contemplates delivering the composition, system, described herein, to one or both lungs.

In some embodiments, as viral vector can be used to deliver the composition, system, or component thereof to the lungs. In some embodiments, the AAV is an AAV-1, AAV-2, AAV-5, AAV-6, and/or AAV-9 for delivery to the lungs. (see, e.g., Li et al., Molecular Therapy, vol. 17 no. 12, 2067-277 December 2009). In some embodiments, the MOI can vary from $1\times10^3$ to $4\times10^5$ vector genomes/cell. In some embodiments, the delivery vector can be an RSV vector as in Zamora et al. (Am J Respir Crit Care Med Vol 183. pp 531-538, 2011. The method of Zamora et al. may be applied to the nucleic acid-targeting system of the present invention and an aerosolized CRISPR Cas, for example with a dosage of 0.6 mg/kg, may be contemplated for the present invention.

Subjects treated for a lung disease may for example receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector. In this instance, the following constructs are provided as examples: Cbh or EF1a promoter for Cas, U6 or H1 promoter for guide RNA). A preferred arrangement is to use a CFTRdelta508 targeting guide, a repair template for deltaF508 mutation and a codon optimized Cas enzyme, with optionally one or more nuclear localization signal or sequence(s) (NLS(s)), e.g., two (2) NLSs.

Treating Diseases of the Skin

The compositions and systems described herein can be used for the treatment of skin diseases. The present invention also contemplates delivering the composition and system, described herein, to the skin.

In some embodiments, delivery to the skin (intradermal delivery) of the composition, system, or component thereof can be via one or more microneedles or microneedle containing device. For example, in some embodiments the device and methods of Hickerson et al. (Molecular Therapy—Nucleic Acids (2013) 2, e129) can be used and/or adapted to deliver the composition, system, described herein, for example, at a dosage of up to 300 µl of 0.1 mg/ml CRISPR-Cas system to the skin.

In some embodiments, the methods and techniques of Leachman et al. (Molecular Therapy, vol. 18 no. 2, 442-446 February 2010) can be used and/or adapted for delivery of a CIRPSR-Cas system described herein to the skin.

In some embodiments, the methods and techniques of Zheng et al. (PNAS, Jul. 24, 2012, vol. 109, no. 30, 11975-11980) can be used and/or adapted for nanoparticle delivery of a CIRPSR-Cas system described herein to the skin. In some embodiments, as dosage of about 25 nM applied in a single application can achieve gene knockdown in the skin.

Treating Cancer

The compositions, systems, described herein can be used for the treatment of cancer. The present invention also contemplates delivering the composition, system, described herein, to a cancer cell. Also, as is described elsewhere herein the compositions, systems, can be used to modify an immune cell, such as a CAR or CAR T cell, which can then in turn be used to treat and/or prevent cancer. This is also described in International Patent Publication No. WO 2015/161276, the disclosure of which is hereby incorporated by reference and described herein below.

Target genes suitable for the treatment or prophylaxis of cancer can include those set forth in Tables 2 and 3. In some embodiments, target genes for cancer treatment and prevention can also include those described in International Patent Publication No. WO 2015/048577 the disclosure of which is hereby incorporated by reference and can be adapted for and/or applied to the composition, system, described herein.

Adoptive Cell Therapy

The compositions, systems, and components thereof described herein can be used to modify cells for an adoptive cell therapy. In an aspect of the invention, methods and compositions which involve editing a target nucleic acid sequence, or modulating expression of a target nucleic acid sequence, and applications thereof in connection with cancer immunotherapy are comprehended by adapting the composition, system, of the present invention. In some examples, the compositions, systems, and methods may be used to modify a stem cell (e.g., induced pluripotent cell) to derive modified natural killer cells, gamma delta T cells, and alpha beta T cells, which can be used for the adoptive cell therapy. In certain examples, the compositions, systems, and methods may be used to modify modified natural killer cells, gamma delta T cells, and alpha beta T cells.

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June; 24(6):724-730; Besser et al., (2010) Clin. Cancer Res 16 (9) 2646-55; Dudley et al., (2002) Science 298 (5594): 850-4; and Dudley et al., (2005)

Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: MR1 (see, e.g., Crowther, et al., 2020, Genome-wide CRISPR-Cas9 screening reveals ubiquitous T cell cancer targeting via the monomorphic MHC class I-related protein MR1, Nature Immunology volume 21, pages 178-185), B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CART cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostate; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRLS); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDCl27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicose antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1 CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triosephosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CIVIL), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088, 379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004, 811; 6,284,240; 6,392,013; 6,410,014; 6,753,162; 8,211,422; and, PCT Publication WO 9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3 or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO 2014/134165; PCT Publication No. WO 2012/079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139. Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ. I.D. No. 2) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NothdI-gested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1,2 or 3) starting with the amino acid sequence IEVMYPPPY and continuing all the way to the carboxy-terminus of the protein. Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in International Patent Publication No. WO 2015/187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signaling domains (CD28-CD3ζ; 4-1BB-CD3ζ; CD27-CD3ζ; CD28-CD27-CD3ζ; 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signaling domain as set forth in Table 1 of No. WO 2015/187528. Preferably, the antigen is CD19, more preferably the antigen-binding element is an anti-CD19 scFv, even more preferably the mouse or human anti-CD19 scFv as described in Example 1 of WO 2015/187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US Patent Publication Nos. US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (International Patent Publication No. WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3t and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CART cells of this kind may for example be used in animal models, for example to treat tumor xenografts.

In certain embodiments, ACT includes co-transferring CD4+ Th1 cells and CD8+ CTLs to induce a synergistic antitumor response (see, e.g., Li et al., Adoptive cell therapy with CD4+ T helper 1 cells and CD8+ cytotoxic T cells enhances complete rejection of an established tumor, leading to generation of endogenous memory responses to non-targeted tumor epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; International Patent Publication WO 2011/146862; International Patent Publication WO 2014/011987; International Patent Publication WO 2013/040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf"

adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. The composition and systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see International Patent Publication Nos. WO 2013/176915, WO 2014/059173, WO 2014/172606, WO 2014/184744, and WO 2014/191128).

In certain embodiments, editing may result in inactivation of a gene. By inactivating a gene, it is intended that the gene of interest is not expressed in a functional protein form. In a particular embodiment, the system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells, particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells, particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells, particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

International Patent Publication No. WO 2014/172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL 10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, International Patent Publication No. WO 2016/196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as the composition or system herein) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CART cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, (such as the composition or system herein) (for example, as described in WO201704916).

In certain embodiments, editing of cells, particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in International Patent Publication Nos. WO 2016/011210 and WO 2017/011804).

In certain embodiments, editing of cells, particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas mRNA and gRNAs targeting endogenous TCR, β-2 microglobulin (B2M) and PD1 simultaneously, to generate gene-disrupted allogeneic CART cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiplied edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (e.g., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MEW class I may be evaluated indirectly by monitoring the ability to promote incorporation of 125I labeled $\beta$2-microglobulin ($\beta$2m) into MHC class I/$\beta$2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™ BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003/057171, U.S. Pat. No. 8,034,334, and U.S. Patent Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in International Patent Publication No. WO 2015/120096, by a method comprising enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO 2015/120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in International Patent Publication No. WO 2017/070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in International Patent Publication No. WO 2016/191756 comprising administering to the patient a dose of cyclophosphamide between 200 mg/m2/day and 2000 mg/m2/day and a dose of fludarabine between 20 mg/m2/day and 900 mg/m$^2$/day.

Diseases

Genetic Diseases and Diseases with a Genetic and/or Epigenetic Aspect

The compositions, systems, or components thereof can be used to treat and/or prevent a genetic disease or a disease with a genetic and/or epigenetic aspect. The genes and conditions exemplified herein are not exhaustive. In some embodiments, a method of treating and/or preventing a genetic disease can include administering a composition, system, and/or one or more components thereof to a subject, where the composition, system, and/or one or more components thereof is capable of modifying one or more copies of one or more genes associated with the genetic disease or a disease with a genetic and/or epigenetic aspect in one or more cells of the subject. In some embodiments, modifying one or more copies of one or more genes associated with a genetic disease or a disease with a genetic and/or epigenetic aspect in the subject can eliminate a genetic disease or a symptom thereof in the subject. In some embodiments, modifying one or more copies of one or more genes associated with a genetic disease or a disease with a genetic and/or epigenetic aspect in the subject can decrease the severity of a genetic disease or a symptom thereof in the subject. In some embodiments, the compositions, systems, or components thereof can modify one or more genes or polynucleotides associated with one or more diseases, including genetic diseases and/or those having a genetic aspect and/or epigenetic aspect, including but not limited to, any one or more set forth in Table 3. It will be appreciated that those diseases and associated genes listed herein are non-exhaustive and non-limiting. Further some genes play roles in the development of multiple diseases.

TABLE 3

Exemplary Genetic and Other Diseases and Associated Genes

| Disease Name | Primary Tissues or System Affected | Additional Tissues/Systems Affected | Genes |
| --- | --- | --- | --- |
| Achondroplasia | Bone and Muscle | | fibroblast growth factor receptor 3 (FGFR3) |
| Achromatopsia | eye | | CNGA3, CNGB3, GNAT2, PDE6C, PDE6H, ACHM2, ACHM3, |
| Acute Renal Injury | kidney | | NFkappaB, AATF, p85alpha, FAS, Apoptosis cascade elements (e.g. FASR, Caspase 2, 3, 4, 6, 7, 8, 9, 10, AKT, TNF alpha, IGF1, IGF1R, RIPK1), p53 |
| Age Related Macular Degeneration | eye | | Aber; CCL2; CC2; CP (ceruloplasmin); Timp3; cathepsinD; VLDLR, CCR2 |
| AIDS | Immune System | | KIR3DL1, NKAT3, NKB1, AMBU, KIR3DS1, IFNG, CXCL12, SDF1 |
| Albinism (including oculocutaneous albinism (types 1-7) and ocular albinism) | Skin, hair, eyes, | | TYR, OCA2, TYRP1, and SLC45A2, SLC24A5 and C10orf11 |
| Alkaptonuria | Metabolism of amino acids | Tissues/organs where homogentisic acid accumulates, particularly cartilage (joints), heart valves, kidneys | HGD |
| alpha-1 antitrypsin deficiency (AATD or A1AD) | Lung | Liver, skin, vascular system, kidneys, GI | SERPINA1, those set forth in WO2017165862, PiZ allele |
| ALS | CNS | | SOD1; ALS2; ALS3; ALS5; ALS7; STEX; FUS; TARDBP; VEGF (VEGF-a; VEGF-b; VEGF-c); DPP6; NEFH, PTGS1, SLC1A2, TNFRSF10B, PRPH, HSP90AA1, CRIA2, IFNG, AMPA2 S100B, FGF2, AOX1, CS, TXN, RAPHJ1, MAP3K5, NBEAL1, GPX1, ICA1L, RAC1, MAPT, ITPR2, ALS2CR4, GLS, ALS2CR8, CNTFR, ALS2CR11, FOLH1, FAM117B, P4HB, CNTF, SQSTM1, STRADB, NAIP, NLR, YWHAQ, SLC33A1, TRAK2, SCA1, NIF3L1, NIF3, |

TABLE 3-continued

Exemplary Genetic and Other Diseases and Associated Genes

| Disease Name | Primary Tissues or System Affected | Additional Tissues/Systems Affected | Genes |
|---|---|---|---|
| | | | PARD3B, COX8A, CDK15, HECW1, HECT, C2, WW 15, NOS1, MET, SOD2, HSPB1, NEFL, CTSB, ANG, HSPA8, RNase A, VAPB, VAMP, SNCA, alpha HGF, CAT, ACTB, NEFM, TH, BCL2, FAS, CASP3, CLU, SMN1, G6PD, BAX, HSF1, RNF19A, JUN, ALS2CR12, HSPA5, MAPK14, APEX1, TXNRD1, NOS2, TIMP1, CASP9, XIAP, GLG1, EPO, VEGFA, ELN, GDNF, NFE2L2, SLC6A3, HSPA4, APOE, PSMB8, DCTN2, TIMP3, KIFAP3, SLC1A1, SMN2, CCNC, STUB1, ALS2, PRDX6, SYP, CABIN1, CASP1, GART, CDK5, ATXN3, RTN4, C1QB, VEGFC, HTT, PARK7, XDH, GFAP, MAP2, CYCS, FCGR3B, CCS, UBL5, MMP9m SLC18A3, TRPM7, HSPB2, AKT1, DEERL1, CCL2, NGRN, GSR, TPPP3, APAF1, BTBD10, GLUD1, CXCR4, S:C1A3, FLT1, PON1, AR, LIF, ERBB3, :GA:S1, CD44, TP53, TLR3, GRIA1, GAPDH, AMP A, GRIK1, DES, CHAT, FLT4, CHMP2B, BAG1, CHRNA4, GSS, BAK1, KDR, GSTP1, OGG1, IL6 |
| Alzheimer's Disease | Brain | | E1; CHIP; UCH; UBB; Tan; LRP; PICALM; CLU; PS1; SORL1; CR1; VLDLR; UBA1; UBA3; CHIP28; AQP1; UCHL1; UCHL3; APP, AAA, CVAP, AD1, APOE, AD2, DCP1, ACE1, MPO, PACIP1, PAXIPIL, PTIP, A2M, BLMH, BMH, PSEN1, AD3, ALAS2, ABCA1, BIN1, BDNF, BTNL8, C1ORF49, CDH4, CHRNB2, CKLFSF2, CLEC4E, CR1L, CSF3R, CST3, CYP2C, DAPK1, ESR1, FCAR, FCGR3B, FFA2, FGA, GAB2, GALP, GAPDHS, GMPB, HP, HTR7, IDE, IF127, IFI6, IFIT2, IL1RN, IL-1RA, IL8RA, IL8RB, JAG1, KCNJ15, LRP6, MAPT, MARK4, MPHOSPH1, MTHFR, NBN, NCSTN, NIACR2, NMNAT3, NTM, ORM1, P2RY13, PBEF1, PCK1, PICALM, PLAU, PLXNC1, PRNP, PSEN1, PSEN2, PTPRA, RALGPS2, RGSL2, SELENBP1, SLC25A37, SORL1, Mitoferrin-1, TF, TEAM, TNF, TNFRSF10C, UBE1C |
| Amyloidosis | | | APOA1, APP, AAA, CVAP, AD1, GSN, FGA, LYZ, TTR, PALB |
| Amyloid neuropathy | | | TTR, PALB |
| Anemia | Blood | | CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT |
| Angelman Syndrome | Nervous system, brain | | UBE3A |
| Attention Deficit Hyperactivity Disorder (ADHD) | Brain | | PTCHD1 |
| Autoimmune lymphoproliferative syndrome | Immune system | | TNFRSF6, APT1, FAS, CD95, ALPS1A |
| Autism, Autism spectrum disorders (ASDs), including Asperger's and a general diagnostic category called | Brain | | PTCHD1; Mecp2; BZRAP1; MDGA2; Sema5A; Neurexin 1; GLO1, RTT, PPMX, MRX16, RX79, NLGN3, NLGN4, KIAA1260, AUTSX2, |

TABLE 3-continued

Exemplary Genetic and Other Diseases and Associated Genes

| Disease Name | Primary Tissues or System Affected | Additional Tissues/Systems Affected | Genes |
|---|---|---|---|
| Pervasive Developmental Disorders (PDDs) | | | FMR1, FMR2; FXR1; FXR2; MGLUR5, ATP10C, CDH10, GRM6, MGLUR6, CDH9, CNTN4, NLGN2, CNTNAP2, SEMA5A, DHCR7, NLGN4X, NLGN4Y, DPP6, NLGN5, EN2, NRCAM, MDGA2, NRXN1, FMR2, AFF2, FOXP2, OR4M2, OXTR, FXR1, FXR2, PAH, GABRA1, PTEN, GABRA5, PTPRZ1, GABRB3, GABRG1, HIRIP3, SEZ6L2, HOXA1, SHANK3, IL6, SHBZRAP1, LAMB1, SLC6A4, SERT, MAPK3, TAS2R1, MAZ, TSC1, MDGA2, TSC2, MECP2, UBE3A, WNT2, see also 20110023145 |
| autosomal dominant polycystic kidney disease (ADPKD) - (includes diseases such as von Hippel-Lindau disease and tubreous sclerosis complex disease) | kidney | liver | PKD1, PKD2 |
| Autosomal Recessive Polycystic Kidney Disease (ARPKD) | kidney | liver | PKDH1 |
| Ataxia-Telangiectasia (a.k.a Louis Bar syndrome) | Nervous system, immune system | various | ATM |
| B-Cell Non-Hodgkin Lymphoma | | | BCL7A, BCL7 |
| Bardet-Biedl syndrome | Eye, musculoskeletal system, kidney, reproductive organs | Liver, ear, gastrointestinal system, brain | ARL6, BBS1, BBS2, BBS4, BBS5, BBS7, BBS9, BBS10, BBS12, CEP290, INPP5E, LZTFL1, MKKS, MKS1, SDCCAG8, TRIM32, TTC8 |
| Bare Lymphocyte Syndrome | blood | | TAPBP, TPSN, TAP2, ABCB3, PSF2, RING11, MHC2TA, C2TA, RFX5, RFXAP, RFX5 |
| Bartter's Syndrome (types I, II, III, IVA and B, and V) | kidney | | SLC12A1 (type I), KCNJ1 (type II), CLCNKB (type III), BSND (type IV A), or both the CLCNKA CLCNKB genes (type IV B), CASR (type V). |
| Becker muscular dystrophy | Muscle | | DMD, BMD, MYF6 |
| Best Disease (Vitelliform Macular Dystrophy type 2 ) | eye | | VMD2 |
| Bleeding Disorders | blood | | TBXA2R, P2RX1, P2X1 |
| Blue Cone Monochromacy | eye | | OPN1LW, OPN1MW, and LCR |
| Breast Cancer | Breast tissue | | BRCA1, BRCA2, COX-2 |
| Bruton's Disease (aka X-linked Agammglobulinemia) | Immune system, specifically B cells | | BTK |
| Cancers (e.g., lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma | Various | | FAS, BID, CTLA4, PDCD1, CBLB, PTPN6, TRAC, TRBC, those described in WO2015048577 |
| Cardiovascular Diseases | heart | Vascular system | IL1B, XDH, TP53, PTGS, MB, IL4, ANGPT1, ABCGu8, CTSK, PTGIR, KCNJ11, INS, CRP, PDGFRB, CCNA2, PDGFB, KCNJ5, KCNN3, CAPN10, ADRA2B, ABCG5, PRDX2, CPAN5, PARP14, MEX3C, ACE, RNF, IL6, TNF, STN, |

TABLE 3-continued

Exemplary Genetic and Other Diseases and Associated Genes

| Disease Name | Primary Tissues or System Affected | Additional Tissues/Systems Affected | Genes |
|---|---|---|---|
| | | | SERPINE1, ALB, ADIPOQ, APOB, APOE, LEP, MTHFR, APOA1, EDN1, NPPB, NOS3, PPARG, PLAT, PTGS2, CETP, AGTR1, HMGCR, IGF1, SELE, REN, PPARA, PON1, KNG1, CCL2, LPL, VWF, F2, ICAM1, TGFB, NPPA, IL10, EPO, SOD1, VCAM1, IFNG, LPA, MPO, ESR1, MAPK, HP, F3, CST3, COG2, MMP9, SERPINC1, F8, HMOX1, APOC3, IL8, PROL1, CBS, NOS2, TLR4, SELP, ABCA1, AGT, LDLR, GPT, VEGFA, NR3C2, IL18, NOS1, NR3C1, FGB, HGF, IL1A, AKT1, LIPC, HSPD1, MAPK14, SPP1, ITGB3, CAT, UTS2, THBD, F10, CP, TNFRSF11B, EGFR, MMP2, PLG, NPY, RHOD, MAPK8, MYC, FN1, CMA1, PLAU, GNB3, ADRB2, SOD2, F5, VDR, ALOX5, HLA-DRB1, PARP1, CD40LG, PON2, AGER, IRS1, PTGS1, ECE1, F7, IRMN, EPHX2, IGFBP1, MAPK10, FAS, ABCB1, JUN, IGFBP3, CD14, PDE5A, AGTR2, CD40, LCAT, CCR5, MMP1, TIMP1, ADM, DYT10, STAT3, MMP3, ELN, USF1, CFH, HSPA4, MMP12, MME, F2R, SELL, CTSB, ANXA5, ADRB1, CYBA, FGA, GGT1, LIPG, HIF1A, CXCR4, PROC, SCARE 1, CD79A, PLTP, ADD1, FGG, SAA1, KCNH2, DPP4, NPR1, VTN, KIAA0101, FOS, TLR2, PPIG, IL1R1, AR, CYP1A1, SERPINA1, MTR, RBP4, APOA4, CDKN2A, FGF2, EDNRB, ITGA2, VLA-2, CABIN1, SHBG, HMGB1, HSP90B2P, CYP3A4, GJA1, CAV1, ESR2, LTA, GDF15, BDNF, CYP2D6, NGF, SP1, TGIF1, SRC, EGF, PIK3CG, HLA-A, KCNQ1, CNR1, FBN1, CHKA, BEST1, CTNNB1, IL2, CD36, PRKAB1, TPO, ALDH7A1, CX3CR1, TH, F9, CH1, TF, HFE, IL17A, PTEN, GSTM1, DMD, GATA4, F13A1, TTR, FABP4, PON3, APOC1, INSR, TNFRSF1B, HTR2A, CSF3, CYP2C9, TXN, CYP11B2, PTH, CSF2, KDR, PLA2G2A, THBS1, GCG, RHOA, ALDH2, TCF7L2, NFE2L2, NOTCH1, UGT1A1, IFNA1, PPARD, SIRT1, GNHR1, PAPPA, ARR3, NPPC, AHSP, PTK2, IL13, MTOR, ITGB2, GSTT1, IL6ST, CPB2, CYP1A2, HNF4A, SLC64A, PLA2G6, TNFSF11, SLC8A1, F2RL1, AKR1A1, ALDH9A1, BGLAP, MTTP, MTRR, SULT1A3, RAGE, C4B, P2RY12, RNLS, CREB1, POMC, RAC1, LMNA, CD59, SCM5A, CYP1B1, MIF, MMP13, TIMP2, CYP19A1, CUP21A2, PTPN22, MYH14, MBL2, SELPLG, AOC3, CTSL1, PCNA, IGF2, ITGB1, CAST, CXCL12, IGHE, KCNE1, TFRC, COL1A1, COL1A2, IL2RB, PLA2G10, ANGPT2, PROCR, NOX4, HAMP, PTPN11, SLCA1, IL2RA, CCL5, IRF1, CF:AR, CA:CA, EIF4E, GSTP1, JAK2, CYP3A5, HSPG2, CCL3, MYD88, VIP, SOAT1, |

TABLE 3-continued

Exemplary Genetic and Other Diseases and Associated Genes

| Disease Name | Primary Tissues or System Affected | Additional Tissues/Systems Affected | Genes |
|---|---|---|---|
| | | | ADRBK1, NR4A2, MMP8, NPR2, GCH1, EPRS, PPARGC1A, F12, PECAM1, CCL4, CERPINA34, CASR, FABP2, TTF2, PROS1, CTF1, SGCB, YME1L1, CAMP, ZC3H12A, AKR1B1, MMP7, AHR, CSF1, HDAC9, CTGF, KCNMA1, UGT1A, PRKCA, COMT, S100B, EGR1, PRL, IL15, DRD4, CAMK2G, SLC22A2, CCL11, PGF, THPO, GP6, TACR1, NTS, HNF1A, SST, KCDN1, LOC646627, TBXAS1, CUP2J2, TBXA2R, ADH1C, ALOX12, AHSG, BHMT, GJA4, SLC25A4, ACLY, ALOX5AP, NUMA1, CYP27B1, CYSLTR2, SOD3, LTC4S, UCN, GHRL, APOC2, CLEC4A, KBTBD10, TNC, TYMS, SHC1, LRP1, SOCS3, ADH1B, KLK3, HSD11B1, VKORC1, SERPINB2, TNS1, RNF19A, EPOR, ITGAM, PITX2, MAPK7, FCGR3A, LEEPR, ENG, GPX1, GOT2, HRH1, NR1I2, CRH, HTR1A, VDAC1, HPSE, SFTPD, TAP2, RMF123, PTK2Bm NTRK2, IL6R, ACHE, GLP1R, GHR, GSR, NQO1, NR5A1, GJB2, SLC9A1, MAOA, PCSK9, FCGR2A, SERPINF1, EDN3, UCP2, TFAP2A, C4BPA, SERPINF2, TYMP, ALPP, CXCR2, SLC3A3, ABCG2, ADA, JAK3, HSPA1A, FASN, FGF1, F11, ATP7A, CR1, GFPA, ROCK1, MECP2, MYLK, BCHE, LIPE, ADORA1, WRN, CXCR3, CD81, SMAD7, LAMC2, MAP3K5, CHGA, IAPP, RHO, ENPP1, PTHLH, NRG1, VEGFC, ENPEP, CEBPB, NAGLU, . F2RL3, CX3CL1, BDKRB1, ADAMTS13, ELANE, ENPP2, CISH, GAST, MYOC, ATP1A2, NF1, GJB1, MEF2A, VCL, BMPR2, TUBB, CDC42, KRT18, HSF1, MYB, PRKAA2, ROCK2, TFP1, PRKG1, BMP2, CTNND1, CTH, CTSS, VAV2, NPY2R, IGFBP2, CD28, GSTA1, PPIA, APOH, S100A8, IL11, ALOX15, FBLN1, NR1H3, SCD, GIP, CHGB, PRKCB, SRD5A1, HSD11B2, CALCRL, GALNT2, ANGPTL4, KCNN4, PIK3C2A, HBEGF, CYP7A1, HLA-DRB5, BNIP3, GCKR, S100A12, PADI4, HSPA14, CXCR1, H19, KRTAP19-3, IDDM2, RAC2, YRY1, CLOCK, NGFR, DBH, CHRNA4, CACNA1C, PRKAG2, CHAT, PTGDS, NR1H2, TEK, VEGFB, MEF2C, MAPKAPK2, TNFRSF11A, HSPA9, CYSLTR1, MATIA, OPRL1, IMPA1, CLCN2, DLD, PSMA6, PSMB8, CHI3L1, ALDH1B1, PARP2, STAR, LBP, ABCC6, RGS2, EFNB2, GJB6, APOA2, AMPD1, DYSF, FDFT1, EMD2, CCR6, GJB3, IL1RL1, ENTPD1, BBS4, CELSR2, F11R, RAPGEF3, HYAL1, ZNF259, ATOX1, ATF6, KHK, SAT1, GGH, TIMP4, SLC4A4, PDE2A, PDE3B, FADS1, FADS2, TMSB4X, TXNIP, LIMS1, RHOB, LY96, FOXO1, |

TABLE 3-continued

Exemplary Genetic and Other Diseases and Associated Genes

Figure 4:
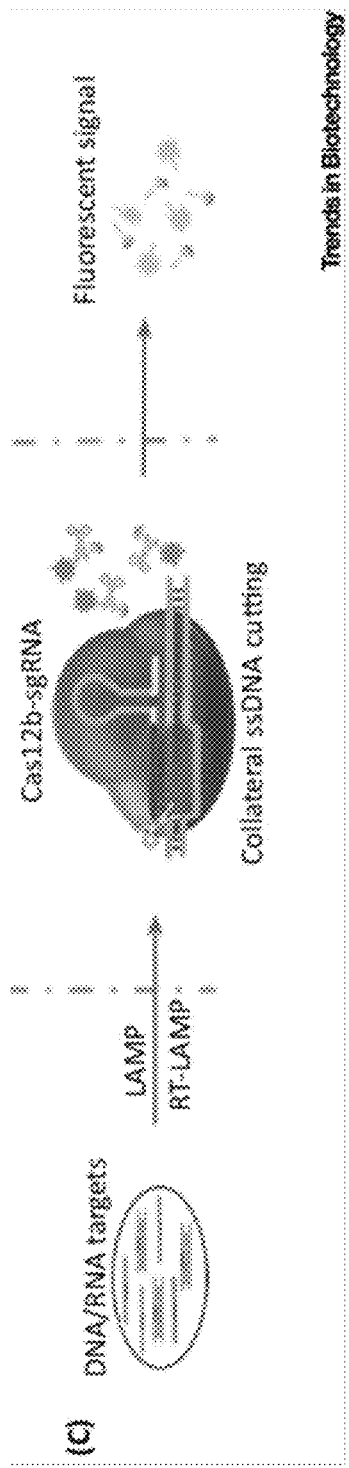
FIG. 4—Schematic for developing a one pot RT-LAMP Cas12b SHERLOCK reaction.
Figure 5:
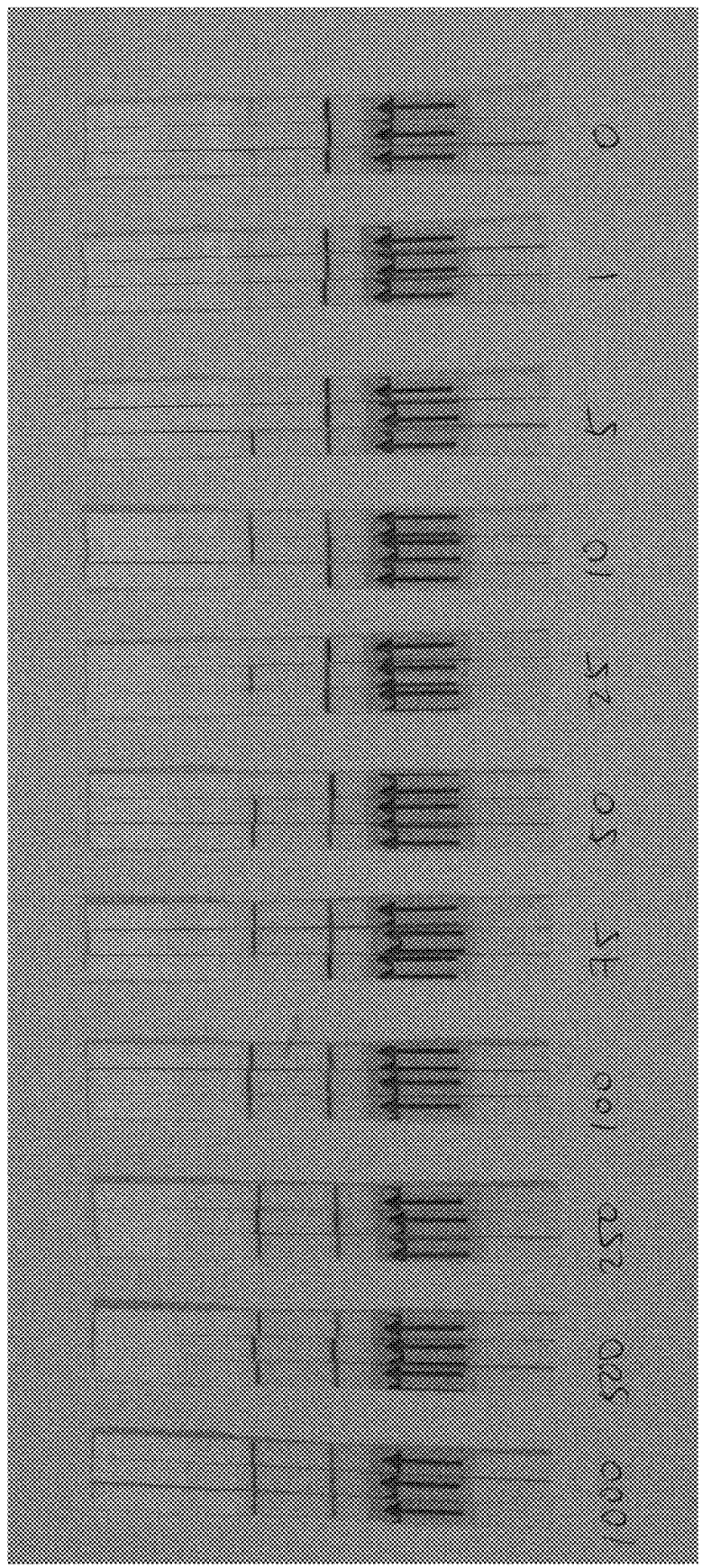
FIG. 5—Figure shows results obtained for assessing limit of detection by lateral flow assay at 60° C. for 60 minutes. The limit of detection was 100 molecules per reaction.

| Disease Name | Primary Tissues or System Affected | Additional Tissues/Systems Affected | Genes |
|---|---|---|---|
| | | | PNPLA2, TRH, GJC1, S:C17A5, FTO, GJD2, PRSC1, CASP12, GPBAR1, PXK, IL33, TRIB1, PBX4, NUPR1, 15-SEP, CILP2, TERC, GGT2, MTCO1, UOX, AVP |
| Cataract | eye | | CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1 |
| CDKL-5 Deficiencies or Mediated Diseases | Brain, CNS | | CDKL5 |
| Charcot-Marie-Tooth (CMT) disease (Types 1, 2, 3, 4, ) | Nervous system | Muscles (dystrophy) | PMP22 (CMT1A and E), MPZ (CMT1B), LITAF (CMT1C), EGR2 (CMT1D), NEFL (CMT1F), GJB1 (CMTIX), MFN2 (CMT2A), KIF1B (CMT2A2B), RAB7A (CMT2B), TRPV4 (CMT2C), GARS (CMT2D), NEFL (CMT2E), GAPD1 (CMT2K), HSPB8 (CMT2L), DYNC1H1, CMT2O, LRSAM1 (CMT2P), IGHMBP2 (CMT2S), MORC2 (CMT2Z), GDAP1 (CMT4A), MTMR2 or SBF2/MTMR13 (CMT4B), SH3TC2 (CMT4C), NDRG1 (CMT4D), PRX (CMT4F), FIG4 (CMT4J), NT-3 |
| Chediak-Higashi Syndrome | Immune system | Skin, hair, eyes, neurons | LYST |
| Choroidermia | | | CHM, REP1, |
| Chorioretinal atrophy | eye | | PRDM13, RGR, TEAD1 |
| Chronic Granulomatous Disease | Immune system | | CYBA, CYBB, NCF1, NCF2, NCF4 |
| Chronic Mucocutaneous Candidiasis | Immune system | | AIRE, CARD9, CLEC7A, IL12B, IL12B1, IL1F, IL17RA, IL17RC, RORC, STAT1, STAT3, TRAF31P2 |
| Cirrhosis | liver | | KRT18, KRT8, CIRH1A, NAIC, TEX292, KIAA1988 |
| Colon cancer (Familial adenomatous polyposis (FAP) and hereditary nonpolyposis colon cancer (HNPCC)) | Gastrointestinal | | FAP: APCHNPCC: MSH2, MLH1, PMS2, SH6, PMS1 |
| Combined Immunodeficiency | Immune System | | IL2RG, SCIDX1, SCIDX, IMD4); HIV-1 (CCL5, SCYA5, D17S136E, TCP228 |
| Cone(-rod) dystrophy | eye | | AIPL1, CRX, GUA1A, GUCY2D, PITPM3, PROM1, PRPH2, RIMS1, SEMA4A, ABCA4, ADAM9, ATF6, C21ORF2, C80RF37, CACNA2D4, CDHR1, CERKL, CNGA3, CNGB3, CNNM4, CNAT2, IFT81, KCNV2, PDE6C, PDE6H, POCIB, RAX2, RDH5, RPGRIP1, TTLL5, RetCG1, GUCY2E |
| Congenital Stationary Night Blindness | eye | | CABP4, CACNA1F, CACNA2D4, GNAT1, CPR179, GRK1, GRM6, LRIT3, NYX, PDE6B, RDH5, RHO, RLBP1, RPE65, SAG, SLC24A1, TRPM1, |
| Congenital Fructose Intolerance | Metabolism | | ALDOB |
| Cori's Disease (Glycogen Storage Disease Type III) | Various- wherever glycogen accumulates, | | AGL |

TABLE 3-continued

Exemplary Genetic and Other Diseases and Associated Genes

| Disease Name | Primary Tissues or System Affected | Additional Tissues/Systems Affected | Genes |
|---|---|---|---|
| | particularly liver, heart, skeletal muscle | | |
| Corneal clouding and dystrophy | eye | | APOA1, TGFB1, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD |
| Cornea plana congenital | | | KERA, CNA2 |
| Cri du chat Syndrome, also known as 5p syndrome and cat cry syndrome | | | Deletions involving only band 5p15.2 to the entire short arm of chromosome 5, e.g. CTNND2, TERT, |
| Cystic Fibrosis (CF) | Lungs and respiratory system | Pancreas, liver, digestive system, reproductive system, exocrine, glands, | CTFR, ABCC7, CF, MRP7, SCNN1A, those described in WO2015157070 |
| Diabetic nephropathy | kidney | | Gremlin, 12/15- lipoxygenase, TIM44, |
| Dent Disease (Types 1 and 2) | Kidney | | Type 1: CLCN5, Type 2: ORCL |
| Dentatorubro-Pallidoluysian Atrophy (DRPLA) (aka Haw River and Naito-Oyanagi Disease) | CNS, brain, muscle | | Atrophin-1 and Atn1 |
| Down Syndrome | various | | Chromosome 21 trisomy |
| Drug Addiction | Brain | | Prkce; Drd2; Drd4; ABAT; GRIA2; Grm5; Grin1; Htr1b; Grin2a; Drd3; Pdyn; Gria1 |
| Duane syndrome (Types 1, 2, and 3, including subgroups A, B and C). Other names for this condition include: Duane's Retraction Syndrome (or DR syndrome), Eye Retraction Syndrome, Retraction Syndrome, Congenital retraction syndrome and Stilling-Turk-Duane Syndrome | eye | | CHN1, indels on chromosomes 4 and 8 |
| Duchenne muscular dystrophy (DMD) | muscle | Cardiovascular, respiratory | DMD, BMD, dystrophin gene, intron flanking exon 51 of DMD gene, exon 51 mutations in DMD gene, see also WO2013163628 and US Pat. Pub. 20130145487 |
| Edward's Syndrome (Trisomy 18) | | | Complete or partial trisomy of chromosome 18 |
| Ehlers-Danlos Syndrome (Types I-VI) | Various depending on type: including musculoskeletal, eye, vasculature, immune, and skin | | COL5A1, COL5A2, COL1A1, COL3A1, TNXB, PLOD1, COL1A2, FKBP14 and ADAMTS2 |
| Emery-Dreifuss muscular dystrophy | muscle | | LMNA, LMN1, EMD2, FPLD, CMD1A, HGPS, LGMD1B, LMNA, LMN1, EMD2, FPLD, CMD1A |
| Enhanced S-Cone Syndrome | eye | | NR2E3, NRL |
| Fabry's Disease | Various - including skin, eyes, and gastrointestinal system, kidney, heart, brain, nervous system | | GLA |
| Facioscapulohumeral muscular dystrophy | muscles | | FSHMD1A, FSHD1A, FRG1, |
| Factor H and Factor H-like 1 | blood | | HF1, CFH, HUS |
| Factor V Leiden thrombophilia and Factor V deficiency | blood | | Factor V (F5) |
| Factor V and Factor VII deficiency | blood | | MCFD2 |
| Factor VII deficiency | blood | | F7 |
| Factor X deficiency | blood | | F10 |

TABLE 3-continued

Exemplary Genetic and Other Diseases and Associated Genes

| Disease Name | Primary Tissues or System Affected | Additional Tissues/Systems Affected | Genes |
|---|---|---|---|
| Factor XI deficiency | blood | | F11 |
| Factor XII deficiency | blood | | F12, HAF |
| Factor XIIIA deficiency | blood | | F13A1, F13A |
| Factor XIIIB deficiency | blood | | F13B |
| Familial Hypercholestereolemia | Cardiovascular system | | APOB, LDLR, PCSK9 |
| Familial Mediterranean Fever (FMF) also called recurrent polyserositis or familial paroxysmal polyserositis | Various-organs/tissues with serous or synovial membranes, skin, joints | Heart, kidney, brain/CNS, reproductive organs | MEFV |
| Fanconi Anemia | Various - blood (anemia), immune system, cognitive, kidneys, eyes, musculoskeletal | | FANCA, FACA, FA1, FA, FAA, FAAP95, FAAP90, FLJ34064, FANCC, FANCG, RAD51, BRCA1, BRCA2, BRIP1, BACH1, FANCJ, FANCB, FANCD1, FANCD2, FANCD, FAD, FANCE, FACE, FANCF, FANCI, ERCC4, FANCL, FANCM, PALB2, RAD51C, SLX4, UBE2T, FANCB, XRCC9, PHF9, KIAA1596 |
| Fanconi Syndrome Types I (Childhood onset) and 11 (Adult Onset) | kidneys | | FRTS1, GATM |
| Fragile X syndrome and related disorders | brain | | FMR1, FMR2; FXR1; FXR2; mGLUR5 |
| Fragile XE Mental Retardation (aka Martin Bell syndrome) | Brain, nervous system | | FMR1 |
| Friedreich Ataxia (FRDA) | Brain, nervous system | heart | FXN/X25 |
| Fuchs endothelial corneal dystrophy | Eye | | TCF4; COL8A2 |
| Galactosemia | Carbohydrate metabolism disorder | Various-where galactose accumulates - liver, brain, eyes | GALT, GALK1, and GALE |
| Gastrointestinal Epithelial Cancer, GI cancer | | | CISH |
| Gaucher Disease (Types 1, 2, and 3, as well as other unusual forms that may not fit into these types) | Fat metabolism disorder | Various-liver, spleen, blood, CNS, skeletal system | GBA |
| Griscelli syndrome | | | |
| Glaucoma | eye | | MYOC, TIGR, GLC1A, JOAG, GPOA, OPTN, GLC1E, FIP2, HYPL, NRP, CYP1B1, GLC3A, OPA1, NTG, NPG, CYP1B1, GLC3A, those described in WO2015153780 |
| Glomerulo sclerosis | kidney | | CC chemokine ligand 2 |
| Glycogen Storage Diseases Types I-VI -See also Cori's Disease, Pompe's Disease, McArdle's disease, Hers Disease, and Von Gierke's disease | Metabolism Diseases | | SLC2A2, GLUT2, G6PC, G6PT, G6PT1, GAA, LAMP2, LAMPB, AGL, GDE, GBE1, GYS2, PYGL, PFKM, see also Cori's Disease, Pompe's Disease, McArdle's disease, Hers Disease, and Von Gierke's disease |
| RBC Glycolytic enzyme deficiency | blood | | any mutations in a gene for an enzyme in the glycolysis pathway including mutations in genes for hexokinases I and II, glucokinase, phosphoglucose isomerase, phosphofructokinase, aldolase Bm triosephosphate isomerease, glyceraldehydee-3-phosphate dehydrogenase, phosphoglycerokinase, phosphoglycerate mutase, enolase 1, pyruvate kinase |
| Hartnup's disease | Malabsorption disease | Various- brain, gastrointestinal, skin, | SLC6A19 |

TABLE 3-continued

Exemplary Genetic and Other Diseases and Associated Genes

| Disease Name | Primary Tissues or System Affected | Additional Tissues/Systems Affected | Genes |
|---|---|---|---|
| Hearing Loss | ear | | NOX3, Hes5, BDNF, |
| Hemochromatosis (HH) | Iron absorption regulation disease | Various- wherever iron accumulates, liver, heart, pancreasjoints, pituitary gland | HFE and H63D |
| Hemophagocytic lymphohistiocytosis disorders | blood | | PRF1, HPLH2, UNC13D, MUNC13-4, HPLH3, HLH3, FHL3 |
| Hemorrhagic disorders | blood | | PI, ATT, F5 |
| Hers disease (Glycogen storage disease Type VI) | liver | muscle | PYGL |
| Hereditary angioedema (HAE) | | | kalikrein B1 |
| Hereditary Hemorrhagic Telangiectasia (Osler-Weber-Rendu Syndrome) | Skin and mucous membranes | | ACVRL1, ENG and SMAD4 |
| Hereditary Spherocytosis | blood | | NK1, EPB42, SLC4A1, SPTA1, and SPTB |
| Hereditary Persistence of Fetal Hemoglobin | blood | | HBG1, HBG2, BCL11A, promoter region of HBG 1 and/or 2 (in the CCAAT box) |
| Hemophilia (hemophilia A (Classic) a B (aka Christmas disease) and C) | blood | | A: FVIII, F8C, HEMA B:FVIX, HEMB C:F9, F11 |
| Hepatic adenoma | liver | | TCF1, HNF1A, MODY3 |
| Hepatic failure, early onset, and neurologic disorder | liver | | SCOD1, SCO1 |
| Hepatic lipase deficiency | liver | | LIPC |
| Hepatoblastoma, cancer and carcinomas | liver | | CTNNB1, PDGFRL, PDGRL, PRLTS, AXIN1, AXIN, CTNNB1, TP53, P53, LFS1, IGF2R, MPRI, MET, CASP8, MCH5 |
| Hermansky-Pudlak syndrome | Skin, eyes, blood, lung, kidneys, intestine | | HPS1, HPS3, HPS4, HPS5, HPS6, HPS7, DTNBP1, BLOC1, BLOC1S2, BLOC3 |
| HIV susceptibility or infection | Immune system | | IL10, CSIF, CMKBR2, CCR2, CMKBR5, CCCKR5 (CCR5), those in WO2015148670A1 |
| Holoprosencephaly (HPE) (Alobar, Semilobar, and Lobar) | brain | | ACVRL1, ENG, SMAD4 |
| Homocystinuria | Metabolic disease | Various- connective tissue, muscles, CNS, cardiovascular system | CBS, MTHFR, MTR, MTRR, and MMADHC |
| HPV | | | HPV16 and HPV18 E6/E7 |
| HSV1, HSV2, and related keratitis | eye | | HSV1 genes (immediate early and late HSV-1 genes (UL1, 1.5, 5, 6, 8, 9, 12, 15, 16, 18, 19, 22, 23, 26, 26.5, 27, 28, 29, 30, 31, 32, 33, 34, 35, 36, 37, 38, 42, 48, 49.5, 50, 52, 54, S6, RL2, RS1, those described in WO2015153789, WO2015153791 |
| Hunter's Syndrome (aka Mucopolysaccharidosis type II) | Lysosomal storage disease | Various- liver, spleen, eye, joint, heart, brain, skeletal | IDS |
| Huntington's disease (HD) and HD-like disorders | Brain, nervous system | | HD, HTT, IT15, PRNP, PRIP, JPH3, JP3, HDL2, TBP, SCA17, PRKCE; IGF1; EP300; RCOR1; PRKCZ; HDAC4; and TGM2, and those described in WO2013130824, WO2015089354 |
| Hurler's Syndrome (aka mucopolysaccharidosis type IH, MPSIH) | Lysosomal storage disease | Various- liver, spleen, eye, joint, heart, brain, skeletal | IDUA, α-L-iduronidase |
| Hurler-Scheie syndrome (aka mucopolysaccharidosis type IH- | Lysosomal storage disease | Various- liver, spleen, eye, | IDUA, α-L-iduronidase |

TABLE 3-continued

Exemplary Genetic and Other Diseases and Associated Genes

| Disease Name | Primary Tissues or System Affected | Additional Tissues/Systems Affected | Genes |
|---|---|---|---|
| S, MPS IH-S) | | joint, heart, brain, skeletal | |
| hyaluronidase deficiency (aka MPS IX) | Soft and connective tissues | | HYAL1 |
| Hyper IgM syndrome | Immune system | | CD40L |
| Hyper- tension caused renal damage | kidney | | Mineral corticoid receptor |
| Immunodeficiencies | Immune System | | CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI |
| Inborn errors of metabolism: including urea cycle disorders, organic acidemias), fatty acid oxidation defects, amino acidopathies, carbohydrate disorders, mitochondrial disorders | Metabolism diseases, liver | Various organs and cells | See also: Carbohydrate metabolism disorders (e.g. galactosemia), Amino acid Metabolism disorders (e.g. phenylketonuria), Fatty acid metabolism (e.g. MCAD deficiency), Urea Cycle disorders (e.g. Citrullinemia), Organic acidemias (e.g. Maple Syrup Urine disease), Mitochondrial disorders (e.g. MELAS), peroxisomal disorders (e.g. Zellweger syndrome) |
| Inflammation | Various | | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3c11 |
| Inflammatory Bowel Diseases (e.g. Ulcerative Colitis and Chron's Disease) | Gastrointestinal | Joints, skin | NOD2, IRGM, LRRK2, ATG5, ATG16L1, IRGM, GATM, ECM1, CDH1, LAMB1, HNF4A, GNA12, IL10, CARD9/15. CCR6, IL2RA, MST1, TNFSF15, REL, STAT3, IL23R, IL12B, FUT2 |
| Interstitial renal fibrosis | kidney | | TGF-β type II receptor |
| Job's Syndrome (aka Hyper IgE Syndrome) | Immune System | | STAT3, DOCK8 |
| Juvenile Retinoschisis | eye | | RS1, XLRS1 |
| Kabuki Syndrome 1 | | | MLL4, KMT2D |
| Kennedy Disease (aka Spinobulbar Muscular Atrophy) | Muscles, brain, nervous system | | SBMA/SMAX1/AR |
| Klinefelter syndrome | Various- particularly those involved in development of male characteristics | | Extra X chromosome in males |
| Lafora Disease | Brain, CNS | | EMP2A and EMP2B |
| Leber Congenital Amaurosis | eye | | CRB1, RP12, CORD2, CRD, CRX, IMPDH1, OTX2, AIPL1, CABP4, CCT2, CEP290, CLUAPI, CRB1, CRX, DTHD1, GDF6, GUCY2D, IFT140, IQCB1, KCNJ13, LCA5, LRAT, NMNAT1, PRPH2, RD3, RDH12, RPE65, RP20, RPGRIP1, SPATA7, TULP1, LCA1, LCA4, GUC2D, CORD6, LCA3, |
| Lesch-Nyhan Syndrome | Metabolism disease | Various - joints, cognitive, brain, nervous system | HPRT1 |
| Leukocyte deficiencies and disorders | blood | | ITGB2, CD18, LCAMB, LAD, EIF2B1, EIF2BA, EIF2B2, EIF2B3, EIF2B5, LVWM, CACH, CLE, EIF2B4 |
| Leukemia | Blood | | TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, |

TABLE 3-continued

Exemplary Genetic and Other Diseases and Associated Genes

| Disease Name | Primary Tissues or System Affected | Additional Tissues/Systems Affected | Genes |
|---|---|---|---|
| | | | CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AFIQ, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN |
| Limb-girdle muscular dystrophy diseases | muscle | | LGMD |
| Lowe syndrome | brain, eyes, kidneys | | OCRL |
| Lupus glomerulo- nephritis | kidney | | MAPK1 |
| Machado-Joseph's Disease (also known as Spinocerebellar ataxia Type 3) | Brain, CNS, muscle | | ATX3 |
| Macular degeneration | eye | | ABC4, CBC1, CHM1, APOE, C1QTNF5, C2, C3, CCL2, CCR2, CD36, CFB, CFH, CFHR1, CFHR3, CNGB3, CP, CRP, CST3, CTSD, CX3CR1, ELOVL4, ERCC6, FBLN5, FBLN6, FSCN2, HMCN1, HTRA1, IL6, IL8, PLEKHA1, PROM1, PRPH2, RPGR, SERPING1, TCOF1, TIMP3, TLR3 |
| Macular Dystrophy | eye | | BEST1, C1QTNF5, CTNNA1, EFEMP1, ELOVL4, FSCN2, GUCAIB, HMCN1, IMPG1, OTX2, PRDM13, PROM1, PRPH2, RP1L1, TIMP3, ABCA4, CFH, DRAM2, IMG1, MFSD8, ADMD, STGD2, STGD3, RDS, RP7, PRPH, AVMD, AOFMD, VMD2 |
| Malattia Leventinesse | eye | | EFEMP1, FBLN3 |
| Maple Syrup Urine Disease | Metabolism disease | | BCKDHA, BCKDHB, and DBT |
| Marfan syndrome | Connective tissue | Musculoskeletal | FBN1 |
| Maroteaux-Lamy Syndrome (aka MPS VI) | Musculoskeletal system, nervous system | Liver, spleen | ARSB |
| McArdle's Disease (Glycogen Storage Disease Type V) | Glycogen storage disease | muscle | PYGM |
| Medullary cystic kidney disease | kidney | | UMOD, HNFJ, FJHN, MCKD2, ADMCKD2 |
| Metachromatic leukodystrophy | Lysosomal storage disease | Nervous system | ARSA |
| Methylmalonic acidemia (MMA) | Metabolism disease | | MMAA, MMAB, MUT, MMACHC, MMADHC, LMBRD1 |
| Morquio Syndrome (aka MPS IV A and B) | Connective tissue, skin, bone, eyes | heart | GALNS |
| Mucopolysaccharidosis diseases (Types IH/S, IH, II, III A B and C, I S, IVA and B, IX, VII, and VI) | Lysosomal storage disease - affects various organs/tissues | | See also Hurler/Scheie syndrome, Hurler disease, Sanfillipo syndrome, Scheie syndrome, Morquio syndrome, hyaluronidase deficiency, Sly syndrome, and Maroteaux-Lamy syndrome |
| Muscular Atrophy | muscle | | VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1 |
| Muscular dystrophy | muscle | | FKRP, MDC1C, LGMD2I, LAMA2, LAMM, LARGE, KIAA0609, MDC1D, FCMD, TTID, MYOT, CAPN3, CANP3, DYSF, LGMD2B, |

TABLE 3-continued

Exemplary Genetic and Other Diseases and Associated Genes

| Disease Name | Primary Tissues or System Affected | Additional Tissues/Systems Affected | Genes |
|---|---|---|---|
| Myotonic dystrophy (Type 1 and Type 2) | Muscles | Eyes, heart, endocrine | SGCG, LGMD2C, DMDA1, SCG3, SGCA, ADL, DAG2, LGMD2D, DMDA2, SGCB, LGMD2E, SGCD, SGD, LGMD2F, CMDIL, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1 CNBP (Type 2) and DMPK (Type 1) |
| Neoplasia | | | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Ape |
| Neurofibromatosis (NF) (NF1, formerly Recklinghausen's NF, andNF2) | brain, spinal cord, nerves, and skin | | NF1, NF2 |
| Niemann-Pick Lipidosis (Types A, B, and C) | Lysosomal Storage Disease | Various- where sphingomyelin accumulates, particularly spleen, liver, blood, CNS | Types A and B: SMPD1; Type C: NPC1 orNPC2 |
| Noonan Syndrome | Various - musculoskeletal, heart, eyes, reproductive organs, blood | | PTPN11, SOS1, RAF1 and KRAS |
| Norrie Disease or X-linked Familial Exudative Vitreoretinopathy | eye | | NDP |
| North Carolina Macular Dystrophy | eye | | MCDR1 |
| Osteogenesis imperfecta (OI) (Types 1, II, III, IV, V, VI, VII) | bones, musculoskeletal | | COL1A1, COL1A2, CRTAP, P3H |
| Osteopetrosis | bones | | LRP5, BMND1, LRP7, LR3, OPPG, VBCH2, CLCN7, CLC7, OPTA2, OSTM1, GL, TCIRG1, TIRC7, OC116, OPTB1 |
| Patau's Syndrome (Trisomy 13) | Brain, heart, skeletal system | | Additional copy of chromosome 13 |
| Parkinson's disease (PD) | Brain, nervous system | | SNCA (PARKI), UCHL1 (PARK 5), and LRRK2 (PARK8), (PARK3), PARK2, PARK4, PARK7 (PARK7), PINK1 (PARK6); x-Synuclein, DJ-1, Parkin, NR4A2, NURR1, NOT, TINUR, SNCAIP, TBP, SCA17, NCAP, PRKN, PDJ, DBH, NDUFV2 |
| Pattern Dystrophy of the RPE | eye | | RDS/peripherin |
| Phenylketonuria (PKU) | Metabolism disorder | Various due to build-up of phenylalanine, phenyl ketones in tissues and CNS | PAH, PKU1, QDPR, DHPR, PTS |

TABLE 3-continued

Exemplary Genetic and Other Diseases and Associated Genes

| Disease Name | Primary Tissues or System Affected | Additional Tissues/Systems Affected | Genes |
|---|---|---|---|
| Polycystic kidney and hepatic disease | Kidney, liver | | FCYT, PKHD1, ARPKD, PKD1, PKD2, PKD4, PKDTS, PRKCSH, G19P1, PCLD, SEC63 |
| Pompe's Disease | Glycogen storage disease | Various - heart, liver, spleen | GAA |
| Porphyria (actually refers to a group of different diseases all having a specific heme production process abnormality) | Various- wherever heme precursors accumulate | | ALAD, ALAS2, CPOX, FECH, HMBS, PPOX, UROD, or UROS |
| posterior polymorphous corneal dystrophy | eyes | | TCF4; COL8A2 |
| Primary Hyperoxaluria (e.g. type 1) | Various - eyes, heart, kidneys, skeletal system | | LDHA (lactate dehydrogenase A) and hydroxyacid oxidase 1 (HAO1) |
| Primary Open Angle Glaucoma (POAG) | eyes | | MYOC |
| Primary sclerosing cholangitis | Liver, gallbladder | | TCF4; COL8A2 |
| Progeria (also called Hutchinson-Gilford progeria syndrome) | All | | LMNA |
| Prader-Willi Syndrome | Musculoskeletal system, brain, reproductive and endocrine system | | Deletion of region of short arm of chromosome 15, including UBE3A |
| Prostate Cancer | prostate | | HOXB13, MSMB, GPRC6A, TP53 |
| Pyruvate Dehydrogenase Deficiency | Brain, nervous system | | PDHA1 |
| Kidney/Renal carcinoma | kidney | | RLIP76, VEGF |
| Rett Syndrome | Brain | | MECP2, RTT, PPMX, MRX16, MRX79, CDKL5, STK9, MECP2, RTT, PPMX, MRX16, MRX79, x-Synuclein, DJ-1 |
| Retinitis pigmentosa (RP) | eye | | ADIPOR1, ABCA4, AGBL5, ARHGEF18, ARL2BP, ARL3, ARL6, BEST1, BBS1, BBS2, C2ORF71, C8ORF37, CA4, CERKL, CLRN1, CNGA1, CMGB1, CRB1, CRX, CYP4V2, DHDDS, DHX38, EMC1, EYS, FAM161A, FSCN2, GPR125, GUCAIB, HK1, HPRPF3, HGSNAT, IDH3B, IMPDH1, IMPG2, IFT140, IFT172, KLHL7, KIAA1549, KIZ, LRAT, MAK, MERTK, MVK, NEK2, NUROD1, NR2E3, NRL, OFD1, PDE6A, PDE6B, PDE6G, POMGNT1, PRCD, PROM1, PRPF3, PRPF4, PRPF6, PRPF8, PRPF31, PRPH2, RPB3, RDH12, REEP6, RP39, RGR, RHO, RLBP1, ROM1, RP1, RP1L1, RPY, RP2, RP9, RPE65, RPGR, SAMD11, SAG, SEMA4A, SLC7A14, SNRNP200, SPP2, SPATA7, TRNT1, TOPORS, TTC8, TULP1, USH2A, ZFN408, ZNF513, see also 20120204282 |
| Scheie syndrome (also known as mucopolysaccharidosis type I S(MPS I-S)) | Various- liver, spleen, eye, joint, heart, brain, skeletal | | IDUA, α-L-iduronidase |
| Schizophrenia | Brain | | Neuregulin1 (Nrg1); Erb4 (receptor for Neuregulin); Complexini (Cplx1); Tph1 Tryptophan hydroxylase; Tph2 Tryptophan hydroxylase 2; Neurexin 1; GSK3; GSK3a; GSK3b; 5-HTT (Slc6a4); COMT; DRD (Drd1a); SLC6A3; DAOA; DTNBP1; Dao (Dao1); TCF4; COL8A2 |

TABLE 3-continued

Exemplary Genetic and Other Diseases and Associated Genes

| Disease Name | Primary Tissues or System Affected | Additional Tissues/Systems Affected | Genes |
|---|---|---|---|
| Secretase Related Disorders | Various | | APH-1 (alpha and beta); PSEN1; NCSTN; PEN-2; Nos1, Parp1, Nat1, Nat2, CTSB, APP, APH1B, PSEN2, PSENEN, BACE1, ITM2B, CTSD, NOTCH1, TNF, INS, DYT10, ADAM17, APOE, ACE, STN, TP53, IL6, NGFR, IL1B, ACHE, CTNNB1, IGF1, IFNG, NRG1, CASP3, MAPK1, CDH1, APBB1, HMGCR, CREB1, PTGS2, HES1, CAT, TGFB1, ENO2, ERBB4, TRAPPC10, MAOB, NGF, MMP12, JAG1, CD40LG, PPARG, FGF2, LRP1, NOTCH4, MAPK8, PREP, NOTCH3, PRNP, CTSG, EGF, REN, CD44, SELP, GHR, ADCYAP1, INSR, GFAP, MMP3, MAPK10, SP1, MYC, CTSE, PPARA, JUN, TIMP1, IL5, IL1A, MMP9, HTR4, HSPG2, KRAS, CYCS, SMG1, IL1R1, PROK1, MAPK3, NTRK1, IL13, MME, TKT, CXCR2, CHRM1, ATXN1, PAWR, NOTCJ2, M6PR, CYP46A1, CSNK1D, MAPK14, PRG2, PRKCA, L1 CAM, CD40, NR1I2, JAG2, CTNND1, CMA1, SORT1, DLK1, THEM4, JUP, CD46, CCL11, CAV3, RNASE3, HSPA8, CASP9, CYP3A4, CCR3, TFAP2A, SCP2, CDK4, JOF1A, TCF7L2, B3GALTL, MDM2, RELA, CASP7, IDE, FANP4, CASK, ADCYAP1R1, ATF4, PDGFA, C21ORF33, SCG5, RMF123, NKFB1, ERBB2, CAV1, MMP7, TGFA, RXRA, STX1A, PSMC4, P2RY2, TNFRSF21, DLG1, NUMBL, SPN, PLSCR1, UBQLN2, UBQLN1, PCSK7, SPON1, SILV, QPCT, HESS, GCC1 |
| Selective IgA Deficiency | Immune system | | Type 1: MSH5; Type 2: TNFRSF13B |
| Severe Combined Immunodeficiency (SCID) and SCID-X1, and ADA-SCID | Immune system | | JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4, those identified in US Pat. App. Pub. 20110225664, 20110091441, 20100229252, 20090271881 and 20090222937; |
| Sickle cell disease | blood | | HBB, BCL11A, BCL11Ae, cis-regulatory elements of the B-globin locus, HBG 1/2 promoter, HBG distal CCAAT box region between -92 and -130 of the HBG Transcription Start Site, those described in WO2015148863, WO 2013/126794, US Pat. Pub. 20110182867 |
| Sly Syndrome (aka MPS VII) | | | GUSB |
| Spinocerebellar Ataxias (SCA types 1, 2, 3, 6, 7, 8, 12 and 17) | | | ATXN1, ATXN2, ATX3 |
| Sorsby Fundus Dystrophy | eye | | TIMP3 |
| Stargardt disease | eye | | ABCR, ELOVL4, ABCA4, PROM1 |
| Tay-Sachs Disease | Lysosomal Storage disease | Various - CNS, brain, eye | HEX-A |
| Thalassemia (Alpha, Beta, Delta) | blood | | HBA1, HBA2 (Alpha), HBB (Beta), HBB and HBD (delta), LCRB, BCL11A, BCL11Ae, cis-regulatory elements of the B-globin locus, HBG 1/2 promoter, those described in WO2015148860, US Pat. Pub. 20110182867, 2015/148860 |

TABLE 3-continued

Exemplary Genetic and Other Diseases and Associated Genes

| Disease Name | Primary Tissues or System Affected | Additional Tissues/Systems Affected | Genes |
|---|---|---|---|
| Thymic Aplasia (DiGeorge Syndrome; 22q11.2 deletion syndrome) | Immune system, thymus | | deletion of 30 to 40 genes in the middle of chromosome 22 at a location known as 22q11.2, including TBX1, DGCR8 |
| Transthyretin amyloidosis (ATTR) | liver | | TTR (transthyretin) |
| trimethylaminuria | Metabolism disease | | FMO3 |
| Trinucleotide Repeat Disorders (generally) | Various | | HTT; SBMA/SMAX1/AR; FXN/X25 ATX3; ATXN1; ATXN2; DMPK; Atrophin-1 and Atn1 (DRPLA Dx); CBP (Creb-BP - global instability); VLDLR; Atxn7; Atxn10; FEN1, TNRC6A, PABPN1, JPH3, MED15, ATXN1, ATXN3, TBP, CACNA1A, ATXN80S, PPP2R2B, ATXN7, TNRC6B, TNRC6C, CELF3, MAB21L1, MSH2, TMEM185A, SIX5, CNPY3, RAXE, GNB2, RPL14, ATXN8, ISR, TTR, EP400, GIGYF2, OGG1, STC1, CNDP1, C10ORF2, MAML3, DKC1, PAXIP1, CASK, MAPT, SP1, POLG, AFF2, THBS1, TP53, ESR1, CGGBP1, ABT1, KLK3, PRNP, JUN, KCNN3, BAX, FRAXA, KBTBD10, MBNL1, RAD51, NCOA3, ERDA1, TSC1, COMP, GGLC, RRAD, MSH3, DRD2, CD44, CTCF, CCND1, CLSPN, MEF2A, PTPRU, GAPDH, TRIM22, WT1, AHR, GPX1, TPMT, NDP, ARX, TYR, EGRI, UNG, NUMBL, FABP2, EN2, CRYGC, SRP14, CRYGB, PDCD1, HOXA1, ATXN2L, PMS2, GLA, CBL, FTH1, IL12RB2, OTX2, HOXA5, POLG, DLX2, AHRR, MANF, RMEM158, see also 20110016540 |
| Turner's Syndrome (XO) | Various - reproductive organs, and sex characteristics, vasculature | | Monosomy X |
| Tuberous Sclerosis | CNS, heart, kidneys | | TSC1, TSC2 |
| Usher syndrome (Types I, II, and III) | Ears, eyes | | ABHD12, CDH23, CIB2, CLRN1, DFNB31, GPR98, HARS, MY07A, PCDH15, USH1C, USH1G, USH2A, USH11A, those described in WO2015134812A1 |
| Velocardiofacial syndrome (aka 22q11.2 deletion syndrome, DiGeorge syndrome, conotruncal anomaly face syndrome (CTAF), autosomal dominant Opitz G/BB syndrome or Cayler cardiofacial syndrome) | Various - skeletal, heart, kidney, immune system, brain | | Many genes are deleted, COM, TBX1, and other are associated with symptoms |
| Von Gierke's Disease (Glycogen Storage Disease type I) | Glycogen Storage disease | Various - liver, kidney | G6PC and SLC37A4 |
| Von Hippel-Lindau Syndrome | Various - cell growth regulation disorder | CNS, Kidney, Eye, visceral organs | VHL |
| Von Willebrand Disease (Types I, II and III) | blood | | VWF |
| Wilson Disease | Various - Copper Storage Disease | Liver, brains, eyes, other tissues where copper builds up | ATP7B |

TABLE 3-continued

Exemplary Genetic and Other Diseases and Associated Genes

| Disease Name | Primary Tissues or System Affected | Additional Tissues/Systems Affected | Genes |
|---|---|---|---|
| Wiskott-Aldrich Syndrome | Immune System | | WAS |
| Xeroderma Pigmentosum | Skin | Nervous system | POLH |
| XXX Syndrome | Endocrine, brain | | X chromosome trisomy |

In some embodiments, the compositions, systems, or components thereof can be used treat or prevent a disease in a subject by modifying one or more genes associated with one or more cellular functions, such as any one or more of those in Table 9. In some embodiments, the disease is a genetic disease or disorder. In some of embodiments, the composition, system, or component thereof can modify one or more genes or polynucleotides associated with one or more genetic diseases such as any set forth in Table 4.

TABLE 4

Exemplary Genes controlling Cellular Functions

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKC1; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPPICC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE21; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKNIA; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKC1; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLH; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPPICC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; |

TABLE 4-continued

Exemplary Genes controlling Cellular Functions

| CELLULAR FUNCTION | GENES |
|---|---|
| Apoptosis Signaling | HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKC1; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; |
| Aryl Hydrocarbon Receptor Signaling | PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKC1; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |

TABLE 4-continued

Exemplary Genes controlling Cellular Functions

| CELLULAR FUNCTION | GENES |
|---|---|
| Neuregulin Signaling | ERBB4; PRKCE; ITGAM; ITGA5; PTEN; PRKCZ; ELK1; MAPK1; PTPN11; AKT2; EGFR; ERBB2; PRKC1; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAPK1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKC1; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKC1; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKC1; PTK2; FOS; PIK3CB; PIK3C3; MAPK8; IGFIR; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKC1; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKC1; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKC1; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; |

TABLE 4-continued

Exemplary Genes controlling Cellular Functions

| CELLULAR FUNCTION | GENES |
|---|---|
| | IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKC1; GNAQ; PPP2R1A; IGFIR; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE21; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKC1; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE21; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |

TABLE 4-continued

Exemplary Genes controlling Cellular Functions

| CELLULAR FUNCTION | GENES |
|---|---|
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; |
| Notch Signaling | PARK2; APP; CASP3 HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GP1; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GP1; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |

TABLE 4-continued

Exemplary Genes controlling Cellular Functions

| CELLULAR FUNCTION | GENES |
| --- | --- |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cm2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 orBm3a); Numb; Reln |

In an aspect, the invention provides a method of individualized or personalized treatment of a genetic disease in a subject in need of such treatment comprising: (a) introducing one or more mutations ex vivo in a tissue, organ or a cell line, or in vivo in a transgenic non-human mammal, comprising delivering to cell(s) of the tissue, organ, cell or mammal a composition comprising the particle delivery system or the delivery system or the virus particle of any one of the above embodiment or the cell of any one of the above embodiment, wherein the specific mutations or precise sequence substitutions are or have been correlated to the genetic disease; (b) testing treatment(s) for the genetic disease on the cells to which the vector has been delivered that have the specific mutations or precise sequence substitutions correlated to the genetic disease; and (c) treating the subject based on results from the testing of treatment(s) of step (b).

Infectious Diseases

In some embodiments, the composition, system,(s) or component(s) thereof can be used to diagnose, prognose, treat, and/or prevent an infectious disease caused by a microorganism, such as bacteria, virus, fungi, parasites, or combinations thereof.

In some embodiments, the system(s) or component(s) thereof can be capable of targeting specific microorganism within a mixed population. Exemplary methods of such techniques are described in e.g. Gomaa A A, Klumpe H E, Luo M L, Selle K, Barrangou R, Beisel C L. 2014. Programmable removal of bacterial strains by use of genome-targeting composition, systems, mBio 5:e00928-13; Citorik R J, Mimee M, Lu T K. 2014. Sequence-specific antimicrobials using efficiently delivered RNA-guided nucleases. Nat Biotechnol 32:1141-1145, the teachings of which can be adapted for use with the compositions, systems, and components thereof described herein.

In some embodiments, the composition, system,(s) and/or components thereof can be capable of targeting pathogenic and/or drug-resistant microorganisms, such as bacteria, virus, parasites, and fungi. In some embodiments, the composition, system,(s) and/or components thereof can be capable of targeting and modifying one or more polynucleotides in a pathogenic microorganism such that the microorganism is less virulent, killed, inhibited, or is otherwise rendered incapable of causing disease and/or infecting and/or replicating in a host cell.

In some embodiments, the pathogenic bacteria that can be targeted and/or modified by the composition, system,(s) and/or component(s) thereof described herein include, but are not limited to, those of the genus *Actinomyces* (e.g. *A. israelii*), *Bacillus* (e.g. *B. anthracis, B. cereus*), Bactereoides (e.g. *B. fragilis*), *Bartonella* (*B. henselae, B. quintana*), *Bordetella* (*B. pertussis*), *Borrelia* (e.g. *B. burgdorferi, B. garinii, B. afzelii*, and *B. recurreentis*), *Brucella* (e.g. *B. abortus, B. canis, B. melitensis*, and *B. suis*), *Campylobacter* (e.g. *C. jejuni*), *Chlamydia* (e.g. *C. pneumoniae* and *C. trachomatis*), *Chlamydophila* (e.g. *C. psittaci*), *Clostridium* (e.g. *C. botulinum, C. difficile, C. perfringens. C. tetani*), *Corynebacterium* (e.g. *C. diptheriae*), *Enterococcus* (e.g. *E. Faecalis, E. faecium*), *Ehrlichia* (*E. canis* and *E. chaffensis*) *Escherichia* (e.g. *E. coli*), *Francisella* (e.g. *F. tularensis*), *Haemophilus* (e.g. *H. influenzae*), *Helicobacter* (*H. pylori*), *Klebsiella* (E.g. *K. pneumoniae*), *Legionella* (e.g. *L. pneumophila*), Leptospira (e.g. *L. interrogans, L. santarosai, L. weilii, L. noguchii*), *Listereia* (e.g. *L. monocytogeenes*), *Mycobacterium* (e.g. *M. leprae, M. tuberculosis, M. ulcerans*), *Mycoplasma* (*M. pneumoniae*), *Neisseria* (*N. gonorrhoeae* and *N. menigitidis*), *Nocardia* (e.g. *N. asteeroides*), *Pseudomonas* (*P. aeruginosa*), *Rickettsia* (*R. rickettsia*), *Salmonella* (*S. typhi* and *S. typhimurium*), *Shigella* (*S. sonnei* and *S. dysenteriae*), *Staphylococcus* (*S. aureus, S.*

*epidermidis*, and *S. saprophyticus*), Streeptococcus (*S. agalactiaee, S. pneumoniae, S. pyogenes*), *Treponema* (*T. pallidum*), Ureeaplasma (e.g. *U. urealyticum*), *Vibrio* (e.g. *V. cholerae*), *Yersinia* (e.g. *Y. pestis, Y. enteerocolitica*, and *Y. pseudotuberculosis*).

In some embodiments, the pathogenic virus that can be targeted and/or modified by the composition, system,(s) and/or component(s) thereof described herein include, but are not limited to, a double-stranded DNA virus, a partly double-stranded DNA virus, a single-stranded DNA virus, a positive single-stranded RNA virus, a negative single-stranded RNA virus, or a double stranded RNA virus. In some embodiments, the pathogenic virus can be from the family Adenoviridae (e.g. Adenovirus), Herpeesviridae (e.g. Herpes simplex, type 1, Herpes simplex, type 2, Varicella-zoster virus, Epstein-Barr virus, Human cytomegalovirus, Human herpesvirus, type 8), Papillomaviridae (e.g. Human papillomavirus), Polyomaviridae (e.g. BK virus, JC virus), Poxviridae (e.g. smallpox), Hepadnaviridae (e.g. Hepatitis B), Parvoviridae (e.g. Parvovirus B19), Astroviridae (e.g. Human astrovirus), Caliciviridae (e.g. Norwalk virus), Picornaviridae (e.g. coxsackievirus, hepatitis A virus, poliovirus, rhinovirus), Coronaviridae (e.g. Severe acute respiratory syndrome-related coronavirus, strains: Severe acute respiratory syndrome virus, Severe acute respiratory syndrome coronavirus 2 (COVID-19)), Flaviviridae (e.g. Hepatitis C virus, yellow fever virus, dengue virus, West Nile virus, TBE virus), Togaviridae (e.g. Rubella virus), Hepeviridae (e.g. Hepatitis E virus), Retroviridae (Human immunodeficiency virus (HIV)), Orthomyxoviridae (e.g. Influenza virus), Arenaviridae (e.g. Lassa virus), Bunyaviridae (e.g. Crimean-Congo hemorrhagic fever virus, Hantaan virus), Filoviridae (e.g. Ebola virus and Marburg virus), Paramyxoviridae (e.g. Measles virus, Mumps virus, Parainfluenza virus, Respiratory syncytial virus), Rhabdoviridae (Rabies virus), Hepatits D virus, Reoviridae (e.g. Rotavirus, Orbivirus, Coltivirus, Banna virus).

In some embodiments, the pathogenic fungi that can be targeted and/or modified by the composition, system,(s) and/or component(s) thereof described herein include, but are not limited to, those of the genus *Candida* (e.g. *C. albicans*), *Aspergillus* (e.g. *A. fumigatus, A. flavus, A. clavatus*), *Cryptococcus* (e.g. *C. neoformans, C. gattii*), *Histoplasma* (e.g., *H. capsulatum*), *Pneumocystis* (e.g. *P. jiroveecii*), *Stachybotrys* (e.g. *S. chartarum*).

In some embodiments, the pathogenic parasites that can be targeted and/or modified by the composition, system,(s) and/or component(s) thereof described herein include, but are not limited to, protozoa, helminths, and ectoparasites. In some embodiments, the pathogenic protozoa that can be targeted and/or modified by the composition, system,(s) and/or component(s) thereof described herein include, but are not limited to, those from the groups Sarcodina (e.g. ameba such as *Entamoeba*), Mastigophora (e.g. *flagellates* such as *Giardia* and *Leishmania*), Cilophora (e.g. ciliates such as *Balantidum*), and sporozoa (e.g. *plasmodium* and *cryptosporidium*). In some embodiments, the pathogenic helminths that can be targeted and/or modified by the composition, system,(s) and/or component(s) thereof described herein include, but are not limited to, flatworms (platyhelminths), thorny-headed worms (acanthoceephalins), and roundworms (nematodes). In some embodiments, the pathogenic ectoparasites that can be targeted and/or modified by the composition, system,(s) and/or component(s) thereof described herein include, but are not limited to, ticks, fleas, lice, and mites.

In some embodiments, the pathogenic parasite that can be targeted and/or modified by the composition, system,(s) and/or component(s) thereof described herein include, but are not limited to, *Acanthamoeba* spp., *Balamuthia mandrillaris, Babesiosis* spp. (e.g. *Babesia B. divergens, B. bigemina, B. equi, B. microfti, B. duncani*), *Balantidiasis* spp. (e.g. *Balantidium coli*), *Blastocystis* spp., *Cryptosporidium* spp., *Cyclosporiasis* spp. (e.g. *Cyclospora cayetanensis*), *Dientamoebiasis* spp. (e.g. *Dientamoeba fragilis*), *Amoebiasis* spp. (e.g. *Entamoeba histolytica*), *Giardiasis* spp. (e.g. *Giardia lamblia*), *Isosporiasis* spp. (e.g. *Isospora belli*), *Leishmania* spp., *Naegleria* spp. (e.g. *Naegleria fowleri*), *Plasmodium* spp. (e.g. *Plasmodium falciparum, Plasmodium vivax, Plasmodium ovale* curtisi, *Plasmodium ovale* wallikeri, *Plasmodium malariae, Plasmodium knowlesi*), *Rhinosporidiosis* spp. (e.g. *Rhinosporidium seeberi*), *Sarcocystosis* spp. (e.g. *Sarcocystis bovihominis, Sarcocystis suihominis*), *Toxoplasma* spp. (e.g. *Toxoplasma gondii*), *Trichomonas* spp. (e.g. *Trichomonas vaginalis*), *Trypanosoma* spp. (e.g. *Trypanosoma brucei*), *Trypanosoma* spp. (e.g. *Trypanosoma cruzi*), Tapeworm (e.g. *Cestoda, Taenia multiceps, Taenia saginata, Taenia solium*), *Diphyllobothrium latum* spp., *Echinococcus* spp. (e.g. *Echinococcus granulosus, Echinococcus multilocularis, E. vogeli, E. oligarthrus*), *Hymenolepis* spp. (e.g. *Hymenolepis nana, Hymenolepis diminuta*), *Bertiella* spp. (e.g. *Bertiella mucronata, Bertiella studeri*), *Spirometra* (e.g. *Spirometra erinaceieuropaei*), *Clonorchis* spp. (e.g. *Clonorchis sinensis; Clonorchis viverrini*), *Dicrocoelium* spp. (e.g. *Dicrocoelium dendriticum*), *Fasciola* spp. (e.g. *Fasciola hepatica, Fasciola gigantica*), *Fasciolopsis* spp. (e.g. *Fasciolopsis buski*), *Metagonimus* spp. (e.g. *Metagonimus yokogawai*), *Metorchis* spp. (e.g. *Metorchis conjunctus*), *Opisthorchis* spp. (e.g. *Opisthorchis viverrini, Opisthorchis felineus*), *Clonorchis* spp. (e.g. *Clonorchis sinensis*), *Paragonimus* spp. (e.g. *Paragonimus westermani; Paragonimus africanus; Paragonimus caliensis; Paragonimus kellicotti; Paragonimus skrjabini; Paragonimus uterobilateralis*), *Schistosoma* sp., *Schistosoma* spp. (e.g. *Schistosoma mansoni, Schistosoma haematobium, Schistosoma japonicum, Schistosoma mekongi*, and *Schistosoma intercalatum*), *Echinostoma* spp. (e.g. *E. echinatum*), *Trichobilharzia* spp. (e.g. *Trichobilharzia regent*), *Ancylostoma* spp. (e.g. *Ancylostoma duodenale*), Necator spp. (e.g. *Necator americanus*), *Angiostrongylus* spp., *Anisakis* spp., *Ascaris* spp. (e.g. *Ascaris lumbricoides*), *Baylisascaris* spp. (e.g. *Baylisascaris procyonis*), *Brugia* spp. (e.g. *Brugia malayi, Brugia timori*), *Dioctophyme* spp. (e.g. *Dioctophyme renale*), *Dracunculus* spp. (e.g. *Dracunculus medinensis*), *Enterobius* spp. (e.g. *Enterobius vermicularis, Enterobius gregorii*), *Gnathostoma* spp. (e.g. *Gnathostoma spinigerum, Gnathostoma hispidum*), *Halicephalobus* spp. (e.g. *Halicephalobus gingivalis*), *Loa loa* spp. (e.g. *Loa boa filaria*), *Mansonella* spp. (e.g. *Mansonella streptocerca*), *Onchocerca* spp. (e.g. *Onchocerca volvulus*), *Strongyloides* spp. (e.g. *Strongyloides stercoralis*), *Thelazia* spp. (e.g. *Thelazia californiensis, Thelazia callipaeda*), *Toxocara* spp. (e.g. *Toxocara canis, Toxocara cati*, Toxascaris leonine), *Trichinella* spp. (e.g. *Trichinella spiralis, Trichinella britovi, Trichinella nelsoni, Trichinella nativa*), *Trichuris* spp. (e.g. *Trichuris trichiura, Trichuris vulpis*), *Wuchereria* spp. (e.g. *Wuchereria bancrofti*), *Dermatobia* spp. (e.g. *Dermatobia hominis*), *Tunga* spp. (e.g. *Tunga penetrans*), *Cochliomyia* spp. (e.g. *Cochliomyia hominivorax*), *Linguatula* spp. (e.g. *Linguatula serrata*), Archiacanthocephala sp., *Moniliformis* sp. (e.g. *Moniliformis moniliformis*), *Pediculus* spp. (e.g. *Pediculus humanus* capitis, *Pediculus humanus humanus*), *Pthirus* spp.

(e.g. *Pthirus pubis*), Arachnida spp. (e.g. *Trombiculidae, Ixodidae, Argaside*), Siphonaptera spp (e.g. *Siphonaptera: Pulicinae*), Cimicidae spp. (e.g. *Cimex lectularius* and *Cimex hemipterus*), Diptera spp., *Demodex* spp. (e.g. *Demodex folliculorum/brevis/canis*), *Sarcoptes* spp. (e.g. *Sarcoptes scabiei*), *Dermanyssus* spp. (e.g. *Dermanyssus gallinae*), *Ornithonyssus* spp. (e.g. *Ornithonyssus sylviarum, Ornithonyssus bursa, Ornithonyssus bacoti*), *Laelaps* spp. (e.g. *Laelaps echidnina*), *Liponyssoides* spp. (e.g. *Liponyssoides sanguineus*).

In some embodiments the gene targets can be any of those as set forth in Table 1 of Strich and Chertow. 2019. J. Clin. Microbio. 57:4 e01307-18, which is incorporated herein as if expressed in its entirety herein.

In some embodiments, the method can include delivering a composition, system, and/or component thereof to a pathogenic organism described herein, allowing the composition, system, and/or component thereof to specifically bind and modify one or more targets in the pathogenic organism, whereby the modification kills, inhibits, reduces the pathogenicity of the pathogenic organism, or otherwise renders the pathogenic organism non-pathogenic. In some embodiments, delivery of the composition, system, occurs in vivo (i.e. in the subject being treated). In some embodiments occurs by an intermediary, such as microorganism or phage that is non-pathogenic to the subject but is capable of transferring polynucleotides and/or infecting the pathogenic microorganism. In some embodiments, the intermediary microorganism can be an engineered bacteria, virus, or phage that contains the composition, system,(s) and/or component(s) thereof and/or CRISPR-Cas vectors and/or vector systems. The method can include administering an intermediary microorganism containing the composition, system,(s) and/or component(s) thereof and/or CRISPR-Cas vectors and/or vector systems to the subject to be treated. The intermediary microorganism can then produce the CRISPR-system and/or component thereof or transfer a composition, system, polynucleotide to the pathogenic organism. In embodiments, where the CRISPR-system and/or component thereof, vector, or vector system is transferred to the pathogenic microorganism, the composition, system, or component thereof is then produced in the pathogenic microorganism and modifies the pathogenic microorganism such that it is less virulent, killed, inhibited, or is otherwise rendered incapable of causing disease and/or infecting and/or replicating in a host or cell thereof.

In some embodiments, where the pathogenic microorganism inserts its genetic material into the host cell's genome (e.g. a virus), the composition, system, can be designed such that it modifies the host cell's genome such that the viral DNA or cDNA cannot be replicated by the host cell's machinery into a functional virus. In some embodiments, where the pathogenic microorganism inserts its genetic material into the host cell's genome (e.g. a virus), the composition, system, can be designed such that it modifies the host cell's genome such that the viral DNA or cDNA is deleted from the host cell's genome.

It will be appreciated that inhibiting or killing the pathogenic microorganism, the disease and/or condition that its infection causes in the subject can be treated or prevented. Thus, also provided herein are methods of treating and/or preventing one or more diseases or symptoms thereof caused by any one or more pathogenic microorganisms, such as any of those described herein.

Mitochondrial Diseases

Some of the most challenging mitochondrial disorders arise from mutations in mitochondrial DNA (mtDNA), a high copy number genome that is maternally inherited. In some embodiments, mtDNA mutations can be modified using a composition, system, described herein. In some embodiments, the mitochondrial disease that can be diagnosed, prognosed, treated, and/or prevented can be MELAS (mitochondrial myopathy encephalopathy, and lactic acidosis and stroke-like episodes), CPEO/PEO (chronic progressive external ophthalmoplegia syndrome/progressive external ophthalmoplegia), KSS (Kearns-Sayre syndrome), MIDD (maternally inherited diabetes and deafness), MERRF (myoclonic epilepsy associated with ragged red fibers), NIDDM (noninsulin-dependent diabetes mellitus), LHON (Leber hereditary optic neuropathy), LS (Leigh Syndrome) an aminoglycoside induced hearing disorder, NARP (neuropathy, ataxia, and pigmentary retinopathy), Extrapyramidal disorder with akinesia-rigidity, psychosis and SNHL, Nonsyndromic hearing loss a cardiomyopathy, an encephalomyopathy, Pearson's syndrome, or a combination thereof.

In some embodiments, the mtDNA of a subject can be modified in vivo or ex vivo. In some embodiments, where the mtDNA is modified ex vivo, after modification the cells containing the modified mitochondria can be administered back to the subject. In some embodiments, the composition, system, or component thereof can be capable of correcting an mtDNA mutation, or a combination thereof.

In some embodiments, at least one of the one or more mtDNA mutations is selected from the group consisting of: A3243G, C3256T, T3271C, G1019A, A1304T, A15533G, C1494T, C4467A, T1658C, G12315A, A3421G, A8344G, T8356C, G8363A, A13042T, T3200C, G3242A, A3252G, T3264C, G3316A, T3394C, T14577C, A4833G, G3460A, G9804A, G11778A, G14459A, A14484G, G15257A, T8993C, T8993G, G10197A, G13513A, T1095C, C1494T, A1555G, G1541A, C1634T, A3260G, A4269G, T7587C, A8296G, A8348G, G8363A, T9957C, T9997C, G12192A, C12297T, A14484G, G15059A, duplication of CCCCCTCCCC-tandem repeats at positions 305-314 and/or 956-965, deletion at positions from 8,469-13,447, 4, 308-14,874, and/or 4,398-14,822, 961ins/delC, the mitochondrial common deletion (e.g. mtDNA 4,977 bp deletion), and combinations thereof.

In some embodiments, the mitochondrial mutation can be any mutation as set forth in or as identified by use of one or more bioinformatic tools available at Mitomap available at mitomap.org. Such tools include, but are not limited to, "Variant Search, aka Market Finder", Find Sequences for Any Haplogroup, aka "Sequence Finder", "Variant Info", "POLG Pathogenicity Prediction Server", "MITOMASTER", "Allele Search", "Sequence and Variant Downloads", "Data Downloads". MitoMap contains reports of mutations in mtDNA that can be associated with disease and maintains a database of reported mitochondrial DNA Base Substitution Diseases: rRNA/tRNA mutations.

In some embodiments, the method includes delivering a composition, system, and/or a component thereof to a cell, and more specifically one or more mitochondria in a cell, allowing the composition, system, and/or component thereof to modify one or more target polynucleotides in the cell, and more specifically one or more mitochondria in the cell. The target polynucleotides can correspond to a mutation in the mtDNA, such as any one or more of those described herein. In some embodiments, the modification can alter a function of the mitochondria such that the mitochondria functions normally or at least is/are less dysfunctional as compared to an unmodified mitochondria. Modification can occur in vivo or ex vivo. Where modification is performed ex vivo, cells containing modified mitochondria can be administered to a subject in need thereof in an autologous or allogenic manner.

Microbiome Modification

Microbiomes play important roles in health and disease. For example, the gut microbiome can play a role in health by controlling digestion, preventing growth of pathogenic microorganisms and have been suggested to influence mood and emotion. Imbalanced microbiomes can promote disease and are suggested to contribute to weight gain, unregulated blood sugar, high cholesterol, cancer, and other disorders. A healthy microbiome has a series of joint characteristics that can be distinguished from non-healthy individuals, thus detection and identification of the disease-associated microbiome can be used to diagnose and detect disease in an individual. The compositions, systems, and components thereof can be used to screen the microbiome cell population and be used to identify a disease associated microbiome. Cell screening methods utilizing compositions, systems, and components thereof are described elsewhere herein and can be applied to screening a microbiome, such as a gut, skin, vagina, and/or oral microbiome, of a subject.

In some embodiments, the microbe population of a microbiome in a subject can be modified using a composition, system, and/or component thereof described herein. In some embodiments, the composition, system, and/or component thereof can be used to identify and select one or more cell types in the microbiome and remove them from the microbiome population. Exemplary methods of selecting cells using a composition, system, and/or component thereof are described elsewhere herein. In this way the make-up or microorganism profile of the microbiome can be altered. In some embodiments, the alteration causes a change from a diseased microbiome composition to a healthy microbiome composition. In this way the ratio of one type or species of microorganism to another can be modified, such as going from a diseased ratio to a healthy ratio. In some embodiments, the cells selected are pathogenic microorganisms.

In some embodiments, the compositions and systems described herein can be used to modify a polynucleotide in a microorganism of a microbiome in a subject. In some embodiments, the microorganism is a pathogenic microorganism. In some embodiments, the microorganism is a commensal and non-pathogenic microorganism. Methods of modifying polynucleotides in a cell in the subject are described elsewhere herein and can be applied to these embodiments.

Models of Diseases and Conditions

In an aspect, the invention provides a method of modeling a disease associated with a genomic locus in a eukaryotic organism or a non-human organism comprising manipulation of a target sequence within a coding, non-coding or regulatory element of said genomic locus comprising delivering a non-naturally occurring or engineered composition comprising a viral vector system comprising one or more viral vectors operably encoding a composition for expression thereof, wherein the composition comprises particle delivery system or the delivery system or the virus particle of any one of the above embodiments or the cell of any one of the above embodiment.

In one aspect, the invention provides a method of generating a model eukaryotic cell that can include one or more a mutated disease genes and/or infectious microorganisms. In some embodiments, a disease gene is any gene associated an increase in the risk of having or developing a disease. In some embodiments, the method includes (a) introducing one or more vectors into a eukaryotic cell, wherein the one or more vectors comprise a composition, system, and/or component thereof and/or a vector or vector system that is capable of driving expression of a composition, system, and/or component thereof including, but not limited to: a guide sequence optionally linked to a tracr mate sequence, a tracr sequence, one or more Cas effectors, and combinations thereof and (b) allowing a composition, system, or complex to bind to one or more target polynucleotides, e.g., to effect cleavage, nicking, or other modification of the target polynucleotide within said disease gene, wherein the composition, system, or complex is composed of one or more CRISPR-Cas effectors complexed with (1) one or more guide sequences that is/are hybridized to the target sequence(s) within the target polynucleotide(s), and optionally (2) the tracr mate sequence(s) that is/are hybridized to the tracr sequence(s), thereby generating a model eukaryotic cell comprising one or more mutated disease gene(s). Thus, in some embodiments the composition and system, contains nucleic acid molecules for and drives expression of one or more of: a Cas effector, a guide sequence linked to a tracr mate sequence, and a tracr sequence and/or a Homologous Recombination template and/or a stabilizing ligand if the Cas effector has a destabilization domain. In some embodiments, said cleavage comprises cleaving one or two strands at the location of the target sequence by the Cas effector(s). In some embodiments, nicking comprises nicking one or two strands at the location of the target sequence by the Cas effector(s). In some embodiments, said cleavage or nicking results in modified transcription of a target polynucleotide. In some embodiments, modification results in decreased transcription of the target polynucleotide. In some embodiments, the method further comprises repairing said cleaved or nicked target polynucleotide by homologous recombination with an recombination template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

The disease modeled can be any disease with a genetic or epigenetic component. In some embodiments, the disease modeled can be any as discussed elsewhere herein, including but not limited to any as set forth in Tables 2 and 3 herein.

In Situ Disease Detection

The compositions, systems, and/or components thereof can be used for diagnostic methods of detection such as in CASFISH (see e.g. Deng et al. 2015. PNAS USA 112(38): 11870-11875), CRISPR-Live FISH (see e.g. Wang et al. 2020. Science; 365(6459):1301-1305), sm-FISH (Lee and Jefcoate. 2017. Front. Endocrinol. doi.org/10.3389/fendo.2017.00289), sequential FISH CRISPRainbow (Ma et al. Nat Biotechnol, 34 (2016), pp. 528-530), CRISPR-Sirius (Nat Methods, 15 (2018), pp. 928-931), Casilio (Cheng et al. Cell Res, 26 (2016), pp. 254-257), Halo-Tag based genomic loci visualization techniques (e.g. Deng et al. 2015. PNAS USA 112(38): 11870-11875; Knight et al., Science, 350 (2015), pp. 823-826), RNA-aptamer based methods (e.g. Ma et al., J Cell Biol, 214 (2016), pp. 529-537), molecular beacon-based methods (e.g. Zhao et al. Biomaterials, 100 (2016), pp. 172-183; Wu et al. Nucleic Acids Res (2018)), Quantum Dot-based systems (e.g. Ma et al. Anal Chem, 89 (2017), pp. 12896-12901), multiplexed methods (e.g. Ma et al., Proc Natl Acad Sci USA, 112 (2015), pp. 3002-3007; Fu et al. Nat Commun, 7 (2016), p. 11707; Ma et al. Nat Biotechnol, 34 (2016), pp. 528-530; Shao et al. Nucleic Acids Res, 44 (2016), Article e86); Wang et al. Sci Rep, 6

(2016), p. 26857), c, and other in situ CRISPR-hybridization based methods (e.g. Chen et al. Cell, 155 (2013), pp. 1479-1491; Gu et al. Science, 359 (2018), pp. 1050-1055; Tanebaum et al. Cell, 159 (2014), pp. 635-646; Ye et al. Protein Cell, 8 (2017), pp. 853-855; Chen et al. Nat Commun, 9 (2018), p. 5065; Shao et al. ACS Synth Biol (2017); Fu et al. Nat Commun, 7 (2016), p. 11707; Shao et al. Nucleic Acids Res, 44 (2016), Article e86; Wang et al., Sci Rep, 6 (2016), p. 26857), all of which are incorporated by reference herein as if expressed in their entirety and whose teachings can be adapted to the compositions, systems, and components thereof described herein in view of the description herein.

In some embodiments, the composition, system, or component thereof can be used in a detection method, such as an in situ detection method described herein. In some embodiments, the composition, system, or component thereof can include a catalytically inactivate Cas effector described herein and use this system in detection methods such as fluorescence in situ hybridization (FISH) or any other described herein. In some embodiments, the inactivated Cas effector, which lacks the ability to produce DNA double-strand breaks may be fused with a marker, such as fluorescent protein, such as the enhanced green fluorescent protein (eEGFP) and co-expressed with small guide RNAs to target pericentric, centric and telomeric repeats in vivo. The dCas effector or system thereof can be used to visualize both repetitive sequences and individual genes in the human genome. Such new applications of labelled dCas effector and compositions, systems, thereof can be important in imaging cells and studying the functional nuclear architecture, especially in cases with a small nucleus volume or complex 3-D structures.

Cell Selection

In some embodiments, the compositions, systems, and/or components thereof described herein can be used in a method to screen and/or select cells. In some embodiments, composition, system,-based screening/selection method can be used to identify diseased cells in a cell population. In some embodiments, selection of the cells results in a modification in the cells such that the selected cells die. In this way, diseased cells can be identified, and removed from the healthy cell population. In some embodiments, the diseased cells can be a cancer cell, pre-cancerous cell, a virus or other pathogenic organism infected cells, or otherwise abnormal cell. In some embodiments, the modification can impart another detectable change in the cells to be selected (e.g. a functional change and/or genomic barcode) that facilitates selection of the desired cells. In some embodiments a negative selection scheme can be used to obtain a desired cell population. In these embodiments, the cells to be selected against are modified, thus can be removed from the cell population based on their death or identification or sorting based the detectable change imparted on the cells. Thus, in these embodiments, the remaining cells after selection are the desired cell population.

In some embodiments, a method of selecting one or more cell(s) containing a polynucleotide modification can include: introducing one or more composition, system,(s) and/or components thereof, and/or vectors or vector systems into the cell(s), wherein the composition, system,(s) and/or components thereof, and/or vectors or vector systems contains and/or is capable of expressing one or more of: a Cas effector, a guide sequence optionally linked to a tracr mate sequence, a tracr sequence, and an recombination template; wherein, for example that which is being expressed is within and expressed in vivo by the composition, system, vector or vector system and/or the recombination template comprises the one or more mutations that abolish Cas effector cleavage; allowing homologous recombination of the recombination template with the target polynucleotide in the cell(s) to be selected; allowing a composition, system, or complex to bind to a target polynucleotide to effect cleavage of the target polynucleotide within said gene, wherein the AAV-complex comprises the Cas effector complexed with (1) the guide sequence that is hybridized to the target sequence within the target polynucleotide, and (2) the tracr mate sequence that is hybridized to the tracr sequence, wherein binding of the complex to the target polynucleotide induces cell death or imparts some other detectable change to the cell, thereby allowing one or more cell(s) in which one or more mutations have been introduced to be selected. In some embodiments, the cell to be selected may be a eukaryotic cell. In some embodiments, the cell to be selected may be a prokaryotic cell. Selection of specific cells via the methods herein can be performed without requiring a selection marker or a two-step process that may include a counter-selection system.

Therapeutic Agent Development

The compositions, systems, and components thereof described herein can be used to develop CRISPR-Cas-based and non-CRISPR-Cas-based biologically active agents, such as small molecule therapeutics. Thus, described herein are methods for developing a biologically active agent that modulates a cell function and/or signaling event associated with a disease and/or disease gene. In some embodiments, the method comprises (a) contacting a test compound with a diseased cell and/or a cell containing a disease gene cell; and (b) detecting a change in a readout that is indicative of a reduction or an augmentation of a cell signaling event or other cell functionality associated with said disease or disease gene, thereby developing said biologically active agent that modulates said cell signaling event or other functionality associated with said disease gene. In some embodiments, the diseased cell is a model cell described elsewhere herein. In some embodiments, the diseased cell is a diseased cell isolated from a subject in need of treatment. In some embodiments, the test compound is a small molecule agent. In some embodiments, test compound is a small molecule agent. In some embodiments, the test compound is a biologic molecule agent.

In some embodiments, the method involves developing a therapeutic based on the composition, system, described herein. In particular embodiments, the therapeutic comprises a Cas effector and/or a guide RNA capable of hybridizing to a target sequence of interest. In particular embodiments, the therapeutic is a vector or vector system that can contain a) a first regulatory element operably linked to a nucleotide sequence encoding the Cas effector protein(s); and b) a second regulatory element operably linked to one or more nucleotide sequences encoding one or more nucleic acid molecules comprising a guide RNA comprising a guide sequence, a direct repeat sequence; wherein components (a) and (b) are located on same or different vectors. In particular embodiments, the biologically active agent is a composition comprising a delivery system operably configured to deliver composition, system, or components thereof, and/or or one or more polynucleotide sequences, vectors, or vector systems containing or encoding said components into a cell and capable of forming a complex with the components of the composition and system herein, and wherein said complex is operable in the cell. In some embodiments, the complex can include the Cas effector protein(s) as described herein, guide RNA comprising the guide sequence, and a direct repeat sequence. In any such compositions, the delivery system can be a yeast system, a lipofection system, a microinjection system, a biolistic system, virosomes, liposomes, immunoliposomes, polycations, lipid:nucleic acid conjugates or artificial virions, or any other system as described herein. In particular embodiments, the delivery is via a particle, a nanoparticle, a lipid or a cell penetrating peptide (CPP).

Also described herein are methods for developing or designing a composition, system, optionally a composition, system, based therapy or therapeutic, comprising (a) selecting for a (therapeutic) locus of interest gRNA target sites, wherein said target sites have minimal sequence variation across a population, and from said selected target sites subselecting target sites, wherein a gRNA directed against said target sites recognizes a minimal number of off-target sites across said population, or (b) selecting for a (therapeutic) locus of interest gRNA target sites, wherein said target sites have minimal sequence variation across a population, or selecting for a (therapeutic) locus of interest gRNA target sites, wherein a gRNA directed against said target sites recognizes a minimal number of off-target sites across said population, and optionally estimating the number of (sub)selected target sites needed to treat or otherwise modulate or manipulate a population, and optionally validating one or more of the (sub)selected target sites for an individual subject, optionally designing one or more gRNA recognizing one or more of said (sub)selected target sites.

In some embodiments, the method for developing or designing a gRNA for use in a composition, system, optionally a composition, system, based therapy or therapeutic, can include (a) selecting for a (therapeutic) locus of interest gRNA target sites, wherein said target sites have minimal sequence variation across a population, and from said selected target sites subselecting target sites, wherein a gRNA directed against said target sites recognizes a minimal number of off-target sites across said population, or (b) selecting for a (therapeutic) locus of interest gRNA target sites, wherein said target sites have minimal sequence variation across a population, or selecting for a (therapeutic) locus of interest gRNA target sites, wherein a gRNA directed against said target sites recognizes a minimal number of off-target sites across said population, and optionally estimating the number of (sub)selected target sites needed to treat or otherwise modulate or manipulate a population, optionally validating one or more of the (sub)selected target sites for an individual subject, optionally designing one or more gRNA recognizing one or more of said (sub)selected target sites.

In some embodiments, the method for developing or designing a composition, system, optionally a composition, system, based therapy or therapeutic in a population, can include (a) selecting for a (therapeutic) locus of interest gRNA target sites, wherein said target sites have minimal sequence variation across a population, and from said selected target sites subselecting target sites, wherein a gRNA directed against said target sites recognizes a minimal number of off-target sites across said population, or (b) selecting for a (therapeutic) locus of interest gRNA target sites, wherein said target sites have minimal sequence variation across a population, or selecting for a (therapeutic) locus of interest gRNA target sites, wherein a gRNA directed against said target sites recognizes a minimal number of off-target sites across said population, and optionally estimating the number of (sub)selected target sites needed to treat or otherwise modulate or manipulate a population, optionally validating one or more of the (sub)selected target sites for an individual subject, optionally designing one or more gRNA recognizing one or more of said (sub)selected target sites.

In some embodiments the method for developing or designing a gRNA for use in a composition, system, optionally a composition, system, based therapy or therapeutic in a population, can include (a) selecting for a (therapeutic) locus of interest gRNA target sites, wherein said target sites have minimal sequence variation across a population, and from said selected target sites subselecting target sites, wherein a gRNA directed against said target sites recognizes a minimal number of off-target sites across said population, or (b) selecting for a (therapeutic) locus of interest gRNA target sites, wherein said target sites have minimal sequence variation across a population, or selecting for a (therapeutic) locus of interest gRNA target sites, wherein a gRNA directed against said target sites recognizes a minimal number of off-target sites across said population, and optionally estimating the number of (sub)selected target sites needed to treat or otherwise modulate or manipulate a population, optionally validating one or more of the (sub)selected target sites for an individual subject, optionally designing one or more gRNA recognizing one or more of said (sub)selected target sites.

In some embodiments, the method for developing or designing a composition, system, such as a composition, system, based therapy or therapeutic, optionally in a population; or for developing or designing a gRNA for use in a composition, system, optionally a composition, system, based therapy or therapeutic, optionally in a population, can include selecting a set of target sequences for one or more loci in a target population, wherein the target sequences do not contain variants occurring above a threshold allele frequency in the target population (i.e. platinum target sequences); removing from said selected (platinum) target sequences any target sequences having high frequency off-target candidates (relative to other (platinum) targets in the set) to define a final target sequence set; preparing one or more, such as a set of compositions, systems, based on the final target sequence set, optionally wherein a number of CRISP-Cas systems prepared is based (at least in part) on the size of a target population.

In certain embodiments, off-target candidates/off-targets, PAM restrictiveness, target cleavage efficiency, or effector protein specificity is identified or determined using a sequencing-based double-strand break (DSB) detection assay, such as described herein elsewhere. In certain embodiments, off-target candidates/off-targets are identified or determined using a sequencing-based double-strand break (DSB) detection assay, such as described herein elsewhere. In certain embodiments, off-targets, or off target candidates have at least 1, preferably 1-3, mismatches or (distal) PAM mismatches, such as 1 or more, such as 1, 2, 3, or more (distal) PAM mismatches. In certain embodiments, sequencing-based DSB detection assay comprises labeling a site of a DSB with an adapter comprising a primer binding site, labeling a site of a DSB with a barcode or unique molecular identifier, or combination thereof, as described herein elsewhere.

It will be understood that the guide sequence of the gRNA is 100% complementary to the target site, i.e. does not comprise any mismatch with the target site. It will be further understood that "recognition" of an (off-)target site by a gRNA presupposes composition, system, functionality, i.e. an (off-)target site is only recognized by a gRNA if binding of the gRNA to the (off-)target site leads to composition, system, activity (such as induction of single or double strand DNA cleavage, transcriptional modulation, etc.).

In certain embodiments, the target sites having minimal sequence variation across a population are characterized by absence of sequence variation in at least 99%, preferably at least 99.9%, more preferably at least 99.99% of the population. In certain embodiments, optimizing target location comprises selecting target sequences or loci having an absence of sequence variation in at least 99%, %, preferably at least 99.9%, more preferably at least 99.99% of a population. These targets are referred to herein elsewhere also as "platinum targets". In certain embodiments, said population comprises at least 1000 individuals, such as at least 5000 individuals, such as at least 10000 individuals, such as at least 50000 individuals.

In certain embodiments, the off-target sites are characterized by at least one mismatch between the off-target site and the gRNA. In certain embodiments, the off-target sites are characterized by at most five, preferably at most four, more preferably at most three mismatches between the off-target site and the gRNA. In certain embodiments, the off-target sites are characterized by at least one mismatch between the off-target site and the gRNA and by at most five, preferably at most four, more preferably at most three mismatches between the off-target site and the gRNA.

In certain embodiments, said minimal number of off-target sites across said population is determined for high-frequency haplotypes in said population. In certain embodiments, said minimal number of off-target sites across said population is determined for high-frequency haplotypes of the off-target site locus in said population. In certain embodiments, said minimal number of off-target sites across said population is determined for high-frequency haplotypes of the target site locus in said population. In certain embodiments, the high-frequency haplotypes are characterized by occurrence in at least 0.1% of the population.

In certain embodiments, the number of (sub)selected target sites needed to treat a population is estimated based on based low frequency sequence variation, such as low frequency sequence variation captured in large scale sequencing datasets. In certain embodiments, the number of (sub)selected target sites needed to treat a population of a given size is estimated.

In certain embodiments, the method further comprises obtaining genome sequencing data of a subject to be treated; and treating the subject with a composition, system, selected from the set of compositions, systems, wherein the composition, system, selected is based (at least in part) on the genome sequencing data of the individual. In certain embodiments, the ((sub)selected) target is validated by genome sequencing, preferably whole genome sequencing.

In certain embodiments, target sequences or loci as described herein are (further) selected based on optimization of one or more parameters, such as PAM type (natural or modified), PAM nucleotide content, PAM length, target sequence length, PAM restrictiveness, target cleavage efficiency, and target sequence position within a gene, a locus or other genomic region. Methods of optimization are discussed in greater detail elsewhere herein.

In certain embodiments, target sequences or loci as described herein are (further) selected based on optimization of one or more of target loci location, target length, target specificity, and PAM characteristics. As used herein, PAM characteristics may comprise for instance PAM sequence, PAM length, and/or PAM GC contents. In certain embodiments, optimizing PAM characteristics comprises optimizing nucleotide content of a PAM. In certain embodiments, optimizing nucleotide content of PAM is selecting a PAM with a motif that maximizes abundance in the one or more target loci, minimizes mutation frequency, or both. Minimizing mutation frequency can for instance be achieved by selecting PAM sequences devoid of or having low or minimal CpG.

In certain embodiments, the effector protein for each composition and system, in the set of compositions, systems, is selected based on optimization of one or more parameters selected from the group consisting of; effector protein size, ability of effector protein to access regions of high chromatin accessibility, degree of uniform enzyme activity across genomic targets, epigenetic tolerance, mismatch/budge tolerance, effector protein specificity, effector protein stability or half-life, effector protein immunogenicity or toxicity. Methods of optimization are discussed in greater detail elsewhere herein.

Optimization of the Systems

The methods of the present invention can involve optimization of selected parameters or variables associated with the composition, system, and/or its functionality, as described herein further elsewhere. Optimization of the composition, system, in the methods as described herein may depend on the target(s), such as the therapeutic target or therapeutic targets, the mode or type of composition, system, modulation, such as composition, system, based therapeutic target(s) modulation, modification, or manipulation, as well as the delivery of the composition, system, components. One or more targets may be selected, depending on the genotypic and/or phenotypic outcome. For instance, one or more therapeutic targets may be selected, depending on (genetic) disease etiology or the desired therapeutic outcome. The (therapeutic) target(s) may be a single gene, locus, or other genomic site, or may be multiple genes, loci or other genomic sites. As is known in the art, a single gene, locus, or other genomic site may be targeted more than once, such as by use of multiple gRNAs.

The activity of the composition and/or system, such as CRISPR-Cas system-based therapy or therapeutics may involve target disruption, such as target mutation, such as leading to gene knockout. The activity of the composition and/or system, such as CRISPR-Cas system-based therapy or therapeutics may involve replacement of particular target sites, such as leading to target correction. CRISPR-Cas system-based therapy or therapeutics may involve removal of particular target sites, such as leading to target deletion. The activity of the composition and/or system, such as CRISPR-Cas system-based therapy or therapeutics may involve modulation of target site functionality, such as target site activity or accessibility, leading for instance to (transcriptional and/or epigenetic) gene or genomic region activation or gene or genomic region silencing. The skilled person will understand that modulation of target site functionality may involve CRISPR effector mutation (such as for instance generation of a catalytically inactive CRISPR effector) and/or functionalization (such as for instance fusion of the CRISPR effector with a heterologous functional domain, such as a transcriptional activator or repressor), as described herein elsewhere.

Accordingly, in an aspect, the invention relates to a method as described herein, comprising selection of one or more (therapeutic) target, selecting one or more functionality of the composition and/or system, and optimization of selected parameters or variables associated with the CRISPR-Cas system and/or its functionality. In a related aspect, the invention relates to a method as described herein, comprising (a) selecting one or more (therapeutic) target loci, (b) selecting one or more CRISPR-Cas system functionalities, (c) optionally selecting one or more modes of delivery, and preparing, developing, or designing a CRISPR-Cas system selected based on steps (a)-(c).

In certain embodiments, the functionality of the composition and/or system comprises genomic mutation. In certain embodiments, the functionality of the composition and/or system comprises single genomic mutation. In certain embodiments, the functionality of the composition and/or system functionality comprises multiple genomic mutation. In certain embodiments, the functionality of the composition and/or system comprises gene knockout. In certain embodiments, the functionality of the composition and/or system comprises single gene knockout. In certain embodiments, the functionality of the composition and/or system comprises multiple gene knockout. In certain embodiments, the functionality of the composition and/or system comprises gene correction. In certain embodiments, the functionality of the composition and/or system comprises single gene correction. In certain embodiments, the functionality of the composition and/or system comprises multiple gene correction. In certain embodiments, the functionality of the composition and/or system comprises genomic region correction. In certain embodiments, the functionality of the composition and/or system comprises single genomic region correction. In certain embodiments, the functionality of the composition and/or system comprises multiple genomic region correction. In certain embodiments, the functionality of the composition and/or system comprises gene deletion. In certain embodiments, the functionality of the composition and/or system comprises single gene deletion. In certain embodiments, the functionality of the composition and/or system comprises multiple gene deletion. In certain embodiments, the functionality of the composition and/or system comprises genomic region deletion. In certain embodiments, the functionality of the composition and/or system comprises single genomic region deletion. In certain embodiments, the functionality of the composition and/or system comprises multiple genomic region deletion. In certain embodiments, the functionality of the composition and/or system comprises modulation of gene or genomic region functionality. In certain embodiments, the functionality of the composition and/or system comprises modulation of single gene or genomic region functionality. In certain embodiments, the functionality of the composition and/or system comprises modulation of multiple gene or genomic region functionality. In certain embodiments, the functionality of the composition and/or system comprises gene or genomic region functionality, such as gene or genomic region activity. In certain embodiments, the functionality of the composition and/or system comprises single gene or genomic region functionality, such as gene or genomic region activity. In certain embodiments, the functionality of the composition and/or system comprises multiple gene or genomic region functionality, such as gene or genomic region activity. In certain embodiments, the functionality of the composition and/or system comprises modulation gene activity or accessibility optionally leading to transcriptional and/or epigenetic gene or genomic region activation or gene or genomic region silencing. In certain embodiments, the functionality of the composition and/or system comprises modulation single gene activity or accessibility optionally leading to transcriptional and/or epigenetic gene or genomic region activation or gene or genomic region silencing. In certain embodiments, the functionality of the composition and/or system comprises modulation multiple gene activity or accessibility optionally leading to transcriptional and/or epigenetic gene or genomic region activation or gene or genomic region silencing.

Optimization of selected parameters or variables in the methods as described herein may result in optimized or improved the system, such as CRISPR-Cas system-based therapy or therapeutic, specificity, efficacy, and/or safety. In certain embodiments, one or more of the following parameters or variables are taken into account, are selected, or are optimized in the methods of the invention as described herein: Cas protein allosteric interactions, Cas protein functional domains and functional domain interactions, CRISPR effector specificity, gRNA specificity, CRISPR-Cas complex specificity, PAM restrictiveness, PAM type (natural or modified), PAM nucleotide content, PAM length, CRISPR effector activity, gRNA activity, CRISPR-Cas complex activity, target cleavage efficiency, target site selection, target sequence length, ability of effector protein to access regions of high chromatin accessibility, degree of uniform enzyme activity across genomic targets, epigenetic tolerance, mismatch/budge tolerance, CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector protein size, CRISPR effector expression level, gRNA expression level, CRISPR-Cas complex expression level, CRISPR effector spatiotemporal expression, gRNA spatiotemporal expression, CRISPR-Cas complex spatiotemporal expression.

By means of example, and without limitation, parameter or variable optimization may be achieved as follows. CRISPR effector specificity may be optimized by selecting the most specific CRISPR effector. This may be achieved for instance by selecting the most specific CRISPR effector orthologue or by specific CRISPR effector mutations which increase specificity. gRNA specificity may be optimized by selecting the most specific gRNA. This can be achieved for instance by selecting gRNA having low homology, i.e. at least one or preferably more, such as at least 2, or preferably at least 3, mismatches to off-target sites. CRISPR-Cas complex specificity may be optimized by increasing CRISPR effector specificity and/or gRNA specificity as above. PAM restrictiveness may be optimized by selecting a CRISPR effector having to most restrictive PAM recognition. This can be achieved for instance by selecting a CRISPR effector orthologue having more restrictive PAM recognition or by specific CRISPR effector mutations which increase or alter PAM restrictiveness. PAM type may be optimized for instance by selecting the appropriate CRISPR effector, such as the appropriate CRISPR effector recognizing a desired PAM type. The CRISPR effector or PAM type may be naturally occurring or may for instance be optimized based on CRISPR effector mutants having an altered PAM recognition, or PAM recognition repertoire. PAM nucleotide content may for instance be optimized by selecting the appropriate CRISPR effector, such as the appropriate CRISPR effector recognizing a desired PAM nucleotide content. The CRISPR effector or PAM type may be naturally occurring or may for instance be optimized based on CRISPR effector mutants having an altered PAM recognition, or PAM recognition repertoire. PAM length may for instance be optimized by selecting the appropriate CRISPR effector, such as the appropriate CRISPR effector recognizing a desired PAM nucleotide length. The CRISPR effector or PAM type may be naturally occurring or may for instance be optimized based on CRISPR effector mutants having an altered PAM recognition, or PAM recognition repertoire.

Target length or target sequence length may be optimized, for instance, by selecting the appropriate CRISPR effector, such as the appropriate CRISPR effector recognizing a desired target or target sequence nucleotide length. Alternatively, or in addition, the target (sequence) length may be optimized by providing a target having a length deviating from the target (sequence) length typically associated with the CRISPR effector, such as the naturally occurring CRISPR effector. The CRISPR effector or target (sequence) length may be naturally occurring or may for instance be optimized based on CRISPR effector mutants having an altered target (sequence) length recognition, or target (sequence) length recognition repertoire. For instance, increasing or decreasing target (sequence) length may influence target recognition and/or off-target recognition. CRISPR effector activity may be optimized by selecting the most active CRISPR effector. This may be achieved for instance by selecting the most active CRISPR effector orthologue or by specific CRISPR effector mutations which increase activity. The ability of the CRISPR effector protein to access regions of high chromatin accessibility, may be optimized by selecting the appropriate CRISPR effector or mutant thereof, and can consider the size of the CRISPR effector, charge, or other dimensional variables etc. The degree of uniform CRISPR effector activity may be optimized by selecting the appropriate CRISPR effector or mutant thereof, and can consider CRISPR effector specificity and/or activity, PAM specificity, target length, mismatch tolerance, epigenetic tolerance, CRISPR effector and/or gRNA stability and/or half-life, CRISPR effector and/or gRNA immunogenicity and/or toxicity, etc. gRNA activity may be optimized by selecting the most active gRNA. In some embodiments, this can be achieved by increasing gRNA stability through RNA modification. CRISPR-Cas complex activity may be optimized by increasing CRISPR effector activity and/or gRNA activity as above.

The target site selection may be optimized by selecting the optimal position of the target site within a gene, locus or other genomic region. The target site selection may be optimized by optimizing target location comprises selecting a target sequence with a gene, locus, or other genomic region having low variability. This may be achieved for instance by selecting a target site in an early and/or conserved exon or domain (i.e. having low variability, such as polymorphisms, within a population).

In certain embodiments, optimizing target (sequence) length comprises selecting a target sequence within one or more target loci between 5 and 25 nucleotides. In certain embodiments, a target sequence is 20 nucleotides.

In certain embodiments, optimizing target specificity comprises selecting targets loci that minimize off-target candidates.

In some embodiments, the target site may be selected by minimization of off-target effects (e.g. off-targets qualified as having 1-5, 1-4, or preferably 1-3 mismatches compared to target and/or having one or more PAM mismatches, such as distal PAM mismatches), preferably also considering variability within a population. CRISPR effector stability may be optimized by selecting CRISPR effector having appropriate half-life, such as preferably a short half-life while still capable of maintaining sufficient activity. In some embodiments, this can be achieved by selecting an appropriate CRISPR effector orthologue having a specific half-life or by specific CRISPR effector mutations or modifications which affect half-life or stability, such as inclusion (e.g. fusion) of stabilizing or destabilizing domains or sequences. CRISPR effector mRNA stability may be optimized by increasing or decreasing CRISPR effector mRNA stability. In some embodiments, this can be achieved by increasing or decreasing CRISPR effector mRNA stability through mRNA modification. gRNA stability may be optimized by increasing or decreasing gRNA stability. In some embodiments, this can be achieved by increasing or decreasing gRNA stability through RNA modification. CRISPR-Cas complex stability may be optimized by increasing or decreasing CRISPR effector stability and/or gRNA stability as above. CRISPR effector protein or mRNA immunogenicity or toxicity may be optimized by decreasing CRISPR effector protein or mRNA immunogenicity or toxicity. In some embodiments, this can be achieved by mRNA or protein modifications. Similarly, in case of DNA based expression systems, DNA immunogenicity or toxicity may be decreased. gRNA immunogenicity or toxicity may be optimized by decreasing gRNA immunogenicity or toxicity. In some embodiments, this can be achieved by gRNA modifications. Similarly, in case of DNA based expression systems, DNA immunogenicity or toxicity may be decreased. CRISPR-Cas complex immunogenicity or toxicity may be optimized by decreasing CRISPR effector immunogenicity or toxicity and/or gRNA immunogenicity or toxicity as above, or by selecting the least immunogenic or toxic CRISPR effector/gRNA combination. Similarly, in case of DNA based expression systems, DNA immunogenicity or toxicity may be decreased. CRISPR effector protein or mRNA dose or titer may be optimized by selecting dosage or titer to minimize toxicity and/or maximize specificity and/or efficacy. gRNA dose or titer may be optimized by selecting dosage or titer to minimize toxicity and/or maximize specificity and/or efficacy. CRISPR-Cas complex dose or titer may be optimized by selecting dosage or titer to minimize toxicity and/or maximize specificity and/or efficacy. CRISPR effector protein size may be optimized by selecting minimal protein size to increase efficiency of delivery, in particular for virus mediated delivery. CRISPR effector, gRNA, or CRISPR-Cas complex expression level may be optimized by limiting (or extending) the duration of expression and/or limiting (or increasing) expression level. This may be achieved for instance by using self-inactivating compositions, systems, such as including a self-targeting (e.g. CRISPR effector targeting) gRNA, by using viral vectors having limited expression duration, by using appropriate promoters for low (or high) expression levels, by combining different delivery methods for individual CRISP-Cas system components, such as virus mediated delivery of CRISPR-effector encoding nucleic acid combined with non-virus mediated delivery of gRNA, or virus mediated delivery of gRNA combined with non-virus mediated delivery of CRISPR effector protein or mRNA. CRISPR effector, gRNA, or CRISPR-Cas complex spatiotemporal expression may be optimized by appropriate choice of conditional and/or inducible expression systems, including controllable CRISPR effector activity optionally a destabilized CRISPR effector and/or a split CRISPR effector, and/or cell- or tissue-specific expression systems.

In an aspect, the invention relates to a method as described herein, comprising selection of one or more (therapeutic) target, selecting the functionality of the composition and/or system, selecting CRISPR-Cas system mode of delivery, selecting CRISPR-Cas system delivery vehicle or expression system, and optimization of selected parameters or variables associated with the CRISPR-Cas system and/or its functionality, optionally wherein the parameters or variables are one or more selected from CRISPR effector specificity, gRNA specificity, CRISPR-Cas complex specificity, PAM restrictiveness, PAM type (natural or modified), PAM nucleotide content, PAM length, CRISPR effector activity, gRNA activity, CRISPR-Cas complex activity, target cleavage efficiency, target site selection, target sequence length, ability of effector protein to access regions of high chromatin accessibility, degree of uniform enzyme activity across genomic targets, epigenetic tolerance, mismatch/budge tolerance, CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector protein size, CRISPR effector expression level, gRNA expression level, CRISPR-Cas complex expression level, CRISPR effector spatiotemporal expression, gRNA spatiotemporal expression, CRISPR-Cas complex spatiotemporal expression.

In an aspect, the invention relates to a method as described herein, comprising selecting one or more (therapeutic) target, selecting one or more the functionality of the composition and/or system, selecting one or more CRISPR-Cas system mode of delivery, selecting one or more delivery vehicle or expression system, and optimization of selected parameters or variables associated with the CRISPR-Cas system and/or its functionality, wherein specificity, efficacy, and/or safety are optimized, and optionally wherein optimization of specificity comprises optimizing one or more parameters or variables selected from CRISPR effector specificity, gRNA specificity, CRISPR-Cas complex specificity, PAM restrictiveness, PAM type (natural or modified), PAM nucleotide content, PAM length, wherein optimization of efficacy comprises optimizing one or more parameters or variables selected from CRISPR effector activity, gRNA activity, CRISPR-Cas complex activity, target cleavage efficiency, target site selection, target sequence length, CRISPR effector protein size, ability of effector protein to access regions of high chromatin accessibility, degree of uniform enzyme activity across genomic targets, epigenetic tolerance, mismatch/budge tolerance, and wherein optimization of safety comprises optimizing one or more parameters or variables selected from CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector expression level, gRNA expression level, CRISPR-Cas complex expression level, CRISPR effector spatiotemporal expression, gRNA spatiotemporal expression, CRISPR-Cas complex spatiotemporal expression.

In an aspect, the invention relates to a method as described herein, comprising optionally selecting one or more (therapeutic) target, optionally selecting one or more the functionality of the composition and/or system, optionally selecting one or more mode of delivery, optionally selecting one or more delivery vehicle or expression system, and optimization of selected parameters or variables associated with the system and/or its functionality, wherein specificity, efficacy, and/or safety are optimized, and optionally wherein optimization of specificity comprises optimizing one or more parameters or variables selected from CRISPR effector specificity, gRNA specificity, CRISPR-Cas complex specificity, PAM restrictiveness, PAM type (natural or modified), PAM nucleotide content, PAM length, wherein optimization of efficacy comprises optimizing one or more parameters or variables selected from CRISPR effector activity, gRNA activity, CRISPR-Cas complex activity, target cleavage efficiency, target site selection, target sequence length, CRISPR effector protein size, ability of effector protein to access regions of high chromatin accessibility, degree of uniform enzyme activity across genomic targets, epigenetic tolerance, mismatch/budge tolerance, and wherein optimization of safety comprises optimizing one or more parameters or variables selected from CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector expression level, gRNA expression level, CRISPR-Cas complex expression level, CRISPR effector spatiotemporal expression, gRNA spatiotemporal expression, CRISPR-Cas complex spatiotemporal expression.

In an aspect, the invention relates to a method as described herein, comprising optimization of selected parameters or variables associated with the system and/or its functionality, wherein specificity, efficacy, and/or safety are optimized, and optionally wherein optimization of specificity comprises optimizing one or more parameters or variables selected from CRISPR effector specificity, gRNA specificity, CRISPR-Cas complex specificity, PAM restrictiveness, PAM type (natural or modified), PAM nucleotide content, PAM length, wherein optimization of efficacy comprises optimizing one or more parameters or variables selected from CRISPR effector activity, gRNA activity, CRISPR-Cas complex activity, target cleavage efficiency, target site selection, target sequence length, CRISPR effector protein size, ability of effector protein to access regions of high chromatin accessibility, degree of uniform enzyme activity across genomic targets, epigenetic tolerance, mismatch/budge tolerance, and wherein optimization of safety comprises optimizing one or more parameters or variables selected from CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector expression level, gRNA expression level, CRISPR-Cas complex expression level, CRISPR effector spatiotemporal expression, gRNA spatiotemporal expression, CRISPR-Cas complex spatiotemporal expression.

It will be understood that the parameters or variables to be optimized as well as the nature of optimization may depend on the (therapeutic) target, the functionality of the composition and/or system, the system mode of delivery, and/or the CRISPR-Cas system delivery vehicle or expression system.

In an aspect, the invention relates to a method as described herein, comprising optimization of gRNA specificity at the population level. Preferably, said optimization of gRNA specificity comprises minimizing gRNA target site sequence variation across a population and/or minimizing gRNA off-target incidence across a population.

In some embodiments, optimization can result in selection of a CRISPR-Cas effector that is naturally occurring or is modified. In some embodiments, optimization can result in selection of a CRISPR-Cas effector that has nuclease, nickase, deaminase, transposase, and/or has one or more effector functionalities deactivated or eliminated. In some embodiments, optimizing a PAM specificity can include selecting a CRISPR-Cas effector with a modified PAM specificity. In some embodiments, optimizing can include selecting a CRISPR-Cas effector having a minimal size. In certain embodiments, optimizing effector protein stability comprises selecting an effector protein having a short half-life while maintaining sufficient activity, such as by selecting an appropriate CRISPR effector orthologue having a specific half-life or stability. In certain embodiments, optimizing immunogenicity or toxicity comprises minimizing effector protein immunogenicity or toxicity by protein modifications. In certain embodiments, optimizing functional specific comprises selecting a protein effector with reduced tolerance of mismatches and/or bulges between the guide RNA and one or more target loci.

In certain embodiments, optimizing efficacy comprises optimizing overall efficiency, epigenetic tolerance, or both. In certain embodiments, maximizing overall efficiency comprises selecting an effector protein with uniform enzyme activity across target loci with varying chromatin complexity, selecting an effector protein with enzyme activity limited to areas of open chromatin accessibility. In certain embodiments, chromatin accessibility is measured using one or more of ATAC-seq, or a DNA-proximity ligation assay. In certain embodiments, optimizing epigenetic tolerance comprises optimizing methylation tolerance, epigenetic mark competition, or both. In certain embodiments, optimizing methylation tolerance comprises selecting an effector protein that modify methylated DNA. In certain embodiments, optimizing epigenetic tolerance comprises selecting an effector protein unable to modify silenced regions of a chromosome, selecting an effector protein able to modify silenced regions of a chromosome, or selecting target loci not enriched for epigenetic markers In certain embodiments, selecting an optimized guide RNA comprises optimizing gRNA stability, gRNA immunogenicity, or both, or other gRNA associated parameters or variables as described herein elsewhere.

In certain embodiments, optimizing gRNA stability and/or gRNA immunogenicity comprises RNA modification, or other gRNA associated parameters or variables as described herein elsewhere. In certain embodiments, the modification comprises removing 1-3 nucleotides form the 3' end of a target complementarity region of the gRNA. In certain embodiments, modification comprises an extended gRNA and/or trans RNA/DNA element that create stable structures in the gRNA that compete with gRNA base pairing at a target of off-target loci, or extended complimentary nucleotides between the gRNA and target sequence, or both.

In certain embodiments, the mode of delivery comprises delivering gRNA and/or CRISPR effector protein, delivering gRNA and/or CRISPR effector mRNA, or delivery gRNA and/or CRISPR effector as a DNA based expression system. In certain embodiments, the mode of delivery further comprises selecting a delivery vehicle and/or expression systems from the group consisting of liposomes, lipid particles, nanoparticles, biolistics, or viral-based expression/delivery systems. In certain embodiments, expression is spatiotemporal expression is optimized by choice of conditional and/or inducible expression systems, including controllable CRISPR effector activity optionally a destabilized CRISPR effector and/or a split CRISPR effector, and/or cell- or tissue-specific expression system.

The methods as described herein may further involve selection of the mode of delivery. In certain embodiments, gRNA (and tracr, if and where needed, optionally provided as a sgRNA) and/or CRISPR effector protein are or are to be delivered. In certain embodiments, gRNA (and tracr, if and where needed, optionally provided as a sgRNA) and/or CRISPR effector mRNA are or are to be delivered. In certain embodiments, gRNA (and tracr, if and where needed, optionally provided as a sgRNA) and/or CRISPR effector provided in a DNA-based expression system are or are to be delivered. In certain embodiments, delivery of the individual system components comprises a combination of the above modes of delivery. In certain embodiments, delivery comprises delivering gRNA and/or CRISPR effector protein, delivering gRNA and/or CRISPR effector mRNA, or delivering gRNA and/or CRISPR effector as a DNA based expression system.

The methods as described herein may further involve selection of the CRISPR-Cas system delivery vehicle and/or expression system. Delivery vehicles and expression systems are described herein elsewhere. By means of example, delivery vehicles of nucleic acids and/or proteins include nanoparticles, liposomes, etc. Delivery vehicles for DNA, such as DNA-based expression systems include for instance biolistics, viral based vector systems (e.g. adenoviral, AAV, lentiviral), etc. the skilled person will understand that selection of the mode of delivery, as well as delivery vehicle or expression system may depend on for instance the cell or tissues to be targeted. In certain embodiments, the delivery vehicle and/or expression system for delivering the compositions, systems, or components thereof comprises liposomes, lipid particles, nanoparticles, biolistics, or viral-based expression/delivery systems.

Considerations for Therapeutic Applications

A consideration in genome editing therapy is the choice of sequence-specific nuclease, such as a variant of a Cas nuclease. Each nuclease variant may possess its own unique set of strengths and weaknesses, many of which must be balanced in the context of treatment to maximize therapeutic benefit. For a specific editing therapy to be efficacious, a sufficiently high level of modification must be achieved in target cell populations to reverse disease symptoms. This therapeutic modification 'threshold' is determined by the fitness of edited cells following treatment and the amount of gene product necessary to reverse symptoms. With regard to fitness, editing creates three potential outcomes for treated cells relative to their unedited counterparts: increased, neutral, or decreased fitness. In the case of increased fitness, corrected cells may be able and expand relative to their diseased counterparts to mediate therapy. In this case, where edited cells possess a selective advantage, even low numbers of edited cells can be amplified through expansion, providing a therapeutic benefit to the patient. Where the edited cells possess no change in fitness, an increase the therapeutic modification threshold can be warranted. As such, significantly greater levels of editing may be needed to treat diseases, where editing creates a neutral fitness advantage, relative to diseases where editing creates increased fitness for target cells. If editing imposes a fitness disadvantage, as would be the case for restoring function to a tumor suppressor gene in cancer cells, modified cells would be outcompeted by their diseased counterparts, causing the benefit of treatment to be low relative to editing rates. This may be overcome with supplemental therapies to increase the potency and/or fitness of the edited cells relative to the diseased counterparts.

In addition to cell fitness, the amount of gene product necessary to treat disease can also influence the minimal level of therapeutic genome editing that can treat or prevent a disease or a symptom thereof. In cases where a small change in the gene product levels can result in significant changes in clinical outcome, the minimal level of therapeutic genome editing is less relative to cases where a larger change in the gene product levels are needed to gain a clinically relevant response. In some embodiments, the minimal level of therapeutic genome editing can range from 0.1 to 1%, 1-5%, 5-10%, 10-15%, 15-20%, 20-25%, 25-30%, 30-35%, 35-40%, 40-45%. 45-50%, or 50-55%. Thus, where a small change in gene product levels can influence clinical outcomes and diseases where there is a fitness advantage for edited cells, are ideal targets for genome editing therapy, as the therapeutic modification threshold is low enough to permit a high chance of success.

The activity of NHEJ and HDR DSB repair can vary by cell type and cell state. NHEJ is not highly regulated by the cell cycle and is efficient across cell types, allowing for high levels of gene disruption in accessible target cell populations. In contrast, HDR acts primarily during S/G2 phase, and is therefore restricted to cells that are actively dividing, limiting treatments that require precise genome modifications to mitotic cells [Ciccia, A. & Elledge, S. J. Molecular cell 40, 179-204 (2010); Chapman, J. R., et al. Molecular cell 47, 497-510 (2012)].

The efficiency of correction via HDR may be controlled by the epigenetic state or sequence of the targeted locus, or the specific repair template configuration (single vs. double stranded, long vs. short homology arms) used [Hacein-Bey-Abina, S., et al. The New England journal of medicine 346, 1185-1193 (2002); Gaspar, H. B., et al. Lancet 364, 2181-2187 (2004); Beumer, K. J., et al. G3 (2013)]. The relative activity of NHEJ and HDR machineries in target cells may also affect gene correction efficiency, as these pathways may compete to resolve DSBs [Beumer, K. J., et al. Proceedings of the National Academy of Sciences of the United States of America 105, 19821-19826 (2008)]. HDR also imposes a delivery challenge not seen with NHEJ strategies, as it uses the concurrent delivery of nucleases and repair templates. Thus, these differences can be kept in mind when designing, optimizing, and/or selecting a CRISPR-Cas based therapeutic as described in greater detail elsewhere herein.

CRISPR-Cas-based polynucleotide modification application can include combinations of proteins, small RNA molecules, and/or repair templates, and can make, in some embodiments, delivery of these multiple parts substantially more challenging than, for example, traditional small molecule therapeutics. Two main strategies for delivery of compositions, systems, and components thereof have been developed: ex vivo and in vivo. In some embodiments of ex vivo treatments, diseased cells are removed from a subject, edited and then transplanted back into the patient. In other embodiments, cells from a healthy allogeneic donor are collected, modified using a CRISPR-Cas system or component thereof, to impart various functionalities and/or reduce immunogenicity, and administered to an allogeneic recipient in need of treatment. Ex vivo editing has the advantage of allowing the target cell population to be well defined and the specific dosage of therapeutic molecules delivered to cells to be specified. The latter consideration may be particularly important when off-target modifications are a concern, as titrating the amount of nuclease may decrease such mutations (Hsu et al., 2013). Another advantage of ex vivo approaches is the typically high editing rates that can be achieved, due to the development of efficient delivery systems for proteins and nucleic acids into cells in culture for research and gene therapy applications.

In vivo polynucleotide modification via compositions, systems, and/or components thereof involves direct delivery of the compositions, systems, and/or components thereof to cell types in their native tissues. In vivo polynucleotide modification via compositions, systems, and/or components thereof allows diseases in which the affected cell population is not amenable to ex vivo manipulation to be treated. Furthermore, delivering compositions, systems, and/or components thereof to cells in situ allows for the treatment of multiple tissue and cell types.

In some embodiments, such as those where viral vector systems are used to generate viral particles to deliver the CRISPR-Cas system and/or component thereof to a cell, the total cargo size of the CRISPR-Cas system and/or component thereof should be considered as vector systems can have limits on the size of a polynucleotide that can be expressed therefrom and/or packaged into cargo inside of a viral particle. In some embodiments, the tropism of a vector system, such as a viral vector system, should be considered as it can impact the cell type to which the CRISPR-Cas system or component thereof can be efficiently and/or effectively delivered.

When delivering a system or component thereof via a viral-based system, it can be important to consider the amount of viral particles that will be needed to achieve a therapeutic effect so as to account for the potential immune response that can be elicited by the viral particles when delivered to a subject or cell(s). When delivering a system or component thereof via a viral based system, it can be important to consider mechanisms of controlling the distribution and/or dosage of the system in vivo. Generally, to reduce the potential for off-target effects, it is optimal but not necessarily required, that the amount of the system be as close to the minimum or least effective dose. In practice this can be challenging to do.

In some embodiments, it can be important to considered the immunogenicity of the system or component thereof. In embodiments, where the immunogenicity of the system or component thereof is of concern, the immunogenicity system or component thereof can be reduced. By way of example only, the immunogenicity of the system or component thereof can be reduced using the approach set out in Tangri et al. Accordingly, directed evolution or rational design may be used to reduce the immunogenicity of the CRISPR enzyme in the host species (human or other species).

Xenotransplantation

The present invention also contemplates use of the CRISPR-Cas system described herein, e.g. Cas effector protein systems, to provide RNA-guided DNA nucleases adapted to be used to provide modified tissues for transplantation. For example, RNA-guided DNA nucleases may be used to knockout, knockdown or disrupt selected genes in an animal, such as a transgenic pig (such as the human heme oxygenase-1 transgenic pig line), for example by disrupting expression of genes that encode epitopes recognized by the human immune system, i.e. xenoantigen genes. Candidate porcine genes for disruption may for example include α(1, 3)-galactosyltransferase and cytidine monophosphate-N-acetylneuraminic acid hydroxylase genes (see PCT Patent Publication WO 2014/066505). In addition, genes encoding endogenous retroviruses may be disrupted, for example the genes encoding all porcine endogenous retroviruses (see Yang et al., 2015, Genome-wide inactivation of porcine endogenous retroviruses (PERVs), Science 27 Nov. 2015: Vol. 350 no. 6264 pp. 1101-1104). In addition, RNA-guided DNA nucleases may be used to target a site for integration of additional genes in xenotransplant donor animals, such as a human CD55 gene to improve protection against hyperacute rejection.

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA•DNA hybrids. McIvor E I, Polak U, Napierala M. RNA Biol. 2010 September-October; 7(5):551-8). The present effector protein systems may be harnessed to correct these defects of genomic instability.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

Immune Orthogonal Orthologs

In some embodiments, when the Cas need to be expressed or administered in a subject, immunogenicity of the Cas may be reduced by sequentially expressing or administering immune orthogonal orthologs of the Cas to the subject. As used herein, the term "immune orthogonal orthologs" refer to orthologous proteins that have similar or substantially the same function or activity, but have no or low cross-reactivity with the immune response generated by one another. In some embodiments, sequential expression or administration of such orthologs elicits low or no secondary immune response. The immune orthogonal orthologs can avoid being neutralized by antibodies (e.g., existing antibodies in the host before the orthologs are expressed or administered). Cells expressing the orthologs can avoid being cleared by the host's immune system (e.g., by activated CTLs). In some examples, CRISPR enzyme orthologs from different species may be immune orthogonal orthologs.

Immune orthogonal orthologs may be identified by analyzing the sequences, structures, and/or immunogenicity of a set of candidates orthologs. In an example method, a set of immune orthogonal orthologs may be identified by a) comparing the sequences of a set of candidate orthologs (e.g., orthologs from different species) to identify a subset of candidates that have low or no sequence similarity; b) assessing immune overlap among the members of the subset of candidates to identify candidates that have no or low immune overlap. In some cases, immune overlap among candidates may be assessed by determining the binding (e.g., affinity) between a candidate ortholog and MHC (e.g., MHC type I and/or MHC II) of the host. Alternatively or additionally, immune overlap among candidates may be assessed by determining B-cell epitopes for the candidate orthologs. In one example, immune orthogonal orthologs may be identified using the method described in Moreno A M et al., BioRxiv, published online Jan. 10, 2018, doi: doi.org/10.1101/245985.

Applications in Plants and Fungi

The compositions, systems, and methods described herein can be used to perform gene or genome interrogation or editing or manipulation in plants and fungi. For example, the applications include investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant or fugus genome. There can accordingly be improved production of plants, new plants with new combinations of traits or characteristics or new plants with enhanced traits. The compositions, systems, and methods can be used with regard to plants in Site-Directed Integration (SDI) or Gene Editing (GE) or any Near Reverse Breeding (NRB) or Reverse Breeding (RB) techniques.

The compositions, systems, and methods herein may be used to confer desired traits (e.g., enhanced nutritional quality, increased resistance to diseases and resistance to biotic and abiotic stress, and increased production of commercially valuable plant products or heterologous compounds) on essentially any plants and fungi, and their cells and tissues. The compositions, systems, and methods may be used to modify endogenous genes or to modify their expression without the permanent introduction into the genome of any foreign gene.

In some embodiments, compositions, systems, and methods may be used in genome editing in plants or where RNAi or similar genome editing techniques have been used previously; see, e.g., Nekrasov, "Plant genome editing made easy: targeted mutagenesis in model and crop plants using the CRISPR-Cas system," Plant Methods 2013, 9:39 (doi: 10.1186/1746-4811-9-39); Brooks, "Efficient gene editing in tomato in the first generation using the CRISPR-Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 November; 6(6): 1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061-*Agrobacterium*-Mediated Plant Transformation Method; U.S. Pat. No. 7,868,149-Plant Genome Sequences and Uses Thereof and US 2009/0100536-Transgenic Plants with Enhanced Agronomic Traits, Morrell et al "Crop genomics: advances and applications," Nat Rev Genet. 2011 Dec. 29; 13(2):85-96, all the contents and disclosure of each of which are herein incorporated by reference in their entirety. Aspects of utilizing the compositions, systems, and methods may be analogous to the use of the CRISPR-Cas system in plants, and mention is made of the University of Arizona website "CRISPR-PLANT" (www.genome.arizona.edu/crispr/) (supported by Penn State and AGI).

The compositions, systems, and methods may also be used on protoplasts. A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The compositions, systems, and methods may be used for screening genes (e.g., endogenous, mutations) of interest. In some examples, genes of interest include those encoding enzymes involved in the production of a component of added nutritional value or generally genes affecting agronomic traits of interest, across species, phyla, and plant kingdom. By selectively targeting e.g. genes encoding enzymes of metabolic pathways, the genes responsible for certain nutritional aspects of a plant can be identified. Similarly, by selectively targeting genes which may affect a desirable agronomic trait, the relevant genes can be identified. Accordingly, the present invention encompasses screening methods for genes encoding enzymes involved in the production of compounds with a particular nutritional value and/or agronomic traits.

It is also understood that reference herein to animal cells may also apply, mutatis mutandis, to plant or fungal cells unless otherwise apparent; and, the enzymes herein having reduced off-target effects and systems employing such enzymes can be used in plant applications, including those mentioned herein.

In some cases, nucleic acids introduced to plants and fungi may be codon optimized for expression in the plants and fungi. Methods of codon optimization include those described in Kwon K C, et al., Codon Optimization to Enhance Expression Yields Insights into Chloroplast Translation, Plant Physiol. 2016 September; 172(1):62-77.

The components (e.g., Cas proteins) in the compositions and systems may further comprise one or more functional domains described herein. In some examples, the functional domains may be an exonuclease. Such exonuclease may increase the efficiency of the Cas proteins' function, e.g., mutagenesis efficiency. An example of the functional domain is Trex2, as described in Weiss T et al., www.biorxiv.org/content/10.1101/2020.04.11.037572v1, doi: doi.org/10.1101/2020.04.11.037572.

Examples of Plants

The compositions, systems, and methods herein can be used to confer desired traits on essentially any plant. A wide variety of plants and plant cell systems may be engineered for the desired physiological and agronomic characteristics. In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants.

The compositions, systems, and methods may be used over a broad range of plants, such as for example with dicotyledonous plants belonging to the orders Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Raffiesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g., those belonging to the orders Pinales, Ginkgoales, Cycadales, Araucariales, Cupressales and Gnetales.

The compositions, systems, and methods herein can be used over a broad range of plant species, included in the non-limitative list of dicot, monocot or gymnosperm genera hereunder: *Atropa, Alseodaphne, Anacardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malta, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis*, and *Vigna*; and the genera *Allium, Andropogon, Aragrostis, Asparagus, Avena, Cynodon, Elaeis, Festuca, Festulolium, Heterocallis, Hordeum, Lemna, Lolium, Musa, Oryza, Panicum, Pannesetum, Phleum, Poa, Secale, Sorghum, Triticum, Zea, Abies, Cunninghamia, Ephedra, Picea, Pinus*, and *Pseudotsuga*.

In some embodiments, target plants and plant cells for engineering include those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini.

The term plant also encompasses Algae, which are mainly photoautotrophs unified primarily by their lack of roots, leaves and other organs that characterize higher plants. The compositions, systems, and methods can be used over a broad range of "algae" or "algae cells." Examples of algae include eukaryotic phyla, including the *Rhodophyta* (red algae), *Chlorophyta* (green algae), *Phaeophyta* (brown algae), *Bacillariophyta* (diatoms), *Eustigmatophyta* and dinoflagellates as well as the prokaryotic phylum *Cyanobacteria* (blue-green algae). Examples of algae species include those of Amphora, *Anabaena, Anikstrodesmis, Botryococcus, Chaetoceros, Chlamydomonas, Chlorella, Chlorococcum, Cyclotella, Cylindrotheca, Dunaliella, Emiliana, Euglena, Hematococcus, Isochrysis, Monochrysis, Monoraphidium, Nannochloris, Nannnochloropsis, Navicula, Nephrochloris, Nephroselmis, Nitzschia, Nodularia, Nostoc, Oochromonas, Oocystis, Oscillartoria, Pavlova, Phaeodactylum, Playtmonas, Pleurochrysis, Porhyra, Pseudoanabaena, Pyramimonas, Stichococcus, Synechococcus, Synechocystis, Tetraselmis, Thalassiosira,* and *Trichodesmium.*

Plant Promoters

In order to ensure appropriate expression in a plant cell, the components of the components and systems herein may be placed under control of a plant promoter. A plant promoter is a promoter operable in plant cells. A plant promoter is capable of initiating transcription in plant cells, whether or not its origin is a plant cell. The use of different types of promoters is envisaged.

In some examples, the plant promoter is a constitutive plant promoter, which is a promoter that is able to express the open reading frame (ORF) that it controls in all or nearly all of the plant tissues during all or nearly all developmental stages of the plant (referred to as "constitutive expression"). One example of a constitutive promoter is the cauliflower mosaic virus 35S promoter. In some examples, the plant promoter is a regulated promoter, which directs gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In some examples, the plant promoter is a tissue-preferred promoters, which can be utilized to target enhanced expression in certain cell types within a particular plant tissue, for instance vascular cells in leaves or roots or in specific cells of the seed.

Exemplary plant promoters include those obtained from plants, plant viruses, and bacteria such as *Agrobacterium* or *Rhizobium* which comprise genes expressed in plant cells. Additional examples of promoters include those described in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

In some examples, a plant promoter may be an inducible promoter, which is inducible and allows for spatiotemporal control of gene editing or gene expression may use a form of energy. The form of energy may include sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc.), or light inducible systems (Phytochrome, LOV domains, or cryptochrome), such as a Light Inducible Transcriptional Effector (LITE) that direct changes in transcriptional activity in a sequence-specific manner. In a particular example, of the components of a light inducible system include a Cas protein, a light-responsive cytochrome heterodimer (e.g. from *Arabidopsis thaliana*), and a transcriptional activation/repression domain.

In some examples, the promoter may be a chemical-regulated promotor (where the application of an exogenous chemical induces gene expression) or a chemical-repressible promoter (where application of the chemical represses gene expression). Examples of chemical-inducible promoters include maize 1n2-2 promoter (activated by benzene sulfonamide herbicide safeners), the maize GST promoter (activated by hydrophobic electrophilic compounds used as pre-emergent herbicides), the tobacco PR-1 a promoter (activated by salicylic acid), promoters regulated by antibiotics (such as tetracycline-inducible and tetracycline-repressible promoters).

Stable Integration in the Genome of Plants

In some embodiments, polynucleotides encoding the components of the compositions and systems may be introduced for stable integration into the genome of a plant cell. In some cases, vectors or expression systems may be used for such integration. The design of the vector or the expression system can be adjusted depending on for when, where and under what conditions the guide RNA and/or the Cas gene are expressed. In some cases, the polynucleotides may be integrated into an organelle of a plant, such as a plastid, mitochondrion or a chloroplast. The elements of the expression system may be on one or more expression constructs which are either circular such as a plasmid or transformation vector, or non-circular such as linear double stranded DNA.

In some embodiments, the method of integration generally comprises the steps of selecting a suitable host cell or host tissue, introducing the construct(s) into the host cell or host tissue, and regenerating plant cells or plants therefrom. In some examples, the expression system for stable integration into the genome of a plant cell may contain one or more of the following elements: a promoter element that can be used to express the RNA and/or Cas enzyme in a plant cell; a 5' untranslated region to enhance expression; an intron element to further enhance expression in certain cells, such as monocot cells; a multiple-cloning site to provide convenient restriction sites for inserting the guide RNA and/or the Cas gene sequences and other desired elements; and a 3' untranslated region to provide for efficient termination of the expressed transcript.

Transient Expression in Plants

In some embodiments, the components of the compositions and systems may be transiently expressed in the plant cell. In some examples, the compositions and systems may modify a target nucleic acid only when both the guide RNA and the Cas protein are present in a cell, such that genomic modification can further be controlled. As the expression of the Cas protein is transient, plants regenerated from such plant cells typically contain no foreign DNA. In certain examples, the Cas protein is stably expressed and the guide sequence is transiently expressed.

DNA and/or RNA (e.g., mRNA) may be introduced to plant cells for transient expression. In such cases, the introduced nucleic acid may be provided in sufficient quantity to modify the cell but do not persist after a contemplated period of time has passed or after one or more cell divisions.

The transient expression may be achieved using suitable vectors. Exemplary vectors that may be used for transient expression include a pEAQ vector (may be tailored for

*Agrobacterium*-mediated transient expression) and Cabbage Leaf Curl virus (CaLCuV), and vectors described in Sainsbury F. et al., Plant Biotechnol J. 2009 September; 7(7): 682-93; and Yin K et al., Scientific Reports volume 5, Article number: 14926 (2015).

Combinations of the different methods described above are also envisaged.

Translocation to and/or Expression in Specific Plant Organelles

The compositions and systems herein may comprise elements for translocation to and/or expression in a specific plant organelle.

Chloroplast Targeting

In some embodiments, it is envisaged that the compositions and systems are used to specifically modify chloroplast genes or to ensure expression in the chloroplast. The compositions and systems (e.g., Cas proteins, guide molecules, or their encoding polynucleotides) may be transformed, compartmentalized, and/or targeted to the chloroplast. In an example, the introduction of genetic modifications in the plastid genome can reduce biosafety issues such as gene flow through pollen.

Examples of methods of chloroplast transformation include Particle bombardment, PEG treatment, and microinjection, and the translocation of transformation cassettes from the nuclear genome to the plastid. In some examples, targeting of chloroplasts may be achieved by incorporating in chloroplast localization sequence, and/or the expression construct a sequence encoding a chloroplast transit peptide (CTP) or plastid transit peptide, operably linked to the 5' region of the sequence encoding the components of the compositions and systems. Additional examples of transforming, targeting and localization of chloroplasts include those described in WO2010061186, Protein Transport into Chloroplasts, 2010, Annual Review of Plant Biology, Vol. 61: 157-180, and US 20040142476, which are incorporated by reference herein in their entireties.

Exemplary Applications in Plants

The compositions, systems, and methods may be used to generate genetic variation(s) in a plant (e.g., crop) of interest. One or more, e.g., a library of, guide molecules targeting one or more locations in a genome may be provided and introduced into plant cells together with the Cas effector protein. For example, a collection of genome-scale point mutations and gene knock-outs can be generated. In some examples, the compositions, systems, and methods may be used to generate a plant part or plant from the cells so obtained and screening the cells for a trait of interest. The target genes may include both coding and non-coding regions. In some cases, the trait is stress tolerance and the method is a method for the generation of stress-tolerant crop varieties.

In some embodiments, the compositions, systems, and methods are used to modify endogenous genes or to modify their expression. The expression of the components may induce targeted modification of the genome, either by direct activity of the Cas nuclease and optionally introduction of recombination template DNA, or by modification of genes targeted. The different strategies described herein above allow Cas-mediated targeted genome editing without requiring the introduction of the components into the plant genome.

In some cases, the modification may be performed without the permanent introduction into the genome of the plant of any foreign gene, including those encoding CRISPR components, so as to avoid the presence of foreign DNA in the genome of the plant. This can be of interest as the regulatory requirements for non-transgenic plants are less rigorous. Components which are transiently introduced into the plant cell are typically removed upon crossing.

For example, the modification may be performed by transient expression of the components of the compositions and systems. The transient expression may be performed by delivering the components of the compositions and systems with viral vectors, delivery into protoplasts, with the aid of particulate molecules such as nanoparticles or CPPs.

Generation of Plants with Desired Traits

The compositions, systems, and methods herein may be used to introduce desired traits to plants. The approaches include introduction of one or more foreign genes to confer a trait of interest, editing or modulating endogenous genes to confer a trait of interest.

Agronomic Traits

In some embodiments, crop plants can be improved by influencing specific plant traits. Examples of the traits include improved agronomic traits such as herbicide resistance, disease resistance, abiotic stress tolerance, high yield, and superior quality, pesticide-resistance, disease resistance, insect and nematode resistance, resistance against parasitic weeds, drought tolerance, nutritional value, stress tolerance, self-pollination voidance, forage digestibility biomass, and grain yield.

In some embodiments, genes that confer resistance to pests or diseases may be introduced to plants. In cases there are endogenous genes that confer such resistance in a plants, their expression and function may be enhanced (e.g., by introducing extra copies, modifications that enhance expression and/or activity).

Examples of genes that confer resistance include plant disease resistance genes (e.g., Cf-9, Pto, RSP2, S1DMR6-1), genes conferring resistance to a pest (e.g., those described in WO96/30517), *Bacillus thuringiensis* proteins, lectins, Vitamin-binding proteins (e.g., avidin), enzyme inhibitors (e.g., protease or proteinase inhibitors or amylase inhibitors), insect-specific hormones or pheromones (e.g., ecdysteroid or a juvenile hormone, variant thereof, a mimetic based thereon, or an antagonist or agonist thereof) or genes involved in the production and regulation of such hormone and pheromones, insect-specific peptides or neuropeptide, Insect-specific venom (e.g., produced by a snake, a wasp, etc., or analog thereof), Enzymes responsible for a hyper-accumulation of a monoterpene, a sesquiterpene, a steroid, hydroxamic acid, a phenylpropanoid derivative or another nonprotein molecule with insecticidal activity, Enzymes involved in the modification of biologically active molecule (e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic), molecules that stimulates signal transduction, Viral-invasive proteins or a complex toxin derived therefrom, Developmental-arrestive proteins produced in nature by a pathogen or a parasite, a developmental-arrestive protein produced in nature by a plant, or any combination thereof.

The compositions, systems, and methods may be used to identify, screen, introduce or remove mutations or sequences lead to genetic variability that give rise to susceptibility to certain pathogens, e.g., host specific pathogens. Such approach may generate plants that are non-host resistance, e.g., the host and pathogen are incompatible or there can be partial resistance against all races of a pathogen, typically controlled by many genes and/or also complete resistance to some races of a pathogen but not to other races.

In some embodiments, the compositions, systems, and methods may be used to modify genes involved in plant diseases. Such genes may be removed, inactivated, or otherwise regulated or modified. Examples of plant diseases include those described in [0045]-[0080] of US20140213619A1, which is incorporated by reference herein in its entirety.

In some embodiments, genes that confer resistance to herbicides may be introduced to plants. Examples of genes that confer resistance to herbicides include genes conferring resistance to herbicides that inhibit the growing point or meristem, such as an imidazolinone or a sulfonylurea, genes conferring glyphosate tolerance (e.g., resistance conferred by, e.g., mutant 5-enolpyruvylshikimate-3-phosphate synthase genes, aroA genes and glyphosate acetyl transferase (GAT) genes, respectively), or resistance to other phosphono compounds such as by glufosinate (phosphinothricin acetyl transferase (PAT) genes from Streptomyces species, including Streptomyces hygroscopicus and Streptomyces viridichromogenes), and to pyridinoxy or phenoxy proprionic acids and cyclohexones by ACCase inhibitor-encoding genes), genes conferring resistance to herbicides that inhibit photosynthesis (such as a triazine (psbA and gs+ genes) or a benzonitrile (nitrilase gene), and glutathione S-transferase), genes encoding enzymes detoxifying the herbicide or a mutant glutamine synthase enzyme that is resistant to inhibition, genes encoding a detoxifying enzyme is an enzyme encoding a phosphinothricin acetyltransferase (such as the bar or pat protein from Streptomyces species), genes encoding hydroxyphenylpyruvatedioxygenases (HPPD) inhibitors, e.g., naturally occurring HPPD resistant enzymes, and genes encoding a mutated or chimeric HPPD enzyme.

In some embodiments, genes involved in Abiotic stress tolerance may be introduced to plants. Examples of genes include those capable of reducing the expression and/or the activity of poly(ADP-ribose) polymerase (PARP) gene, transgenes capable of reducing the expression and/or the activity of the PARG encoding genes, genes coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase, enzymes involved in carbohydrate biosynthesis, enzymes involved in the production of polyfructose (e.g., the inulin and levan-type), the production of alpha-1,6 branched alpha-1,4-glucans, the production of alternan, the production of hyaluronan.

In some embodiments, genes that improve drought resistance may be introduced to plants. Examples of genes Ubiquitin Protein Ligase protein (UPL) protein (UPL3), DR02, DR03, ABC transporter, and DREB1A.

Nutritionally Improved Plants

In some embodiments, the compositions, systems, and methods may be used to produce nutritionally improved plants. In some examples, such plants may provide functional foods, e.g., a modified food or food ingredient that may provide a health benefit beyond the traditional nutrients it contains. In certain examples, such plants may provide nutraceuticals foods, e.g., substances that may be considered a food or part of a food and provides health benefits, including the prevention and treatment of disease. The nutraceutical foods may be useful in the prevention and/or treatment of diseases in animals and humans, e.g., cancers, diabetes, cardiovascular disease, and hypertension.

An improved plant may naturally produce one or more desired compounds and the modification may enhance the level or activity or quality of the compounds. In some cases, the improved plant may not naturally produce the compound(s), while the modification enables the plant to produce such compound(s). In some cases, the compositions, systems, and methods used to modify the endogenous synthesis of these compounds indirectly, e.g. by modifying one or more transcription factors that controls the metabolism of this compound.

Examples of nutritionally improved plants include plants comprising modified protein quality, content and/or amino acid composition, essential amino acid contents, oils and fatty acids, carbohydrates, vitamins and carotenoids, functional secondary metabolites, and minerals. In some examples, the improved plants may comprise or produce compounds with health benefits. Examples of nutritionally improved plants include those described in Newell-Mc-Gloughlin, Plant Physiology, July 2008, Vol. 147, pp. 939-953.

Examples of compounds that can be produced include carotenoids (e.g., α-Carotene or β-Carotene), lutein, lycopene, Zeaxanthin, Dietary fiber (e.g., insoluble fibers, β-Glucan, soluble fibers, fatty acids (e.g., ω-3 fatty acids, Conjugated linoleic acid, GLA,), Flavonoids (e.g., Hydroxycinnamates, flavonols, catechins and tannins), Glucosinolates, indoles, isothiocyanates (e.g., Sulforaphane), Phenolics (e.g., stilbenes, caffeic acid and ferulic acid, epicatechin), Plant stanols/sterols, Fructans, inulins, fructo-oligosaccharides, Saponins, Soybean proteins, Phytoestrogens (e.g., isoflavones, lignans), Sulfides and thiols such as diallyl sulphide, Allyl methyl trisulfide, dithiolthiones, Tannins, such as proanthocyanidins, or any combination thereof.

The compositions, systems, and methods may also be used to modify protein/starch functionality, shelf life, taste/aesthetics, fiber quality, and allergen, antinutrient, and toxin reduction traits.

Examples of genes and nucleic acids that can be modified to introduce the traits include stearyl-ACP desaturase, DNA associated with the single allele which may be responsible for maize mutants characterized by low levels of phytic acid, Tf RAP2.2 and its interacting partner SINAT2, Tf Dof1, and DOF Tf AtDof1.1 (OBP2).

Modification of Polyploid Plants

The compositions, systems, and methods may be used to modify polyploid plants. Polyploid plants carry duplicate copies of their genomes (e.g. as many as six, such as in wheat). In some cases, the compositions, systems, and methods may be can be multiplexed to affect all copies of a gene, or to target dozens of genes at once. For instance, the compositions, systems, and methods may be used to simultaneously ensure a loss of function mutation in different genes responsible for suppressing defenses against a disease. The modification may be simultaneous suppression the expression of the TaMLO-A1, TaMLO-B1 and TaMLO-D1 nucleic acid sequence in a wheat plant cell and regenerating a wheat plant therefrom, in order to ensure that the wheat plant is resistant to powdery mildew (e.g., as described in WO2015109752).

Regulation of Fruit-Ripening

The compositions, systems, and methods may be used to regulate ripening of fruits. Ripening is a normal phase in the maturation process of fruits and vegetables. Only a few days after it starts it may render a fruit or vegetable inedible, which can bring significant losses to both farmers and consumers.

In some embodiments, the compositions, systems, and methods are used to reduce ethylene production. In some examples, the compositions, systems, and methods may be used to suppress the expression and/or activity of ACC synthase, insert a ACC deaminase gene or a functional fragment thereof, insert a SAM hydrolase gene or functional fragment thereof, suppress ACC oxidase gene expression Alternatively or additionally, the compositions, systems, and methods may be used to modify ethylene receptors (e.g., suppressing ETR1) and/or Polygalacturonase (PG). Suppression of a gene may be achieved by introducing a mutation, an antisense sequence, and/or a truncated copy of the gene to the genome.

Increasing Storage Life of Plants

In some embodiments, the compositions, systems, and methods are used to modify genes involved in the production of compounds which affect storage life of the plant or plant part. The modification may be in a gene that prevents the accumulation of reducing sugars in potato tubers. Upon high-temperature processing, these reducing sugars react with free amino acids, resulting in brown, bitter-tasting products and elevated levels of acrylamide, which is a potential carcinogen. In particular embodiments, the methods provided herein are used to reduce or inhibit expression of the vacuolar invertase gene (VInv), which encodes a protein that breaks down sucrose to glucose and fructose.

Reducing Allergens in Plants

In some embodiments, the compositions, systems, and methods are used to generate plants with a reduced level of allergens, making them safer for consumers. To this end, the compositions, systems, and methods may be used to identify and modify (e.g., suppress) one or more genes responsible for the production of plant allergens. Examples of such genes include Lol p5, as well as those in peanuts, soybeans, lentils, peas, lupin, green beans, mung beans, such as those described in Nicolaou et al., Current Opinion in Allergy and Clinical Immunology 2011; 11(3):222), which is incorporated by reference herein in its entirety.

Generation of Male Sterile Plants

The compositions, systems, and methods may be used to generate male sterile plants. Hybrid plants typically have advantageous agronomic traits compared to inbred plants. However, for self-pollinating plants, the generation of hybrids can be challenging. In different plant types (e.g., maize and rice), genes have been identified which are important for plant fertility, more particularly male fertility. Plants that are as such genetically altered can be used in hybrid breeding programs.

The compositions, systems, and methods may be used to modify genes involved male fertility, e.g., inactivating (such as by introducing mutations to) genes required for male fertility. Examples of the genes involved in male fertility include cytochrome P450-like gene (MS26) or the meganuclease gene (MS45), and those described in Wan X et al., Mol Plant. 2019 Mar. 4; 12(3):321-342; and Kim Y J, et al., Trends Plant Sci. 2018 January; 23(1):53-65.

Increasing the Fertility Stage in Plants

In some embodiments, the compositions, systems, and methods may be used to prolong the fertility stage of a plant such as of a rice. For instance, a rice fertility stage gene such as Ehd3 can be targeted in order to generate a mutation in the gene and plantlets can be selected for a prolonged regeneration plant fertility stage.

Production of Early Yield of Products

In some embodiments, the compositions, systems, and methods may be used to produce early yield of the product. For example, flowering process may be modulated, e.g., by mutating flowering repressor gene such as SPSG. Examples of such approaches include those described in Soyk S, et al., Nat Genet. 2017 January; 49(1):162-168.

Oil and Biofuel Production

The compositions, systems, and methods may be used to generate plants for oil and biofuel production. Biofuels include fuels made from plant and plant-derived resources. Biofuels may be extracted from organic matter whose energy has been obtained through a process of carbon fixation or are made through the use or conversion of biomass. This biomass can be used directly for biofuels or can be converted to convenient energy containing substances by thermal conversion, chemical conversion, and biochemical conversion. This biomass conversion can result in fuel in solid, liquid, or gas form. Biofuels include bioethanol and biodiesel. Bioethanol can be produced by the sugar fermentation process of cellulose (starch), which may be derived from maize and sugar cane. Biodiesel can be produced from oil crops such as rapeseed, palm, and soybean. Biofuels can be used for transportation.

Generation of Plants for Production of Vegetable Oils and Biofuels

The compositions, systems, and methods may be used to generate algae (e.g., diatom) and other plants (e.g., grapes) that express or overexpress high levels of oil or biofuels.

In some cases, the compositions, systems, and methods may be used to modify genes involved in the modification of the quantity of lipids and/or the quality of the lipids. Examples of such genes include those involved in the pathways of fatty acid synthesis, e.g., acetyl-CoA carboxylase, fatty acid synthase, 3-ketoacyl_acyl-carrier protein synthase III, glycerol-3-phospate deshydrogenase (G3PDH), Enoyl-acyl carrier protein reductase (Enoyl-ACP-reductase), glycerol-3-phosphate acyltransferase, lysophosphatidic acyl transferase or diacylglycerol acyltransferase, phospholipid: diacylglycerol acyltransferase, phoshatidate phosphatase, fatty acid thioesterase such as palmitoyi protein thioesterase, or malic enzyme activities.

In further embodiments, it is envisaged to generate diatoms that have increased lipid accumulation. This can be achieved by targeting genes that decrease lipid catabolization. Examples of genes include those involved in the activation of triacylglycerol and free fatty acids, β-oxidation of fatty acids, such as genes of acyl-CoA synthetase, 3-ketoacyl-CoA thiolase, acyl-CoA oxidase activity and phosphoglucomutase.

In some examples, algae may be modified for production of oil and biofuels, including fatty acids (e.g., fatty esters such as acid methyl esters (FAME) and fatty acid ethyl esters (FAEE)). Examples of methods of modifying microalgae include those described in Stovicek et al. Metab. Eng. Comm., 2015; 2:1; U.S. Pat. No. 8,945,839; and International Patent Publication No. WO 2015/086795.

In some examples, one or more genes may be introduced (e.g., overexpressed) to the plants (e.g., algae) to produce oils and biofuels (e.g., fatty acids) from a carbon source (e.g., alcohol). Examples of the genes include genes encoding acyl-CoA synthases, ester synthases, thioesterases (e.g., tesA, 'tesA, tesB, fatB, fatB2, fatB3, fatA1, or fatA), acyl-CoA synthases (e.g., fadD, JadK, BH3103, pfl-4354, EAV15023, fadD1, fadD2, RPC_4074, fadDD35, fadDD22, faa39), ester synthases (e.g., synthase/acyl-CoA:diacylglycerl acyltransferase from *Simmondsia chinensis, Acinetobacter* sp. ADP, *Alcanivorax borkumensis, Pseudomonas aeruginosa, Fundibacter jadensis, Arabidopsis thaliana*, or *Alkaligenes eutrophus*, or variants thereof).

Additionally or alternatively, one or more genes in the plants (e.g., algae) may be inactivated (e.g., expression of the genes is decreased). For examples, one or more mutations may be introduced to the genes. Examples of such genes include genes encoding acyl-CoA dehydrogenases (e.g., fade), outer membrane protein receptors, and transcriptional regulator (e.g., repressor) of fatty acid biosynthesis (e.g., fabR), pyruvate formate lyases (e.g., pflB), lactate dehydrogenases (e.g., IdhA).

Organic Acid Production

In some embodiments, plants may be modified to produce organic acids such as lactic acid. The plants may produce organic acids using sugars, pentose or hexose sugars. To this end, one or more genes may be introduced (e.g., and overexpressed) in the plants. An example of such genes include LDH gene.

In some examples, one or more genes may be inactivated (e.g., expression of the genes is decreased). For examples, one or more mutations may be introduced to the genes. The genes may include those encoding proteins involved an endogenous metabolic pathway which produces a metabolite other than the organic acid of interest and/or wherein the endogenous metabolic pathway consumes the organic acid.

Examples of genes that can be modified or introduced include those encoding pyruvate decarboxylases (pdc), fumarate reductases, alcohol dehydrogenases (adh), acetaldehyde dehydrogenases, phosphoenolpyruvate carboxylases (ppc), D-lactate dehydrogenases (d-ldh), L-lactate dehydrogenases (l-ldh), lactate 2-monooxygenases, lactate dehydrogenase, cytochrome-dependent lactate dehydrogenases (e.g., cytochrome B2-dependent L-lactate dehydrogenases).

Enhancing Plant Properties for Biofuel Production

In some embodiments, the compositions, systems, and methods are used to alter the properties of the cell wall of plants to facilitate access by key hydrolyzing agents for a more efficient release of sugars for fermentation. By reducing the proportion of lignin in a plant the proportion of cellulose can be increased. In particular embodiments, lignin biosynthesis may be downregulated in the plant so as to increase fermentable carbohydrates.

In some examples, one or more lignin biosynthesis genes may be down regulated. Examples of such genes include 4-coumarate 3-hydroxylases (C3H), phenylalanine ammonia-lyases (PAL), cinnamate 4-hydroxylases (C4H), hydroxycinnamoyl transferases (HCT), caffeic acid O-methyltransferases (COMT), caffeoyl CoA 3-O-methyltransferases (CCoAOMT), ferulate 5-hydroxylases (F5H), cinnamyl alcohol dehydrogenases (CAD), cinnamoyl CoA-reductases (CCR), 4-coumarate-CoA ligases (4CL), monolignol-lignin-specific glycosyltransferases, and aldehyde dehydrogenases (ALDH), and those described in WO 2008064289.

In some examples, plant mass that produces lower level of acetic acid during fermentation may be reduced. To this end, genes involved in polysaccharide acetylation (e.g., Cas1L and those described in WO 2010096488) may be inactivated.

Other Microorganisms for Oils and Biofuel Production

In some embodiments, microorganisms other than plants may be used for production of oils and biofuels using the compositions, systems, and methods herein. Examples of the microorganisms include those of the genus of *Escherichia, Bacillus, Lactobacillus, Rhodococcus*, Synechococcus, Synechoystis, *Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, or *Streptomyces*.

Plant Cultures and Regeneration

In some embodiments, the modified plants or plant cells may be cultured to regenerate a whole plant which possesses the transformed or modified genotype and thus the desired phenotype. Examples of regeneration techniques include those relying on manipulation of certain phytohormones in a tissue culture growth medium, relying on a biocide and/or herbicide marker which has been introduced together with the desired nucleotide sequences, obtaining from cultured protoplasts, plant callus, explants, organs, pollens, embryos or parts thereof.

Detecting Modifications in the Plant Genome—Selectable Markers

When the compositions, systems, and methods are used to modify a plant, suitable methods may be used to confirm and detect the modification made in the plant. In some examples, when a variety of modifications are made, one or more desired modifications or traits resulting from the modifications may be selected and detected. The detection and confirmation may be performed by biochemical and molecular biology techniques such as Southern analysis, PCR, Northern blot, S1 RNase protection, primer-extension or reverse transcriptase-PCR, enzymatic assays, ribozyme activity, gel electrophoresis, Western blot, immunoprecipitation, enzyme-linked immunoassays, in situ hybridization, enzyme staining, and immunostaining.

In some cases, one or more markers, such as selectable and detectable markers, may be introduced to the plants. Such markers may be used for selecting, monitoring, isolating cells and plants with desired modifications and traits. A selectable marker can confer positive or negative selection and is conditional or non-conditional on the presence of external substrates. Examples of such markers include genes and proteins that confer resistance to antibiotics, such as hygromycin (hpt) and kanamycin (nptII), and genes that confer resistance to herbicides, such as phosphinothricin (bar) and chlorosulfuron (als), enzyme capable of producing or processing a colored substances (e.g., the β-glucuronidase, luciferase, B or C1 genes).

Applications in Fungi

The compositions, systems, and methods described herein can be used to perform efficient and cost effective gene or genome interrogation or editing or manipulation in fungi or fungal cells, such as yeast. The approaches and applications in plants may be applied to fungi as well.

A fungal cell may be any type of eukaryotic cell within the kingdom of fungi, such as phyla of Ascomycota, Basidiomycota, Blastocladiomycota, Chytridiomycota, Glomeromycota, Microsporidia, and Neocallimastigomycota. Examples of fungi or fungal cells in include yeasts, molds, and filamentous fungi.

In some embodiments, the fungal cell is a yeast cell. A yeast cell refers to any fungal cell within the phyla Ascomycota and Basidiomycota. Examples of yeasts include budding yeast, fission yeast, and mold, *S. cerervisiae, Kluyveromyces marxianus, Issatchenkia orientalis, Candida* spp. (e.g., *Candida albicans*), *Yarrowia* spp. (e.g., *Yarrowia lipolytica*),*Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis, Pichia kudriavzevii* and *Candida acidothermophilum*).

In some embodiments, the fungal cell is a filamentous fungal cell, which grow in filaments, e.g., hyphae or mycelia. Examples of filamentous fungal cells include *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is of an industrial strain. Industrial strains include any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes include fermentation (e.g., in production of food or beverage products), distillation, biofuel production, production of a compound, and production of a polypeptide. Examples of industrial strains include, without limitation, JAY270 and ATCC4124.

In some embodiments, the fungal cell is a polyploid cell whose genome is present in more than one copy. Polyploid cells include cells naturally found in a polyploid state, and cells that has been induced to exist in a polyploid state (e.g., through specific regulation, alteration, inactivation, activation, or modification of meiosis, cytokinesis, or DNA replication). A polyploid cell may be a cell whose entire genome is polyploid, or a cell that is polyploid in a particular genomic locus of interest. In some examples, the abundance of guide RNA may more often be a rate-limiting component in genome engineering of polyploid cells than in haploid cells, and thus the methods using the CRISPR system described herein may take advantage of using certain fungal cell types.

In some embodiments, the fungal cell is a diploid cell, whose genome is present in two copies. Diploid cells include cells naturally found in a diploid state, and cells that have been induced to exist in a diploid state (e.g., through specific regulation, alteration, inactivation, activation, or modification of meiosis, cytokinesis, or DNA replication). A diploid cell may refer to a cell whose entire genome is diploid, or it may refer to a cell that is diploid in a particular genomic locus of interest.

In some embodiments, the fungal cell is a haploid cell, whose genome is present in one copy. Haploid cells include cells naturally found in a haploid state, or cells that have been induced to exist in a haploid state (e.g., through specific regulation, alteration, inactivation, activation, or modification of meiosis, cytokinesis, or DNA replication). A haploid cell may refer to a cell whose entire genome is haploid, or it may refer to a cell that is haploid in a particular genomic locus of interest.

The compositions and systems, and nucleic acid encoding thereof may be introduced to fungi cells using the delivery systems and methods herein. Examples of delivery systems include lithium acetate treatment, bombardment, electroporation, and those described in Kawai et al., 2010, Bioeng Bugs. 2010 November-December; 1(6): 395-403.

In some examples, a yeast expression vector (e.g., those with one or more regulatory elements) may be used. Examples of such vectors include a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2μ plasmids, yeast integrative plasmids, yeast replicative plasmids, shuttle vectors, and episomal plasmids.

Biofuel and Materials Production by Fungi

In some embodiments, the compositions, systems, and methods may be used for generating modified fungi for biofuel and material productions. For instance, the modified fungi for production of biofuel or biopolymers from fermentable sugars and optionally to be able to degrade plant-derived lignocellulose derived from agricultural waste as a source of fermentable sugars. Foreign genes required for biofuel production and synthesis may be introduced in to fungi In some examples, the genes may encode enzymes involved in the conversion of pyruvate to ethanol or another product of interest, degrade cellulose (e.g., cellulase), endogenous metabolic pathways which compete with the biofuel production pathway.

In some examples, the compositions, systems, and methods may be used for generating and/or selecting yeast strains with improved xylose or cellobiose utilization, isoprenoid biosynthesis, and/or lactic acid production. One or more genes involved in the metabolism and synthesis of these compounds may be modified and/or introduced to yeast cells. Examples of the methods and genes include lactate dehydrogenase, PDC1 and PDC5, and those described in Ha, S. J., et al. (2011) Proc. Natl. Acad. Sci. USA 108(2): 504-9 and Galazka, J. M., et al. (2010) Science 330(6000): 84-6; Jakočiūnas T et al., Metab Eng. 2015 March; 28:213-222; Stovicek V, et al., FEMS Yeast Res. 2017 Aug. 1; 17(5).

Improved Plants and Yeast Cells

The present disclosure further provides improved plants and fungi. The improved and fungi may comprise one or more genes introduced, and/or one or more genes modified by the compositions, systems, and methods herein. The improved plants and fungi may have increased food or feed production (e.g., higher protein, carbohydrate, nutrient or vitamin levels), oil and biofuel production (e.g., methanol, ethanol), tolerance to pests, herbicides, drought, low or high temperatures, excessive water, etc.

The plants or fungi may have one or more parts that are improved, e.g., leaves, stems, roots, tubers, seeds, endosperm, ovule, and pollen. The parts may be viable, nonviable, regeneratable, and/or non-regeneratable.

The improved plants and fungi may include gametes, seeds, embryos, either zygotic or somatic, progeny and/or hybrids of improved plants and fungi. The progeny may be a clone of the produced plant or fungi, or may result from sexual reproduction by crossing with other individuals of the same species to introgress further desirable traits into their offspring. The cell may be in vivo or ex vivo in the cases of multicellular organisms, particularly plants.

Further Applications of the CRISPR-Cas System in Plants

Further applications of the compositions, systems, and methods on plants and fungi include visualization of genetic element dynamics (e.g., as described in Chen B, et al., Cell. 2013 Dec. 19; 155(7):1479-91), targeted gene disruption positive-selection in vitro and in vivo (as described in Malina A et al., Genes Dev. 2013 Dec. 1; 27(23):2602-14), epigenetic modification such as using fusion of Cas and histone-modifying enzymes (e.g., as described in Rusk N, Nat Methods. 2014 January; 11(1):28), identifying transcription regulators (e.g., as described in Waldrip Z J, Epigenetics. 2014 September; 9(9):1207-11), anti-virus treatment for both RNA and DNA viruses (e.g., as described in Price A A, et al., Proc Natl Acad Sci USA. 2015 May 12; 112(19):6164-9; Ramanan V et al., Sci Rep. 2015 Jun. 2; 5:10833), alteration of genome complexity such as chromosome numbers (e.g., as described in Karimi-Ashtiyani R et al., Proc Natl Acad Sci USA. 2015 Sep. 8; 112(36):11211-6; Anton T, et al., Nucleus. 2014 March-April; 5(2):163-72), self-cleavage of the CRISPR system for controlled inactivation/activation (e.g., as described Sugano S S et al., Plant Cell Physiol. 2014 March; 55(3):475-81), multiplexed gene editing (as described in Kabadi A M et al., Nucleic Acids Res. 2014 Oct. 29; 42(19):e147), development of kits for multiplex genome editing (as described in Xing H L et al., BMC Plant Biol. 2014 Nov. 29; 14:327), starch production (as described in Hebelstrup K H et al., Front Plant Sci. 2015 Apr. 23; 6:247), targeting multiple genes in a family or pathway (e.g., as described in Ma X et al., Mol Plant. 2015 August; 8(8):1274-84), regulation of non-coding genes and sequences (e.g., as described in Lowder L G, et al., Plant Physiol. 2015 October; 169(2):971-85), editing genes in trees (e.g., as described in Belhaj K et al., Plant Methods. 2013 Oct. 11; 9(1):39; Harrison M M, et al., Genes Dev. 2014 Sep. 1; 28(17):1859-72; Zhou X et al., New Phytol. 2015 October; 208(2):298-301), introduction of mutations for resistance to host-specific pathogens and pests.

Additional examples of modifications of plants and fungi that may be performed using the compositions, systems, and methods include those described in International Patent Publication Nos. WO2016/099887, WO2016/025131, WO2016/073433, WO2017/066175, WO2017/100158, WO 2017/105991, WO2017/106414, WO2016/100272, WO2016/100571, WO 2016/100568, WO 2016/100562, and WO 2017/019867.

Applications in Non-Human Animals

The compositions, systems, and methods may be used to study and modify non-human animals, e.g., introducing desirable traits and disease resilience, treating diseases, facilitating breeding, etc. In some embodiments, the compositions, systems, and methods may be used to improve breeding and introducing desired traits, e.g., increasing the frequency of trait-associated alleles, introgression of alleles from other breeds/species without linkage drag, and creation of de novo favorable alleles. Genes and other genetic elements that can be targeted may be screened and identified. Examples of application and approaches include those described in Tait-Burkard C, et al., Livestock 2.0-genome editing for fitter, healthier, and more productive farmed animals. Genome Biol. 2018 Nov. 26; 19(1):204; Lillico S, Agricultural applications of genome editing in farmed animals. Transgenic Res. 2019 August; 28(Suppl 2):57-60; Houston R D, et al., Harnessing genomics to fast-track genetic improvement in aquaculture. Nat Rev Genet. 2020 Apr. 16. doi: 10.1038/s41576-020-0227-y, which are incorporated herein by reference in their entireties. Applications described in other sections such as therapeutic, diagnostic, etc. can also be used on the animals herein.

The compositions, systems, and methods may be used on animals such as fish, amphibians, reptiles, mammals, and birds. The animals may be farm and agriculture animals, or pets. Examples of farm and agriculture animals include horses, goats, sheep, swine, cattle, llamas, alpacas, and birds, e.g., chickens, turkeys, ducks, and geese. The animals may be a non-human primate, e.g., baboons, capuchin monkeys, chimpanzees, lemurs, macaques, marmosets, tamarins, spider monkeys, squirrel monkeys, and vervet monkeys. Examples of pets include dogs, cats horses, wolfs, rabbits, ferrets, gerbils, hamsters, chinchillas, fancy rats, guinea pigs, *canaries*, parakeets, and parrots.

In some embodiments, one or more genes may be introduced (e.g., overexpressed) in the animals to obtain or enhance one or more desired traits. Growth hormones, insulin-like growth factors (IGF-1) may be introduced to increase the growth of the animals, e.g., pigs or salmon (such as described in Pursel V G et al., J Reprod Fertil Suppl. 1990; 40:235-45; Waltz E, Nature. 2017; 548:148). Fat-1 gene (e.g., from *C elegans*) may be introduced for production of larger ratio of n-3 to n-6 fatty acids may be induced, e.g. in pigs (such as described in Li M, et al., Genetics. 2018; 8:1747-54). Phytase (e.g., from *E coli*) xylanase (e.g., from *Aspergillus niger*), beta-glucanase (e.g., from *Bacillus lichenformis*) may be introduced to reduce the environmental impact through phosphorous and nitrogen release reduction, e.g. in pigs (such as described in Golovan S P, et al., Nat Biotechnol. 2001; 19:741-5; Zhang X et al., elife. 2018). shRNA decoy may be introduced to induce avian influenza resilience e.g. in chicken (such as described in Lyall et al., Science. 2011; 331:223-6). Lysozyme or lysostaphin may be introduced to induce mastitis resilience e.g., in goat and cow (such as described in Maga E A et al., Foodborne Pathog Dis. 2006; 3:384-92; Wall R J, et al., Nat Biotechnol. 2005; 23:445-51). Histone deacetylase such as HDAC6 may be introduced to induce PRRSV resilience, e.g., in pig (such as described in Lu T., et al., PLoS One. 2017; 12:e0169317). CD163 may be modified (e.g., inactivated or removed) to introduce PRRSV resilience in pigs (such as described in Prather R S et al., Sci Rep. 2017 Oct. 17; 7(1):13371). Similar approaches may be used to inhibit or remove viruses and bacteria (e.g., Swine Influenza Virus (SIV) strains which include influenza C and the subtypes of influenza A known as H1N1, H1N2, H2N1, H3N1, H3N2, and H2N3, as well as pneumonia, meningitis and oedema) that may be transmitted from animals to humans.

In some embodiments, one or more genes may be modified or edited for disease resistance and production traits. Myostatin (e.g., GDF8) may be modified to increase muscle growth, e.g., in cow, sheep, goat, catfish, and pig (such as described in Crispo M et al., PLoS One. 2015; 10:e0136690; Wang X, et al., Anim Genet. 2018; 49:43-51; Khalil K, et al., Sci Rep. 2017; 7:7301; Kang J-D, et al., RSC Adv. 2017; 7:12541-9). Pc POLLED may be modified to induce hornlessness, e.g., in cow (such as described in Carlson D F et al., Nat Biotechnol. 2016; 34:479-81). KISS1R may be modified to induce boretaint (hormone release during sexual maturity leading to undesired meat taste), e.g., in pigs. Dead end protein (dnd) may be modified to induce sterility, e.g., in salmon (such as described in Wargelius A, et al., Sci Rep. 2016; 6:21284). Nano2 and DDX may be modified to induce sterility (e.g., in surrogate hosts), e.g., in pigs and chicken (such as described Park K-E, et al., Sci Rep. 2017; 7:40176; Taylor L et al., Development. 2017; 144:928-34). CD163 may be modified to induce PRRSV resistance, e.g., in pigs (such as described in Whitworth K M, et al., Nat Biotechnol. 2015; 34:20-2) RELA may be modified to induce ASFV resilience, e.g., in pigs (such as described in Lillico S G, et al., Sci Rep. 2016; 6:21645). CD18 may be modified to induce Mannheimia (*Pasteurella*) *haemolytica* resilience, e.g., in cows (such as described in Shanthalingam S, et al., roc Natl Acad Sci USA. 2016; 113:13186-90). NRAMP1 may be modified to induce tuberculosis resilience, e.g., in cows (such as described in Gao Y et al., Genome Biol. 2017; 18:13). Endogenous retrovirus genes may be modified or removed for xenotransplantation such as described in Yang L, et al. Science. 2015; 350:1101-4; Niu D et al., Science. 2017; 357:1303-7). Negative regulators of muscle mass (e.g., Myostatin) may be modified (e.g., inactivated) to increase muscle mass, e.g., in dogs (as described in Zou Q et al., J Mol Cell Biol. 2015 December; 7(6):580-3).

Animals such as pigs with severe combined immunodeficiency (SCID) may generated (e.g., by modifying RAG2) to provide useful models for regenerative medicine, xenotransplantation (discussed also elsewhere herein), and tumor development. Examples of methods and approaches include those described Lee K, et al., Proc Natl Acad Sci USA. 2014 May 20; 111(20):7260-5; and Schomberg et al. FASEB Journal, April 2016; 30(1):Suppl 571.1.

SNPs in the animals may be modified. Examples of methods and approaches include those described Tan W. et al., Proc Natl Acad Sci USA. 2013 Oct. 8; 110(41):16526-31; Mali P, et al., Science. 2013 Feb. 15; 339(6121):823-6.

Stem cells (e.g., induced pluripotent stem cells) may be modified and differentiated into desired progeny cells, e.g., as described in Heo Y T et al., Stem Cells Dev. 2015 Feb. 1; 24(3):393-402.

Profile analysis (such as Igenity) may be performed on animals to screen and identify genetic variations related to economic traits. The genetic variations may be modified to introduce or improve the traits, such as carcass composition, carcass quality, maternal and reproductive traits and average daily gain.

The present application also provides aspects and embodiments as set forth in the following numbered Statements:

Statement 1. A non-naturally occurring or engineered composition comprising a Cas12b protein from *Alicyclobacillus acidiphilis*; and a guide molecule derived from another CRISPR-Cas system and capable of forming a complex with the Cas12b protein and directing the complex to bind to a target polynucleotide.

Statement 2. The composition of Statement 1, wherein the guide molecule is derived from *Alicyclobacillus acidoterrestris*.

Statement 3. The composition of Statement 1 or 2, wherein the guide sequence comprises SEQ ID NOs: 61957-61961.

Statement 4. The composition of any one of the preceding Statements, wherein the Cas12b protein is fused to one or more localization signals.

Statement 5. The composition of Statement 4, wherein the Cas12b protein is catalytically inactive.

Statement 6. The composition of Statement 5, wherein the functional domain is a nickase, a nucleotide deaminase or a reverse transcriptase.

Statement 7. The composition of Statement 6, wherein the functional domain is a reverse transcriptase and the guide molecule is a prime editor guide molecule.

Statement 8. The composition of any one of the preceding Statements, further comprising a detection construct comprising a non-target polynucleotide, wherein the Cas protein exhibits collateral activity and cleaves the non-target polynucleotide component once activated by the target polynucleotide.

Statement 9. The composition of Statement 8, further comprising one or more isothermal amplification reagents.

Statement 10. The composition of Statement 9, wherein the isothermal amplification reagents are LAMP reagents.

Statement 11. The composition of Statement 10, wherein the guide molecule is designed to bind to a polynucleotide sequence of SARS-CoV-2.

Statement 12. The composition of Statement 11, wherein the LAMP reagents comprise primers selected from SEQ ID NOs: 61983-61988 and guide molecules is SEQ ID NO: 61989.

Statement 13. A vector system comprising one or more polynucleotide sequences encoding the Cas12b protein and the guide molecule in the composition of any one of Statements 1-12, optionally wherein the polynucleotide sequences are codon optimized for expression in a eukaryotic cell.

Statement 14. A cell comprising the composition of any one of Statements 1-12 or the vector system of Statement 13, or progeny thereof.

Statement 15. A method of targeting one or more target polynucleotides, the method comprising contacting the one or more target polynucleotides with a non-naturally occurring or engineered composition of any one of Statements 1-12, wherein targeting comprises modifying the one or more target polynucleotides comprises increasing or decreasing expression of the one or more genes in the one or more target polynucleotides, insertion of a recombination template or a portion thereof to the tar one or more target polynucleotides.

Statement 16. The method of Statement 15, wherein the Cas12b is a catalytically inactive Cas12b fused to a functional domain.

Statement 17. The method of Statement 16, wherein the functional domain is a nickase, a reverse transcriptase, or a nucleotide deaminase.

Statement 18. The method of Statement 17, wherein the functional domain is a reverse transcriptase and the guide molecule is a primer editor guide molecule.

Statement 19. A method for detecting a target polynucleotide in a sample, comprising contacting the sample with the composition of any one of Statements 8-12, wherein the Cas protein exhibits collateral activity and cleaves the detection construct once activated by the target polynucleotide, and the cleaved detection construct generate a signal; and detecting the signal thereby determining presence of the target polynucleotide in the sample.

Statement 20. A kit for modifying or detecting a target polynucleotide in a sample, comprising the composition of any one of Statements 1-12 or the vector system of Statement 13.

EXAMPLES

Example 1—Coronavirus Assay Development

Systems and methods can be designed for the detection and diagnosis of viruses and viral infections, including Covid-2019, optionally with acute respiratory infections using the disclosure detailed herein. The systems can comprise two or more CRISPR Cas systems to multiplex, for example, detection of Covid-2019, and other coronaviruses such as SARS-CoV and MERS-CoV. Sequences of the 2019-nCoV are available at GISAID accession no. EPI_ISL_402124 and EPI_ISL_402127-402130, and described in DOI: 10.1101/2020.01.22.914952. Further deposits of the Wuhan coronavirus deposited in the GISAID platform include EP_ISL_402119-402121 and EP_ISL 402123-402124; see also GenBank Accession No. MN908947, and guide design can be predicated on genome sequences disclosed therein and in Tian et al, "Potent binding of 2019 novel coronavirus spike protein by a SARS coronavirus-specific human monoclonal antibody"; doi: 10.1101/2020.01.28.923011, incorporated by reference, which details human monoclonal antibody, CR3022 binding of the 2019-nCoV RBD (KD of 6.3 nM). Guide design can target unique viral genomic regions of the 2019-nCoV or conserved genomic regions across one or more viruses of the coronavirus family. Gene targets may comprise ORF1ab, N protein, RNA-dependent RNA polymerase (RdRP), E protein, ORF1b-nsp14, Spike glycoprotein (S), or pancorona targets, including guide molecules based on the 8a protein, which was present in SARS-CoV but absent in 2019-nCoV, utilized to differentiate between the viruses. Similarly, the 8b and 3b proteins have different lengths in SARS-CoV and 2019-nCoV and can be utilized to design guide molecules to detect non-overlapping portions of nucleotides encoding in the two viruses. Wu et al., Genome Composition and Divergence of the Novel Coronavirus (2019-nCoV) Originating in China, Cell Host & Microbe (2020), DOI: 10.1016/ j.chom.2020.02.001, incorporated herein by reference, including all supplemental information, in particular Table S1. Molecular assays have been under development and can be used as a starting point to develop guide molecules for the methods and systems described herein.

Detection of respiratory viruses such as coronavirus may include a thermostable CRISPR-Cas protein as described herein, which may be a Cas12b ortholog. As described elsewhere herein, one or more Cas12b orthologs may be utilized in a multiplex design, including the thermostable Cas12b orthologs described herein, where such thermostability confers further rapidity to the diagnostic and detections platforms and methods disclosed herein.

Coronavirus detection can comprise two or more detection systems utilizing RNA targeting Cas effector proteins; DNA targeting Cas effector proteins, or a combination thereof. The RNA-targeting effector proteins may be a Cas13 protein, such as Cas13a, Cas13b, or Cas13c, including one of the thermostable Cas13a proteins described herein. The DNA-targeting effector protein may be a Type V protein, e.g. Cas12 protein such as Cpf1 and Cas12b. Multiplexing systems can be designed such that different Cas proteins with different sequence specificities or other motif cutting preferences can be used, including, in certain embodiments, at least one Cas13a thermostable protein described herein. See International Publication WO 2019/126577. Type VI and Type V Cas proteins are known to possess different cutting motif preferences. See Gootenberg et al. "Multiplexed and portable nucleic acid detection platform with Cas13b, Cas12a, and Csm6." Science. Apr. 27, 2018, 360:439-444; International Publication WO 2019/051318. Thus, embodiments disclosed herein may further comprise multiplex embodiments comprising two or more Type VI Cas proteins with different cutting preferences, or one or more Type VI Cas proteins and one or more Type V case proteins.

In certain example embodiments, the coronavirus assay comprises a Type VI Cas protein disclosed herein and guide molecule comprising a guide sequence configured to direct binding of the CRISPR-Cas complex to a target molecule and a labeled detection molecule ("RNA-based masking construct"). A multiplex embodiment can be designed to track one or more variants of coronavirus or one or more variants of coronavirus, including the 2019-nCoV, in combination with other viruses, for example, Human respiratory syncytial virus, Middle East respiratory syndrome (MERS) coronavirus, Severe acute respiratory syndrome-related (SARS) coronavirus, and influenza.

In certain embodiments, the detection assay can be provided on a lateral flow device, as described herein. The lateral flow device may comprise a flexible substrate, such as a paper substrate or a flexible polymer-based substrate, which can include freeze-dried reagents for detection assays with a visual readout of the assay results. See, WO 2019/071051 at [0145]-[0151] and Example 2, specifically incorporated herein by reference. Accordingly, the assay can be adapted for field diagnostics, including use of visual readout on a lateral flow device, rapid, sensitive detection and can be deployed for early and direct detection.

Example 2—Lateral Flow Coronavirus Detection

Detection of coronavirus targets was performed using RPA amplification for 25 minutes followed by a 30 minute Cas 13 reaction using the following primers and guides:

TABLE 5

| | |
|---|---|
| S gene RPA Forward | GAAATTAATACGACTCACTATAGGGAGGTTTCAAACTT TACTTGCTTTACATAGA (SEQ ID NO: 61977) |
| S gene RPA Reverse | TCCTAGGTTGAAGATAACCCACATAATAAG (SEQ ID NO: 61978) |
| S gene LwCas13a crRNA | GAUUUAGACUACCCCAAAAACGAAGGGGACUAAAACGC AGCACCAGCUGUCCAACCUGAAGAAG (SEQ ID NO: 61979) |
| Orf1ab RPA Forward | GAAATTAATACGACTCACTATAGGGCGAAGTTGTAGGA GACATTATACTTAAACC (SEQ ID NO: 61980) |
| Orf1ab RPA Reverse | TAGTAAGACTAGAATTGTCTACATAAGCAGC (SEQ ID NO: 61981) |
| Orf1ab LwCas13a crRNA | GAUUUAGACUACCCCAAAAACGAAGGGGACUAAAACCC AACCUCUUCUGUAAUUUUUAAACUAU (SEQ ID NO: 61982) |

Figure 1:
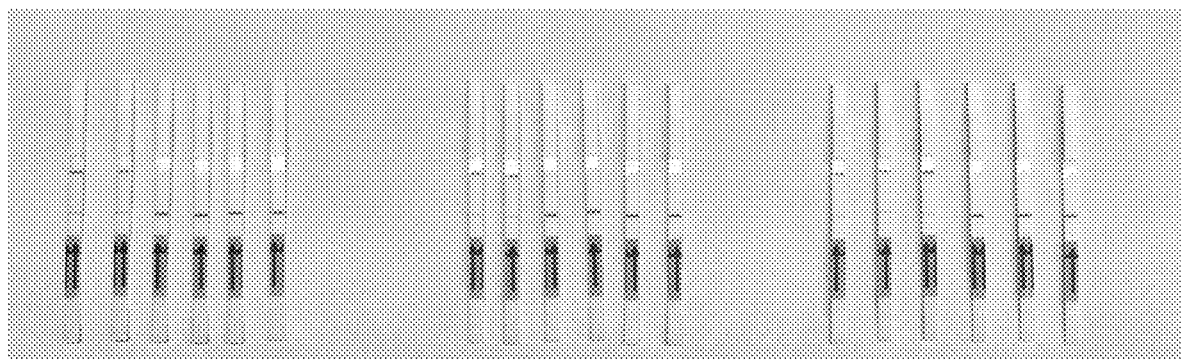
FIG. 1—includes lateral flow assay detection for three n2019-CoV targets, left, middle and right groups. Testing for each target shown with decreasing concentrations from left to right, with far right at 0 concentration S protein (left), middle, synthetic S (synthego) and right (Orflab).
Figures 2A, 2B:
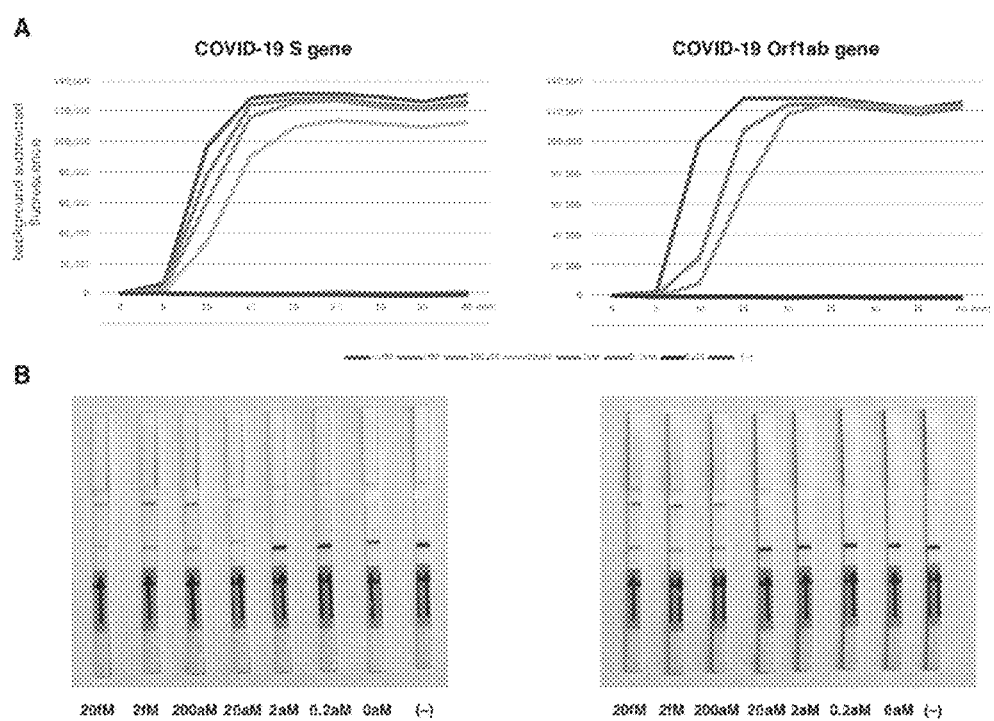
FIGS. 2A-2B FIG. 2A—Detection of synthetic COVID-19 sequences using a two-step SHERLOCK reaction (25 min RPA). Readout using fluorescence RNaseAlert reporter.
Figures 3A, 3B:
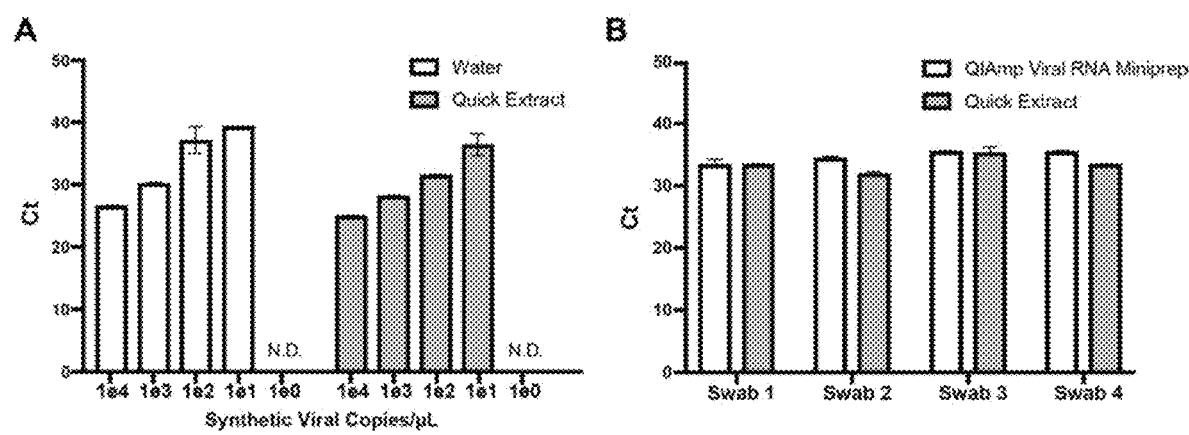
FIGS. 3A-3B.

Results are provided in FIG. 1, with S gene detection shown on the left and Orf1ab on the right, and FIG. 2B. The assay has been further validated by fluorescence in FIG. 2A.

Example 3. RNA Preparation for COVID-19 Detection

One of the major bottlenecks for COVID-19 diagnosis is the limited availability of RNA extraction kits for preparing virus RNA from patient samples and the low-throughput nature of the extraction procedure. Here, Applicants describe a one-step extraction-free RNA preparation method that can be carried out in 5 minutes and the reaction can be used directly with the CDC COVID-19 RT-qPCR testing protocol, thus increasing throughput, and alleviating supply chain issues.

Materials and Reagents

Quick Extract™ DNA Extraction Solution (QE09050), Lucigen

Protocol

Step 1. Dilute nasopharyngeal swab stored in Viral Transport Medium or Human Specimen Control (HSC) 1:1 with Quick Extract™ DNA Extraction Solution. For example, in a fresh PCR tube, mix 20 ul of swab sample with 20 ul of Quick Extract.

Step 2. Incubate swab-Quick Extract mix at 95° C. for 5 minutes. Allow reaction to cool on ice before proceeding.

Step 3. Use reaction from step (2) for qRT-PCR. Make sure the amount from step (2) does not exceed 10% of the total qRT-PCR reaction volume. For example, if a RT-qPCR reaction has a total volume of 50 ul, do not use more than 5 ul of the reaction mix from step (2).

Assay Development and Preliminary Validation

Applicants evaluated a number of buffer compositions to identify one that achieved efficient lysis of enveloped virus while preserving the activity of the CDC recommended RT-qPCR reaction (TaqPath™ 1-Step RT-qPCR Master Mix). Of all of the buffers tested, Quick Extract™ DNA Extraction Solution provided satisfactory results.

To confirm that the presence of QE does not interfere with RT-qPCR activity, comparison of RT-qPCR reactions using synthetic SARS-CoV-2 gene fragment (Twist Synthetic SARS-CoV-2 RNA Control 1, SKU:102019) dissolved in either ddH$_2$O or in a 50:50 ddH$_2$O:Quick Extract mixture was performed. Each RT-qPCR reaction was set up with a total volume of 10 ul (1 ul of RNA sample, 0.5 ul of CDC probe N1, 2.5 ul of TaqPath RT-qPCR master mix, and 6 ul of ddH$_2$O). From these reactions, Applicants found that Quick Extract at a final concentration of 5% did not negatively affect the RT-qPCR reaction (FIG. 1A).

Preliminary validation of the Quick Extract RNA preparation procedure was conducted on coronavirus positive nasopharyngeal swabs where it was found that RNA samples prepared using Quick Extract supported similarly sensitive detection of coronavirus as QIAmp Viral RNA Miniprep for all 4 swab samples (FIG. 1B). To simulate low viral load, coronavirus positive swabs were diluted 1:10 in pooled nasopharyngeal swabs from 5 unique, healthy donors (Lee Biosolutions, SKU:991-31-NC-5) prior to purification or Quick Extract treatment. For the QIAmp Viral RNA Miniprep conditions, 100 ul of diluted swab sample was used for extraction and was eluted using 100 ul of ddH$_2$O. 1 ul of the elution was used in a 10 ul RT-qPCR reaction. For the Quick Extract conditions, 1 ul of Quick Extract preparation was used for each 10 ul RT-qPCR reaction.

Example 4. Development of a One Pot RT-LAMP Cas12b SHERLOCK Reaction

Applicants developed a research protocol for a SHERLOCK-based COVID-19 coronavirus detection. The basic protocol is outlined in FIG. 16. A nasopharyngeal swab or saliva sample is collected from a patient. The sample is added to a tube containing SHERLOCK reagents. The tube is heated for 60 minutes at 60° C. A SHERLOCK detection lateral flow strip is then dipped into the reaction in the tube and the strip is then analyzed for results. Table 2 shows final reaction parameters for reagents in the tube.

Figure 16:
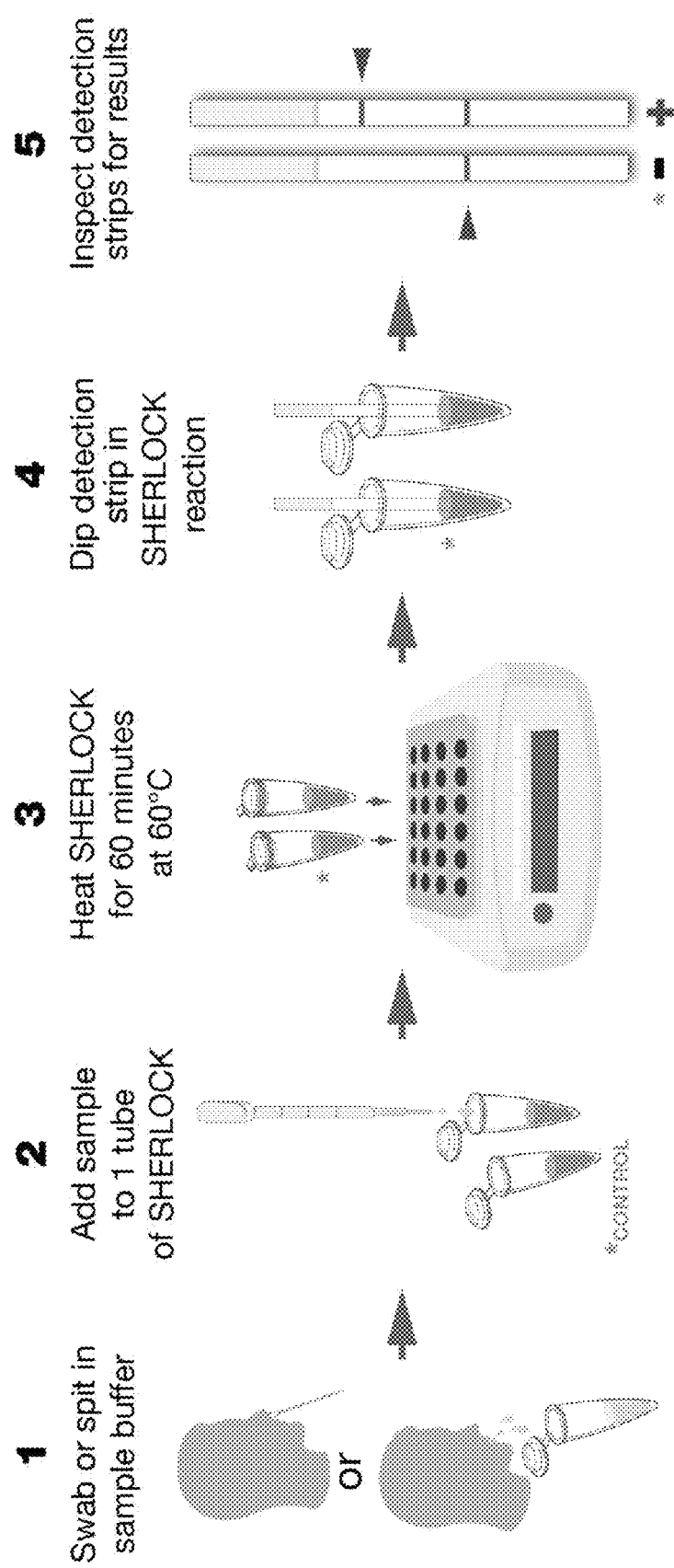
FIG. 16—A schematic for the SHERLOCK diagnostic assay.

The lateral flow strip is inserted directly into this reaction as shown in FIG. 16.

TABLE 6

Final Reaction Parameters

| | Initial Concentration | Final Concentration | Amount (µL) |
|---|---|---|---|
| Isothermal amplification buffer | 10× | 1× | 5 |
| dNTPs | 10 mM | 1.4 mM | 7 |
| MgSO4 | 100 mM | 8 mM | 4 |
| Bst 2.0 | 8000 units/mL | 320 units/mL | 2 |
| WS RTx | 15,000 units/mL | 300 units/mL | 1 |
| Aap Cas 12b | 2 mg/mL or 15.4 µM | 500 nM | 1.625 |
| Aac Cas 12b crRNA | 360 ng/µL or 10 µM | 500 nM | 2.5 |
| WCV332 | 100 µM | 125 nm | 0.0625 |
| Taurine | 500 mM | 50 nm | 5 |
| LAMP primer pool | 10× | 1× | 5 |
| Sample | | | 5 |
| H2O | | | 11.8125 |
| Total | | | 50 |

Figure 17:
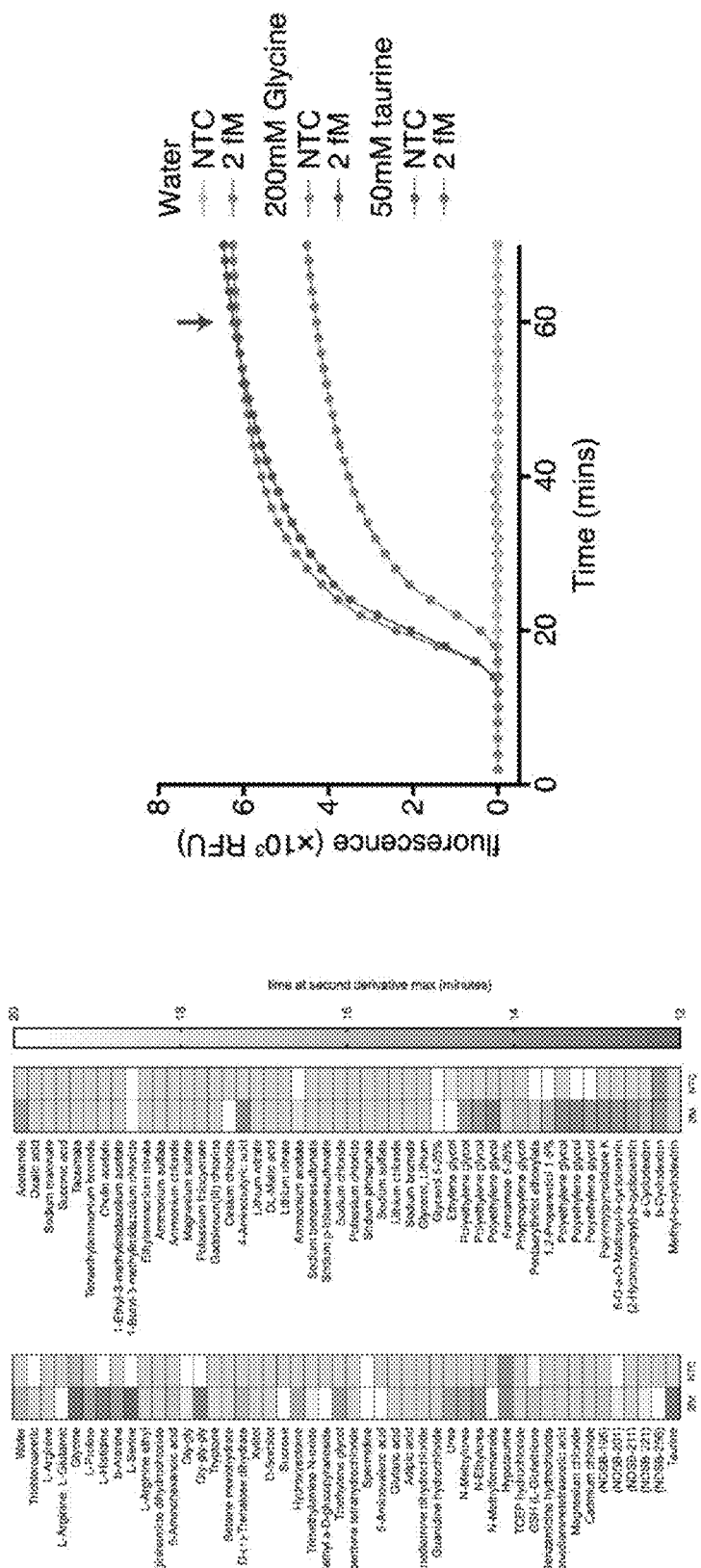
FIG. 17—Shows the different additives that may be used to optimize assay sensitivity and/or kinetics.
Figure 18:
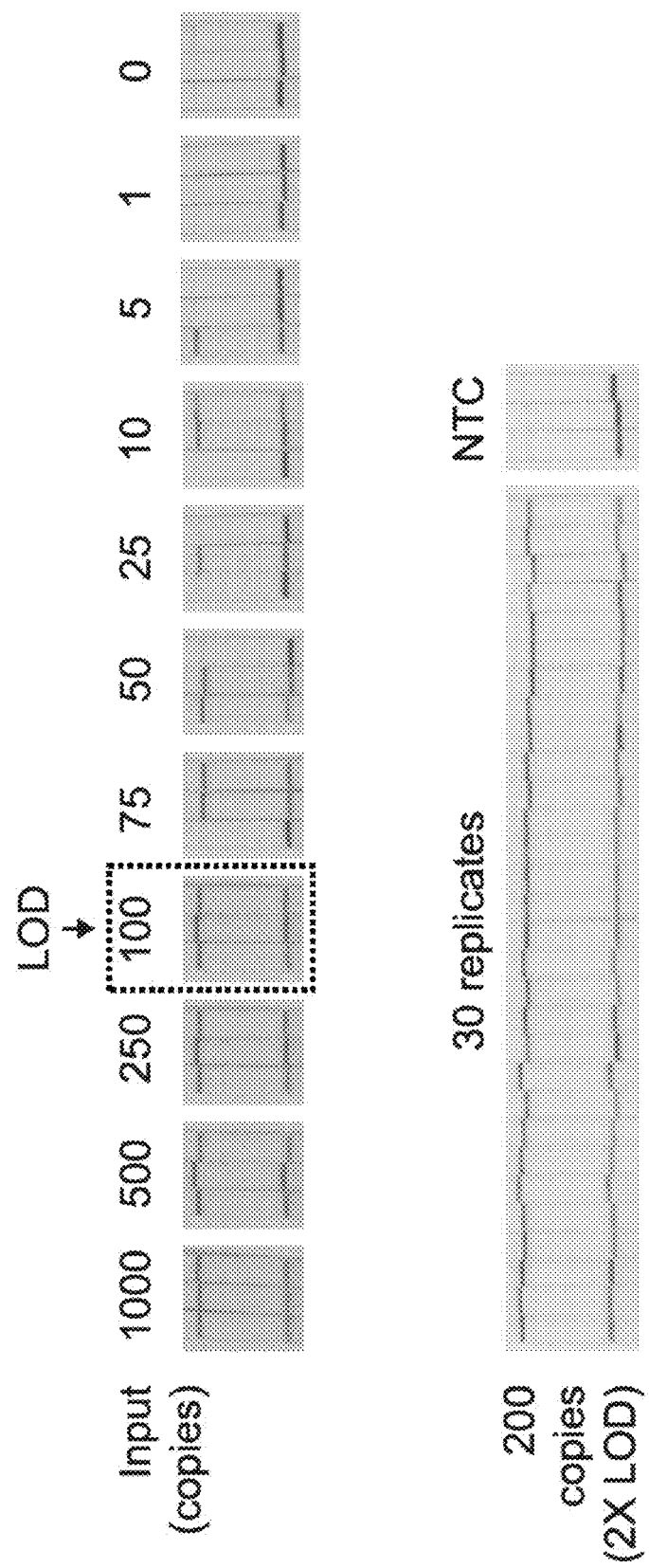
FIG. 18—Shows that the limit of detection is at 100 molecules per reaction.

The different reaction additives that were used to optimize the assay is shown in FIG. 17. FIG. 18 shows results obtained for assessing limit of detection by lateral flow assay at 60° C. for 60 minutes. The limit of detection was 100 molecules per reaction.

Figure 20:
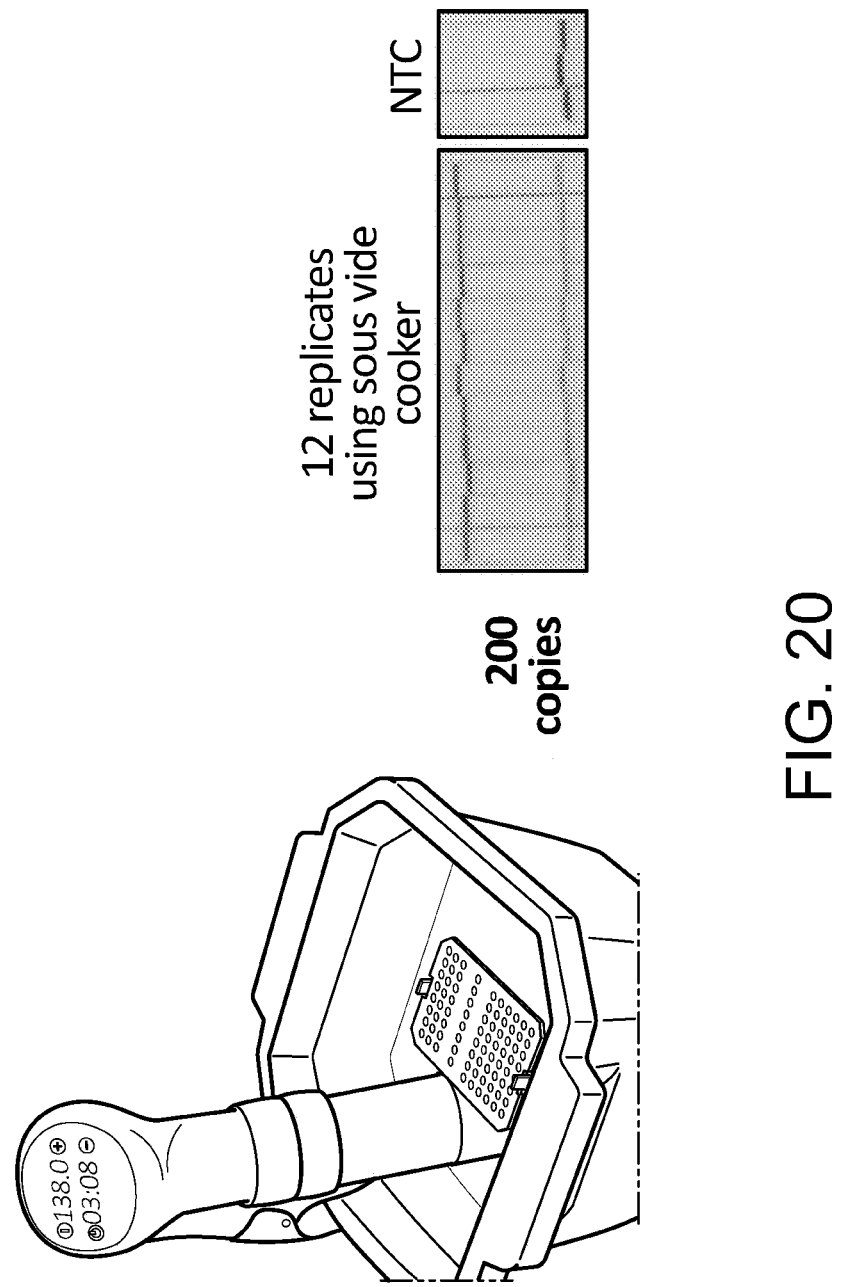
FIG. 20—Illustrates a low cost assay setup using a sous vide cooker.

Results obtained by SHERLOCK assay were compared to results obtained by qRT-PCR, as shown in FIG. 19. The assay can also be performed using a sous vide cooker, as illustrated in FIG. 20, 41.

Example 5. Exemplary Use of Device in Diagnostic Methods

Figure 21:
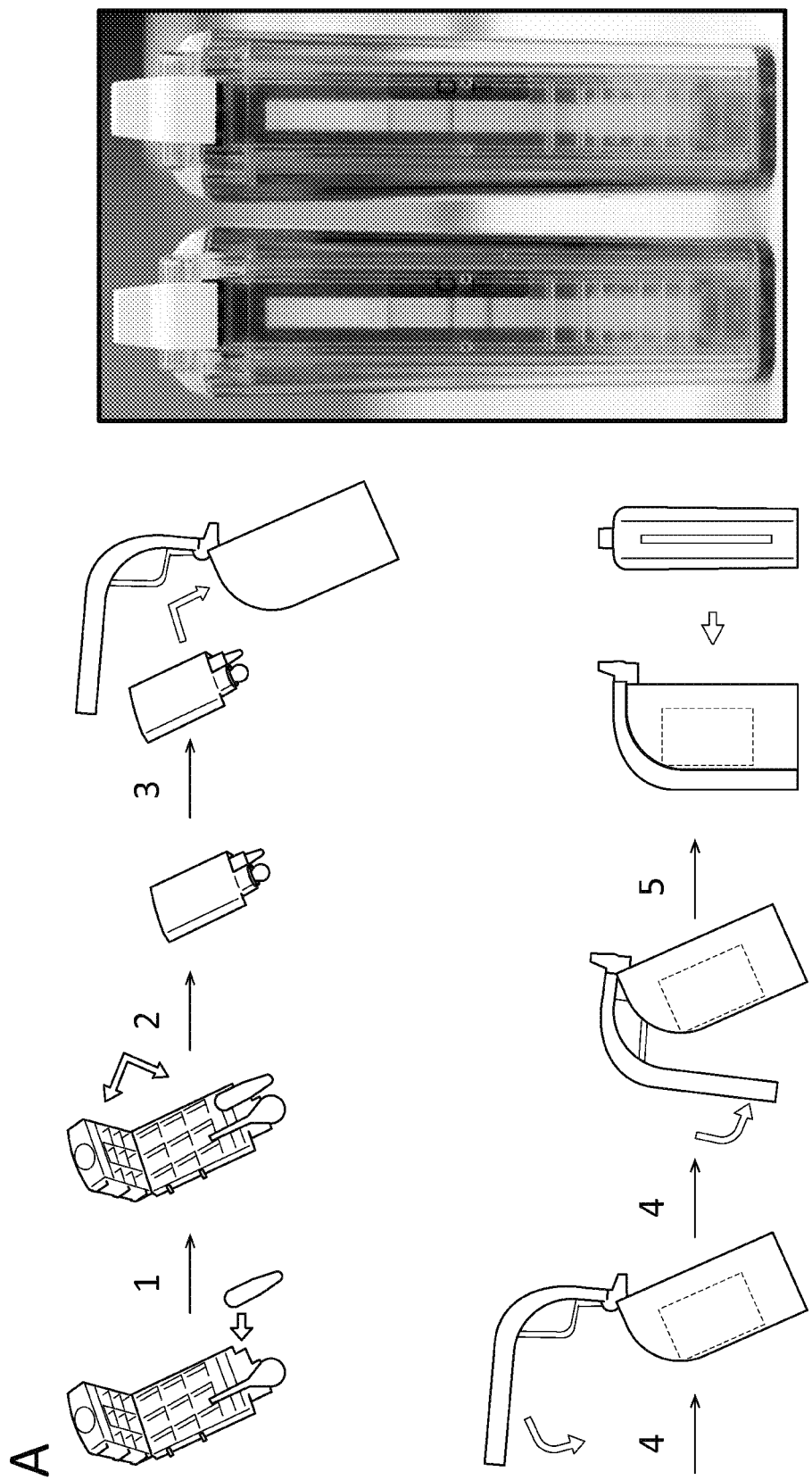
FIG. 21—Shows a point-of-care device that is compatible with SHERLOCK.
Figure 22:
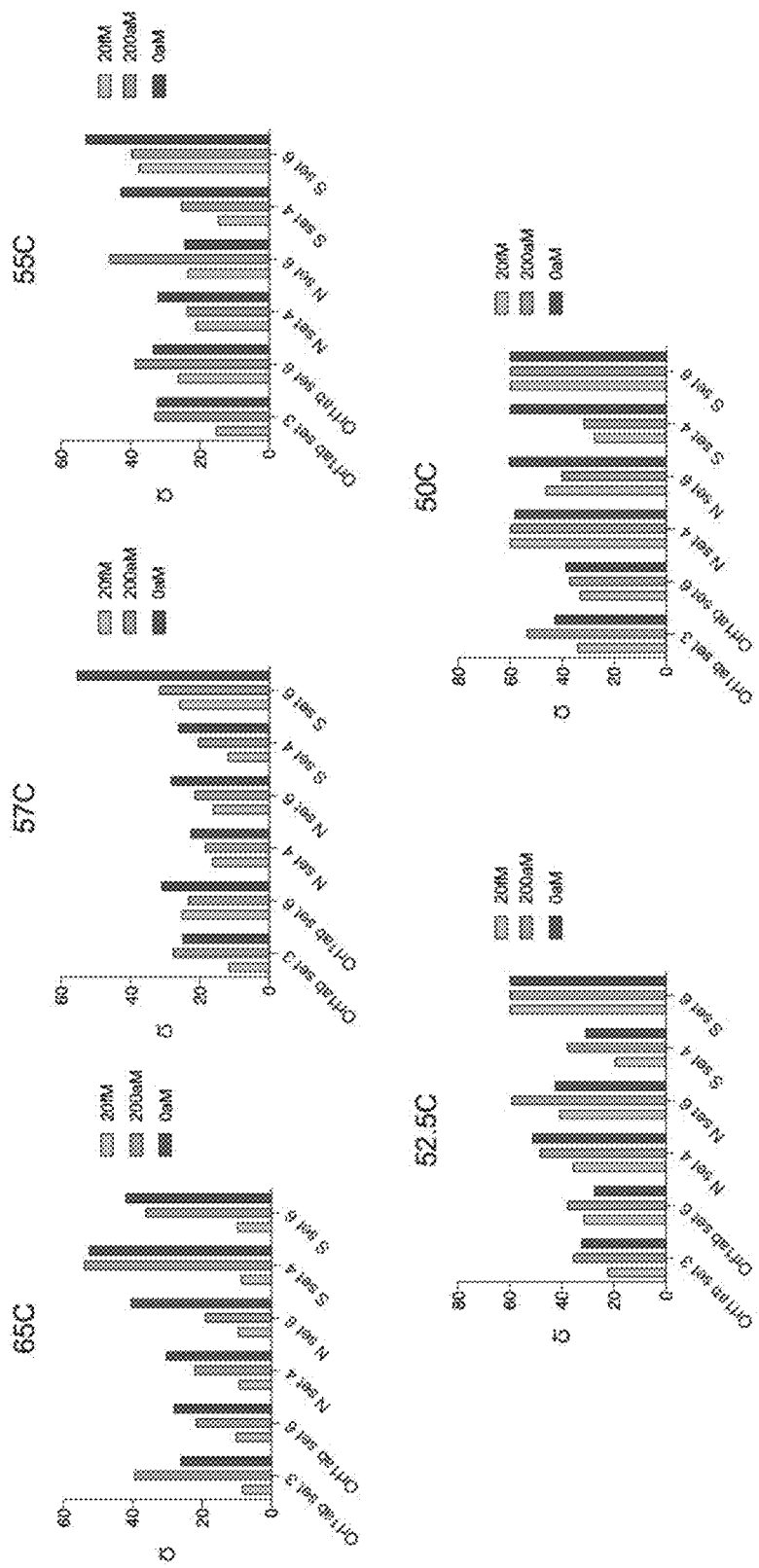
FIG. 22—Demonstrates that LAMP primers are active at lower temperatures.
Figure 23:
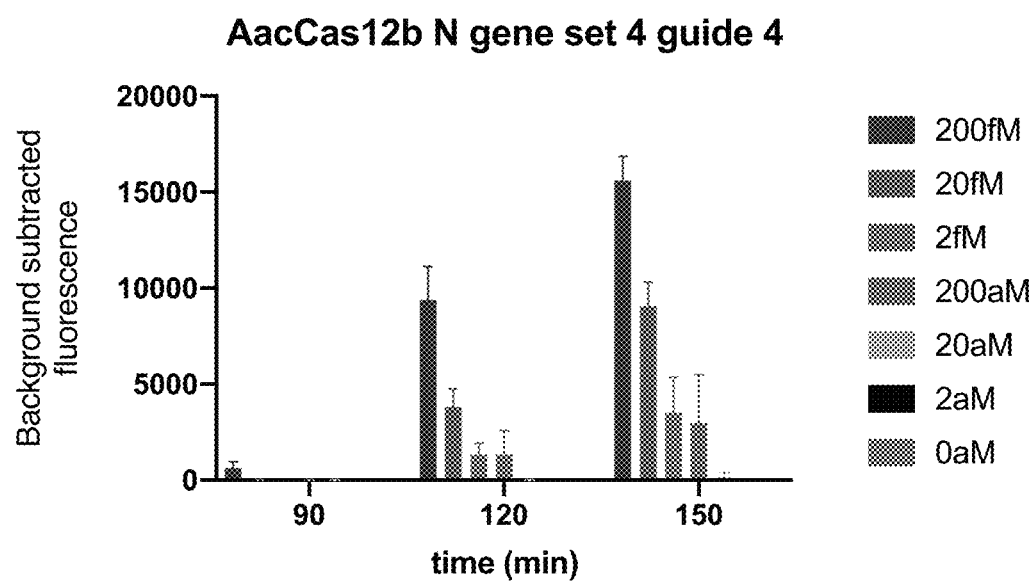
FIG. 23—Demonstrates that combining *Alicyclobacillus acidoterrestris* Cas12b (AacCas12b) with LAMP at 55° C. enables one-pot COVID-19 detection. Input comprised RNA genome of COVID-19 broken into 5 kb fragments.
Figure 24:
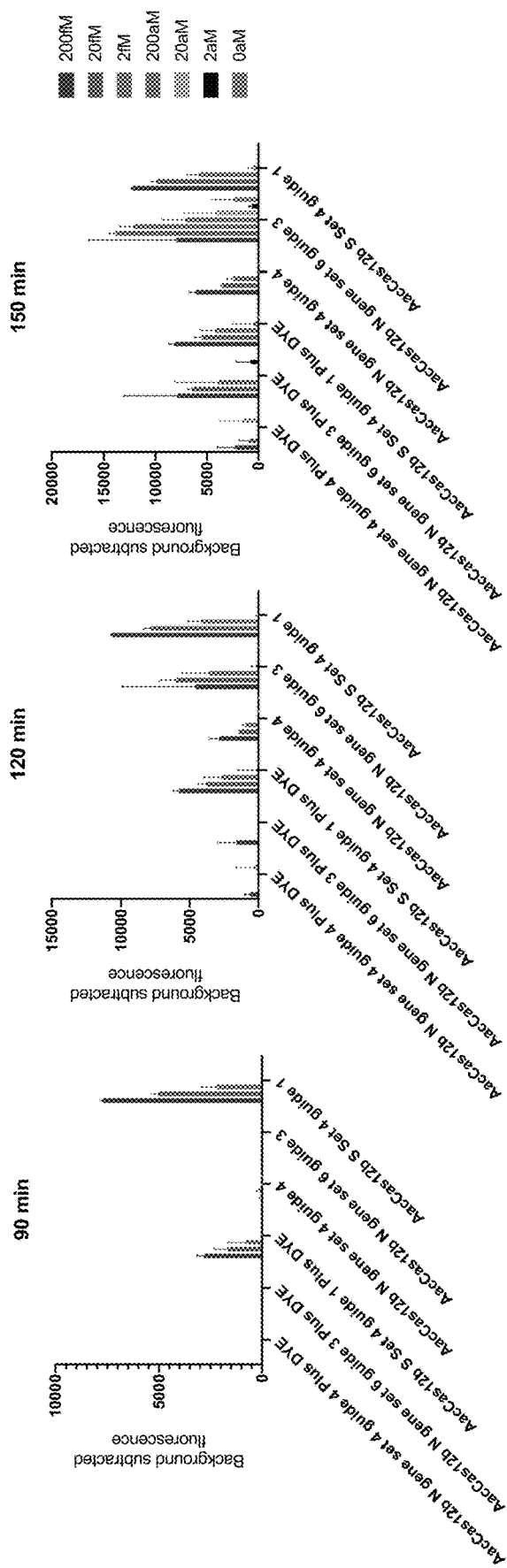
FIG. 24—Demonstrates multiple primer-set and guide combination work targeting different COVID-19 genes. 200aM detection limit was achieve by 150 minutes. Input comprised RNA genome of COVID-19 broken into 5 kb fragments.

One exemplary device that can be utilized at point of care, in home environments, and/or for distribution as a take home device is shown in FIG. 21. The device can advantageously be disposable and can offer rapid instrument-free visualization of the nucleic acid amplification products of the methods disclosed herein. In an exemplary embodiment, the disposable device is compatible with nucleic acid amplification technologies, including LAMP. The device comprises an ampule which can contain the lateral flow buffer for the lateral flow readout of the amplification result. A sample can be loaded into a container which may comprise the reagents for the SHERLOCK reaction, including amplification reagents and CRISPR-Cas protein and guide molecules, which may optionally be stored in the container as lyophilized reagents. (See FIG. 21 at step 1). The device can further comprise a container for the contents of the SHERLOCK reaction, including LAMP amplification reagents and CRISPR-Cas protein and guide molecules. The device can also be configured to comprise the lateral flow strip, such that after the reaction is conducted, a lateral flow readout is provided in the device utilizing an instrument-free method for the visualization of the reaction products without cross-contamination.

Example 6. Point-of-Care Testing for COVID-19 Using SHERLOCK Diagnostics

Rapid point-of-care (POC) tests capable of being run in any low-resource setting, including at home, are needed to adequately combat the COVID-19 pandemic and re-open society. Applicants previously described a protocol for using the CRISPR-based SHERLOCK (Specific High Sensitivity Enzymatic Reporter UnLOCKing) technique (Gootenberg et al., 2017, 2018) for the detection of SARS-CoV-2. SHERLOCK achieves sensitive detection of SARS-CoV-2 through two consecutive reactions: (1) amplification of the virus RNA using an isothermal amplification reaction, and (2) detection of the resulting amplicon using CRISPR-mediated collateral reporter unlocking. Additional CRISPR-based tests have also been recently developed (Broughton et al., 2020; Ding et al., 2020; Guo et al., 2020; Lucia et al., 2020), but these all rely on two separate reaction steps, which requires liquid handling and opening of tubes. These steps add complexity and can lead to contamination, prohibiting their use outside laboratory environments and precluding use by lay individuals. Other POC tests for COVID-19 have been authorized by the U.S. Food and Drug Administration (FDA), including the Abbott ID NOW and Cepheid Genexpert, but these require complex and expensive instrumentation, limiting use to complex labs and hospitals by trained professionals. Some isothermal pre-amplification methods, such as Loop-mediated Isothermal Amplification (LAMP), have been developed as POC tests (Zhang et al., 2020), but these rely on amplification that can be nonspecific.

Currently, the only tests readily available for at-home or low-resource settings are serology paper-based tests (Whitman et al., 2020). However, these are not adequate for diagnosing live infection as antibodies take 1-2 weeks to become detectable in blood and only signify previous exposure. Therefore, Applicants sought to create a POC COVID-19 nucleic acid test that can be run in any setting. Through a series of optimizations, Applicants developed a streamlined, 1-hour SHERLOCK based test that requires no sample extraction and can be performed at one temperature in a single reaction with minimal fluid handling and visual colorimetric readout (FIG. 16).

The one-pot SHERLOCK SARS-CoV-2 detection protocol works in the following three steps, without requiring separate virus RNA extraction:

| Step (1) | 5 mins at 95° C. | lysis of virus-containing patient sample using QuickExtract to release virus RNA; |
|---|---|---|
| Step (2) | 1 hr at 60° C. | detection of virus RNA using one-step SHERLOCK reaction; |
| Step (3) | 2 mins at room temp | visual read out of the detection result by eye using a commercially-available paper dipstick. |

In order to integrate the isothermal amplification step with the CRISPR-mediated detection step, Applicants sought to establish a common reaction condition capable of supporting both steps. Due to the supply chain constraints for the commercially-available recombinase polymerase amplification (RPA) reagents and difficulties in producing a rapid one-pot RPA test for sensitive RNA detection, Applicants chose loop-mediated isothermal amplification (LAMP) reaction for amplifying the virus RNA. The requisite enzymes for LAMP are more readily available from a number of commercial suppliers and the LAMP buffers are simpler and more amenable to systematic optimization with Cas enzymes.

Figure 25:
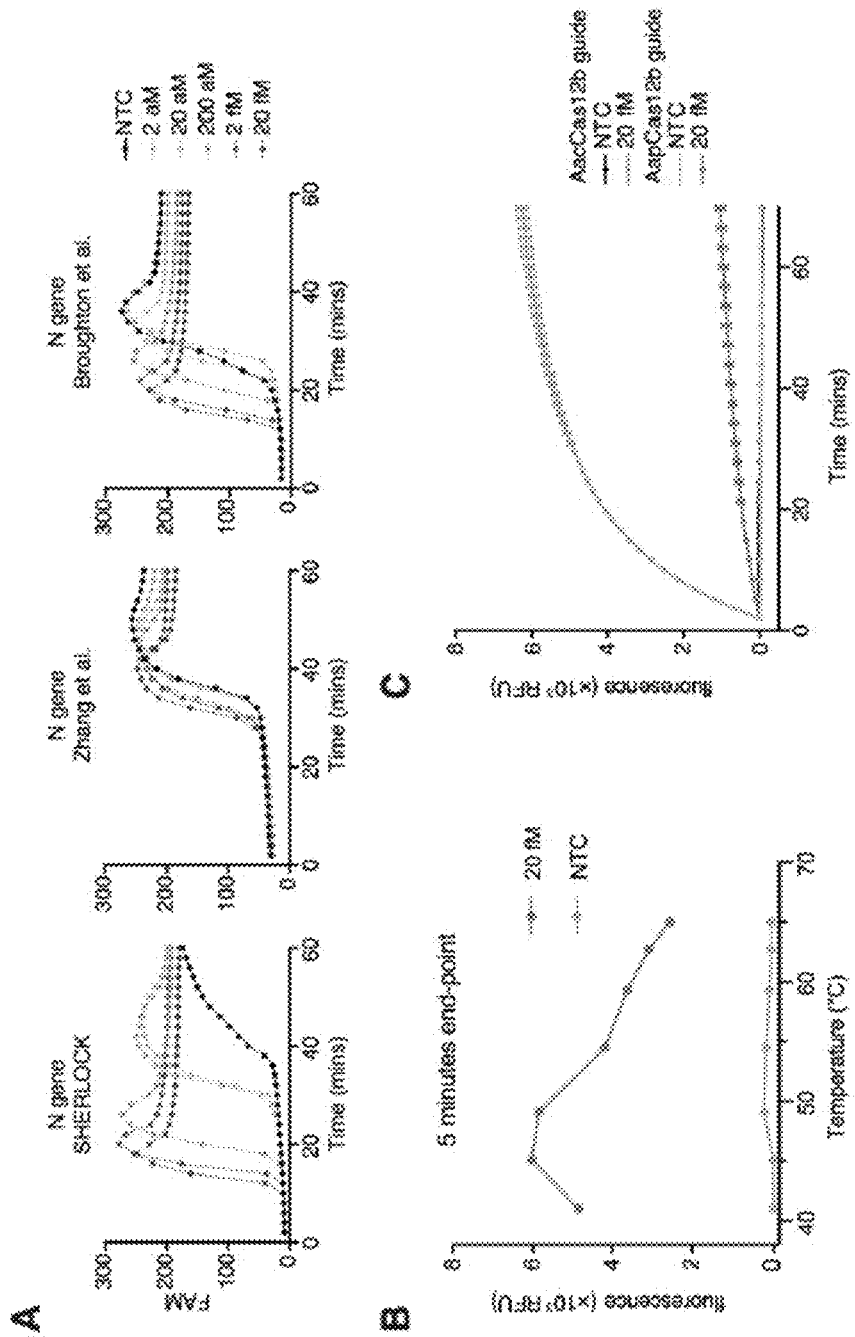
FIG. 25—Development of POC-SHERLOCK using RT-LAMP and thermophilic AapCas12b. (25A) Comparison of the POC-SHERLOCK N gene LAMP primer set to two established LAMP primer sets measured by real-time fluorescence at varying levels of SARS-CoV-2 standard genomes. (25B) Temperature comparison of AapCas12b collateral activity activated by RT-LAMP amplified inputs, including 20 fM SARS-CoV-2 standards and NTC controls. (25C) AapCas12b collateral activity when incubated with AapCas12b or AacCas12b crRNAs and RT-LAMP amplified 20 fM SARS-CoV-2 standards or NTC. (25D) AapCas12b collateral activity measured using different guides for RT-LAMP amplified 20 fM SARS-CoV-2 standards or NTC. (25E) POC-SHERLOCK (One-pot Cas12b and RT-LAMP) results when using AapCas12b or AacCas12b and varying amounts of SARS-CoV-2 inputs or NTC. (25F) POC-SHERLOCK real-time fluorescence performance measured with glycine or taurine additives at 2 fM SARS-CoV-2 input or NTC.
Figure 25:
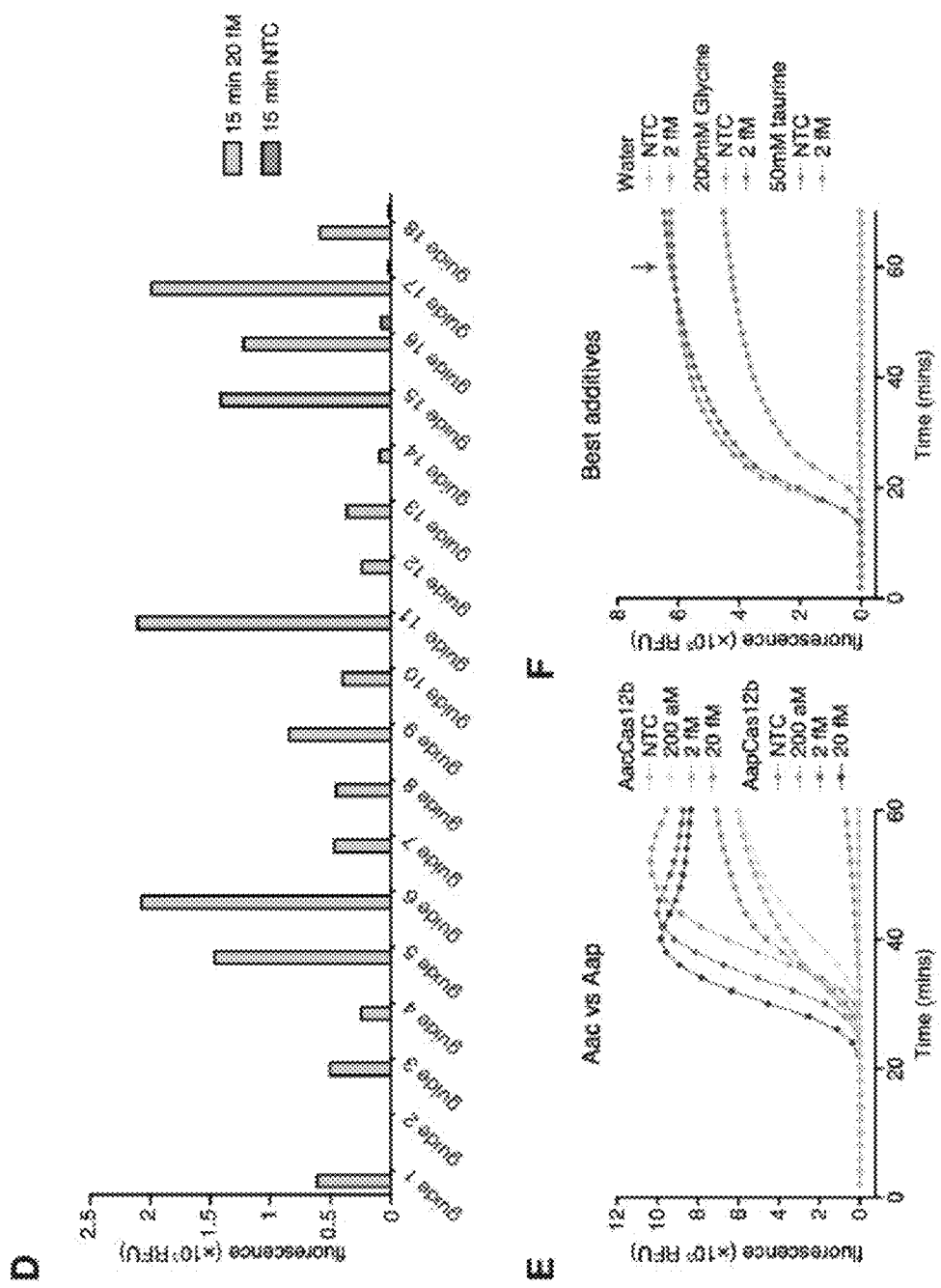

To determine the optimal combination of LAMP primers and guides, Applicants designed 29 sets of LAMP primers targeting different regions of the SARS-CoV-2 genome and identified the best primer set for amplifying gene N (FIG. 25A). As LAMP operates at a higher temperature than RPA (55-65° C. compared to 42° C.), a one-pot reaction demands a Cas enzyme with collateral activity that is thermostable. Of the various Cas proteins Applicants explored, Cas12b from *Alicyclobacillus acidiphilus* (AapCas12b) (Teng et al., 2018) maintained sufficient activity in the same temperature range as LAMP (FIG. 25B). However, because the AapCas12b locus did not contain a CRISPR array, the published single guide RNA (sgRNA) for AapCas12b used a direct repeat (DR) sequence from *Alicyclobacillus macrosporangiidus* Cas12b, which could impede activity. To remedy this, Applicants searched for alternative orthologs with similar protein sequences to AapCas12b and found that *Alicyclobacillus acidoterrestris* Cas12b (AacCas12b) shared a 95% sequence homology (Shmakov et al., 2015). Additionally, the AacCas12b tracrRNA and predicted AapCas12b tracrRNA are 97% identical. Given the high degree of similarity between AapCas12b and AacCas12b protein and tracrRNA, Applicants surmised that the sgRNA for AacCas12b should closely match the cognate AapCas12b DR-tracrRNA hybrid. Indeed, reactions combining AapCas12b enzyme with AacCas12b sgRNA produced more robust and specific nuclease activity compared to the published AapCas12b sgRNA (FIG. 25C).

For the best LAMP amplicon, Applicants tested 18 sgRNAs to identify the optimal combination of primers and guide sequence (FIG. 25D). Using this combination in a one pot reaction, Applicants found that AapCas12b generated faster and higher collateral activity than AacCas12b protein (FIG. 25E). Applicants further optimized one-pot reaction components by screening 94 additives to improve thermal stability, finding that addition of taurine significantly improved reaction kinetics (FIG. 25F).

Figure 6:
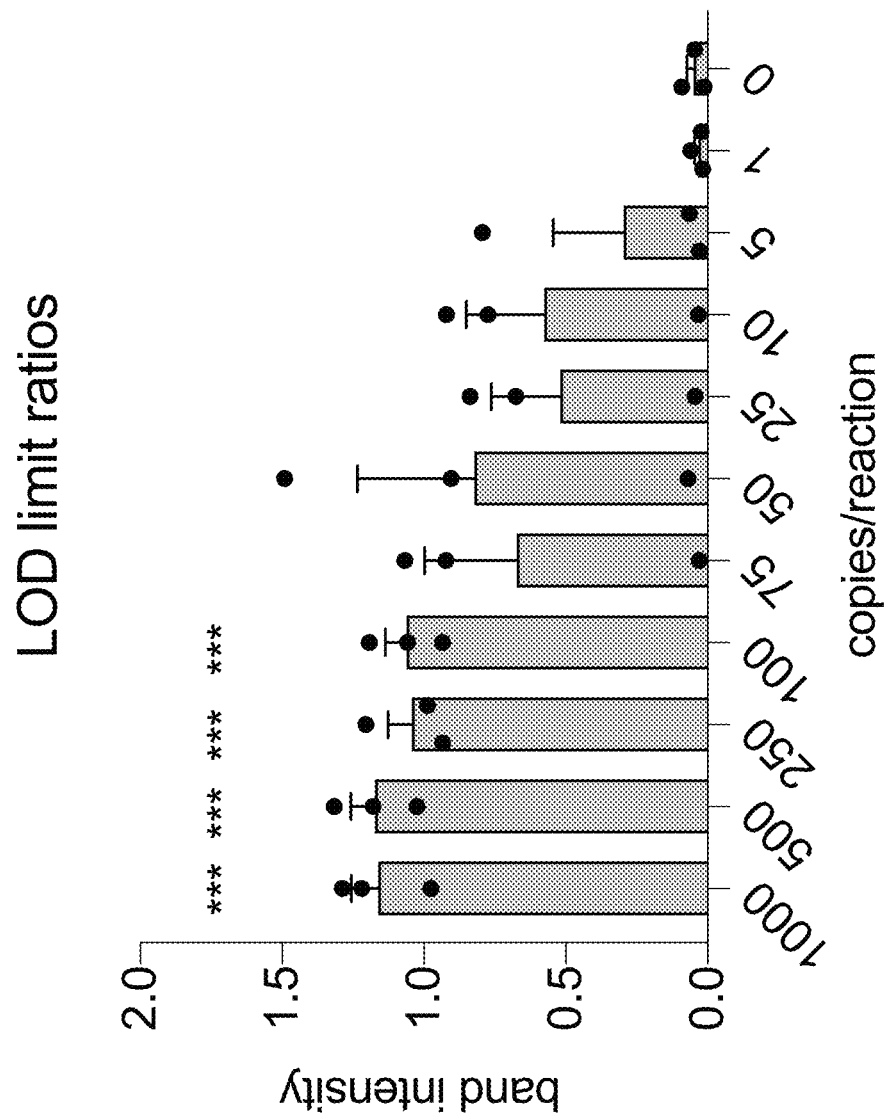
FIG. 6—Graph shows quantification of lateral flow assay from FIG. 5. The bar graph represents quantification of top band intensity/bottom band intensity.
Figure 7:
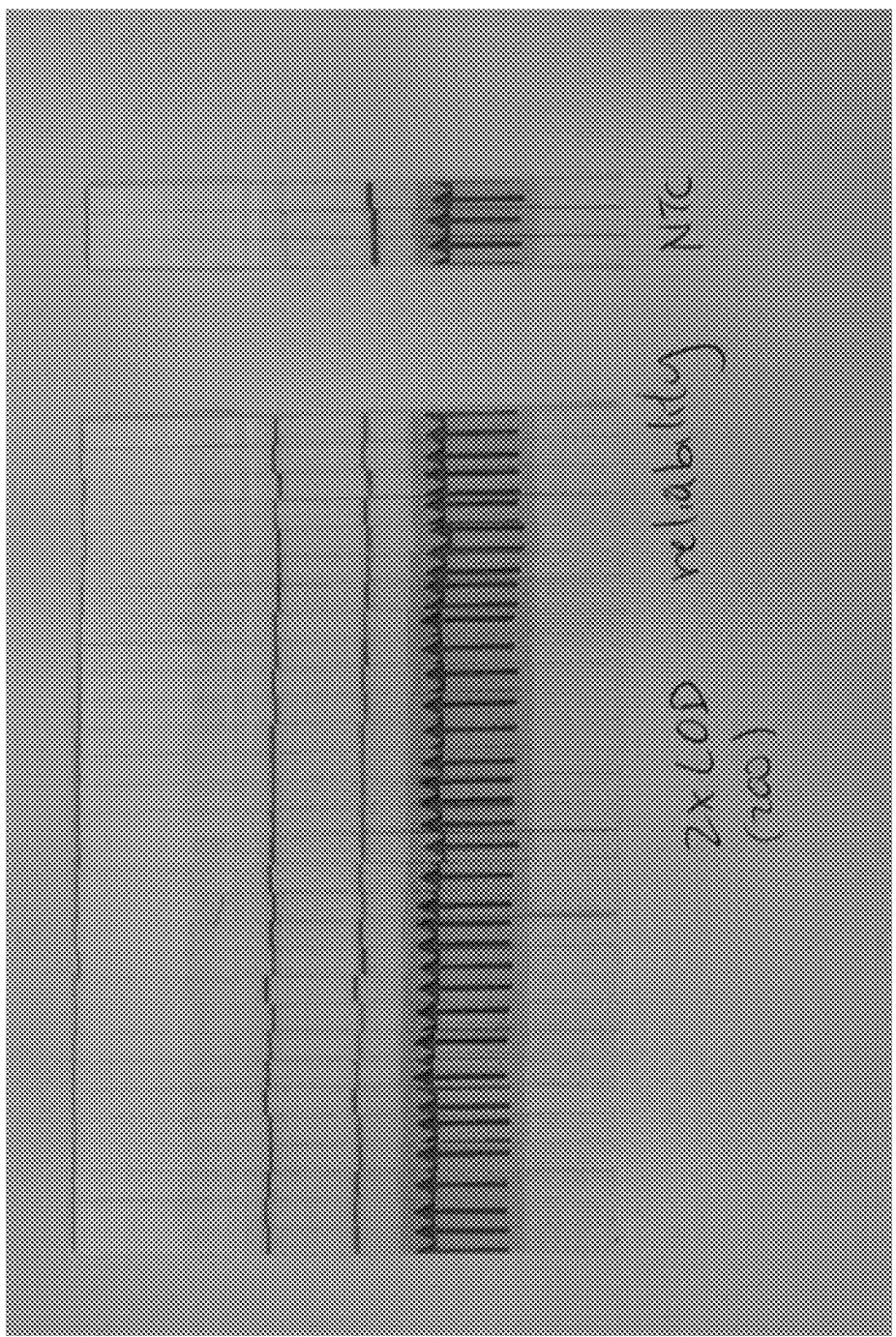
FIG. 7—Shows that SHERLOCK can reliably perform at 2× the limit of detection.
Figure 8:
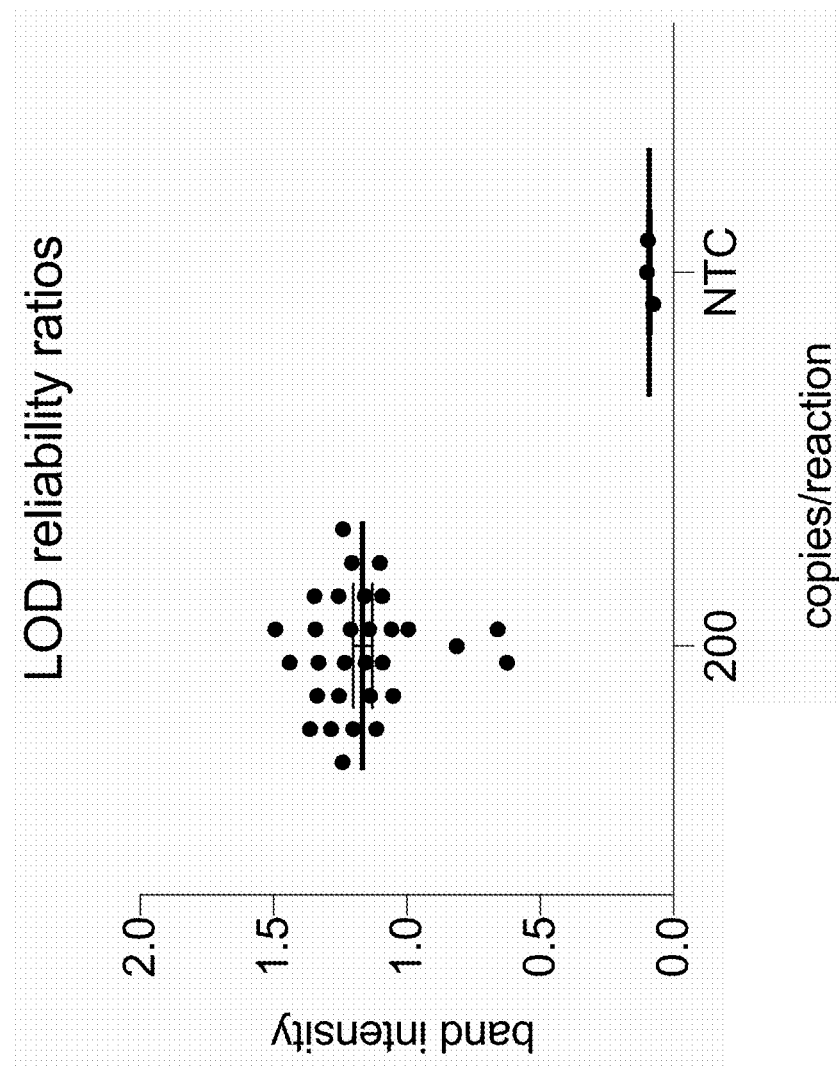
FIG. 8—Graph showing that SHERLOCK can reliably perform at 2× the limit of detection. The graph represents quantification of top band intensity/bottom band intensity of lateral flow assays from FIG. 7.
Figure 9:
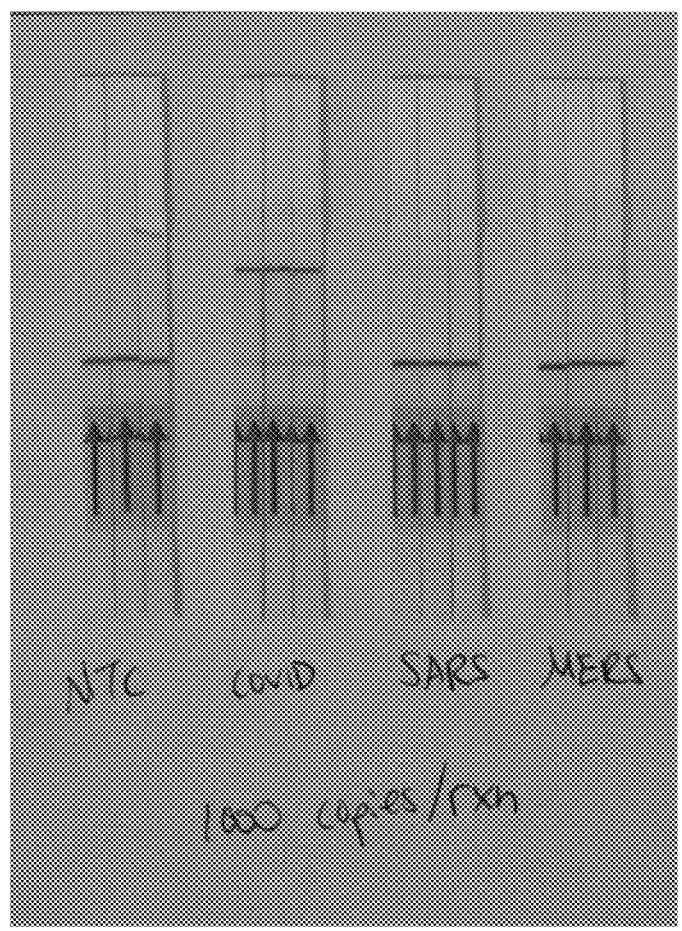
FIG. 9—Shows that the SHERLOCK assay has no cross-reactivity with SARS-CoV or MERS-CoV.
Figure 10:
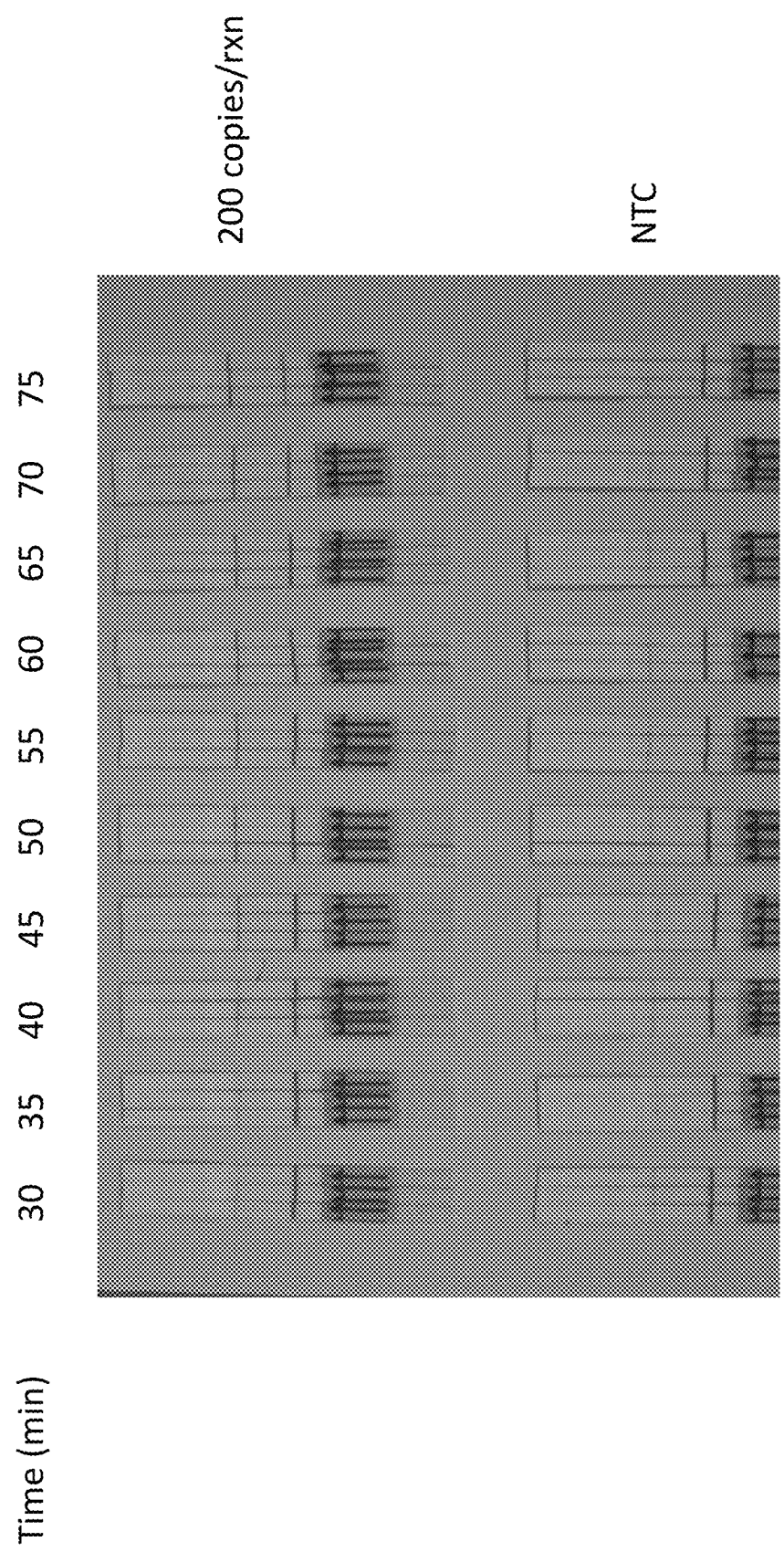
FIG. 10—Shows that a 50 minute incubation is sufficient to reach reaction saturation at 2× limit of detection.
Figure 11:
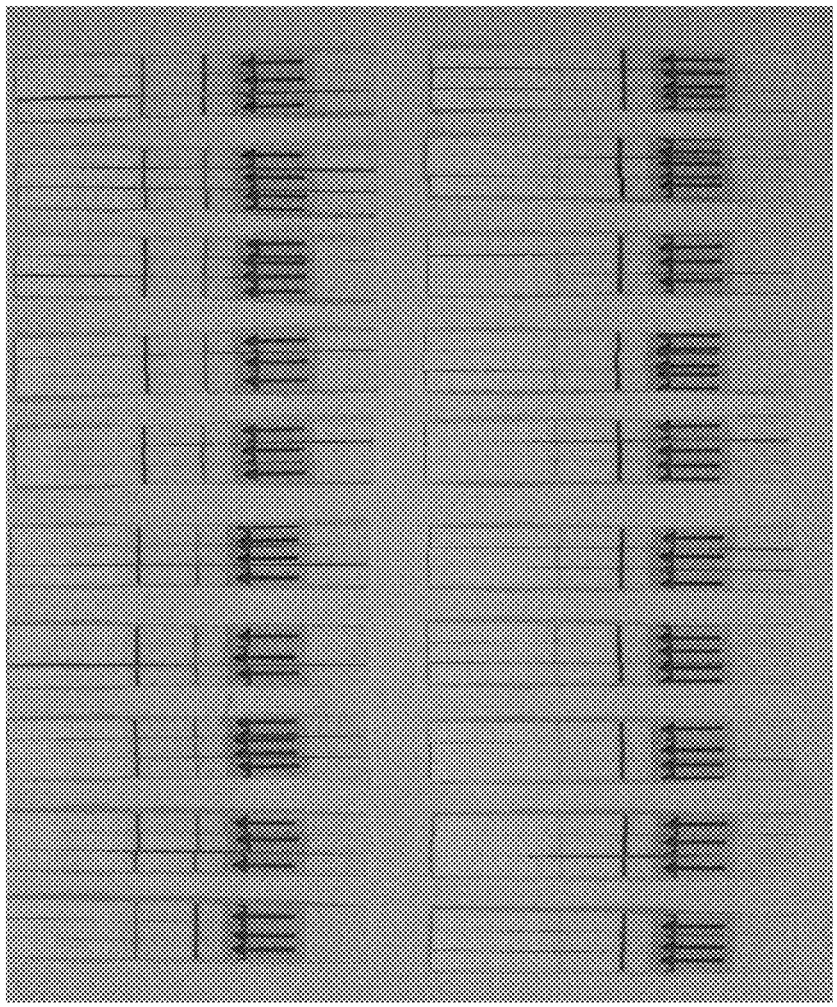
FIG. 11—Shows that SHERLOCK is robust across a 10° C. window.
Figure 12:
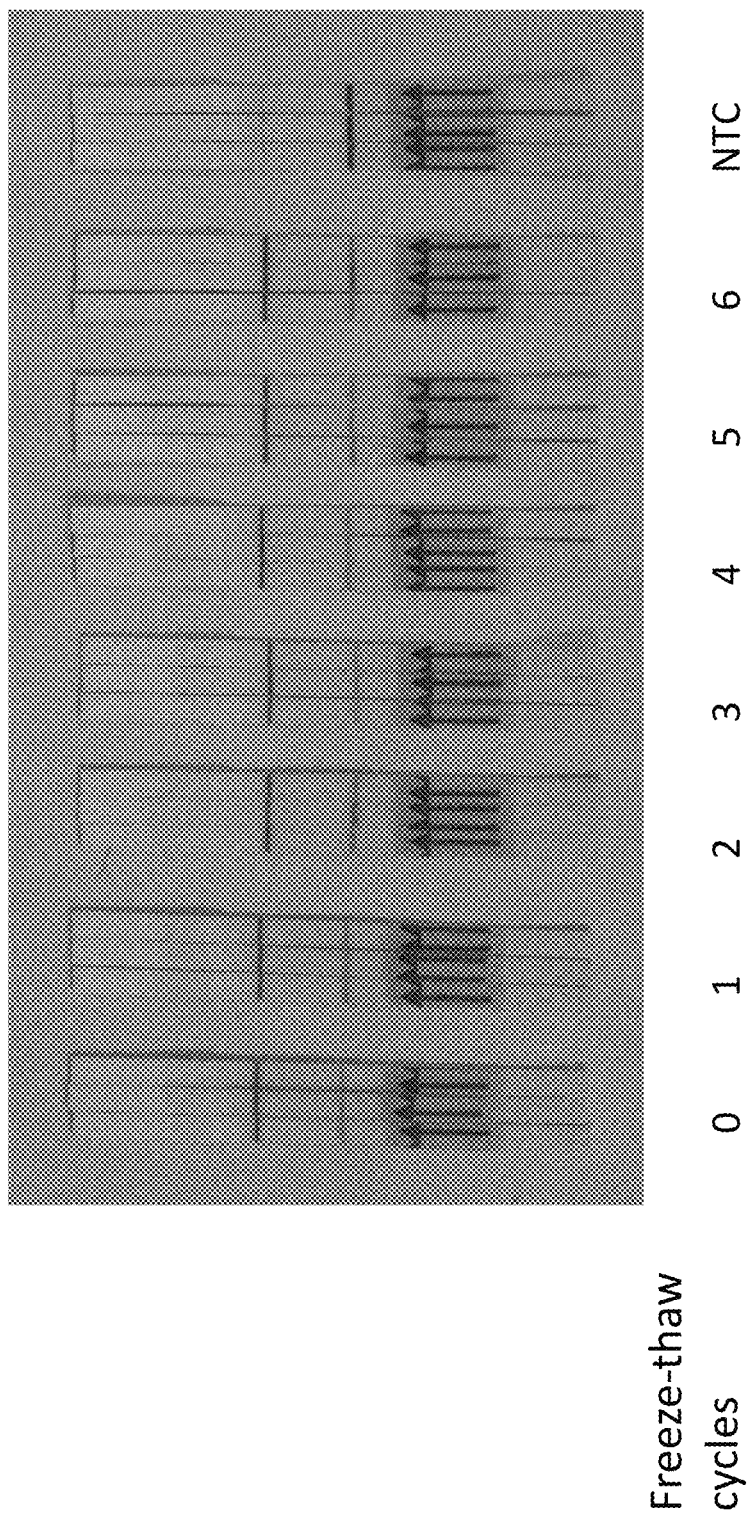
FIG. 12—Shows that SHERLOCK can be master mixed and freeze-thawed for six freeze-thaw cycles or more.
Figure 13:
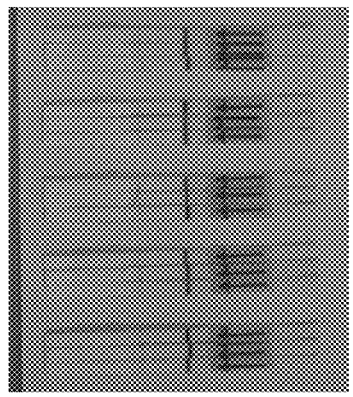
FIG. 13—Shows positive detection of COVID in 12 patients using the SHERLOCK assay.
Figure 13:
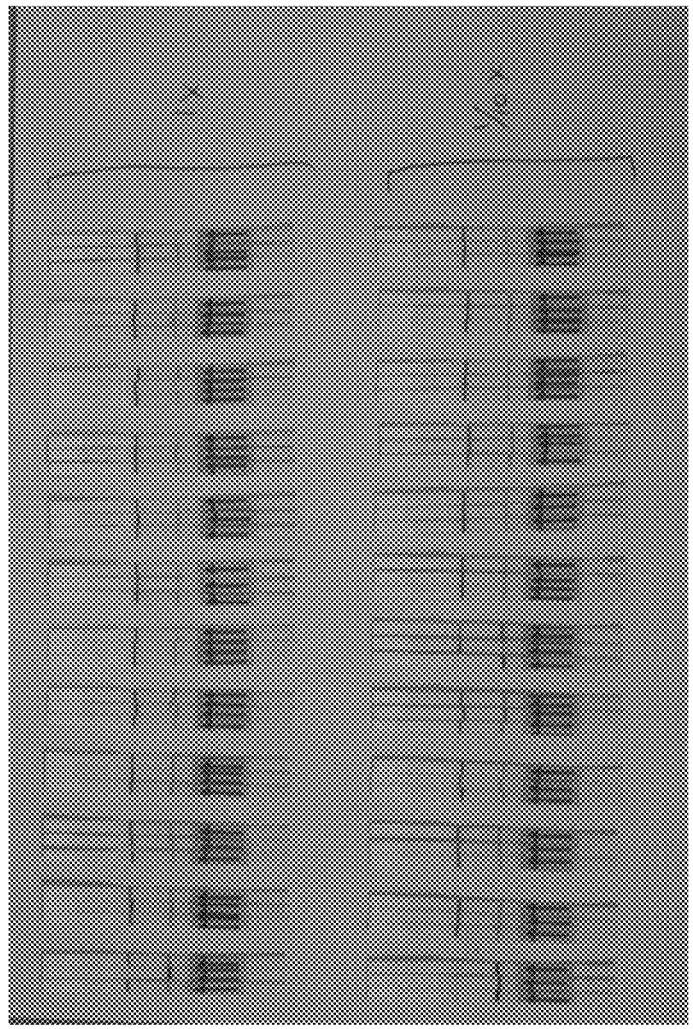
Figure 14:
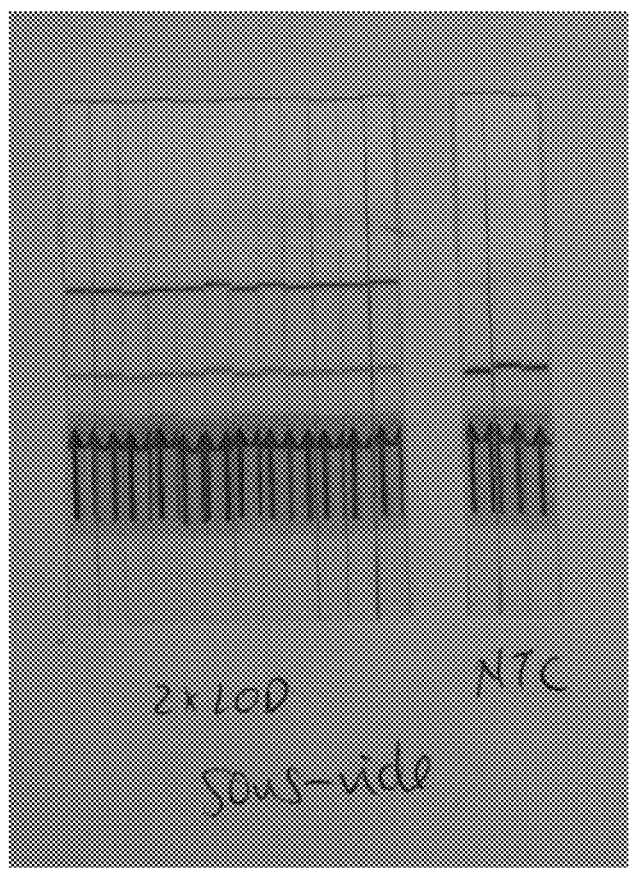
FIG. 14—The SHERLOCK assay can be run with a <$40 using conventional heating devices such as a sous vide heater FIG. 15—Shows SHERLOCK assays strips for 9 different patients using a nasopharyngeal swab sample. The results were compared to qPCR tests.
Figure 15:
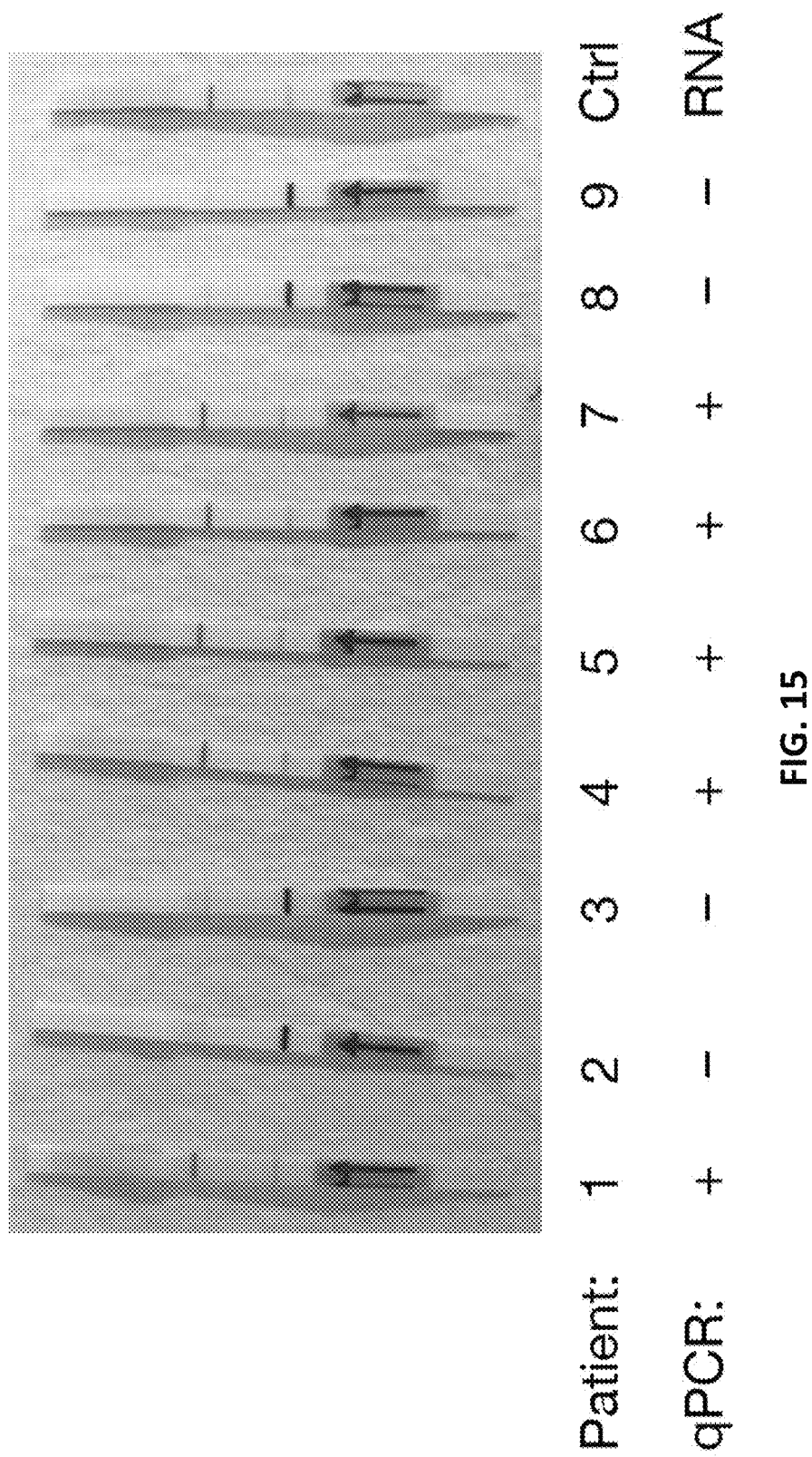
Figure 26:
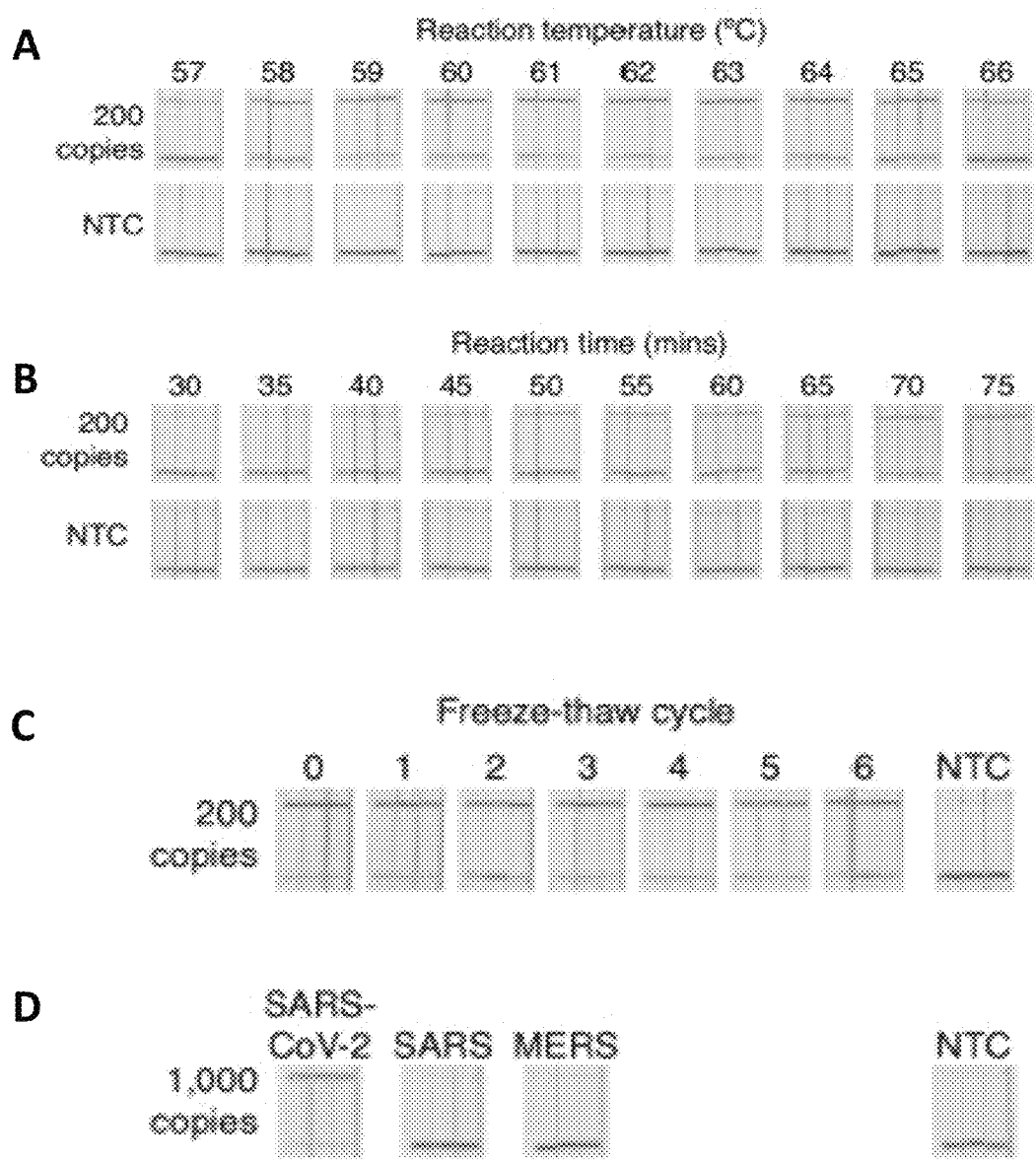
FIG. 26—POC-SHERLOCK performance on lateral flow strips. (25A) Effect of reaction temperature on POC-SHERLOCK lateral flow detection for 200 SARS-CoV-2 copies per reaction and NTC. (25B) Effect of reaction incubation time on POC-SHERLOCK lateral flow detection for 100 SARS-CoV-2 copies per reaction and NTC. (25C) Effect of master mix freeze-thaw cycles on POC-SHERLOCK lateral flow detection for 200 SARS-CoV-2 copies per reaction and NTC. (25D) Measurement of cross-reactivity for COVID-19

Applicants profiled the optimized reaction with a lateral flow readout and an RNA extraction-free input using SARS-CoV-2 genome standards spiked into nasopharyngeal (NP) swab to determine limit of detection (LOD), ideal incubation temperature, readout time, and robustness. Applicants found that the LOD of the reaction was 100 copies of SARS-CoV-2 (FIG. 18). This LOD was reliable and reproducible over 30 replicates (FIG. 6). At twice the LOD, the ideal incubation parameters were 60° C. for at least 50 minutes (FIG. 26A, 26B). The reaction components could be formulated as a mastermix and maintained functionality after 6 freeze-thaw cycles (FIG. 26C). The assay exhibited no cross-reactivity with the SARS or MERS coronavirus genomes (FIG. 26D). The reaction could be performed using either a standard heat block or via a water bath maintained by a commercially-available low-cost (under $40USD) sous-vide cooker (FIG. 20).

Finally, Applicants evaluated the one-pot SHERLOCK detection on 12 positive and 5 negative patient NP swabs. Applicants' assay correctly identified 35/36 positive patient replicates and 15/15 negative patient replicates, resulting in a sensitivity of 97% and specificity of 100% (FIGS. 19 and 27, 42A). To further simplify the assay workflow, Applicants tested whether lysis using QuickExtract at room temperature (22° C.) or the one-pot incubation temperature (60° C.) for 10 mins would be sufficient for detection. As QuickExtract contains Proteinase K that inhibits SHERLOCK without heat inactivation at 95° C., Applicants added Proteinase K Inhibitor to the SHERLOCK reaction. In both cases, Applicants could identify 33/36 positive patient replicates (FIGS. 28A, 28B). Comparison of RT-qPCR Ct values between the lysis methods suggested that both lysis methods are viable alternatives for streamlining the assay workflow, though with a slight decrease (0.2/0.4 Ct at 60° C. and 0.4/0.7 Ct for 22° C. for CDC N1/N2) in sensitivity (FIG. 29).

Materials and Methods

Design of LAMP and SHERLOCK reactions. Applicants designed LAMP amplification primers and SHERLOCK AapCas12b guide RNAs to target the N gene of SARS-CoV-2. The N gene is known to be present at higher copy numbers than other segments of the SARS-CoV-2 genome, which helps to increase the detection sensitivity. Below are the LAMP primer sequences and SHERLOCK AapCas12b guide RNAs:

LAMP Primers:

```
F3:
                                        (SEQ ID NO: 61983)
5'-GCTGCTGAGGCTTCTAAG-3'

B3:
                                        (SEQ ID NO: 61984)
5'-GCGTCAATATGCTTATTCAGC-3'

FIP:
                                        (SEQ ID NO: 61985)
5'-GCGGCCAATGTTTGTAATCAGTAGACGTGGTCCAGAACAA-3'

BIP:
                                        (SEQ ID NO: 61986)
5'-TCAGCGTTCTTCGGAATGTCGCTGTGTAGGTCAACCACG-3'

Loop Forward:
                                        (SEQ ID NO: 61987)
5'-CCTTGTCTGATTAGTTCCTGGT-3'

Loop Reverse:
                                        (SEQ ID NO: 61988)
5'-TGGCATGGAAGTCACACC-3'
```

AapCas12b Guide RNA Targeting SARS-CoV-2 N Gene:

(SEQ ID NO: 61989)
5'-GUCUAGAGGACAGAAUUUUCAACGGGUGUGCCAAUGGCCACUUUCC

AGGUGGCAAAGCCCGUUGAGCUUCUCAAAUCUGAGAAGUGGCACCGAAGA

ACGCUGAAGCGCUG-3'
(The spacer matching N gene is underlined.)

AapCas12b Protein Sequence:

(SEQ ID NO: 61990)
MAVKSMKVKLRLDNMPEIRAGLWKLHTEVNAGVRYYTEWLSLLRQENLYR

RSPNGDGEQECYKTAEECKAELLERLRARQVENGHCGPAGSDDELLQLAR

QLYELLVPQAIGAKGDAQQIARKFLSPLADKDAVGGLGIAKAGNKPRWVR

MREAGEPGWEEEKAKAEARKSTDRTADVLRALADFGLKPLMRVYTDSDMS

SVQWKPLRKGQAVRTWDRDMFQQAIERMMSWESWNQRVGEAYAKLVEQKS

RFEQKNFVGQEHLVQLVNQLQQDMKEASHGLESKEQTAHYLTGRALRGSD

KVFEKWEKLDPDAPFDLYDTEIKNVQRRNTRRFGSHDLFAKLAEPKYQAL

WREDASFLTRYAVYNSIVRKLNHAKMFATFTLPDATAHPIWTRFDKLGGN

LHQYTFLFNEFGEGRHAIRFQKLLTVEDGVAKEVDDVTVPISMSAQLDDL

LPRDPHELVALYFQDYGAEQHLAGEFGGAKIQYRRDQLNHLHARRGARDV

YLNLSVRVQSQSEARGERRPPYAAVFRLVGDNHRAFVHFDKLSDYLAEHP

DDGKLGSEGLLSGLRVMSVDLGLRTSASISVFRVARKDELKPNSEGRVPF

CFPIEGNENLVAVHERSQLLKLPGETESKDLRAIREERQRTLRQLRTQLA

YLRLLVRCGSEDVGRRERSWAKLIEQPMDANQMTPDWREAFEDELQKLKS

LYGICGDREWTEAVYESVRRVWRHMGKQVRDWRKDVRSGERPKIRGYQKD

VVGGNSIEQIEYLERQYKFLKSWSFFGKVSGQVIRAEKGSRFAITLREHI

DHAKEDRLKKLADRIIMEALGYVYALDDERGKGKWVAKYPPCQLILLEEL

SEYQFNNDRPPSENNQLMQWSHRGVFQELLNQAQVHDLLVGTMYAAFSSR

FDARTGAPGIRCRRVPARCAREQNPEPFPWWLNKFVAEHKLDGCPLRADD

LIPTGEGEFFVSPFSAEEGDFHQIHADLNAAQNLQRRLWSDFDISQIRLR

CDWGEVDGEPVLIPRTTGKRTADSYGNKVFYTKTGVTYYERERGKKRRKV

FAQEELSEEEAELLVEADEAREKSVVLMRDPSGIINRGDWTRQKEFWSMV

NQRIEGYLVKQIRSRVRLQESACENTGDI*

Specimen and nucleic acid extraction. Two types of patient samples have been tested for compatibility with one-pot SHERLOCK. All samples should be collected and processed according to the appropriate biosafety procedure.

a. RNA extracted from patient samples: The patient sample should be collected according to the appropriate biosafety procedures. Please reference the 2020 CDC COVID-19 test protocol for details on specimen collection and subsequent nucleic acid extraction. The input for this protocol, beginning with Step (1), can be the same extracted nucleic acid as used in qRT-PCR assays.

b. Nasopharyngeal (NP) swabs: NP swabs dissolved in viral transport media (VTM) or TE can be directly used.
Reagents.
For Step (1)—lysis of viral sample:
QuickExtract DNA Extraction Solution (QE09050), Lucigen. Once thawed, aliquot and store at −20° C. to avoid >3 freeze-thaw cycles.

For Step (2)—one-pot SHERLOCK detection reaction:
Bst 2.0 WarmStart® DNA Polymerase (M0538L), New England BioLabs
WarmStart® RTx Reverse Transcriptase (M0380L), New England BioLabs
10× Isothermal Amplification Buffer (B0374S), New England BioLabs, supplied with M0538L and M0380L
100 mM MgSO4 (B1003S), New England BioLabs, supplied with M0538L and M0380L
10 mM Deoxynucleotide (dNTP) Solution Mix (N0447L), New England BioLabs
Taurine (86329-100G), Millipore Sigma
AapCas12b protein purified according to Kellner et al., Nature Protocols 2019, stored as 10 μL aliquots at 2 mg/mL.
Guide RNA for detecting N gene can be ordered from Synthego
Reporter DNA for lateral flow read out (Lateral Flow Reporter: /56-FAM/TTTTTTT/3Bio/), can be ordered from IDT
(Optional) Proteinase K Inhibitor (539470-10MG), Millipore Sigma. Resuspend 10 mg of Proteinase K Inhibitor with 150 μL of DMSO to make the stock solution. Dilute stock solution 1:100 with ddH2O to make working aliquots. Store both stock and working solutions at −20° C.
10×LAMP Primer Mix:

TABLE 7

| LAMP Primer Mix. | |
|---|---|
| LAMP Primer (100 μM) | Amount (μL) |
| F3 | 2 |
| B3 | 2 |
| FIP | 16 |
| BIP | 16 |
| Loop F | 4 |
| Loop B | 4 |
| ddH$_2$O | 56 |
| Total | 100 |

A Sherlock mastermix can be prepared as follows:

TABLE 8

| | Initial concentration | Final concentration | Amount (uL) |
|---|---|---|---|
| Isothermal amplification buffer | 10× | 1× | 5 |
| dNTPs | 10 mM | 1.4 mM | 7 |
| MgSO$_4$ | 100 mM | 8 mM | 4 |
| WS Bst 2.0 | 8000 units/mL | 320 units/mL | 2 |
| WS RTx | 15,000 units/mL | 300 units/mL | 1 |
| Aap Cas12b | 2 mg/mL or 15.4 uM | 500 nM | 1.625 |
| Aac Cas12b crRNA | 360 ng/uL or 10 uM | 500 nM | 2.5 |
| Lateral Flow Reporter | 100 uM | 125 nM | 0.0625 |
| Taurine | 500 mM | 50 mM | 5 |
| LAMP primer mix | 10× | 1× | 5 |
| ddHO | | | 11.8125 |
| Total | | | 45 |

If lysing samples at 22° C. or 60° C. instead of 95° C., replace 2 uL of ddH2O with 2 uL of Proteinase K Inhibitor working solution.

For Step (3) reading out using lateral flow dipstick:
HybriDetect Dipstick (MGHD 1), Milenia Biotec GmbH
Positive Control Sequences
SARS-CoV-2 RNA control (102019), Twist Bioscience
Equipment.
95° C. heat block or water bath
60° C. heat block or water bath
Alternative: a sous vide immersion cooker capable of supporting the temperature range of 55° C. to 95° C. can also be used (example).

One-Step SHERLOCK Protocol for SARS-CoV-2 Detection

***IMPORTANT NOTE: To prevent sample contamination from confounding detection result, two different work areas should be used for performing Steps (1)/(2) and (3). Steps (1)/(2) should be performed in a pre-amplification area and is especially sensitive to contamination. Amplified samples should not be opened in the work area for Steps (1)/(2). A separate area for post-amplification reactions should be used for performing Step (3) of the protocol. After incubation, reactions from Step (2) should be thoroughly spun down after incubation before opening in the post-amplification area to carry out Step (3).

Step (1)—Lysis of patients sample. *PERFORMED IN THE PRE-AMPLIFICATION AREA*

NP swab sample should be lysed using the QuickExtract lysis buffer.

Mix 10 μL of NP swab sample with 10 μL of Quick Extract in an eppendorf tube.

Incubate the sample-QuickExtract mixture at 95° C. for 5 minutes (or at room temperature or 60° C. for 10 mins) and proceed to Step (2).

Step (2)—One pot SHERLOCK detection. *PERFORMED IN THE PRE-AMPLIFICATION AREA*

For each sample, set up one reaction as follows. In addition, a positive control can be set up using the SARS-CoV-2 control RNA. A negative control with Isothermal Amplification Buffer, MgSO4, dNTPs, Lateral Flow Reporter, and sample should also be set up to control for DNAse contamination that may produce false positive results.

TABLE 9

| Reagent | Amount (μL) |
| --- | --- |
| Sherlock mastermix | 45 |
| Lysed sample | 5 |
| Total | 50 |

Mix thoroughly and incubate each reaction at 60° C. for 1 hour. Spin down the reaction in a centrifuge at maximum speed. Transfer the reaction tubes to the post-amplification area before proceeding to Step (3).

Step (3)—Visual readout of detection result via lateral flow strip. *PERFORMED IN THE POST-AMPLIFICATION AREA*

Before opening each tube, spin down each reaction tube in a centrifuge at maximum speed to prevent aerosol contamination. Place a HybriDetect Dipstick into each reaction tube and wait for the reaction to flow through the dipstick.

Positive control samples should show the top line and a faint bottom line. Negative control samples should show the bottom line.

For each test sample, check to see the top line appears, indicating positive SARS-CoV-2 detection.

ADDITIONAL INFORMATION

A detailed general protocol for setting up SHERLOCK-based detection can be found in the following reference: SHERLOCK: nucleic acid detection with CRISPR nucleases. Kellner M J, Koob J G, Gootenberg J S, Abudayyeh O O, and Zhang F. Nature Protocols. 2019 October; 14(10): 2986-3012. doi: 10.1038/s41596-019-0210-2.

CONCLUSIONS

Applicants' one-pot SHERLOCK detection method is capable of rapid, point-of-care diagnosis of COVID-19. With 97% sensitivity and 100% specificity on patient samples, Applicants were able to detect presence of SARS-CoV-2 down to 100 molecules of viral genome per reaction in a simplified format that any user could perform in a non-laboratory setting. Because of the rapid speed and lack of instrumentation, we envision that this protocol could be used in low resource clinics, workplaces, and even at home. While Applicants tested on nasopharyngeal swabs, saliva samples have similar viral loads and would be a simpler alternative sample source. Future versions of the protocol could benefit from an all-in-one integrated device that could heat the reaction and transfer the reaction to a paper strip to reduce amplicon spread and streamline the workflow.

TABLE 10

Methods Comparison.

| | SHERLOCKV2, RT-LAMP/AapCas12b | SHERLOCKv1 RPA-Cas13 | SARS-Cov2 DETECTR | CDC SARS-Cov2 qRT-PCR |
| --- | --- | --- | --- | --- |
| Reference | This study | (Zhang et al. 2020) | (Broughton et al., 2020) | (CDC) |
| Target | N gene | N gene and S gene | E gene and N gene | N gene |
| LoD (per 50 ul reaction) | 100 copies | 50-500 copies | 50 copies | 5-15 copies |
| Assay reaction time | 60 min | 55 min | 40 min | 120 min |
| Assay sample-to-result time | 70 min | 90 min (including RNA extraction) | 75 min (including RNA extraction) | 4 h (including RNA extraction) |

TABLE 10-continued

Methods Comparison.

| | SHERLOCKV2, RT-LAMP/AapCas1 2b | SHERLOCKv1, RPA-Cas13 | SARS-Cov2 DETECTR | CDC SARS-Cov2 qRT-PCR |
|---|---|---|---|---|
| Assay results | Visual | Visual | Visual | Fluorescent |
| Laboratory instrumentation required | None | Centrifuges, water baths | Centrifuges, water baths | Centrifuges, qPCR machine |
| Sample extraction required | None | Yes | Yes | Yes |
| Liquid transfer steps | 1 | 3 | 3 | 1 |

REFERENCES

Broughton, J. P., Deng, X., Yu, G., Fasching, C. L., Servellita, V., Singh, J., Miao, X., Streithorst, J. A., Granados, A., Sotomayor-Gonzalez, A., et al. (2020). CRISPR-Cas12-based detection of SARS-CoV-2. Nat. Biotechnol.

Ding, X., Yin, K., Li, Z., and Liu, C. (2020). All-in-One Dual CRISPR-Cas12a (AIOD-CRISPR) Assay: A Case for Rapid, Ultrasensitive and Visual Detection of Novel Coronavirus SARS-CoV-2 and HIV virus.

Gootenberg, J. S., Abudayyeh, O. O., Lee, J. W., Essletzbichler, P., Dy, A. J., Joung, J., Verdine, V., Donghia, N., Daringer, N. M., Freije, C. A., et al. (2017). Nucleic acid detection with CRISPR-Cas13a/C2c2. Science 356, 438-442.

Gootenberg, J. S., Abudayyeh, O. O., Kellner, M. J., Joung, J., Collins, J. J., and Zhang, F. (2018). Multiplexed and portable nucleic acid detection platform with Cas13, Cas12a, and Csm6. Science 360, 439-444.

Guo, L., Sun, X., Wang, X., Liang, C., Jiang, H., Gao, Q., Dai, M., Qu, B., Fang, S., Mao, Y., et al. (2020). SARS-CoV-2 detection with CRISPR diagnostics.

Lucia, C., Federico, P.-B., and Alejandra, G. C. (2020). An ultrasensitive, rapid, and portable coronavirus SARS-CoV-2 sequence detection method based on CRISPR-Cas12.

Shmakov, S., Abudayyeh, O. O., Makarova, K. S., Wolf, Y. I., Gootenberg, J. S., Semenova, E., Minakhin, L., Joung, J., Konermann, S., Severinov, K., et al. (2015). Discovery and Functional Characterization of Diverse Class 2 CRISPR-Cas Systems. Mol. Cell 60, 385-397.

Teng, F., Cui, T., Feng, G., Guo, L., Xu, K., Gao, Q., Li, T., Li, J., Zhou, Q., and Li, W. (2018). Repurposing CRISPR-Cas12b for mammalian genome engineering. Cell Discov 4, 63.

Whitman, J. D., Hiatt, J., Mowery, C. T., Shy, B. R., Yu, R., Yamamoto, T. N., Rathore, U., Goldgof, G. M., Whitty, C., Woo, J. M., et al. (2020). Test performance evaluation of SARS-CoV-2 serological assays. medRxiv 2020.04.25.20074856.

Zhang, Y., Odiwuor, N., Xiong, J., Sun, L., Nyaruaba, R. O., Wei, H., and Tanner, N. A. (2020). Rapid Molecular Detection of SARS-CoV-2 (COVID-19) Virus RNA Using Colorimetric LAMP. medRxiv 2020.02.26.20028373.

Example 7—Optimization and Enhancement of Detection Methods

Rather than a multi-step process for the extraction and washing when using beads as is explained in previous prior art methods, the present disclosure improves upon the methods:

A bead and lysis buffer mix is added to the sample, for about 5 to 10 minutes. At this time, the virus is lysed and bound to the beads.

Sample with beads is palced upon magxit, after separation, supernatant is aspirated and reaction buffer mix is added and sample can be subjected in pPCR. Thus, lysis and bead preparation steps are merged rather than multi-steps, and elimination of washes and elution steps are eliminated, with elution merged with the addition of reaction buffer mix.

The bead mix can include potassium chloride, with the typical amount of potassium chloride being reduced or eliminated from the reaction buffer mix. Additionally, the lysis buffer according to methods as provided herein can comprise proteinase K. Without the typical wash steps utilized after lysis, proteinase K carries over from the lysis step in the current methods, and proteinase K inhibitor is added to the reaction buffer mix.

Beads can be optionally used with the methods described herein, including with the one-pot methods that allow for concentration of viral nucleic acids from large volume samples, such as saliva or swab samples to allow for a single one-pot reaction method.

An exemplary method of making the beads are as follows:
Reagents
500 mL 5M NaCl
1M Tris-HCl, pH 8.0
500 mM EDTA, pH 8.0
Dry Poly-Ethylene Glycol 8000, PEG-8000 (Fisher, P/N BP233-1)
Carboxy-Modified Sera-Mag Speed Beads (Fisher, P/N 09-981-124)
Protocol
Vortex the Sera-Mag speedbeads bottle for 1 minutes.
Add 0.1% (w/v) of your intended production amount, which is 10 mL of the Sera-Mag Speedbeads solution to a 50 mL conical tube.
Using a 50 mL magnetic separator, pellet the magnetic beads.
Aspirate the supernatant and discard.
The beads contain residual azide. Wash them twice with 10 mL of DI water, resuspending the pellet each time by vortexing for 30 seconds.
Pellet the beads for the last time.
Prepare the bead buffer by mixing orderly the following in a 500 mL reagent bottle.

| Component | Volume |
|---|---|
| 5M NaCl | 100 mL |
| 1M Tris-HCl | 5 mL |

| Component | Volume |
| --- | --- |
| 500 mM EDTA | 1 mL |
| PEG-8000 | 90 g |

Invert mix 10 times and fill with DI water until it reaches the 500 mL mark.

Filter using a vacuum filtration unit according to the manufacturer's instructions and store filtered buffer in container of filtration unit until needed.

Remove the final wash fluid on the beads and add 10 mL of the sterile bead buffer to the beads.

Vortex for 30 seconds to resuspend the beads.

Add the bead slurry to the 500 mL bottle containing the remainder of the sterile buffer.

Twirl the bottle to homogenize the beads with the buffer.

The beads can now be aliquoted and stored at −20° C. Optimization of reagents For ease of reference, optimization is described using LAMP amplification, but the design paradigm is applicable to any other isothermal amplification approach detailed herein. Further optimization of the methods as disclosed herein can include first screening primers to identify one or more sets of primers that work well for a particular target, Cas protein and/or reaction. Once the primers have been screened, titration of Magnesium concentration can be performed to identify an optimal magnesium concentration for higher signal to noise. Once an optimum magnesium concentration is identified, additional additives are screened at around 20-25% of the reaction, and once additives are identified, these additives, such as those components identified in FIG. 17, can be evaluated and varied in concentration to identify optimal reaction kinetics for specific reaction parameters, for example, specific primers, target, Cas protein, temperature, and other additive concentrations within the reaction. As described herein, a change from NaCl to KCl allows for the bead and lysis buffer mix to n reduce carryover and optimize reactions, allowing for merger of bead preparation, and washing/elution steps. Additionally, optimization of salt types and concentrations may further aid one-pot reactions Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11639523B2). An electronic copy of the "Sequence Listing" will also be available from the USPTO upon request and payment of the fee set forth in 37 CFR 1.19(b)(3).

What is claimed is:

1. A non-naturally occurring or engineered composition comprising
a Cas12b protein from *Alicyclobacillus acidiphilus*; and
a guide molecule that does not impede the Cas12b's activity at elevated temperatures above 55° C., comprising a guide sequence with at least 95% or more sequence similarity to a direct repeat and tracrRNA sequence from the *Alicyclobacillus acidoterrestris* CRISPR-Cas12b system and capable of forming a complex with the Cas12b protein and directing the complex to bind to a target polynucleotide.

2. The composition of claim 1, wherein the guide sequence comprises one of SEQ ID NOs: 61957-61961.

3. The composition of claim 1, wherein the Cas12b protein is fused to one or more localization signals.

4. The composition of claim 1, further comprising a detection construct comprising a non-target polynucleotide, wherein the Cas protein exhibits collateral activity and cleaves the non-target polynucleotide component once activated by the target polynucleotide.

5. The composition of claim 4, further comprising one or more isothermal amplification reagents.

6. The composition of claim 5, wherein the isothermal amplification reagents are loop-mediated isothermal amplification (LAMP) reagents, wherein the LAMP reagents are primers selected from SEQ ID NOs: 61983-61988.

7. The composition of claim 6, wherein the guide molecule is designed to bind to a polynucleotide sequence of SARS-CoV-2, wherein the guide molecule is SEQ ID NO: 61989.

8. A vector composition comprising one or more polynucleotide sequences encoding the Cas12b protein and the guide molecule in the composition of claim 1.

9. A non-naturally occurring or engineered prokaryotic or eukaryotic isolated host cell comprising the composition of claim 1, or progeny thereof.

10. A method of targeting one or more target polynucleotides, the method comprising contacting the one or more target polynucleotides with a non-naturally occurring or engineered composition of claim 1, wherein targeting comprises modifying the one or more target polynucleotides comprises increasing or decreasing expression of the one or more genes in the one or more target polynucleotides, insertion of a recombination template or a portion thereof to the one or more target polynucleotides.

11. A method for detecting a target polynucleotide in a sample, comprising contacting the sample with the composition of claim 4, wherein the Cas protein exhibits collateral activity and cleaves the detection construct once activated by the target polynucleotide, and the cleaved detection construct generate a signal; and detecting the signal thereby determining presence of the target polynucleotide in the sample.

12. A kit for modifying or detecting a target polynucleotide in a sample, comprising the composition of claim 1.

13. The composition of claim 1, wherein the guide molecule comprises a sequence with at least 95% or more sequence similarity to one of SEQ ID NOs: 61957-61961.

14. The vector composition of claim 8, wherein the polynucleotide sequences are codon optimized for expression in a eukaryotic cell.

* * * * *

UNITED STATES PATENT AND TRADEMARK OFFICE
CERTIFICATE OF CORRECTION

PATENT NO. : 11,639,523 B2
APPLICATION NO. : 16/894678
DATED : May 2, 2023
INVENTOR(S) : Feng Zhang et al.

It is certified that error appears in the above-identified patent and that said Letters Patent is hereby corrected as shown below:

On the Title Page

On the Page 2, in Column 1, under "Other Publications", Line 29, delete "Off-arget" and insert -- Off-target --.

On the Page 3, in Column 1, under "Other Publications", Line 26, delete "116/" and insert -- 16/ --.

In the Specification

In Column 2, Line 28, delete "acidiphilis;" and insert -- acidophilus; --.

In Column 8, Line 34, delete "acidiphilis" and insert -- acidophilus --.

In Column 22, Line 6, delete "acidiphilis" and insert -- acidophilus --.

In Column 24, Lines 24-25, delete "acidoterrestrus" and insert -- acidoterrestris --.

In Column 46, Line 55, delete "acidoterrestrus" and insert -- acidoterrestris --.

In Column 154, Line 18, delete "CRISRP" and insert -- CRISPR --.

In Column 156, Line 4, delete "CIRPSR" and insert -- CRISPR --.

In Column 156, Line 8, delete "CIRPSR" and insert -- CRISPR --.

In Column 261, Line 19, delete "acidiphilis;" and insert -- acidophilus; --.

Signed and Sealed this
Fifth Day of December, 2023

Katherine Kelly Vidal
*Director of the United States Patent and Trademark Office*